US006720324B2

(12) United States Patent
Marzabadi et al.

(10) Patent No.: US 6,720,324 B2
(45) Date of Patent: Apr. 13, 2004

(54) SELECTIVE MELANIN CONCENTRATING HORMONE-1 (MCH1) RECEPTOR ANTAGONISTS AND USES THEREOF

(75) Inventors: Mohammad R. Marzabadi, Ridgewood, NJ (US); John Wetzel, Fairlawn, NJ (US); John E. DeLeon, North Bergen, NJ (US); Bharat Lagu, Belle Mead, NJ (US); Charles Gluchowski, Danville, CA (US); Stewart Noble, Lake Forest, IL (US); Dhanapalan Nagarathnam, Bethany, CT (US)

(73) Assignee: Synaptic Pharmaceutical Corporation, Paramus, NJ (US)

( * ) Notice: Subject to any disclaimer, the term of this patent is extended or adjusted under 35 U.S.C. 154(b) by 0 days.

(21) Appl. No.: 09/899,635

(22) Filed: Jul. 5, 2001

(65) Prior Publication Data

US 2003/0069261 A1 Apr. 10, 2003

Related U.S. Application Data

(60) Provisional application No. 60/216,218, filed on Jul. 5, 2000.

(51) Int. Cl.[7] ..................... C07D 239/32; A61K 31/505
(52) U.S. Cl. .................. 514/252.14; 514/274; 544/316
(58) Field of Search ................ 544/316; 514/274, 514/252.14

(56) References Cited

U.S. PATENT DOCUMENTS

| | | | |
|---|---|---|---|
| 4,438,117 A | 3/1984 | Cherkofsky et al. | 424/251 |
| 4,684,653 A | 8/1987 | Taylor et al. | 514/258 |
| 4,684,655 A | 8/1987 | Atwal | 514/274 |
| 4,684,656 A | 8/1987 | Atwal | 514/274 |
| 4,703,120 A | 10/1987 | Press | 544/278 |
| 4,728,652 A | 3/1988 | Atwal | 514/274 |
| 4,845,216 A | 7/1989 | Taylor et al. | 544/279 |
| 4,855,301 A | 8/1989 | Atwal et al. | 514/269 |
| 4,882,334 A | 11/1989 | Shih et al. | 514/258 |
| 4,902,796 A | 2/1990 | Taylor et al. | 544/279 |
| 4,946,846 A | 8/1990 | Nomura et al. | 514/258 |
| 5,134,145 A | 7/1992 | Brouwer et al. | 514/214 |
| 5,149,810 A | 9/1992 | Perrior et al. | 544/309 |
| 5,202,330 A | 4/1993 | Atwal et al. | 514/274 |
| 5,250,531 A | 10/1993 | Cooper et al. | 514/256 |
| 5,292,740 A | 3/1994 | Burri et al. | 514/256 |
| 5,500,424 A | 3/1996 | Nagamine et al. | 514/235.5 |
| 5,521,189 A | 5/1996 | Boykin et al. | 514/256 |
| 5,541,186 A | 7/1996 | Breu et al. | 514/256 |
| 5,594,141 A | 1/1997 | Yuan et al. | 544/242 |
| 5,942,517 A | 8/1999 | Nagarathnam et al. | 514/274 |
| 6,037,354 A | 3/2000 | Patane et al. | 514/318 |
| 6,245,773 B1 | 6/2001 | Wong et al. | 514/272 |

FOREIGN PATENT DOCUMENTS

| | | |
|---|---|---|
| EP | 627427 | 12/1974 |
| EP | 162208 | 11/1985 |
| EP | 204317 | 12/1986 |
| EP | 234830 | 9/1987 |
| EP | 236902 | 9/1987 |
| EP | 237347 | 9/1987 |
| EP | 280227 | 8/1988 |
| EP | 400665 | 12/1990 |
| EP | 459666 | 12/1991 |
| EP | 622366 | 11/1994 |
| EP | 622369 | 11/1994 |
| FR | 2610625 | 8/1988 |
| JP | 5659778 | 5/1981 |
| JP | 61282367 | 12/1986 |
| JP | 6287574 | 4/1987 |
| JP | 62265271 | 11/1987 |
| WO | 9200741 | 1/1992 |
| WO | 9214453 | 9/1992 |
| WO | 9410989 | 5/1994 |
| WO | 9422829 | 10/1994 |
| WO | WO 96/14846 | 5/1996 |
| WO | 9742956 | 11/1997 |
| WO | 9851311 | 11/1998 |
| WO | 9907695 | 2/1999 |
| WO | 9948530 | 9/1999 |
| WO | WO 02/06245 | 1/2002 |

OTHER PUBLICATIONS

Dhar et al., Design and Synthesis of Novel alpha 1a Adrenoceptor–Selective Antagonists, J. Med. Chem. 42(23), pp. 4778–4793, 1999.

Yoshida et al., PubMed Abstract (Int J Obes Relat Metab Disord 18(5): 339–43), 1994.

(List continued on next page.)

Primary Examiner—Deepak Rao
(74) Attorney, Agent, or Firm—John P. White; Cooper & Dunham LLP

(57) ABSTRACT

This invention is directed to compounds which are selective antagonists for melanin concentrating hormone-1 (MCH1) receptors. The invention provides a pharmaceutical composition comprising a therapeutically effective amount of the compound of the invention and a pharmaceutically acceptable carrier. This invention provides a pharmaceutical composition made by combining a therapeutically effective amount of the compound of this invention and a pharmaceutically acceptable carrier. This invention further provides a process for making a pharmaceutical composition comprising combining a therapeutically effective amount of the compound of the invention and a pharmaceutically acceptable carrier.

This invention also provides a method of modifying feeding behavior of a subject which comprises administering to the subject an amount of a compound of the invention effective to decrease the consumption of food by the subject. This invention further provides a method of treating a feeding disorder in a subject which comprises administering to the subject an amount of a compound of the invention effective to decrease the consumption of food by the subject. In an embodiment of the invention, the feeding disorder is bulimia, bulimia nervosa or obesity.

18 Claims, No Drawings

OTHER PUBLICATIONS

Savontaus et al., PubMed Abstract (Eur J Pharmacol 328(2–3): 207–15), 1997.

Zahorska–Markiewicz et al., PubMed Abstract (Horm Metab Res 18(10): 693–7), 1986.

Atwal, K.S. et al., "Synthesis of Substituted 1,2,3, 4–Tetrahydro–6–Methyl–2–Thioxo–5–Pyrimidinecarboxylic Acid Esters," Heterocycles (1987) 26(5): 1189–1192 (Exhibit 47).

Atwal, K. S. et al., "Substituted 1,4–Dihydropyrimidines. 3. Synthesis of Selectively Functionalized 2–Hetero–1,4–dihyropyrimidines," Journal of Organic Chemistry (1989) 54: 5898–5907 (Exhibit 48).

Atwal, K. S. et al., Dihydropyimidines Calcium Channel Blockers: 2–Heterosubstituted 4–aryl–1,4–dihydro–6–methyl–5–pyrimidinecarboxylic Acid Esters as Potent Mimics of Dihydropyridines, Journal of Medicinal Chemistry (1990) 33(5): 1510–1515 (Exhibit 49).

Atwal, K.S. et al., "Dihydropyrimidines Calcium Channel Blockers. 2. 3–Substituted–4–aryl–1,4–diydro–6–methyl–5–pyrimidinecarboxylic Acid Esters as Potent Mimics of Dihydropyridines," *Journal of Medicinal Chemistry* (1990) 33(9):2629–2635 (Exhibit 50).

Atwal, K. S. et al., "Dihydropyrimidine Calcium Channel Blockers. 3. 3–Carbamoyl–4–aryl–1,2,3,4–tetrahydro–6–methyl–5–pyrimidenecarboxylic Acid Esters as Orally Effective Antihypertensive Agents," *Journal of Medicinal Chemistry* (1991) 34(2) : 806–811 (Exhibit 51).

Barrio, et al., "A Direct Method For Preparation of 2–Hydroxyethoxymethyl Derivatives of Guanine, Adenine, and Cytosine," *Journal of Medicinal Chemistry* (1980) 23(5):572–574 (Exhibit 52).

Boer, R. et al., "(+)–Niguldipine binds with very high affinity to $Ca^{2+}$ channels and to a subtype of $\alpha_1$–adrenoceptors," *European Journal of Pharmacology*—Molecular Pharmacology Section (1989) 172: 131–145 (Exhibit 53).

Brown, et al., "Inhibitors of *Bacillus subtilis* DNA Polymerase III. 6–(Arylalkylamino)uracils and 6–Anilinouracils, "*Journal of Medicinal Chemistry* (1997) 20(9): 1186–1189 (Exhibit 54).

Cho H., Takeuchi Y., Ueda M., and Mizuno A. Regioselective synthesis of N–substitued dihydropyrimidine–2 (1–H) or (3H)–One. *Tetrahedron Letters*, vol. 29 (42) : 5405–5408, 1988 (Exhibit 55).

Cho, H. et al., "Dihydropyrimidines: Novel Calcium Antagonists with Potent and Long–Lasting Vasodilative and Antihypertensive Activity," *Journal of Medicinal Chemistry* (1989) 32:2399–2406 (Exhibit 56).

D'Eletto, R. D. and Javitt, N.B., "Effect of Doxazosin on Cholestorol Synthesis In Cell Culture," Journal of Cardiovascular Pharmacology (1989) 13, Supp. 2: S1–S4 (Exhibit 57).

Forray et al., "The $\alpha_1$–Adrenergic Receptor That Mediates Smooth Muscle Contraction in Human Prostate Has The Pharmacological Properties of the Cloned Human $\alpha_{1c}$ Subtype," *Molecular Pharmacology* (1994) 45: 703–708 (Exhibit 58).

Khanina, E. L. et al., Alkylation of derivatives of 2–oxo–4–phenyl–6–methyl–1,2,3,4–tetrahydropyrimidine–5–carboxlic acid. *Chemical Abstracts* 89: 43319 (1978) (Exhibit 59).

Mamaev, V.P. and Dubovenko, Z.D., Pyrimidines. XXI. 5–Substituted 2–hydroxy–4,6–diphenylpyrimidines. *Chemical Abstracts* 73: 77187 (1970) (Exhibit 60).

McGrath, J. C. et al., "Alpha–Adrenoceptors: A Critical Review," *Medicinal Research Reviews* (1989) 9(4): 407–553 (Exhibit 61).

Rovnyak, G. C. et al., "Dihydropyrimidine Calcium Channel Blockers. 4. Basic 3–Substituted–4–aryl–1,4–dihydropyrimidine–5–carboxylic Acid Esters. Potent Antihypertensive Agents," *Journal of Medicinal Chemistry* (1992) 35(17): 3254–3263 (Exhibit 62).

Spiers, J. P. et al., "UK–52,046 (A Novel $\alpha_1$–Adrenoceptor Antagonist) and the Role of $\alpha$–Adrenoceptor Stimulation and Blockade on Antriventricular Conduction," *Journal of Cardiovascular Pharamacology* (1990) 16(5): 824–830 (Exhibit 63).

Triggle, D. J., "Dihydropyrimidine Calcium Channel Blockers. 2.3–Substituted 4–Aryl–1,4–dihdro–6–methyl–5–pyrimidine–carboxylic Acid Esters as Potent Mimics of Dihyropyridines," Chemtracts—*Organic Chemistry* (Jan./Feb. 1991) 68–72 (Exhibit 64).

Wetzel, J. M., et al., "Discovery of $\alpha_{1a}$–Adrenergic Receptor Antagonists Based on the L–Type $Ca^{2+}$ Channel Antagonist Niguldipine" *Journal of Medicinal Chemistry* (1995) 38(10): 1579–1581 (Exhibit 65).

Zhan, G. L. et al., "Bunazosin Reduces Intraocular Pressure By Increasing Uveocleral Outflow In Rabbits,"*Investigative Ophthalmology and Visual Science* (1993) 34(4): Abst. No. 1133–49, p. 928 (Exhibit 66).

SELECTIVE MELANIN CONCENTRATING HORMONE-1 (MCH1) RECEPTOR ANTAGONISTS AND USES THEREOF

This application claims the benefit of U.S. Provisional Application No. 60/216,218, filed Jul. 5, 2000, the contents of which are hereby incorporated by reference.

BACKGROUND OF THE INVENTION

Throughout this application, various publications are referenced in parentheses by author and year. Full citations for these references may be found at the end of the specification immediately preceding the sequence listings and the claims. The disclosure of these publications in their entireties are hereby incorporated by reference into this application to describe more fully the state of the art to which this invention pertains.

Melanin-concentrating hormone (MCH) is a cyclic peptide originally isolated from salmonid (teleost fish) pituitaries (Kawauchi et al., 1983). In fish the 17 amino acid peptide causes aggregation of melanin within the melanophores and inhibits the release of ACTH, acting as a functional antagonist of α-MSH. Mammalian MCH (19 amino acids) is highly conserved between rat, mouse, and human, exhibiting 100% amino acid identity, but its physiological roles are less clear. MCH has been reported to participate in a variety of processes including feeding, water balance, energy metabolism, general arousal/attention state, memory and cognitive functions, and psychiatric disorders (for reviews, see Baker, 1991; Baker, 1994; Nahon, 1994; Knigge et al., 1996). Its role in feeding or body weight regulation is supported by a recent Nature publication (Qu et al., 1996) demonstrating that MCH is overexpressed in the hypothalamus of ob/ob mice compared with ob/+ mice, and that fasting further increased MCH mRNA in both obese and normal mice during fasting. MCH also stimulated feeding in normal rats when injected into the lateral ventricles (Rossi et al., 1997). MCH also has been reported to functionally antagonize the behavioral effects of α-MSH (Miller et al., 1993; Gonzalez et al, 1996; Sanchez et al., 1997); in addition, stress has been shown to increase POMC mRNA levels while decreasing the MCH precursor preproMCH (ppMCH) mRNA levels (Presse et al., 1992). Thus MCH may serve as an integrative neuropeptide involved in the reaction to stress, as well as in the regulation of feeding and sexual activity (Baker, 1991; Knigge et al., 1996).

Although the biological effects of MCH are believed to be mediated by specific receptors, binding sites for MCH have not been well described. A tritiated ligand ([$^3$H]-MCH) was reported to exhibit specific binding to brain membranes but was unusable for saturation analyses, so neither affinity nor $B_{max}$ were determined (Drozdz and Eberle, 1995). Radio-iodination of the tyrosine at position thirteen resulted in a ligand with dramatically reduced biological activity (see Drozdz and Eberle, 1995). In contrast, the radioiodination of the MCH analogue [Phe$^{13}$,Tyr$^{19}$]-MCH was successful (Drozdz et al., 1995); the ligand retained biological activity and exhibited specific binding to a variety of cell lines including mouse melanoma (B16-F1, G4F, and G4F-7), PC12, and COS cells. In G4F-7 cells, the $K_D$=0.118 nM and the $B_{max}$ ~1100 sites/cell. Importantly, the binding was not inhibited by α-MSH but was weakly inhibited by rat ANF (Ki=116 nM vs. 12 nM for native MCH) (Drozdz et al., 1995). More recently specific MCH binding was reported in transformed keratinocytes (Burgaud et al., 1997) and melanoma cells (Drozdz et al., 1998), where photo-crosslinking studies suggest that the receptor is a membrane protein with an apparent molecular weight of 45–50 kDaltons, compatible with the molecular weight range of the GPCR superfamily of receptors. No radioautoradiographic studies of MCH receptor localization using this ligand have been reported as yet.

The localization and biological activities of MCH peptide suggest that the modulation of MCH receptor activity may be useful in a number of therapeutic applications. The role of MCH in feeding is the best characterized of its potential clinical uses. MCH is expressed in the lateral hypothalamus, a brain area implicated in the regulation of thirst and hunger (Grillon et al., 1997); recently orexins A and B, which are potent orexigenic agents, have been shown to have very similar localization to MCH in the lateral hypothalamus (Sakurai et al., 1998). MCH mRNA levels in this brain region are increased in rats after 24 hours of food-deprivation (Hervé and Fellman, 1997); after insulin injection, a significant increase in the abundance and staining intensity of MCH immunoreactive perikarya and fibres was observed concurrent with a significant increase in the level of MCH mRNA (Bahjaoui-Bouhaddi et al., 1994). Consistent with the ability of MCH to stimulate feeding in rats (Rossi et al., 1997) is the observation that MCH mRNA levels are upregulated in the hypothalami of obese ob/ob mice (Qu et al., 1996), and decreased in the hypothalami of rats treated with leptin, whose food intake and body weight gains are also decreased (Sahu, 1998). MCH appears to act as a functional antagonist of the melanocortin system in its effects on food intake and on hormone secretion within the HPA (hypothalamopituitary/adrenal axis) (Ludwig et al., 1998). Together these data suggest a role for endogenous MCH in the regulation of energy balance and response to stress, and provide a rationale for the development of specific compounds acting at MCH receptors for use in the treatment of obesity and stress-related disorders.

In all species studied to date, a major portion of the neurons of the MCH cell group occupies a rather constant location in those areas of the lateral hypothalamus and subthalamus where they lie and may be a part of some of the so-called "extrapyramidal" motor circuits. These involve substantial striato- and pallidofugal pathways involving the thalamus and cerebral cortex, hypothalamic areas, and reciprocal connections to subthalamic nucleus, substantia nigra, and mid-brain centers (Bittencourt et al., 1992). In their location, the MCH cell group may offer a bridge or mechanism for expressing hypothalamic visceral activity with appropriate and coordinated motor activity. Clinically it may be of some value to consider the involvement of this MCH system in movement disorders, such as Parkinson's disease and Huntingdon's Chorea in which extrapyramidal circuits are known to be involved.

Human genetic linkage studies have located authentic hMCH loci on chromosome 12 (12q23–24) and the variant hMCH loci on chromosome 5 (5q12–13) (Pedeutour et al., 1994). Locus 12q23–24 coincides with a locus to which autosomal dominant cerebellar ataxia type II (SCA2) has been mapped (Auburger et al., 1992; Twells et al., 1992). This disease comprises neurodegenerative disorders, including an olivopontocerebellar atrophy. Furthermore, the gene for Darier's disease, has been mapped to locus 12q23–24 (Craddock et al., 1993). Dariers' disease is characterized by abnormalities I keratinocyte adhesion and mental illnesses in some families. In view of the functional and neuroanatomical patterns of the MCH neural system in the rat and human brains, the MCH gene may represent a good candidate for SCA2 or Darier's disease. Interestingly, diseases with high social impact have been mapped to this locus. Indeed, the gene responsible for chronic or acute forms of spinal muscular atrophies has been assigned to chromosome 5q12–13 using genetic linkage analysis (Melki et al., 1990; Westbrook et al., 1992). Furthermore, independent lines of evidence support the assignment of a major schizophrenia locus to chromosome 5q11.2–13.3 (Sherrington et al., 1988; Bassett et al., 1988; Gilliam et al., 1989). The above studies suggest that MCH may play a role in neurodegenerative diseases and disorders of emotion.

Additional therapeutic applications for MCH-related compounds are suggested by the observed effects of MCH in other biological systems. For example, MCH may regulate reproductive functions in male and female rats. MCH transcripts and MCH peptide were found within germ cells in testes of adult rats, suggesting that MCH may participate in stem cell renewal and/or differentiation of early spermatocytes (Hervieu et al., 1996). MCH injected directly into the medial preoptic area (MPOA) or ventromedial nucleus (VMN) stimulated sexual activity in female rats (Gonzalez et al., 1996). In ovariectomized rats primed with estradiol, MCH stimulated luteinizing hormone (LH) release while anti-MCH antiserum inhibited LH release (Gonzalez et al., 1997). The zona incerta, which contains a large population of MCH cell bodies, has previously been identified as a regulatory site for the pre-ovulatory LH surge (MacKenzie et al., 1984). MCH has been reported to influence release of pituitary hormones including ACTH and oxytocin. MCH analogues may also be useful in treating epilepsy. In the PTZ seizure model, injection of MCH prior to seizure induction prevented seizure activity in both rats and guinea pigs, suggesting that MCH-containing neurons may participate in the neural circuitry underlying PTZ-induced seizure (Knigge and Wagner, 1997). MCH has also been observed to affect behavioral correlates of cognitive functions. MCH treatment hastened extinction of the passive avoidance response in rats (McBride et al., 1994), raising the possibility that MCH receptor antagonists may be beneficial for memory storage and/or retention. A possible role for MCH in the modulation or perception of pain is supported by the dense innervation of the periaqueductal grey (PAG) by MCH-positive fibers. Finally, MCH may participate in the regulation of fluid intake. ICV infusion of MCH in conscious sheep produced diuretic, natriuretic, and kaliuretic changes in response to increased plasma volume (Parkes, 1996). Together with anatomical data reporting the presence of MCH in fluid regulatory areas of the brain, the results indicate that MCH may be an important peptide involved in the central control of fluid homeostasis in mammals.

As used in this invention, the term "antagonist" refers to a compound which binds to, and decreases the activity of, a receptor in the presence of an agonist. In the case of a G-protein coupled receptor, activation may be measured using any appropriate second messenger system which is coupled to the receptor in a cell or tissue in which the receptor is expressed. Some specific, but by no means limiting, examples of well-known second messenger systems are adenylate cyclase, intracellular calcium mobilization, ion channel activation, guanylate cyclase and inositol phospholipid hydrolysis. Conversely, the term "agonist" refers to a compound which binds to, and increases activity of, a receptor as compared with the activity of the receptor in the absence of any agonist.

In one embodiment of this invention, the synthesis of novel compounds which bind selectively to the cloned human melanin-concentrating hormone-1 (MCH1) receptor, compared to other cloned G-protein coupled receptors, and inhibit the activation of the cloned receptors as measured in in vitro assays is disclosed. The in vitro receptor binding and activation assays described hereinafter were performed using various cultured cell lines, each transfected with and expressing only a single cloned receptor.

Furthermore, the compounds of the present invention may also be used to treat abnormal conditions such as feeding disorders (obesity, bulimia and bulimia nervosa), sexual/reproductive disorders, depression, anxiety, depression and anxiety, epileptic seizure, hypertension, cerebral hemorrhage, congestive heart failure, sleep disturbances, or any condition in which antagonism of an MCH1 receptor may be beneficial. In addition, the compounds of the present invention may be used to reduce the body mass of a subject.

SUMMARY OF THE INVENTION

This invention provides a compound having the structure:

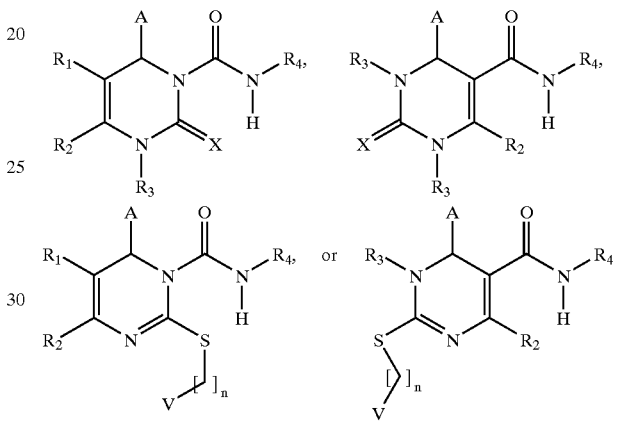

wherein A is

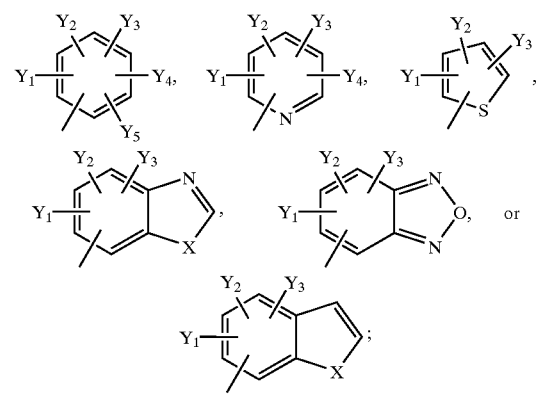

wherein each of $Y_1$, $Y_2$, $Y_3$, $Y_4$ and $Y_5$ is independently —H; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —F, —Cl, —Br, or —I; —NO$_2$; —N$_3$; —CN; —OR$_3$, —OCOR$_3$, —COR$_3$, —CON(R$_3$)$_2$, or —COOR$_3$; or any two of $Y_1$, $Y_2$, $Y_3$, $Y_4$ and $Y_5$ present on adjacent carbon atoms can constitute a methylenedioxy group;

wherein each X is independently S; O; or NR$_3$;

wherein R$_1$ is —H; —NO$_2$; —CN; straight chained or branched $C_1$–$C_7$ alkyl, monofluoroalkyl or polyfluoroalkyl; straight chained or branched C₂–C₇ alkenyl or alkynyl; C₃–C₇ cycloalkyl, monofluorocycloalkyl, polyfluorocycloalkyl or cycloalkenyl; —N(R₃)₂; —OR₃; —(CH₂)ₚOR₃; —COR₃; —CO₂R₃; —CON(R₃)₂; or —CO₂(CH₂)ₙV;

wherein R₂ is —H; straight chained or branched C₁–C₇ alkyl, hydroxyalkyl, alkoxyalkyl, monofluoroalkyl or polyfluoroalkyl; straight chained or branched C₂–C₇ alkenyl or alkynyl; C₃–C₇ cycloalkyl, monofluorocycloalkyl, polyfluorocycloalkyl or cycloalkenyl; C₃–C₁₀ cycloalkyl-C₁–C₁₀-alkyl, C₃–C₁₀ cycloalkyl-C₁–C₁₀-monofluoroalkyl or C₃–C₁₀ cycloalkyl-C₁–C₁₀-polyfluoroalkyl; —CN; —CH₂XR₃, —CH₂X(CH₂)ₚNHR₃, —(CH₂)ₙNHR₃, —CH₂X(CH₂)ₚN(R₃)₂, —CH₂X(CH₂)ₚN₃, —CH₂X(CH₂)ₚNHCXR₇; or —OR₃; or wherein R₁ and R₂ together may form a lactone ring;

wherein each R₃ is independently —H; straight chained or branched C₁–C₇ alkyl, monofluoroalkyl or polyfluoroalkyl; straight chained or branched C₂–C₇ alkenyl or alkynyl; C₃–C₇ cycloalkyl, monofluorocycloalkyl, polyfluorocycloalkyl or cycloalkenyl;

wherein R₄ is

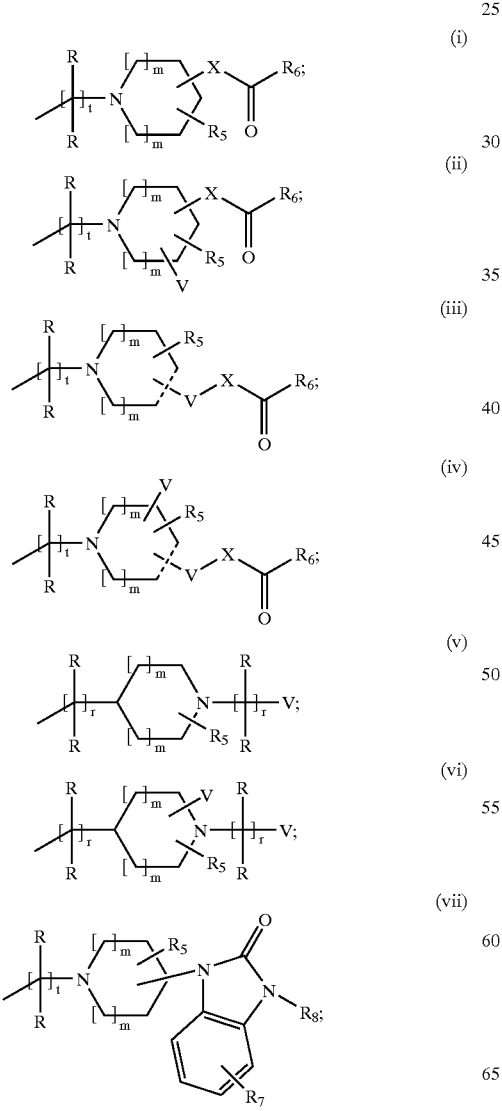

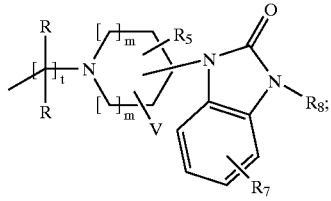

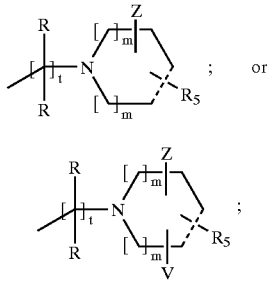

wherein the dashed line represents a single bond or a double bond;

wherein each R is independently —H; —F; straight chained or branched C₁–C₇ alkyl, monofluoroalkyl or polyfluoroalkyl; straight chained or branched C₂–C₇ alkenyl or alkynyl; —N(R₃)₂; —NO₂; —CN; —CO₂R₃; —OR₃; or —CON(R₃)₂;

wherein each V is independently aryl or heteroaryl, optionally substituted with one or more F; Cl; Br; I; COR₃; CO₂R₃; —CON(R₃)₂; CN; —NO₂; —N(R₃)₂; —OR₃; —SR₃; (CH₂)qOR₃; (CH₂)qSR₃; straight chained or branched C₁–C₇ alkyl, monofluoroalkyl, polyfluoroalkyl, aminoalkyl, or carboxamidoalkyl; straight chained or branched C₂–C₇ alkenyl, C₂–C₇ alkynyl; C₃–C₇ cycloalkyl, monofluorocycloalkyl, polyfluorocycloalkyl or cycloalkenyl;

wherein each R₅ is —H; —NO₂; —N₃; —CN; straight chained or branched C₁–C₇ alkyl, monofluoroalkyl or polyfluoroalkyl; straight chained or branched C₂–C₇ alkenyl or alkynyl; C₃–C₇ cycloalkyl, monofluorocycloalkyl, polyfluorocycloalkyl or cycloalkenyl; —N(R₃)₂; —OR₃; —(CH₂)ₚOR₃; —COR₃; —CO₂R₃; —CON(R₃)₂; aryl or heteroaryl, wherein the aryl or heteroaryl is optionally substituted with one or more F; Cl; Br; I; COR₃; CO₂R₃; —CON(R₃)₂; CN; —NO₂; —N(R₃)₂; —OR₃; —SR₃; (CH₂)qOR₃; (CH₂)qSR₃; straight chained or branched C₁–C₇ alkyl, monofluoroalkyl, polyfluoroalkyl, aminoalkyl, or carboxamidoalkyl; straight chained or branched C₂–C₇ alkenyl, C₂–C₇ alkynyl; C₃–C₇ cycloalkyl, monofluorocycloalkyl, polyfluorocycloalkyl or cycloalkenyl;

wherein R₆ is —H; straight chained or branched C₁–C₇ alkyl, monofluoroalkyl or polyfluoroalkyl; straight chained or branched C₂–C₇ alkenyl or alkynyl; C₃–C₇ cycloalkyl, monofluorocycloalkyl, polyfluorocycloalkyl or cycloalkenyl; —N(R₃)₂; —OR₃; —(CH₂)ₚOR₃; —COR₃; —CO₂R₃; —CON(R₃)₂; aryl or heteroaryl, optionally substituted with one or more F; Cl; Br; I; COR₃; CO₂R₃; —CON(R₃)₂; CN; —NO₂; —N(R₃)₂; —OR₃; —SR₃; (CH₂)qOR₃; (CH₂)qSR₃; straight chained or branched C₁–C₇ alkyl, monofluoroalkyl, polyfluoroalkyl, aminoalkyl, or carboxamidoalkyl; straight chained or branched C₂–C₇ alkenyl, C₂–C₇ alkynyl; C₃–C₇ cycloalkyl, monofluorocycloalkyl, polyfluorocycloalkyl or cycloalkenyl;

wherein $R_7$ is H; F; Cl; Br; I; —$NO_2$; —$N_3$; —CN; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —$N(R_3)_2$; —$OR_3$; —$(CH_2)_pOR_3$; —$COR_3$; —$CO_2R_3$; or —$CON(R_3)_2$;

wherein $R_8$ is independently straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl;

wherein Z is naphthyl, quinolinyl, isoquinolinyl, quinazolinyl, phthalazinyl, quinoxalinyl, indolyl, benzo[b]furanyl, or benzo[b]thiophenyl; wherein the naphthyl, quinolinyl, isoquinolinyl, quinazolinyl, phthalazinyl, quinoxalinyl, indolyl, benzo[b]furanyl, or benzo[b]thiophenyl may be substituted with one or more F; Cl; Br; I; $COR_3$; $CO_2R_3$; —$CON(R_3)_2$; CN; —$NO_2$; —$N(R_3)_2$; —$OR_3$; —$SR_3$; $(CH_2)_qOR_3$; $(CH_2)_qSR_3$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl, $C_2$–$C_7$ alkynyl; $C_3$–$C_7$ cycloalkyl, monofluorocycloalkyl, polyfluorocycloalkyl or cycloalkenyl;

wherein each m is independently an integer from 0 to 3 inclusive;

wherein each n is independently an integer from 0 to 5 inclusive;

wherein each p is independently an integer from 1 to 7 inclusive;

wherein q is an integer from 1 to 3 inclusive;

wherein r is an integer from 0 to 3 inclusive;

wherein t is an integer from 2 to 6 inclusive;

or a pharmaceutically acceptable salt thereof.

This invention further provides a compound having the structure:

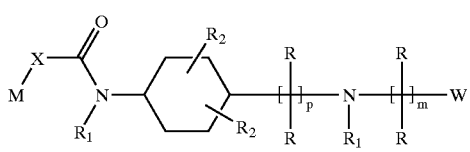

wherein each R is independently —H; —F; straight chained or branched $C_1$–$C_7$ alkyl, monofluoroalkyl or polyfluoroalkyl; straight chained or branched $C_2$–$C_7$ alkenyl or alkynyl; —$N(R_3)_2$; —$NO_2$; —CN; —$SR_3$; —$CO_2R_3$; or —$OR_3$;

wherein each $R_1$ is independently —H; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —$(CH_2)_pOR_3$; —$COR_3$; —$CO_2R_3$; or —$CON(R_3)_2$;

wherein each $R_2$ is —H; —$NO_2$; —$N_3$; —CN; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —$N(R_3)_2$; —$OR_3$; —$(CH_2)_pOR_3$; —$COR_3$; —$CO_2R_3$; or —$CON(R_3)_2$; or aryl or heteroaryl, optionally substituted with one or more F; Cl; Br; I; $COR_3$; $CO_2R_3$; —$CON(R_3)_2$; CN; —$NO_2$; —$N(R_3)_2$; —$OR_3$; —$SR_3$; $(CH_2)_qOR_3$; $(CH_2)_qSR_3$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl, $C_2$–$C_7$ alkynyl; $C_3$–$C_7$ cycloalkyl, monofluorocycloalkyl, polyfluorocycloalkyl or cycloalkenyl;

wherein each $R_3$ is independently —H; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl;

wherein M is aryl or heteroaryl, optionally substituted with one or more F; Cl; Br; I; $COR_3$; $CO_2R_3$; —$CON(R_3)_2$; CN; —$NO_2$; —$N(R_3)_2$; —$OR_3$; —$SR_3$; $(CH_2)_qOR_3$; $(CH_2)_qSR_3$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl, $C_2$–$C_7$ alkynyl; $C_3$–$C_7$ cycloalkyl, monofluorocycloalkyl, polyfluorocycloalkyl or cycloalkenyl;

wherein X is $(CH_2)_n$, O, S or $NR_3$;

wherein W is (a) $C_3$–$C_7$ cycloalkyl, monofluorocycloalkyl, polyfluorocycloalkyl or cycloalkenyl optionally substituted with one or more $COR_3$; $CO_2R_3$; —$CON(R_3)_2$; CN; —$NO_2$; —$N(R_3)_2$; —$OR_3$; —$SR_3$; $(CH_2)_qOR_3$; $(CH_2)_qSR_3$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl, $C_2$–$C_7$ alkynyl; $C_3$–$C_7$ cycloalkyl; or (b) aryl or heteroaryl optionally substituted with one or more F; Cl; Br; I; $COR_3$; $CO_2R_3$; —$CON(R_3)_2$; CN; —$NO_2$; —$N(R_3)_2$; —$OR_3$; —$SR_3$; $(CH_2)_qOR_3$; $(CH_2)_qSR_3$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl, $C_2$–$C_7$ alkynyl; $C_3$–$C_7$ cycloalkyl;

wherein m is an integer from 0 to 4 inclusive;

wherein n is an integer from 0 to 6 inclusive;

wherein p is an integer from 1 to 4 inclusive;

wherein q is an integer from 1 to 3 inclusive;

or a pharmaceutically acceptable salt thereof.

This invention also provides a compound having the structure:

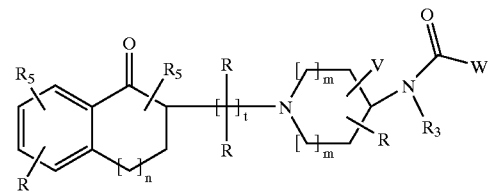

wherein each R is independently —H; —F; straight chained or branched $C_1$–$C_7$ alkyl, monofluoroalkyl or polyfluoroalkyl; straight chained or branched $C_2$–$C_7$ alkenyl or alkynyl; —$N(R_3)_2$; —$NO_2$; —CN; —$CO_2R_3$; —$OR_3$; or —$CON(R_3)_2$;

wherein each $R_1$ is independently —H; F; Cl; Br; I; —$NO_2$; —$N_3$; —CN; straight chained or branched $C_1$–$C_7$ alkyl, monofluoroalkyl or polyfluoroalkyl; straight chained or branched $C_2$–$C_7$ alkenyl or alkynyl;

$C_3$–$C_7$ cycloalkyl, monofluorocycloalkyl, polyfluorocycloalkyl or cycloalkenyl; —N($R_3$)$_2$; —O$R_3$; —(CH$_2$)$_p$O$R_3$; —CO$R_3$; —CO$_2R_3$; —CON($R_3$)$_2$; aryl or heteroaryl, wherein the aryl or heteroaryl is optionally substituted with one or more F; Cl; Br; I; CO$R_3$; CO$_2R_3$; —CON($R_3$)$_2$; CN; —NO$_2$; —N($R_3$)$_2$; —O$R_3$; —S$R_3$; (CH$_2$)$_q$O$R_3$; (CH$_2$)$_q$S$R_3$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl, $C_2$–$C_7$ alkynyl; $C_3$–$C_7$ cycloalkyl, monofluorocycloalkyl, polyfluorocycloalkyl or cycloalkenyl;

wherein each $R_3$ is independently —H; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl;

wherein $R_5$ is —H; —NO$_2$; —N$_3$; —CN; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —N($R_3$)$_2$; —O$R_3$; —(CH$_2$)$_p$O$R_3$; —CO$R_3$; —CO$_2R_3$; —CON($R_3$)$_2$; aryl or heteroaryl, wherein the aryl or heteroaryl is optionally substituted with one or more F; Cl; Br; I; CO$R_3$; CO$_2R_3$; —CON($R_3$)$_2$; CN; —NO$_2$; —N($R_3$)$_2$; —O$R_3$; —S$R_3$; (CH$_2$)$_q$O$R_3$; (CH$_2$)$_q$S$R_3$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl, $C_2$–$C_7$ alkynyl; $C_3$–$C_7$ cycloalkyl, monofluorocycloalkyl, polyfluorocycloalkyl or cycloalkenyl;

wherein V is H; aryl or heteroaryl, optionally substituted with one or more F; Cl; Br; I; CO$R_3$; CO$_2R_3$; —CON($R_3$)$_2$; CN; —NO$_2$; —N($R_3$)$_2$; —O$R_3$; —S$R_3$; (CH$_2$)$_q$ O$R_3$; (CH$_2$)$_q$S$R_3$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl, $C_2$–$C_7$ alkynyl; $C_3$–$C_7$ cycloalkyl, monofluorocycloalkyl, polyfluorocycloalkyl or cycloalkenyl;

wherein W is
(a) $C_3$–$C_7$ cycloalkyl, monofluorocycloalkyl, polyfluorocycloalkyl or cycloalkenyl optionally substituted with one or more CO$R_3$; CO$_2R_3$; —CON($R_3$)$_2$; CN; —NO$_2$; —N($R_3$)$_2$; —O$R_3$; —S$R_3$; (CH$_2$)$_q$O$R_3$; (CH$_2$)$_q$S$R_3$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl, $C_2$–$C_7$ alkynyl; $C_3$–$C_7$ cycloalkyl; or
(b) aryl or heteroaryl optionally substituted with one or more F; Cl; Br; I; CO$R_3$; CO$_2R_3$; —CON($R_3$)$_2$; CN; —NO$_2$; —N($R_3$)$_2$; —O$R_3$; —S$R_3$; (CH$_2$)$_q$O$R_3$; (CH$_2$)$_q$S$R_3$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl, $C_2$–$C_7$ alkynyl; $C_3$–$C_7$ cycloalkyl;

wherein each m is independently an integer from 0 to 3 inclusive;
wherein n is an integer from 0 to 2 inclusive;
wherein p is an integer from 1 to 7 inclusive;
wherein q is an integer from 1 to 3 inclusive;
wherein t is an integer from 2 to 6 inclusive;
or a pharmaceutically acceptable salt thereof.

This invention further provides a method of modifying feeding behavior of a subject which comprises administering to the subject an amount of a compound effective to decrease the consumption of food by the subject wherein the compound has the structure:

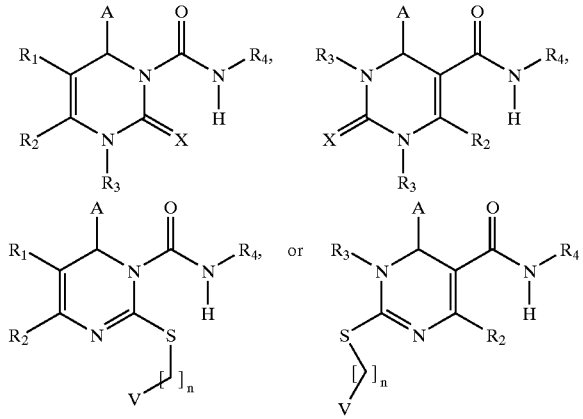

wherein A is

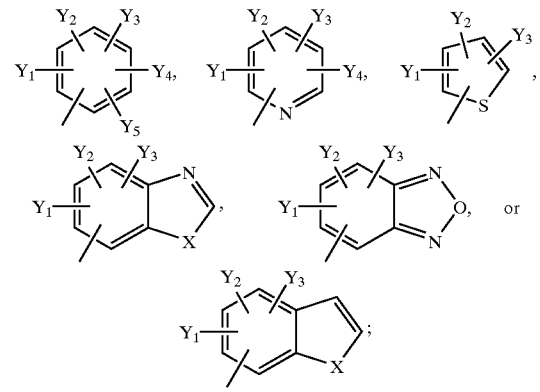

wherein each of $Y_1$, $Y_2$, $Y_3$, $Y_4$ and $Y_5$ is independently —H; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —F, —Cl, —Br, or —I; —NO$_2$; —N$_3$; —CN; —O$R_3$, —OCO$R_3$, —CO$R_3$, —CON($R_3$)$_2$, or —COO$R_3$; or any two of $Y_1$, $Y_2$, $Y_3$, $Y_4$ and $Y_5$ present on adjacent carbon atoms can constitute a methylenedioxy group;

wherein each X is independently S; O; or N$R_3$;

wherein $R_1$ is —H; —NO$_2$; —CN; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —N($R_3$)$_2$; —O$R_3$; —(CH$_2$)$_p$O$R_3$; —CO$R_3$; —CO$_2R_3$; —CON($R_3$)$_2$; or CO$_2$(CH$_2$)$_n$V;

wherein $R_2$ is —H; straight chained or branched $C_1$–$C_7$ alkyl, hydroxyalkyl, alkoxyalkyl, aminoalkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; $C_3$–$C_{10}$ cycloalkyl-$C_1$–$C_{10}$-alkyl, $C_3$–$C_{10}$ cycloalkyl-$C_1$–$C_{10}$-monofluoroalkyl or $C_3$–$C_{10}$ cycloalkyl-$C_1$–$C_{10}$-polyfluoroalkyl; —CN; —CH$_2$X$R_3$, —CH$_2$X(CH$_2$)$_p$NH$R_3$, —(CH$_2$)$_n$NH$R_3$, —CH$_2$X(CH$_2$)$_p$N($R_3$)$_2$, —CH$_2$X(CH$_2$)$_p$N$_3$, —CH$_2$X $(CH_2)_pNHCXR_5$; $-OR_3$; or wherein $R_1$ and $R_2$ together form a lactone ring;

wherein each $R_3$ is independently —H; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl;

wherein $R_4$ is

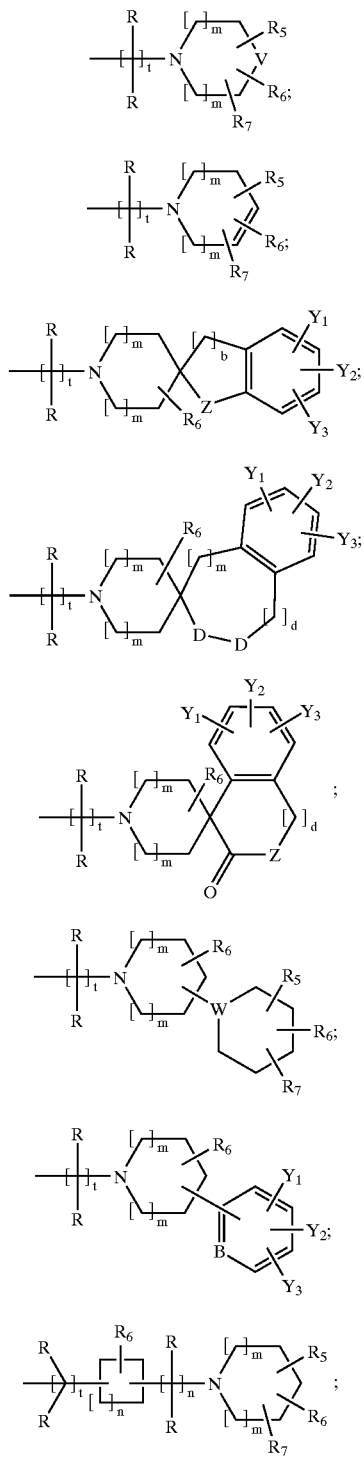

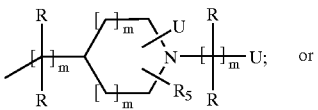

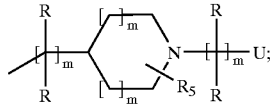

wherein each R is independently —H; —F; straight chained or branched $C_1$–$C_7$ alkyl, monofluoroalkyl or polyfluoroalkyl; straight chained or branched $C_2$–$C_7$ alkenyl or alkynyl; $-N(R_3)_2$; $-NO_2$; $-CN$; $-CO_2R_3$; $-OR_3$; or $-CN(R_3)_2$;

wherein B is N or $CY_4$;

wherein each D is independently $C(R_3)_2$; O; S; $NR_3$; CO; or CS;

wherein each U is independently aryl or heteroaryl, optionally substituted with one or more F; Cl; Br; I; $COR_3$; $CO_2R_3$; $-CON(R_3)_2$; CN; $-NO_2$; $-N(R_3)_2$; $-OR_3$; $-SR_3$; $(CH_2)_qOR_3$; $(CH_2)_qSR_3$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl, $C_2$–$C_7$ alkynyl; $C_3$–$C_7$ cycloalkyl, monofluorocycloalkyl, polyfluorocycloalkyl or cycloalkenyl;

wherein V is $C(R_5)_2$; $CR_5R_6$; $NR_5$ or $NR_6$;

wherein W is $CR_5$; $CR_6$ or N;

wherein Z is S; O; $C(R_3)_2$; or $NR_3$;

wherein each $R_5$ is —H; $-NO_2$; $-N_3$; $-CN$; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; $-N(R_3)_2$; $-OR_3$; $-(CH_2)_pOR_3$; $-COR_3$; $-CO_2R_3$; or $-CON(R_3)_2$; $-XCOR_8$; or aryl or heteroaryl, wherein the aryl or heteroaryl is optionally substituted with one or more F; Cl; Br; I; $COR_3$; $CO_2R_3$; $-CON(R_3)_2$; CN; $-NO_2$; $-N(R_3)_2$; $-OR_3$; $-SR_3$; $(CH_2)_qOR_3$; $(CH_2)_qSR_3$; $-XCOR_8$; straight chained or branched $C_1$–$C_7$ alkyl, monofluoroalkyl, polyfluoroalkyl, or aminoalkyl; straight chained or branched $C_2$–$C_7$ alkenyl, $C_2$–$C_7$ alkynyl; $C_3$–$C_7$ cycloalkyl, monofluorocycloalkyl, polyfluorocycloalkyl or cycloalkenyl;

wherein each $R_6$ is independently —H; straight chained or branched $C_1$–$C_7$ alkyl, hydroxyalkyl, aminoalkyl, alkoxyalkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; $-N(R_3)_2$; $-OR_3$; $-(CH_2)_pOR_3$; $-COR_3$; $-CO_2R_3$; or $-CON(R_3)_2$;

wherein $R_7$ is —H; aryl or heteroaryl, optionally substituted with one or more F; Cl; Br; I; $COR_3$; $CO_2R_3$; $-CON(R_3)_2$; CN; $-NO_2$; $-N(R_3)_2$; $-OR_3$; $-SR_3$; $(CH_2)_qOR_3$; $(CH_2)_qSR_3$; $-XCOR_8$; straight chained or branched $C_1$–$C_7$ alkyl, monofluoroalkyl, polyfluoroalkyl, or aminoalkyl; straight chained or branched $C_2$–$C_7$ alkenyl, $C_2$–$C_7$ alkynyl; $C_3$–$C_7$ cycloalkyl, monofluorocycloalkyl, polyfluorocycloalkyl or cycloalkenyl;

wherein $R_8$ is —H; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —N($R_3$)$_2$; —O$R_3$; —(CH$_2$)$_p$O$R_3$; —CO$R_3$; —CO$_2R_3$; or —CON($R_3$)$_2$; aryl or heteroaryl, optionally substituted with one or more F; Cl; Br; I; CO$R_3$; CO$_2R_3$; —CON($R_3$)$_2$; CN; —NO$_2$; —N($R_3$)$_2$; —O$R_3$; —S$R_3$; (CH$_2$)$_q$O$R_3$; (CH$_2$)$_q$S$R_3$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl, $C_2$–$C_7$ alkynyl; $C_3$–$C_7$ cycloalkyl, monofluorocycloalkyl, polyfluorocycloalkyl or cycloalkenyl;

wherein b is 1 or 2;

wherein d is an integer from 0 to 2 inclusive;

wherein each m is independently an integer from 0 to 3 inclusive;

wherein each n is independently an integer from 0 to 5 inclusive;

wherein each p is independently an integer from 1 to 7 inclusive;

wherein q is an integer from 1 to 3 inclusive;

wherein t is an integer from 2 to 6 inclusive;

or a pharmaceutically acceptable salt thereof.

This invention further provides a method of reducing the body mass of a subject which comprises administering to the subject an amount of a compound effective to reduce the body mass of the subject wherein the compound has the structure:

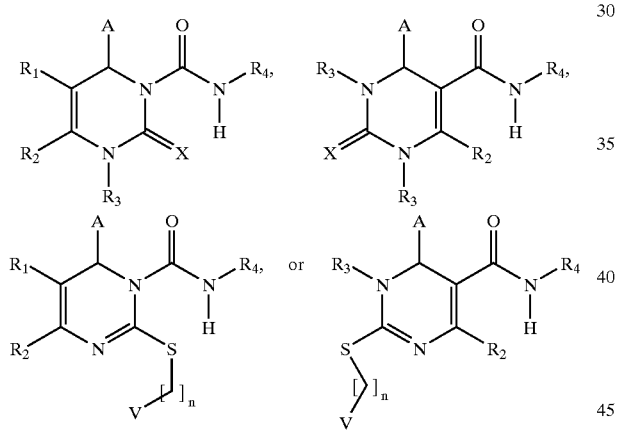

wherein A is

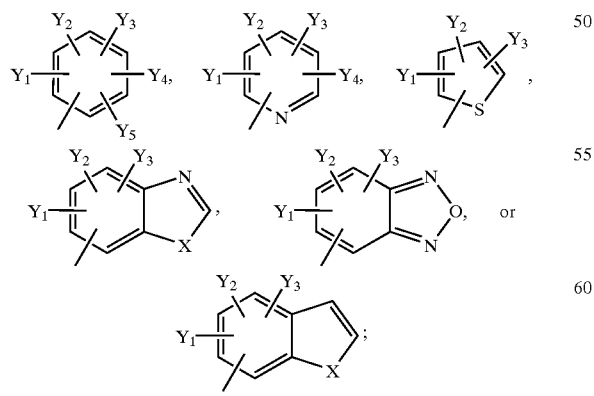

wherein each of $Y_1$, $Y_2$, $Y_3$, $Y_4$ and $Y_5$ is independently —H; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —F, —Cl, —Br, or —I; —NO$_2$; —N$_3$; —CN; —O$R_3$, —OCO$R_3$, —CO$R_3$, —CON($R_3$)$_2$, or —COO$R_3$; or any two of $Y_1$, $Y_2$, $Y_3$, $Y_4$ and $Y_5$ present on adjacent carbon atoms can constitute a methylenedioxy group;

wherein each X is independently S; O; or N$R_3$;

wherein $R_1$ is —H; —NO$_2$; —CN; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —N($R_3$)$_2$; —O$R_3$; —(CH$_2$)$_p$O$R_3$; —CO$R_3$; —CO$_2R_3$; —CON($R_3$)$_2$; or CO$_2$(CH$_2$)$_n$V;

wherein $R_2$ is —H; straight chained or branched $C_1$–$C_7$ alkyl, hydroxyalkyl, alkoxyalkyl, aminoalkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; $C_3$–$C_{10}$ cycloalkyl-$C_1$–$C_{10}$-alkyl, $C_3$–$C_{10}$ cycloalkyl-$C_1$–$C_{10}$-monofluoroalkyl or $C_3$–$C_{10}$ cycloalkyl-$C_1$–$C_{10}$-polyfluoroalkyl; —CN; —CH$_2$X$R_3$, —CH$_2$X(CH$_2$)$_p$NH$R_3$, —(CH$_2$)$_n$NH$R_3$, —CH$_2$X(CH$_2$)$_p$N($R_3$)$_2$, —CH$_2$X(CH$_2$)$_p$N$_3$, —CH$_2$X(CH$_2$)$_p$NHCX$R_5$; —O$R_3$; or wherein $R_1$ and $R_2$ together form a lactone ring;

wherein each $R_3$ is independently —H; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl;

wherein $R_4$ is

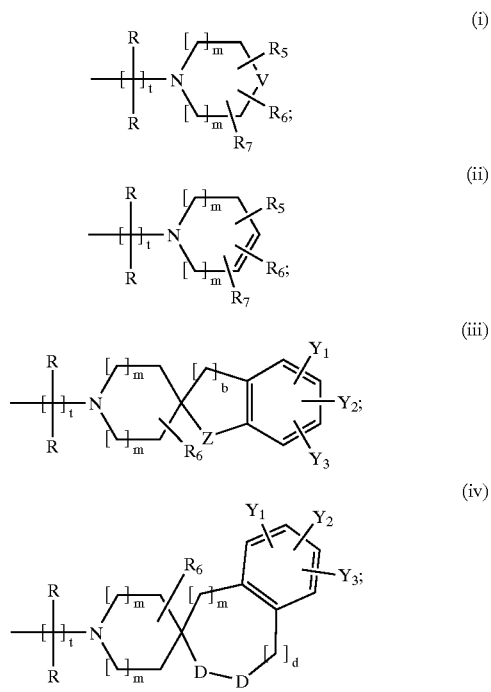

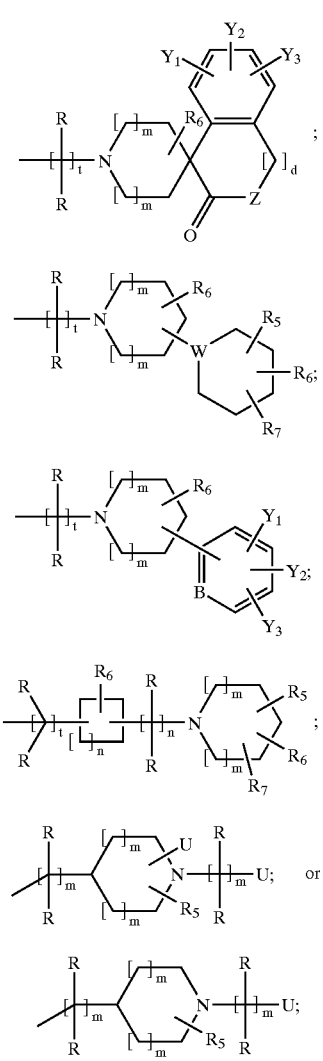

wherein each R is independently —H; —F; straight chained or branched $C_1-C_7$ alkyl, monofluoroalkyl or polyfluoroalkyl; straight chained or branched $C_2-C_7$ alkenyl or alkynyl; —N(R$_3$)$_2$; —NO$_2$; —CN; —CO$_2$R$_3$; —OR$_3$; or —CN(R$_3$)$_2$;

wherein B is N or CY$_4$;

wherein each D is independently C(R$_3$)$_2$; O; S; NR$_3$; CO; or CS;

wherein each U is independently aryl or heteroaryl, optionally substituted with one or more F; Cl; Br; I; COR$_3$; CO$_2$R$_3$; —CON(R$_3$)$_2$; CN; —NO$_2$; —N(R$_3$)$_2$; —OR$_3$; —SR$_3$; (CH$_2$)$_q$OR$_3$; (CH$_2$)$_q$SR$_3$; straight chained or branched $C_1-C_7$ alkyl, monofluoroalkyl, polyfluoroalkyl, aminoalkyl, or carboxamidoalkyl; straight chained or branched $C_2-C_7$ alkenyl, $C_2-C_7$ alkynyl; $C_3-C_7$ cycloalkyl, monofluorocycloalkyl, polyfluorocycloalkyl or cycloalkenyl;

wherein V is C(R$_5$)$_2$; CR$_5$R$_6$; NR$_5$ or NR$_6$;

wherein W is CR$_5$; CR$_6$ or N;

wherein Z is S; O; C(R$_3$)$_2$; or NR$_3$;

wherein each R$_5$ is —H; —NO$_2$; —N$_3$; —CN; straight chained or branched $C_1-C_7$ alkyl, monofluoroalkyl or polyfluoroalkyl; straight chained or branched $C_2-C_7$ alkenyl or alkynyl; $C_3-C_7$ cycloalkyl, monofluorocycloalkyl, polyfluorocycloalkyl or cycloalkenyl; —N(R$_3$)$_2$; —OR$_3$; —(CH$_2$)$_p$OR$_3$; —COR$_3$; —CO$_2$R$_3$; or —CON(R$_3$)$_2$; —XCOR$_8$; or aryl or heteroaryl, wherein the aryl or heteroaryl is optionally substituted with one or more F; Cl; Br; I; COR$_3$; CO$_2$R$_3$; —CON(R$_3$)$_2$; CN; —NO$_2$; —N(R$_3$)$_2$; —OR$_3$; —SR$_3$; (CH$_2$)$_q$OR$_3$; (CH$_2$)$_q$SR$_3$; —XCOR$_8$; straight chained or branched $C_1-C_7$ alkyl, monofluoroalkyl, polyfluoroalkyl, or aminoalkyl; straight chained or branched $C_2-C_7$ alkenyl, $C_2-C_7$ alkynyl; $C_3-C_7$ cycloalkyl, monofluorocycloalkyl, polyfluorocycloalkyl or cycloalkenyl;

wherein each R$_6$ is independently —H; straight chained or branched $C_1-C_7$ alkyl, hydroxyalkyl, aminoalkyl, alkoxyalkyl, monofluoroalkyl or polyfluoroalkyl; straight chained or branched $C_2-C_7$ alkenyl or alkynyl; $C_3-C_7$ cycloalkyl, monofluorocycloalkyl, polyfluorocycloalkyl or cycloalkenyl; —N(R$_3$)$_2$; —OR$_3$; —(CH$_2$)$_p$OR$_3$; —COR$_3$; —CO$_2$R$_3$; or —CON(R$_3$)$_2$;

wherein R$_7$ is —H; aryl or heteroaryl, optionally substituted with one or more F; Cl; Br; I; COR$_3$; CO$_2$R$_3$; —CON(R$_3$)$_2$; CN; —NO$_2$; —N(R$_3$)$_2$; —OR$_3$; —SR$_3$; (CH$_2$)$_q$OR$_3$; (CH$_2$)$_q$SR$_3$; —XCOR$_8$; straight chained or branched $C_1-C_7$ alkyl, monofluoroalkyl, polyfluoroalkyl, or aminoalkyl; straight chained or branched $C_2-C_7$ alkenyl, $C_2-C_7$ alkynyl; $C_3-C_7$ cycloalkyl, monofluorocycloalkyl, polyfluorocycloalkyl or cycloalkenyl;

wherein R$_8$ is —H; straight chained or branched $C_1-C_7$ alkyl, monofluoroalkyl or polyfluoroalkyl; straight chained or branched $C_2-C_7$ alkenyl or alkynyl; $C_3-C_7$ cycloalkyl, monofluorocycloalkyl, polyfluorocycloalkyl or cycloalkenyl; —N(R$_3$)$_2$; —OR$_3$; —(CH$_2$)$_p$OR$_3$; —OR$_3$; —CO$_2$R$_3$; or —CON(R$_3$)$_2$; aryl or heteroaryl, optionally substituted with one or more F; Cl; Br; I; COR$_3$; CO$_2$R$_3$; —CON(R$_3$)$_2$; CN; —NO$_2$; —N(R$_3$)$_2$; —OR$_3$; —SR$_3$; (CH$_2$)$_q$OR$_3$; (CH$_2$)$_q$SR$_3$; straight chained or branched $C_1-C_7$ alkyl, monofluoroalkyl, polyfluoroalkyl, aminoalkyl, or carboxamidoalkyl; straight chained or branched $C_2-C_7$ alkenyl, $C_2-C_7$ alkynyl; $C_3-C_7$ cycloalkyl, monofluorocycloalkyl, polyfluorocycloalkyl or cycloalkenyl;

wherein b is 1 or 2;

wherein d is an integer from 0 to 2 inclusive;

wherein each m is independently an integer from 0 to 3 inclusive;

wherein each n is independently an integer from 0 to 5 inclusive;

wherein each p is independently an integer from 1 to 7 inclusive;

wherein q is an integer from 1 to 3 inclusive;

wherein t is an integer from 2 to 6 inclusive;

or a pharmaceutically acceptable salt thereof.

In addition, the present invention provides a method of treating a subject suffering from depression and/or anxiety which comprises administering to the subject a compound of the aforementioned formula in an amount effective to treat the subject's depression and/or anxiety.

This invention also provides a method of modifying feeding behavior of a subject which comprises administering to the subject an amount of a compound effective to decrease the consumption of food by the subject wherein the compound is selected from the group consisting of:

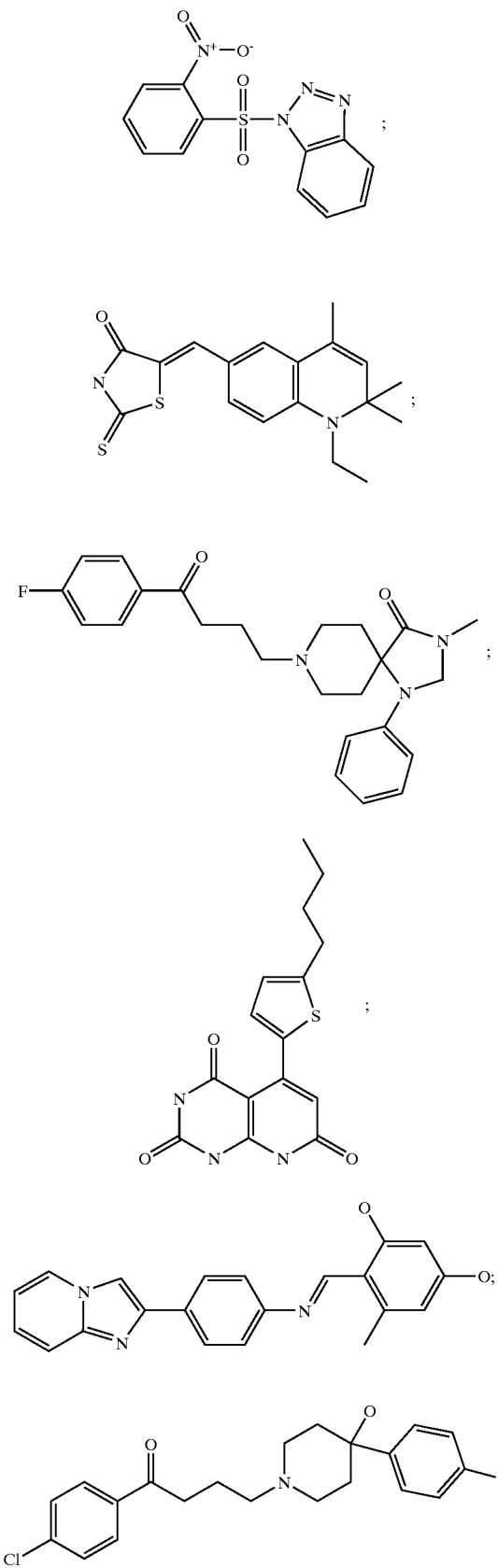

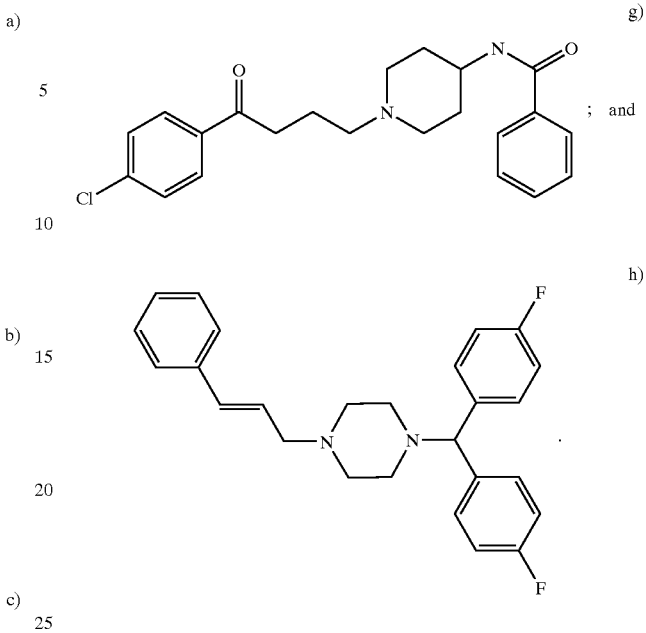

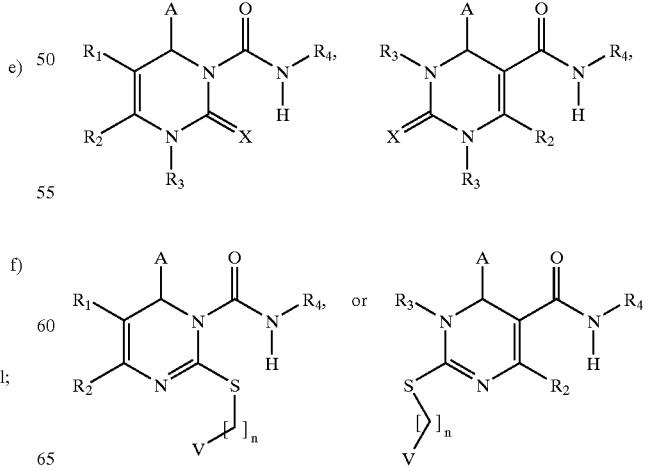

This invention further provides a method of treating a feeding disorder in a subject which comprises administering to the subject an amount of a compound of the invention effective to decrease the consumption of food by the subject.

This invention also provides a pharmaceutical composition comprising a therapeutically effective amount of the compound of the invention and a pharmaceutically acceptable carrier.

This invention further provides a pharmaceutical composition made by combining a therapeutically effective amount of the compound of this invention and a pharmaceutically acceptable carrier. This invention further provides a process for making a pharmaceutical composition comprising combining a therapeutically effective amount of the compound of the invention and a pharmaceutically acceptable carrier.

DETAILED DESCRIPTION OF THE INVENTION

This invention provides a compound having the structure:

wherein A is

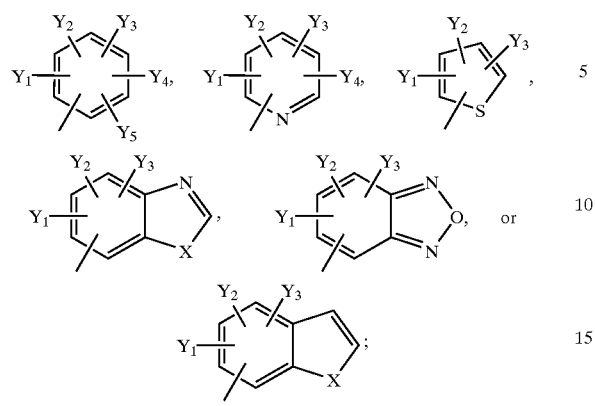

wherein each of $Y_1$, $Y_2$, $Y_3$, $Y_4$ and $Y_5$ is independently —H; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —F, —Cl, —Br, or —I; —$NO_2$; —$N_3$; —CN; —$OR_3$, —$OCOR_3$, —$COR_3$, —$CON(R_3)_2$, or —$COOR_3$; or any two of $Y_1$, $Y_2$, $Y_3$, $Y_4$ and $Y_5$ present on adjacent carbon atoms can constitute a methylenedioxy group;

wherein each X is independently S; O; or $NR_3$;

wherein $R_1$ is —H; —$NO_2$; —CN; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —$N(R_3)_2$; —$OR_3$; —$(CH_2)_pOR_3$; —$COR_3$; —$CO_2R_3$; —$CON(R_3)_2$; or —$CO_2(CH_2)_nV$;

wherein $R_2$ is —H; straight chained or branched $C_1$–$C_7$ alkyl, hydroxyalkyl, alkoxyalkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; $C_3$–$C_{10}$ cycloalkyl-$C_1$–$C_{10}$-alkyl, $C_3$–$C_{10}$ cycloalkyl-$C_1$–$C_{10}$-monofluoroalkyl or $C_3$–$C_{10}$ cycloalkyl-$C_1$–$C_{10}$-polyfluoroalkyl; —CN; —$CH_2XR_3$, —$CH_2X(CH_2)_pNHR_3$, —$(CH_2)_pNHR_3$, —$CH_2X(CH_2)_pN(R_3)_2$, —$CH_2X(CH_2)_pN_3$, —$CH_2X(CH_2)_pNHCXR_7$; —$OR_3$; or wherein $R_1$ and $R_2$ together form a lactone ring;

wherein each $R_3$ is independently —H; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl;

wherein $R_4$ is

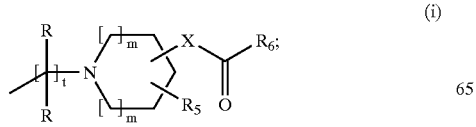

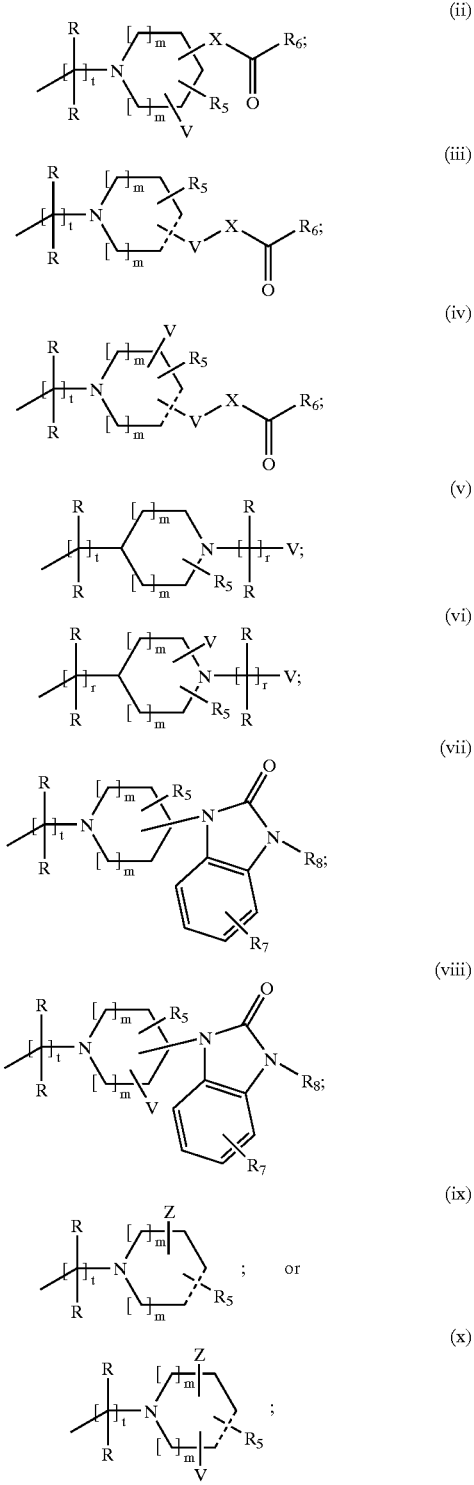

wherein the dashed line represents a single bond or a double bond;

wherein each R is independently —H; —F; straight chained or branched $C_1$–$C_7$ alkyl, monofluoroalkyl or polyfluoroalkyl; straight chained or branched $C_2$–$C_7$ alkenyl or alkynyl; —$N(R_3)_2$; —$NO_2$; —CN; —$CO_2R_3$; —$OR_3$; or —$CON(R_3)_2$;

wherein each V is independently aryl or heteroaryl, optionally substituted with one or more F; Cl; Br; I;

COR$_3$; CO$_2$R$_3$; —CON(R$_3$)$_2$; CN; —NO$_2$; —N(R$_3$)$_2$; —OR$_3$; —SR$_3$; (CH$_2$)$_q$OR$_3$; (CH$_2$)$_q$SR$_3$; straight chained or branched C$_1$–C$_7$ alkyl, monofluoroalkyl, polyfluoroalkyl, aminoalkyl, or carboxamidoalkyl; straight chained or branched C$_2$–C$_7$ alkenyl, C$_2$–C$_7$ alkynyl; C$_3$–C$_7$ cycloalkyl, monofluorocycloalkyl, polyfluorocycloalkyl or cycloalkenyl;

wherein each R$_5$ is —H; —NO$_2$; —N$_3$; —CN; straight chained or branched C$_1$–C$_7$ alkyl, monofluoroalkyl or polyfluoroalkyl; straight chained or branched C$_2$–C$_7$ alkenyl or alkynyl; C$_3$–C$_7$ cycloalkyl, monofluorocycloalkyl, polyfluorocycloalkyl or cycloalkenyl; —N(R$_3$)$_2$; —OR$_3$; —(CH$_2$)$_p$OR$_3$; —COR$_3$; —CO$_2$R$_3$; —CON(R$_3$)$_2$; aryl or heteroaryl, wherein the aryl or heteroaryl is optionally substituted with one or more F; Cl; Br; I; COR$_3$; CO$_2$R$_3$; —CON(R$_3$)$_2$; CN; —NO$_2$; —N(R$_3$)$_2$; —OR$_3$; —SR$_3$; (CH$_2$)$_q$OR$_3$; (CH$_2$)$_q$SR$_3$; straight chained or branched C$_1$–C$_7$ alkyl, monofluoroalkyl, polyfluoroalkyl, aminoalkyl, or carboxamidoalkyl; straight chained or branched C$_2$–C$_7$ alkenyl, C$_2$–C$_7$ alkynyl; C$_3$–C$_7$ cycloalkyl, monofluorocycloalkyl, polyfluorocycloalkyl or cycloalkenyl;

wherein R$_6$ is —H; straight chained or branched C$_1$–C$_7$ alkyl, monofluoroalkyl or polyfluoroalkyl; straight chained or branched C$_2$–C$_7$ alkenyl or alkynyl; C$_3$–C$_7$ cycloalkyl, monofluorocycloalkyl, polyfluorocycloalkyl or cycloalkenyl; —N(R$_3$)$_2$; —OR$_3$; (CH$_2$)$_p$OR$_3$; —COR$_3$; —CO$_2$R$_3$; —CON(R$_3$)$_2$; aryl or heteroaryl, optionally substituted with one or more F; Cl; Br; I; COR$_3$; CO$_2$R$_3$; —CON(R$_3$)$_2$; CN; —NO$_2$; —N(R$_3$)$_2$; —OR$_3$; —SR$_3$; (CH$_2$)$_q$OR$_3$; (CH$_2$)$_q$SR$_3$; straight chained or branched C$_1$–C$_7$ alkyl, monofluoroalkyl, polyfluoroalkyl, aminoalkyl, or carboxamidoalkyl; straight chained or branched C$_2$–C$_7$ alkenyl, C$_2$–C$_7$ alkynyl; C$_3$–C$_7$ cycloalkyl, monofluorocycloalkyl, polyfluorocycloalkyl or cycloalkenyl;

wherein R$_7$ is H; F; Cl; Br; I; —NO$_2$; —N$_3$; —CN; straight chained or branched C$_1$–C$_7$ alkyl, monofluoroalkyl or polyfluoroalkyl; straight chained or branched C$_2$–C$_7$ alkenyl or alkynyl; C$_3$–C$_7$ cycloalkyl, monofluorocycloalkyl, polyfluorocycloalkyl or cycloalkenyl; —N(R$_3$)$_2$; —OR$_3$; —(CH$_2$)$_p$OR$_3$; —COR$_3$; —CO$_2$R$_3$; or —CON(R$_3$)$_2$;

wherein R$_8$ is independently straight chained or branched C$_1$–C$_7$ alkyl, monofluoroalkyl or polyfluoroalkyl; straight chained or branched C$_2$–C$_7$ alkenyl or alkynyl; C$_3$–C$_7$ cycloalkyl, monofluorocycloalkyl, polyfluorocycloalkyl or cycloalkenyl;

wherein Z is naphthyl, quinolinyl, isoquinolinyl, quinazolinyl, phthalazinyl, quinoxalinyl, indolyl, benzo[b]furanyl, or benzo[b]thiophenyl; wherein the naphthyl, quinolinyl, isoquinolinyl, quinazolinyl, phthalazinyl, quinoxalinyl, indolyl, benzo[b]furanyl, or benzo[b]thiophenyl may be substituted with one or more F; Cl; Br; I; COR$_3$; CO$_2$R$_3$; —CON(R$_3$)$_2$; CN; —NO$_2$; —N(R$_3$)$_2$; —OR$_3$; —SR$_3$; (CH$_2$)$_q$OR$_3$; (CH$_2$)$_q$SR$_3$; straight chained or branched C$_1$–C$_7$ alkyl, monofluoroalkyl, polyfluoroalkyl, aminoalkyl, or carboxamidoalkyl; straight chained or branched C$_2$–C$_7$ alkenyl, C$_2$–C$_7$ alkynyl; C$_3$–C$_7$ cycloalkyl, monofluorocycloalkyl, polyfluorocycloalkyl or cycloalkenyl;

wherein each m is independently an integer from 0 to 3 inclusive;

wherein each n is independently an integer from 0 to 5 inclusive;

wherein each p is independently an integer from 1 to 7 inclusive;

wherein q is an integer from 1 to 3 inclusive;

wherein r is an integer from 0 to 3 inclusive;

wherein t is an integer from 2 to 6 inclusive;

or a pharmaceutically acceptable salt thereof.

In one embodiment the compounds of this invention comprise the (+) enantiomer. In another embodiment, the compounds comprise the (−) enantiomer.

In one embodiment, the compound has the structure:

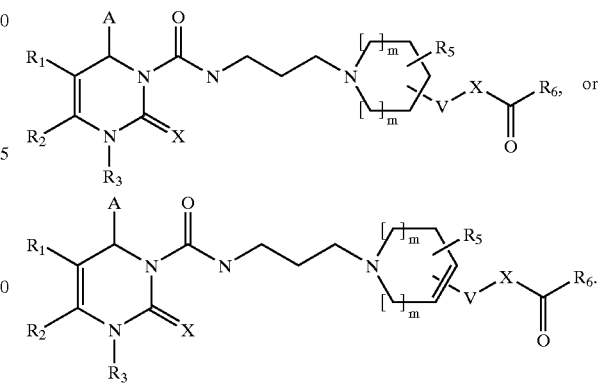

In another embodiment, the compound has the structure:

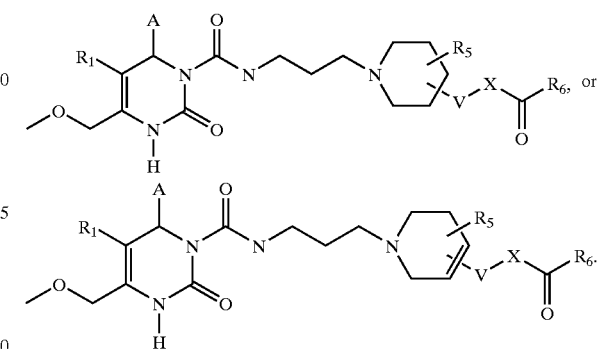

In a further embodiment, the compound has the structure:

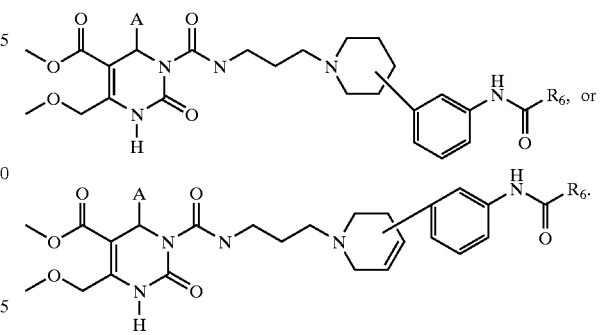

In yet another embodiment of the present invention variable A is

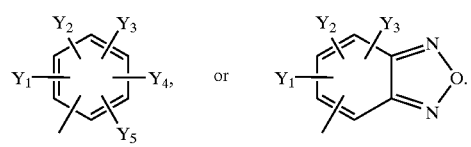

In an embodiment of the present invention, the compound is
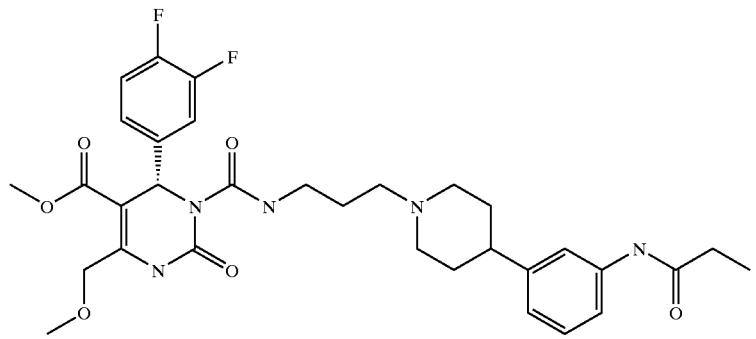
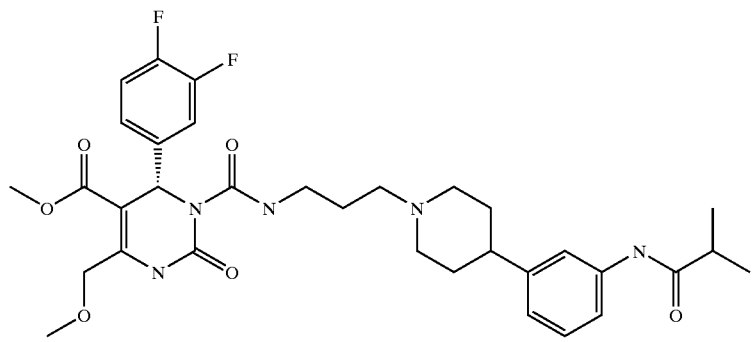
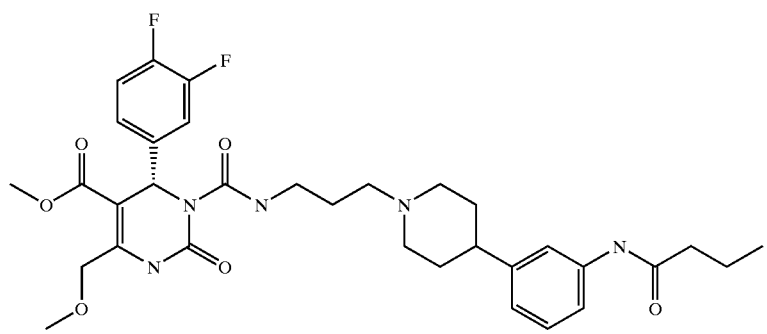
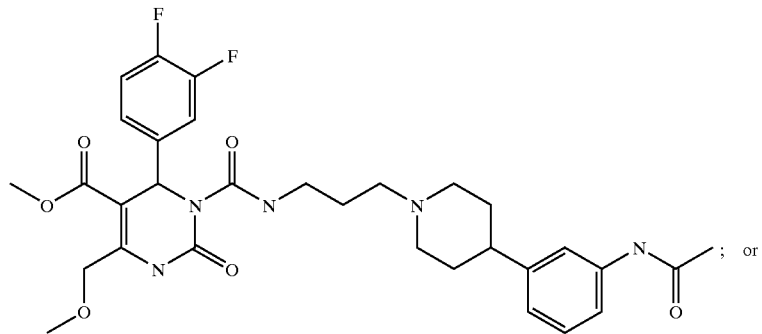
; or -continued

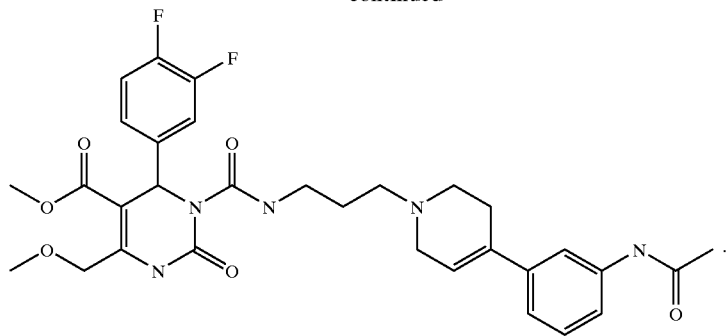

In another embodiment, the compound has the structure:

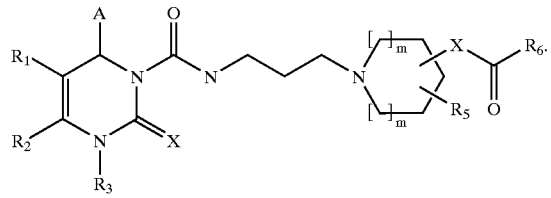

In further embodiments, the compound has the structure:

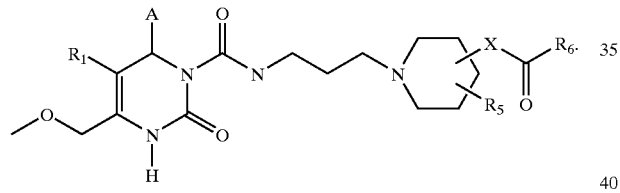

In an embodiment, the compound has the structure:

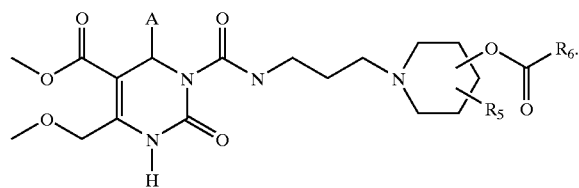

In other embodiments, A is

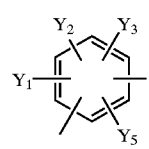 or 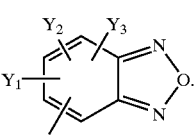

In an embodiment of the invention, the compound has the structure:

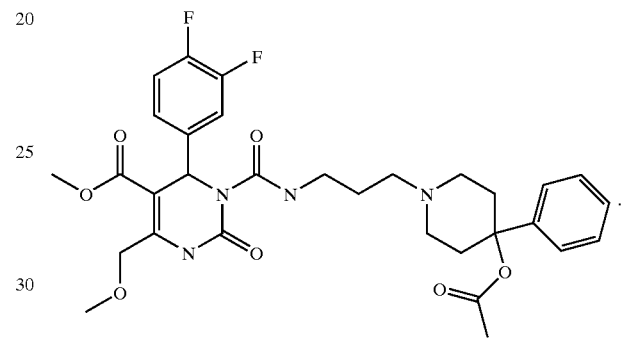

In other embodiments, the compound has the structure:

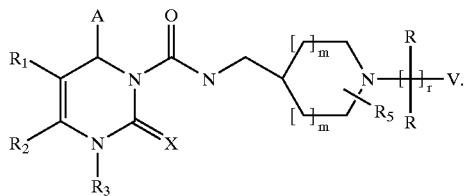

In additional embodiments, the compound has the structure:

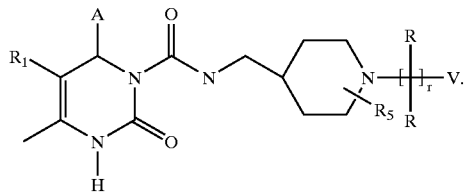

In one embodiment of the present invention, the compound has the structure:

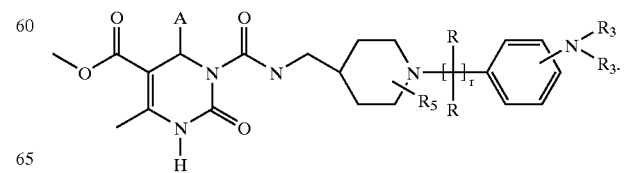

In another embodiment of the instant invention, A is

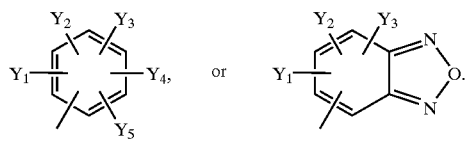

In other embodiments of the invention, the compound has the structure:

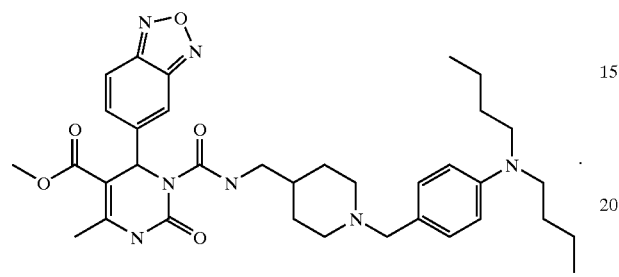

In an embodiment, the compound has the structure:

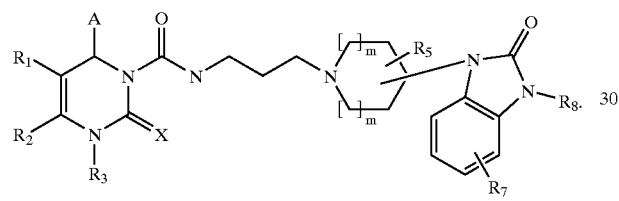

In another embodiment, the compound has the structure:

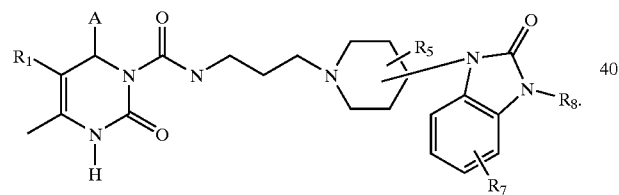

In yet another embodiment, the compound has the structure:

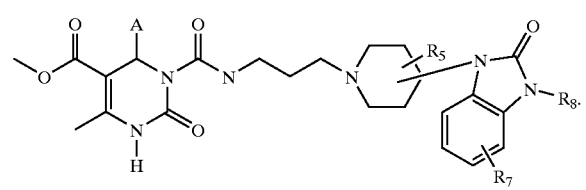

In an embodiment, A is

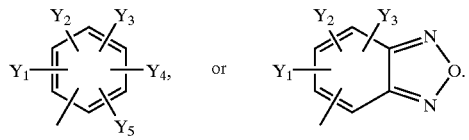

In a further embodiment, the compound has the structure

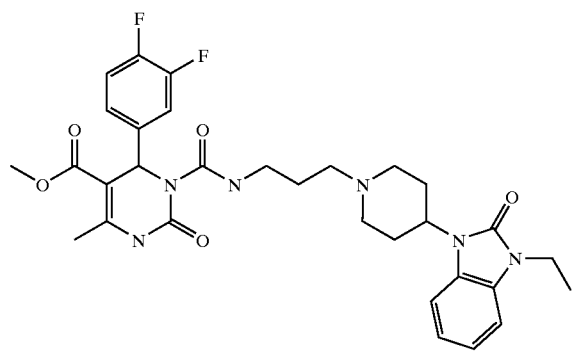

In another embodiment, the compound has the structure:

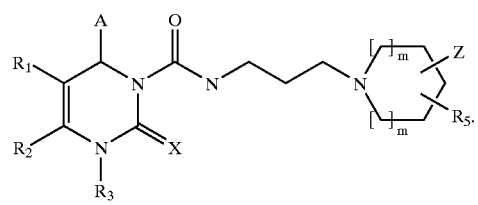

In yet another embodiment, the compound has the structure:

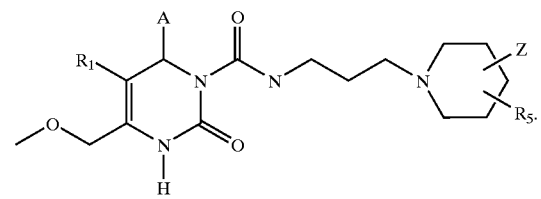

In an additional embodiment, the compound has the structure:

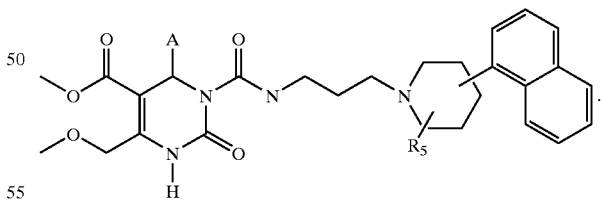

In other embodiments, A is

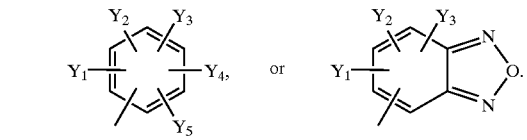

In an embodiment, the compound has the structure:

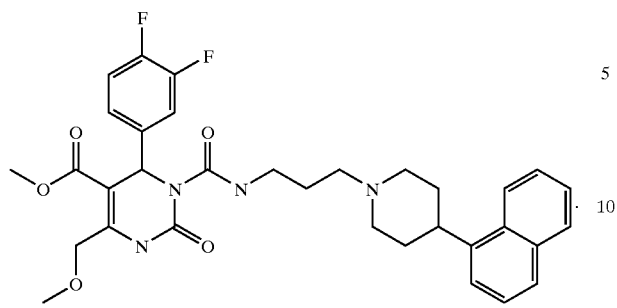

In yet another embodiment, the compound is (+)-1,2,3,6-tetra-hydro-1-{n-[4-(3,-acetamido)-phenylpiperidin-1-yl]propyl}carboxamido-4-methoxymethyl-6-(3,4-difluoro-phenyl)-2-oxopyrimidine-5-carboxylic acid methyl ester. In a further embodiment, the compound is (−)-1,2,3,6-tetra-hydro-1-{n-[4-(3,-acet-amido)-phenylpiperidin-1-yl]propyl}carboxamido-4-methoxymethyl-6-(3,4-difluoro-phenyl)-2-oxopyrimidine-5-carboxylic acid methyl ester.

In a further embodiment, the compound is:

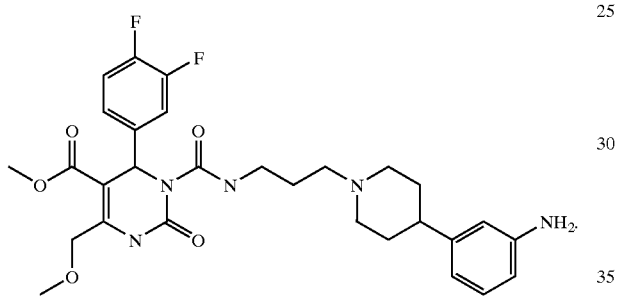

In a further embodiment, the compound has the structure:

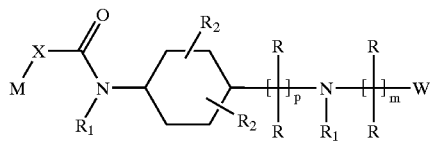

wherein each R is independently —H; —F; straight chained or branched $C_1$–$C_7$ alkyl, monofluoroalkyl or polyfluoroalkyl; straight chained or branched $C_2$–$C_7$ alkenyl or alkynyl; —N(R$_3$)$_2$; —NO$_2$; —CN; —SR$_3$; —CO$_2$R$_3$; or —OR$_3$;

wherein each $R_1$ is independently —H; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —(CH$_2$)$_p$OR$_3$; —COR$_3$; —CO$_2$R$_3$; or —CON(R$_3$)$_2$;

wherein each $R_2$ is —H; —NO$_2$; —N$_3$; —CN; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —N(R$_3$)$_2$; —OR$_3$; —(CH$_2$)$_p$OR$_3$; —COR$_3$; —CO$_2$R$_3$; or —CON(R$_3$)$_2$; or aryl or heteroaryl, optionally substituted with one or more F; Cl; Br; I; COR$_3$; CO$_2$R$_3$; —CON(R$_3$)$_2$; CN; —NO$_2$; —N(R$_3$)$_2$; —OR$_3$; —SR$_3$; (CH$_2$)$_q$OR$_3$; (CH$_2$)$_q$SR$_3$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl, $C_2$–$C_7$ alkynyl; $C_3$–$C_7$ cycloalkyl, monofluorocycloalkyl, polyfluorocycloalkyl or cycloalkenyl;

wherein each $R_3$ is independently —H; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl;

wherein M is aryl or heteroaryl, optionally substituted with one or more F; Cl; Br; I; COR$_3$; CO$_2$R$_3$; —CON(R$_3$)$_2$; CN; —NO$_2$; —N(R$_3$)$_2$; —OR$_3$; —SR$_3$; (CH$_2$)$_q$OR$_3$; (CH$_2$)$_q$SR$_3$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl, $C_2$–$C_7$ alkynyl; $C_3$–$C_7$ cycloalkyl, monofluorocycloalkyl, polyfluorocycloalkyl or cycloalkenyl;

wherein X is (CH$_2$)$_n$, O, S or NR$_3$;

wherein W is
  (a) $C_3$–$C_7$ cycloalkyl, monofluorocycloalkyl, polyfluorocycloalkyl or cycloalkenyl optionally substituted with one or more COR$_3$; CO$_2$R$_3$; —CON(R$_3$)$_2$; CN; —NO$_2$; —N(R$_3$)$_2$; —OR$_3$; —SR$_3$; (CH$_2$)$_q$OR$_3$; (CH$_2$)$_q$SR$_3$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl, $C_2$–$C_7$ alkynyl; $C_3$–$C_7$ cycloalkyl; or
  (b) aryl or heteroaryl optionally substituted with one or more F; Cl; Br; I; COR$_3$; CO$_2$R$_3$; —CON(R$_3$)$_2$; CN; —NO$_2$; —N(R$_3$)$_2$; —OR$_3$; —SR$_3$; (CH$_2$)$_q$OR$_3$; (CH$_2$)$_q$SR$_3$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl, $C_2$–$C_7$ alkynyl; $C_3$–$C_7$ cycloalkyl;

wherein m is an integer from 0 to 4 inclusive;
wherein n is an integer from 0 to 6 inclusive;
wherein p is an integer from 1 to 4 inclusive;
wherein q is an integer from 1 to 3 inclusive;
or a pharmaceutically acceptable salt thereof.

In one embodiment the compounds of this invention comprise the (+) enantiomer. In another embodiment, the compounds comprise the (−) enantiomer.

In an embodiment, the compound has the structure:

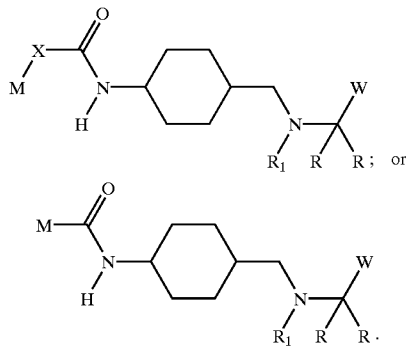

In a further embodiment, W is phenyl optionally substituted with one or more F; Cl; Br; I; COR$_3$; CO$_2$R$_3$; —CON(R$_3$)$_2$; CN; —NO$_2$; —N(R$_3$)$_2$; —OR$_3$; —SR$_3$; (OH$_2$)$_q$OR$_3$; or (CH$_2$)$_q$SR$_3$.

In another embodiment, the compound has the structure

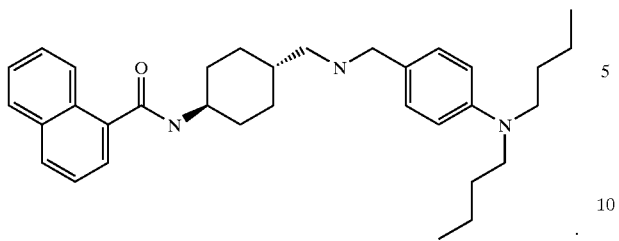

In one embodiment, the compound has the structure:

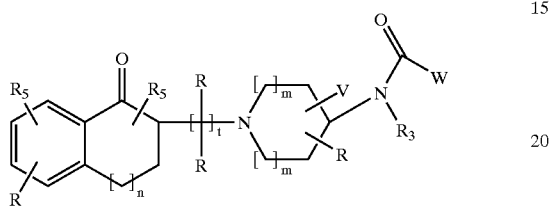

wherein each R is independently —H; —F; straight chained or branched $C_1$–$C_7$ alkyl, monofluoroalkyl or polyfluoroalkyl; straight chained or branched $C_2$–$C_7$ alkenyl or alkynyl; —N($R_3$)$_2$; —NO$_2$; —CN; —CO$_2$$R_3$; —OR$_3$; or —CON($R_3$)$_2$;

wherein each $R_1$ is independently —H; F; Cl; Br; I; —NO$_2$; —N$_3$; —CN; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —N($R_3$)$_2$; —OR$_3$; —(CH$_2$)$_p$OR$_3$; —COR$_3$; —CO$_2$$R_3$; —CON($R_3$)$_2$; aryl or heteroaryl, wherein the aryl or heteroaryl is optionally substituted with one or more F; Cl; Br; I; COR$_3$; CO$_2$$R_3$; —CON($R_3$)$_2$; CN; —NO$_2$; —N($R_3$)$_2$; —OR$_3$; —SR$_3$; (CH$_2$)$_q$OR$_3$; (CH$_2$)$_q$SR$_3$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl, $C_2$–$C_7$ alkynyl; $C_3$–$C_7$ cycloalkyl, monofluorocycloalkyl, polyfluorocycloalkyl or cycloalkenyl;

wherein each $R_3$ is independently —H; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl;

wherein $R_5$ is —H; —NO$_2$; —N$_3$; —CN; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —N($R_3$)$_2$; —OR$_3$; —(CH$_2$)$_p$OR$_3$; —COR$_3$; —CO$_2$$R_3$; —CON($R_3$)$_2$; aryl or heteroaryl, wherein the aryl or heteroaryl is optionally substituted with one or more F; Cl; Br; I; COR$_3$; CO$_2$$R_3$; —CON($R_3$)$_2$; CN; —NO$_2$; —N($R_3$)$_2$; —OR$_3$; —SR$_3$; (CH$_2$)$_q$OR$_3$; (CH$_2$)$_q$SR$_3$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl, $C_2$–$C_7$ alkynyl; $C_3$–$C_7$ cycloalkyl, monofluorocycloalkyl, polyfluorocycloalkyl or cycloalkenyl;

wherein V is H; aryl or heteroaryl, optionally substituted with one or more F; Cl; Br; I; COR$_3$; CO$_2$$R_3$; —CON($R_3$)$_2$; CN; —NO$_2$; —N($R_3$)$_2$; —OR$_3$; —SR$_3$; (CH$_2$)$_q$OR$_3$; (CH$_2$)$_q$SR$_3$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl, $C_2$–$C_7$ alkynyl; $C_3$–$C_7$ cycloalkyl, monofluorocycloalkyl, polyfluorocycloalkyl or cycloalkenyl;

wherein W is
(a) $C_3$–$C_7$ cycloalkyl, monofluorocycloalkyl, polyfluorocycloalkyl or cycloalkenyl optionally substituted with one or more COR$_3$; CO$_2$$R_3$; —CON($R_3$)$_2$; CN; —NO$_2$; —N($R_3$)$_2$; —OR$_3$; —SR$_3$; (CH$_2$)$_q$OR$_3$; (CH$_2$)$_q$SR$_3$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl, $C_2$–$C_7$ alkynyl; $C_3$–$C_7$ cycloalkyl; or
(b) aryl or heteroaryl optionally substituted with one or more F; Cl; Br; I; COR$_3$; CO$_2$$R_3$; —CON($R_3$)$_2$; CN; —NO$_2$; —N($R_3$)$_2$; —OR$_3$; —SR$_3$; (CH$_2$)$_q$OR$_3$; (CH$_2$)$_q$SR$_3$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl, $C_2$–$C_7$ alkynyl; $C_3$–$C_7$ cycloalkyl;

wherein each m is independently an integer from 0 to 3 inclusive;

wherein n is an integer from 0 to 2 inclusive;

wherein p is an integer from 1 to 7 inclusive;

wherein q is an integer from 1 to 3 inclusive;

wherein t is an integer from 2 to 6 inclusive;

or a pharmaceutically acceptable salt thereof.

In one embodiment the compounds of this invention comprise the (+) enantiomer. In another embodiment, the compounds comprise the (−) enantiomer.

In an additional embodiment, the compound has the structure:

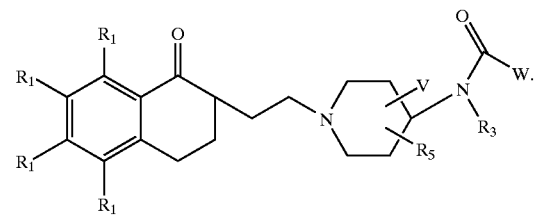

In a further embodiment, the compound has the structure

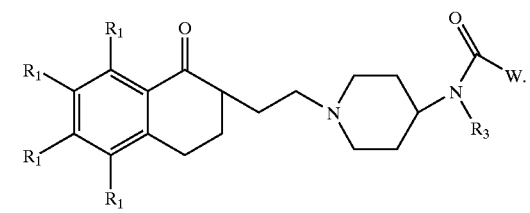

In yet another embodiment, W is phenyl optionally substituted with one or more F; Cl; Br; I; COR$_3$; CO$_2$$R_3$; —CON($R_3$)$_2$; CN; —NO$_2$; —N($R_3$)$_2$; —OR$_3$; —SR$_3$; (CH$_2$)$_q$OR$_3$; (CH$_2$)$_q$SR$_3$; or straight chained or branched $C_1$–$C_7$ alkyl groups.-

In yet another embodiment, the compound has the structure

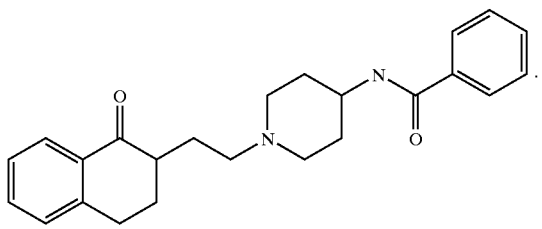

In the present invention, the term "aryl" includes phenyl and naphthyl and the term "heteroaryl" is used to include five and six membered unsaturated rings that may contain one or more heteroatoms such as oxygen, sulfur, and nitrogen. Examples of heteroaryl groups include, but are not limited to, furanyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, and triazinyl.

In addition the term "heteroaryl" is used to include fused bicyclic ring systems that may contain one or more heteroatoms such as oxygen, sulfur and nitrogen. Examples of such heteroaryl groups include, but are not limited to, indolizinyl, indolyl, isoindolyl, benzo[b]furanyl, benzo[b]thiophenyl, indazolyl, benzimidazolyl, benzthiazolyl, purinyl, imidazo[2,1-b]thiazolyl, quinolinyl, isoquinolinyl, quinolizinyl, and 2,1,3-benzothiazolyl.

Included in this invention are pharmaceutically acceptable salts and complexes of all of the compounds described herein. The salts include but are not limited to the acids and bases listed herein. The salts include, but are not limited to the following inorganic acids: hydrochloric acid, hydrobromic acid, hydroiodic acid, sulfuric acid and boric acid. The salts include, but are not limited to the following organic acids: acetic acid, malonic acid, succinic acid, fumaric acid, tartaric acid, maleic acid, citric acid, methanesulfonic acid, benzoic acid, glycolic acid, lactic acid and mandelic acid. The salts include, but are not limited to the inorganic base, ammonia. The salts include, but are not limited to the following organic bases: methylamine, ethylamine, propylamine, dimethylamine, diethylamine, trimethylamine, triethylamine, ethylenediamine, hydroxyethylamine, morpholine, piperazine and guanidine. This invention further provides for the hydrates and polymorphs of all of the compounds described herein.

The present invention includes within its scope prodrugs of the compounds of the invention. In general, such prodrugs will be functional derivatives of the compounds of the invention which are readily convertible in vivo into the required compound. Thus, in the present invention, the term "administering" shall emcompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in Design of Prodrugs, ed. H. Bundgaard, Elsevier, 1985.

The present invention further includes metabolites of the compounds of the present invention. Metabolites include active species produced upon introduction of compounds of this invention into the biological milieu.

This invention further provides a pharmaceutical composition comprising a therapeutically effective amount of the compound of the invention and a pharmaceutically acceptable carrier. In one embodiment, the amount of the compound is an amount from about 0.01 mg to about 800 mg. In another embodiment, the amount of the compound is an amount from about 0.01 mg to about 500 mg. In another embodiment, the amount of the compound is an amount from about 0.01 mg to about 250 mg. In another embodiment, the amount of the compound is an amount from about 0.1 mg to about 60 mg. In another embodiment, the amount of the compound is an amount from about 1 mg to about 20 mg. In a further embodiment, the carrier is a liquid and the composition is a solution. In another embodiment, the carrier is a solid and the composition is a tablet. In a further embodiment, the carrier is a gel and the composition is a suppository.

This invention provides a pharmaceutical composition made by combining a therapeutically effective amount of the compound of this invention and a pharmaceutically acceptable carrier.

This invention provides a process for making a pharmaceutical composition comprising combining a therapeutically effective amount of the compound of this invention and a pharmaceutically acceptable carrier.

In the practice of this invention the "pharmaceutically acceptable carrier" is any physiological carrier known to those of ordinary skill in the art useful in formulating pharmaceutical compositions.

In one preferred embodiment the pharmaceutical carrier may be a liquid and the pharmaceutical composition would be in the form of a solution. In another equally preferred embodiment, the pharmaceutically acceptable carrier is a solid and the composition is in the form of a powder or tablet. In a further embodiment, the pharmaceutical carrier is a gel and the composition is in the form of a suppository or cream. In a further embodiment the compound may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The compounds may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The compound can be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like.

The compound can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

The present invention also provides a method of modifying feeding behavior of a subject which comprises administering to the subject an amount of a compound effective to decrease the consumption of food by the subject wherein the compound has the structure:

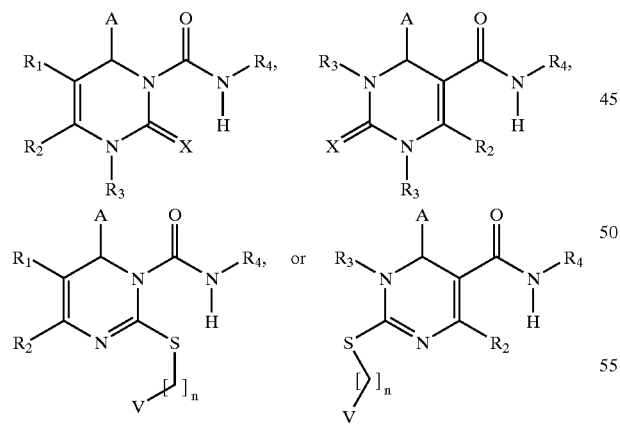

wherein A is

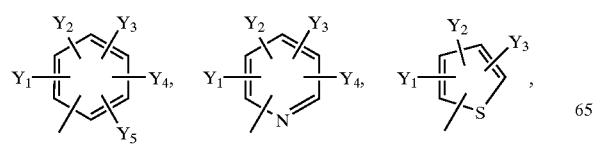

-continued

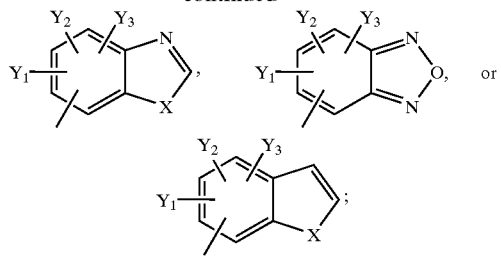

wherein each of $Y_1$, $Y_2$, $Y_3$, $Y_4$ and $Y_5$ is independently —H; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —F, —Cl, —Br, or —I; —$NO_2$; —$N_3$; —CN; —$OR_3$, —$OCOR_3$, —$COR_3$, —$CON(R_3)_2$, or —$COOR_3$; or any two of $Y_1$, $Y_2$, $Y_3$, $Y_4$ and $Y_5$ present on adjacent carbon atoms can constitute a methylenedioxy group;

wherein each X is independently S; O; or $NR_3$;

wherein $R_1$ is —H; —$NO_2$; —CN; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —$N(R_3)_2$; —$OR_3$; —$(CH_2)_pOR_3$; —$COR_3$; —$CO_2R_3$; —$CON(R_3)_2$; or $CO_2(CH_2)_nV$;

wherein $R_2$ is —H; straight chained or branched $C_1$–$C_7$ alkyl, hydroxyalkyl, alkoxyalkyl, aminoalkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; $C_3$–$C_{10}$ cycloalkyl-$C_1$–$C_{10}$-alkyl, $C_3$–$C_{10}$ cycloalkyl-$C_1$–$C_{10}$-monofluoroalkyl or $C_3$–$C_{10}$ cycloalkyl-$C_1$–$C_{10}$-polyfluoroalkyl; —CN; —$CH_2XR_3$, —$CH_2X(CH_2)_pNHR_3$, —$(CH_2)_nNHR_3$, —$CH_2X(CH_2)_pN(R_3)_2$, —$CH_2X(CH_2)_pN_3$, —$CH_2X(CH_2)_pNHCXR_5$; —$OR_3$; or $R_1$ and $R_2$ together form a lactone ring;

wherein each $R_3$ is independently —H; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl;

wherein $R_4$ is

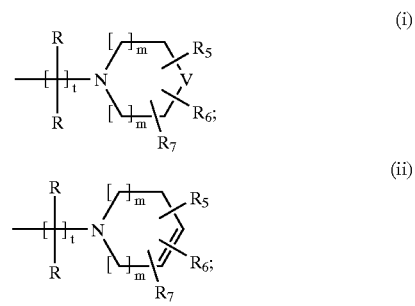

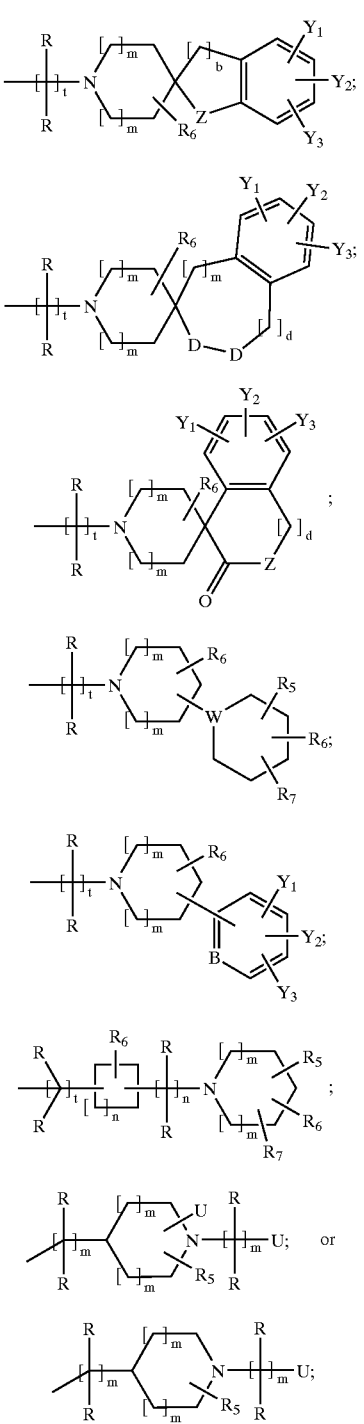

wherein each R is independently —H; —F; straight chained or branched $C_1$–$C_7$ alkyl, monofluoroalkyl or polyfluoroalkyl; straight chained or branched $C_2$–$C_7$ alkenyl or alkynyl; —N($R_3$)$_2$; —NO$_2$; —CN; —CO$_2$R$_3$; —OR$_3$; or —CN(R$_3$)$_2$;

wherein B is N or CY$_4$;

wherein each D is independently C(R$_3$)$_2$; O; S; NR$_3$; CO; or CS;

wherein each U is independently aryl or heteroaryl, optionally substituted with one or more F; Cl; Br; I; COR; CO$_2$R$_3$; —CON(R$_3$)$_2$; CN; —NO$_2$; —N(R$_3$)$_2$; —OR$_3$; —SR$_3$; (CH$_2$)$_q$OR$_3$; (CH$_2$)$_q$SR$_3$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl, $C_2$–$C_7$ alkynyl; $C_3$–$C_7$ cycloalkyl, monofluorocycloalkyl, polyfluorocycloalkyl or cycloalkenyl;

wherein V is C(R$_5$)$_2$; CR$_5$R$_6$; NR$_5$ or NR$_6$;

wherein W is CR$_5$; CR$_6$ or N;

wherein Z is S; O; C(R$_3$)$_2$; or NR$_3$;

wherein each R$_5$ is —H; —NO$_2$; —N$_3$; —CN; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —N(R$_3$)$_2$; —OR$_3$; —(CH$_2$)$_p$OR$_3$; —COR$_3$; —CO$_2$R$_3$; or —CON(R$_3$)$_2$; —XCOR$_8$; or aryl or heteroaryl, wherein the aryl or heteroaryl is optionally substituted with one or more F; Cl; Br; I; COR$_3$; CO$_2$R$_3$; —CON(R$_3$)$_2$; CN; —NO$_2$; —N(R$_3$)$_2$; —OR$_3$; —SR$_3$; (CH$_2$)$_q$OR$_3$; (CH$_2$)$_q$SR$_3$; —XCOR$_8$; straight chained or branched $C_1$–$C_7$ alkyl, monofluoroalkyl, polyfluoroalkyl, or aminoalkyl; straight chained or branched $C_2$–$C_7$ alkenyl, $C_2$–$C_7$ alkynyl; $C_3$–$C_7$ cycloalkyl, monofluorocycloalkyl, polyfluorocycloalkyl or cycloalkenyl;

wherein each R$_6$ is independently —H; straight chained or branched $C_1$–$C_7$ alkyl, hydroxyalkyl, aminoalkyl, alkoxyalkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —N(R$_3$)$_2$; —OR$_3$; —(CH$_2$)$_p$OR$_3$; —COR$_3$; —CO$_2$R$_3$; or —CON(R$_3$)$_2$;

wherein R$_7$ is —H; aryl or heteroaryl, optionally substituted with one or more F; Cl; Br; I; COR$_3$; CO$_2$R$_3$; —CON(R$_3$)$_2$; CN; —NO$_2$; —N(R$_3$)$_2$; —OR$_3$; —SR$_3$; (CH$_2$)$_q$OR$_3$; (CH$_2$)$_q$SR$_3$; —XCOR$_8$; straight chained or branched $C_1$–$C_7$ alkyl, monofluoroalkyl, polyfluoroalkyl, or aminoalkyl; straight chained or branched $C_2$–$C_7$ alkenyl, $C_2$–$C_7$ alkynyl; $C_3$–$C_7$ cycloalkyl, monofluorocycloalkyl, polyfluorocycloalkyl or cycloalkenyl;

wherein R$_8$ is —H; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —N(R$_3$)$_2$; —OR$_3$; —(CH$_2$)$_p$OR$_3$; —COR$_3$; —CO$_2$R$_3$; or —CON(R$_3$)$_2$; aryl or heteroaryl, optionally substituted with one or more F; Cl; Br; I; COR$_3$; CO$_2$R$_3$; —CON(R$_3$)$_2$; CN; —NO$_2$; —N(R$_3$)$_2$; —OR$_3$; —SR$_3$; (CH$_2$)$_q$OR$_3$; (CH$_2$)$_q$SR$_3$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl, $C_2$–$C_7$ alkynyl; $C_3$–$C_7$ cycloalkyl, monofluorocycloalkyl, polyfluorocycloalkyl or cycloalkenyl;

wherein b is 1 or 2;

wherein d is an integer from 0 to 2 inclusive;

wherein each m is independently an integer from 0 to 3 inclusive;

wherein each n is independently an integer from 0 to 5 inclusive;

wherein each p is independently an integer from 1 to 7 inclusive;

wherein q is an integer from 1 to 3 inclusive;

wherein t is an integer from 2 to 6 inclusive;

or a pharmaceutically acceptable salt thereof.

In one embodiment, the compound has the structure

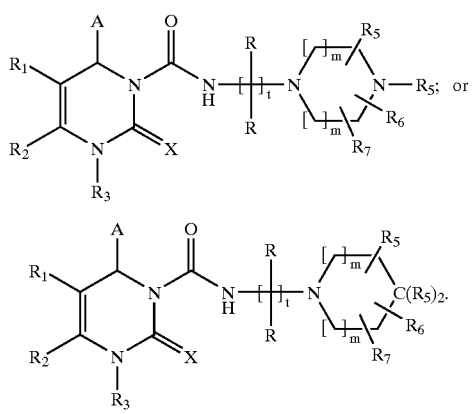

In a further embodiment, the compound has the structure

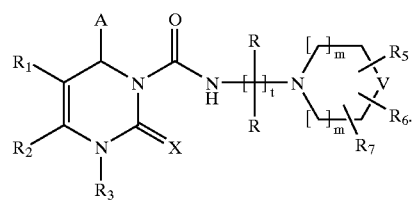

In an additional embodiment, the compound has the structure

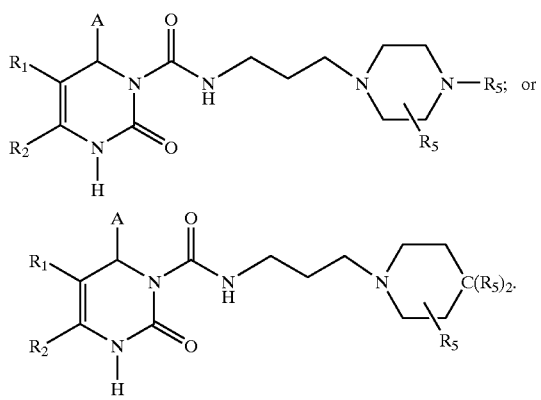

In a further embodiment, at least one $R_5$ group is an aryl or heteroaryl group optionally substituted with one or more F; Cl; Br; I; —$NO_2$; —$N(R_3)_2$; —$OR_3$; —$XCOR_8$; or straight chained or branched $C_1$–$C_7$ alkyl.

In another embodiment, A is:

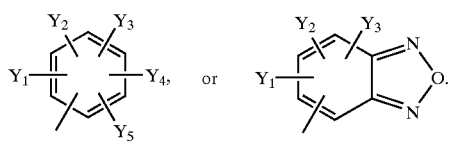

In further embodiments, the compound is selected from the group consisting of:

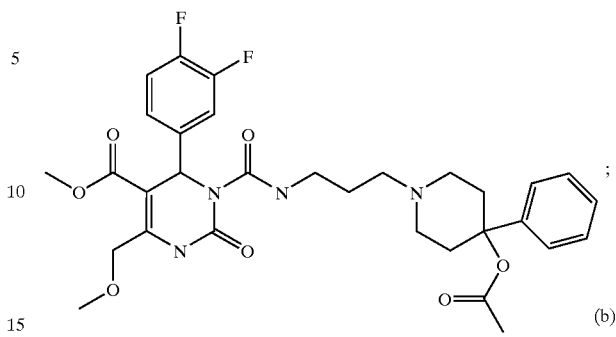

(a)

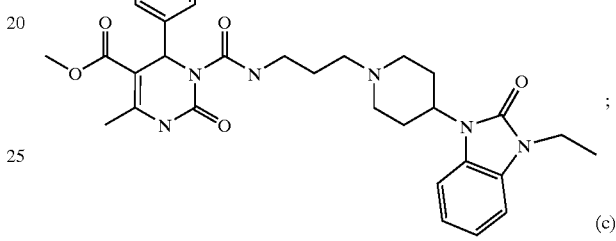

(b)

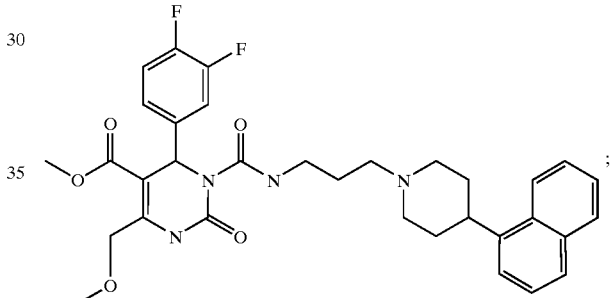

(c)

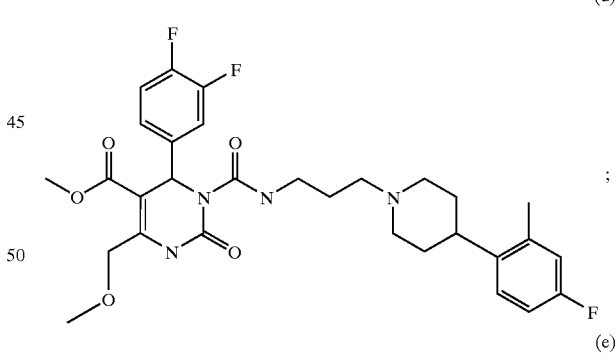

(d)

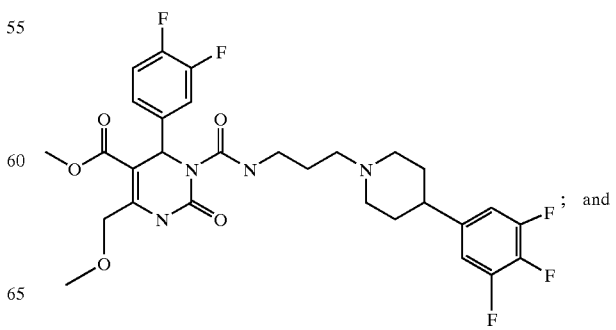

(e)

; and

-continued (f)

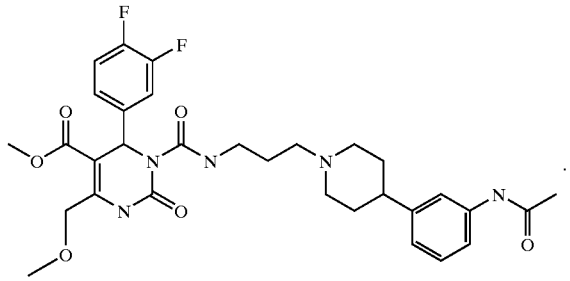

In other embodiments, the compound has the structure

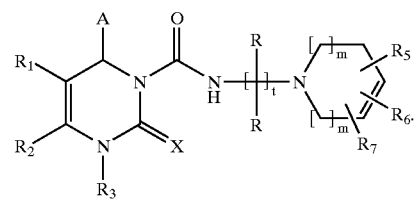

In a further embodiment, the compound has the structure

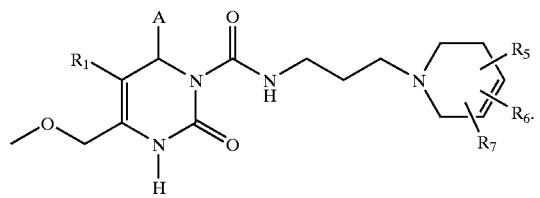

In additional embodiments, A is

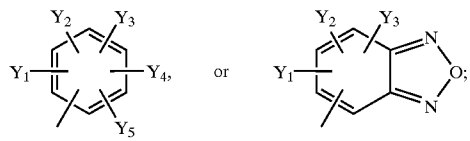

and $R_7$ is phenyl, optionally substituted with one or more F; Cl; Br; I; $COR_3$; $CO_2R_3$; —$CON(R_3)_2$; CN; —$NO_2$; —$N(R_3)_2$; —$OR_3$; —$SR_3$; $(CH_2)_qOR_3$; $(CH_2)SR_3$; —$XCOR_8$; or straight chained or branched $C_1$–$C_7$ alkyl.

In one embodiment, the compound has the structure

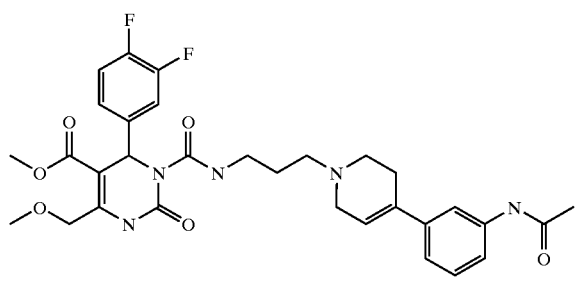

In an embodiment of the present invention, the compound has the structure

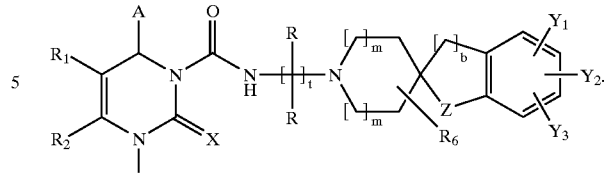

In yet another embodiment, the compound has the structure

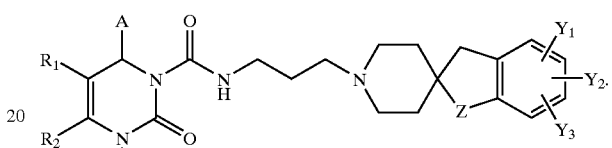

In further embodiments, A is

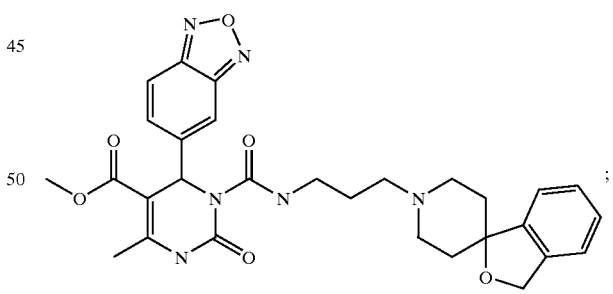

and Z is O or $CH_2$.

In an additional embodiment, the compound is selected from the group consisting of -continued

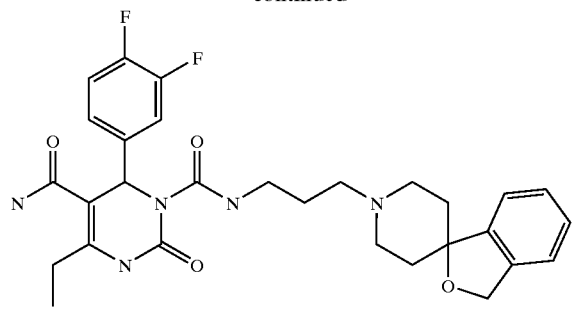

In one embodiment, the compound has the structure

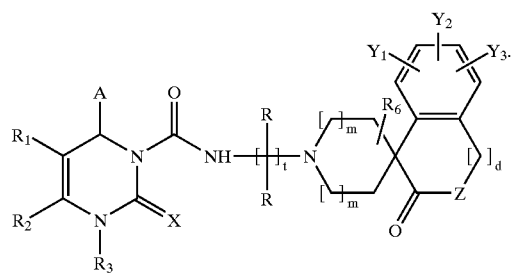

In a further embodiment, the compound has the structure

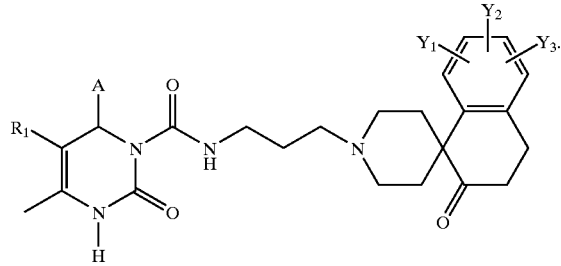

In another embodiment, A is

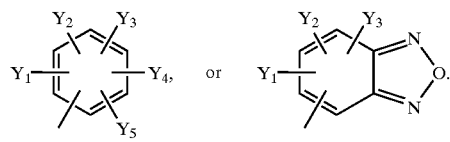

In yet another embodiment, the compound is

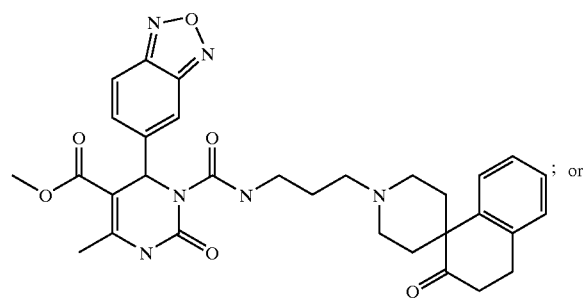

-continued

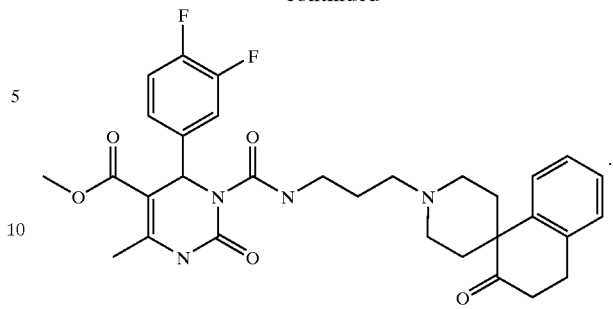

In a further embodiment, the compound has the structure

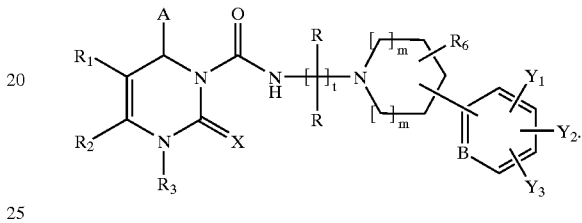

In another embodiment, the compound has the structure

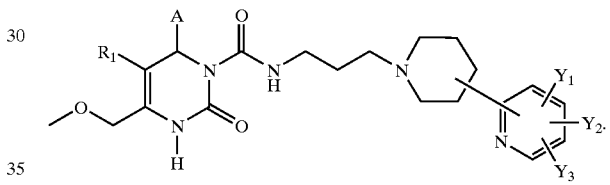

In yet another embodiment, the compound has the structure

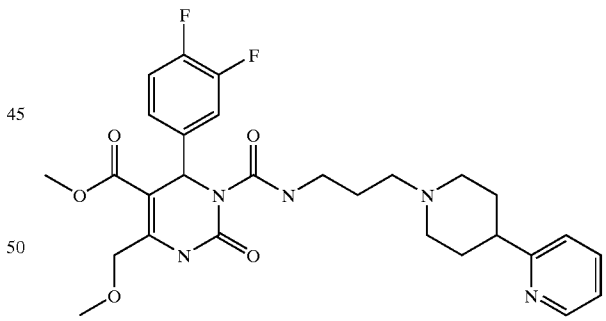

In one embodiment, the compound has the structure

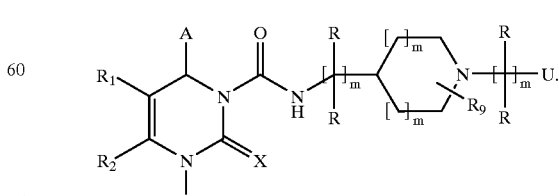

In another embodiment, the compound has the structure

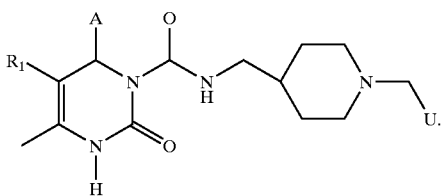

In another embodiment, the compound has the structure

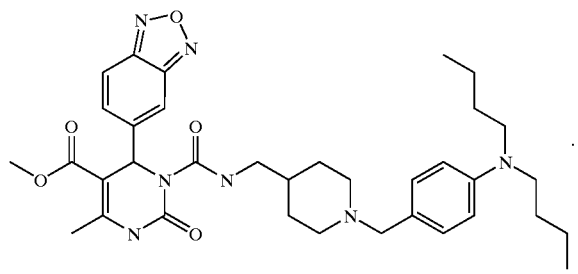

This invention further provides a method of reducing the body mass of a subject which comprises administering to the subject an amount of a compound effective to reduce the body mass of the subject wherein the compound has the structure:

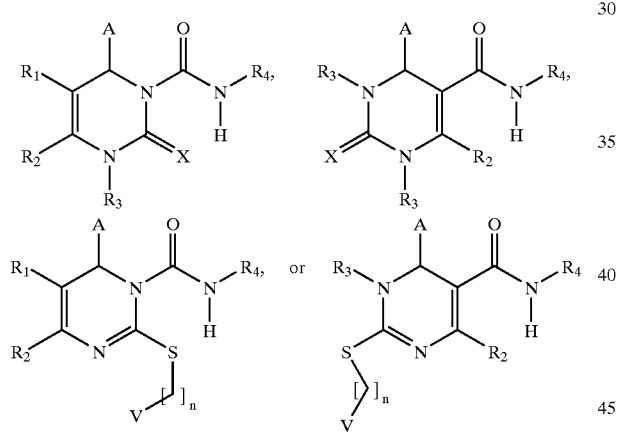

wherein A is

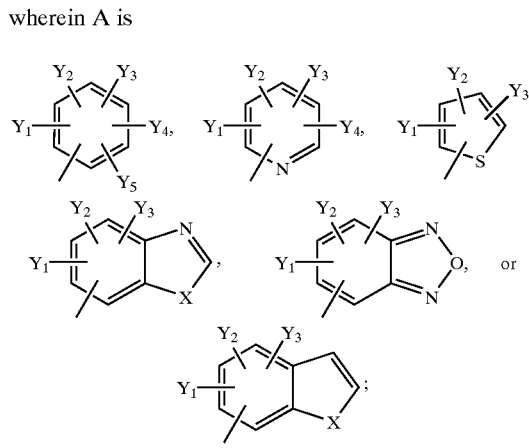

wherein each of $Y_1$, $Y_2$, $Y_3$, $Y_4$ and $Y_5$ is independently —H; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —F, —Cl, —Br, or —I; —$NO_2$; —$N_3$; —CN; —$OR_3$, —$OCOR_3$, —$COR_3$, —$CON(R_3)_2$, or —$COOR_3$; or any two of $Y_1$, $Y_2$, $Y_3$, $Y_4$ and $Y_5$ present on adjacent carbon atoms can constitute a methylenedioxy group;

wherein each X is independently S; O; or $NR_3$;

wherein $R_1$ is —H; —$NO_2$; —CN; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —$N(R_3)_2$; —$OR_3$; —$(CH_2)_pOR_3$; —$COR_3$; —$CO_2R_3$; —$CON(R_3)_2$; or $CO_2(CH_2)_nV$;

wherein $R_2$ is —H; straight chained or branched $C_1$–$C_7$ alkyl, hydroxyalkyl, alkoxyalkyl, aminoalkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; $C_3$–$C_{10}$ cycloalkyl-$C_1$–$C_{10}$-alkyl, $C_3$–$C_{10}$ cycloalkyl-$C_1$–$C_{10}$-monofluoroalkyl or $C_3$–$C_{10}$ cycloalkyl-$C_1$–$C_{10}$-polyfluoroalkyl; —CN; —$CH_2XR_3$, —$CH_2X(CH_2)_pNHR_3$, —$(CH_2)_nNHR_3$, —$CH_2X(CH_2)_pN(R_3)_2$, —$CH_2X(CH_2)_pN_3$, —$CH_2X(CH_2)_pNHCXR_5$; —$OR_3$; or wherein $R_1$ and $R_2$ together form a lactone ring;

wherein each $R_3$ is independently —H; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl;

wherein $R_4$ is

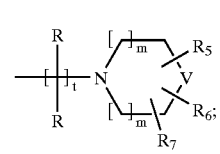 (i)

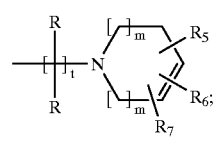 (ii)

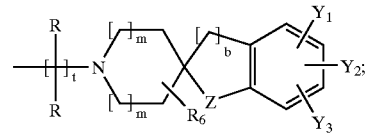 (iii)

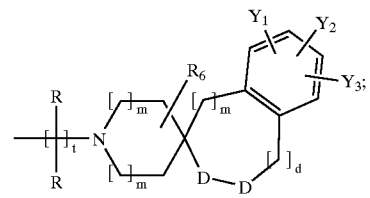 (iv)

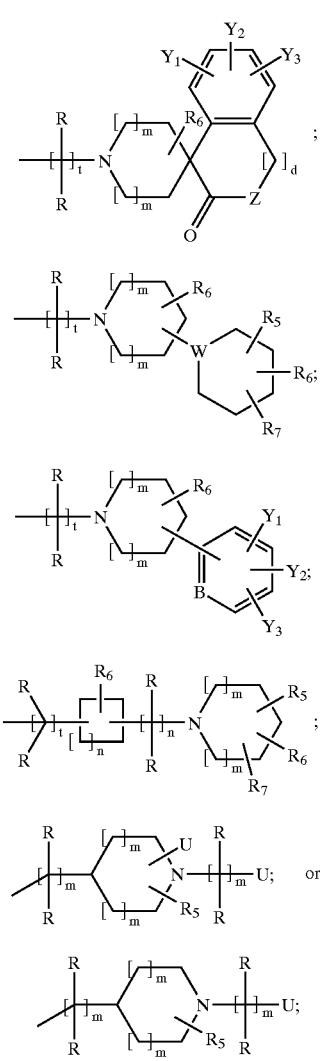

wherein each R is independently —H; —F; straight chained or branched $C_1$–$C_7$ alkyl, monofluoroalkyl or polyfluoroalkyl; straight chained or branched $C_2$–$C_7$ alkenyl or alkynyl; —N($R_3$)$_2$; —NO$_2$; —CN; —CO$_2R_3$; —OR$_3$; or —CN(R$_3$)$_2$;

wherein B is N or $CY_4$;

wherein each D is independently C($R_3$)$_2$; O; S; NR$_3$; CO; or CS;

wherein each U is independently aryl or heteroaryl, optionally substituted with one or more F; Cl; Br; I; COR$_3$; CO$_2$R$_3$; —CON(R$_3$)$_2$; CN; —NO$_2$; —N(R$_3$)$_2$; —OR$_3$; —SR$_3$; (CH$_2$)$_q$OR$_3$; (CH$_2$)$_q$SR$_3$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl, $C_2$–$C_7$ alkynyl; $C_3$–$C_7$ cycloalkyl, monofluorocycloalkyl, polyfluorocycloalkyl or cycloalkenyl;

wherein V is C($R_5$)$_2$; CR$_5$R$_6$; NR$_5$ or NR$_6$;

wherein W is CR$_5$; CR$_6$ or N;

wherein Z is S; O; C($R_3$)$_2$; or NR$_3$;

wherein each R$_5$ is —H; —NO$_2$; —N$_3$; —CN; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —N($R_3$)$_2$; —OR$_3$; —(CH$_2$)$_p$OR$_3$; —COR$_3$; —CO$_2$R$_3$; or —CON(R$_3$)$_2$; —XCOR$_8$; or aryl or heteroaryl, wherein the aryl or heteroaryl is optionally substituted with one or more F; Cl; Br; I; COR$_3$; CO$_2$R$_3$; —CON(R$_3$)$_2$; CN; —NO$_2$; —N(R$_3$)$_2$; —OR$_3$; —SR$_3$; (CH$_2$)$_q$OR$_3$; (CH$_2$)$_q$SR$_3$; —XCOR$_8$; straight chained or branched $C_1$–$C_7$ alkyl, monofluoroalkyl, polyfluoroalkyl, or aminoalkyl; straight chained or branched $C_2$–$C_7$ alkenyl, $C_2$–$C_7$ alkynyl; $C_3$–$C_7$ cycloalkyl, monofluorocycloalkyl, polyfluorocycloalkyl or cycloalkenyl;

wherein each R$_6$ is independently —H; straight chained or branched $C_1$–$C_7$ alkyl, hydroxyalkyl, aminoalkyl, alkoxyalkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —N(R$_3$)$_2$; —OR$_3$; —(CH$_2$)$_p$OR$_3$; —COR$_3$; —CO$_2$R$_3$; or —CON(R$_3$)$_2$;

wherein R$_7$ is —H; aryl or heteroaryl, optionally substituted with one or more F; Cl; Br; I; COR$_3$; CO$_2$R$_3$; —CON(R$_3$)$_2$; CN; —NO$_2$; —N(R$_3$)$_2$; —OR$_3$; —SR$_3$; (CH$_2$)$_q$OR$_3$; (CH$_2$)$_q$SR$_3$; —XCOR$_8$; straight chained or branched $C_1$–$C_7$ alkyl, monofluoroalkyl, polyfluoroalkyl, or aminoalkyl; straight chained or branched $C_2$–$C_7$ alkenyl, $C_2$–$C_7$ alkynyl; $C_3$–$C_7$ cycloalkyl, monofluorocycloalkyl, polyfluorocycloalkyl or cycloalkenyl;

wherein R$_8$ is —H; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —N(R$_3$)$_2$; —OR$_3$; —(CH$_2$)$_p$OR$_3$; —COR$_3$; —CO$_2$R$_3$; or —CON(R$_3$)$_2$; aryl or heteroaryl, optionally substituted with one or more F; Cl; Br; I; COR$_3$; CO$_2$R$_3$; —CON(R$_3$)$_2$; CN; —NO$_2$; —N(R$_3$)$_2$; —OR$_3$; —SR$_3$; (CH$_2$)$_q$OR$_3$; (CH$_2$)$_q$SR$_3$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl, $C_2$–$C_7$ alkynyl; $C_3$–$C_7$ cycloalkyl, monofluorocycloalkyl, polyfluorocycloalkyl or cycloalkenyl;

wherein b is 1 or 2;

wherein d is an integer from 0 to 2 inclusive;

wherein each m is independently an integer from 0 to 3 inclusive;

wherein each n is independently an integer from 0 to 5 inclusive;

wherein each p is independently an integer from 1 to 7 inclusive;

wherein q is an integer from 1 to 3 inclusive;

wherein t is an integer from 2 to 6 inclusive;

or a pharmaceutically acceptable salt thereof.

In addition, the present invention provides a method of treating a subject suffering from depression and/or anxiety which comprises administering to the subject a compound of the aforementioned formula in an amount effective to treat the subject's depression and/or anxiety.

This invention also provides a method of modifying feeding behavior of a subject which comprises administering to the subject an amount of a compound effective to decrease the consumption of food by the subject wherein the compound is selected from the group consisting of:

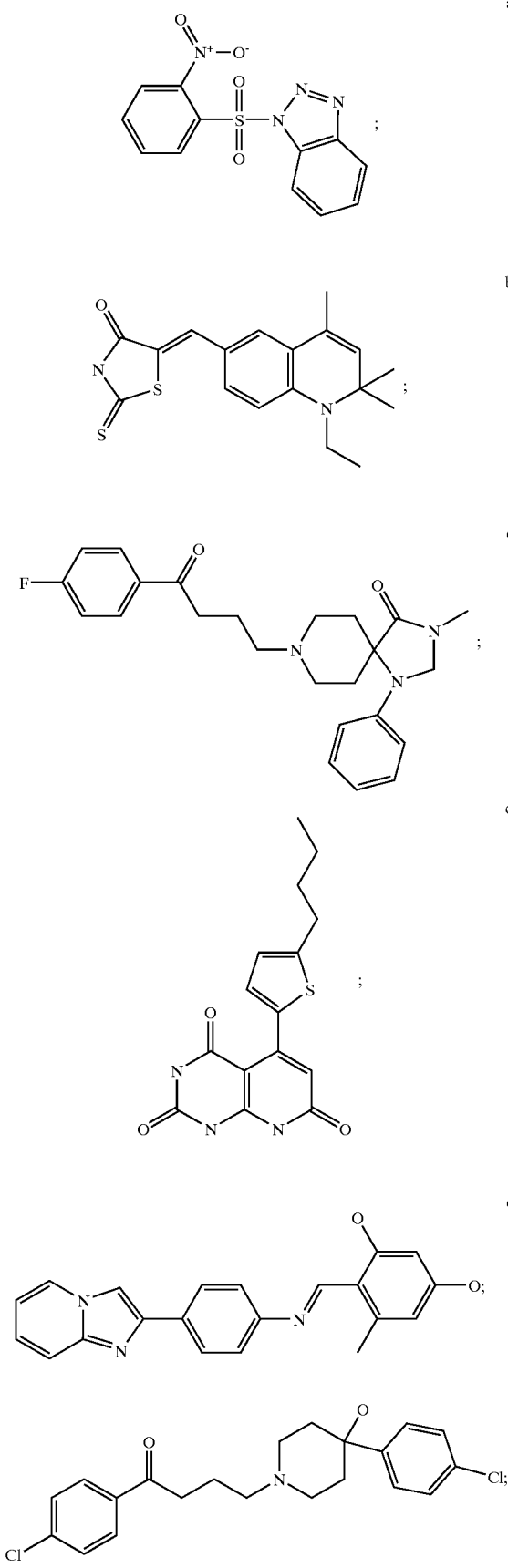

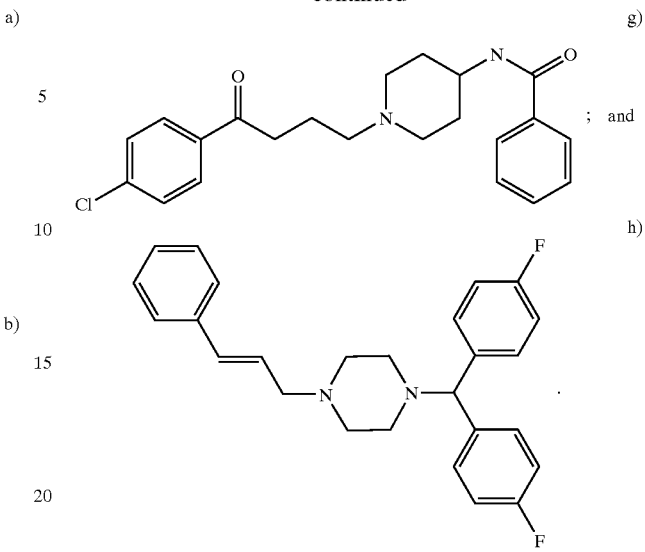

This invention further provides a method of modifying feeding behavior of a subject which comprises administering to the subject an amount of a compound of the present invention effective to decrease the consumption of food by the subject.

This invention also provides a method of treating a feeding disorder in a subject which comprises administering to the subject an amount of a compound of the present invention effective to decrease the consumption of food by the subject. In an embodiment of the present invention, the feeding disorder is bulimia, obesity or bulimia nervosa. In a further embodiment, the subject is a vertebrate, a mammal, a human or a canine. In yet another embodiment, the compound is administered in combination with food.

In the subject invention a "therapeutically effective amount" is any amount of a compound which, when administered to a subject suffering from a disease against which the compounds are effective, causes reduction, remission, or regression of the disease.

One skilled in the art will readily appreciate that appropriate biological assays will be used to determine the therapeutic potential of the claimed compounds for treating the above noted disorders.

Optimal dosages to be administered may be determined by those skilled in the art, and will vary with the particular compound in use, the strength of the preparation, the mode of administration, and the advancement of the disease condition. Additional factors depending on the particular subject being treated will result in a need to adjust dosages, including subject age, weight, gender, diet, and time of administration.

This invention further provides compositions which need not be pharmaceutical as that term is understood in the art. Such compositions comprise a compound in accordance with the subject invention in an amount effective to antagonize an MCH1 receptor and a suitable carrier.

Still further, the invention provides a method of agonizing and/or antagonizing an MCH1 receptor which comprises contacting the receptor, e.g. in vitro or in in vivo, with an amount of a compound of this invention effective to agonize and/or antagonize the receptor.

This invention will be better understood from the Experimental Details which follow. However, one skilled in the art will readily appreciate that the specific methods and results discussed are merely illustrative of the invention as described more fully in the claims which follow thereafter.

EXPERIMENTAL SECTION

I. Synthetic Methods for Examples

General Methods: All reactions (except for those done by parallel synthesis reaction arrays) were performed under an Argon atmosphere and the reagents, neat or in appropriate solvents, were transferred to the reaction vessel via syringe and cannula techniques. The parallel synthesis reaction arrays were performed in vials (without an inert atmosphere) using J-KEM heating shakers (Saint Louis, Mo.). Anhydrous solvents were purchased from Aldrich Chemical Company and used as received. The examples described in the patent (1–37) were named using ACD/Name program (version 2.51, Advanced Chemistry Development Inc., Toronto, Ontario, M5H2L3, Canada). Unless otherwise noted, the $^1$H and $^{13}$C NMR spectra were recorded at 300 and 75 MHz (QE Plus) with $CDCl_3$ as solvent and tetramethylsilane as internal standard. s=singlet; d=doublet; t=triplet; q=quartet; p=pentet; sextet; septet; br=broad; m=multiplet. Elemental analyses were performed by Robertson Microlit Laboratories, Inc. Unless otherwise noted, mass spectra were obtained using low-resolution electrospray (ESMS) and MH+ is reported. Thin-layer chromatography (TLC) was carried out on glass plates precoated with silica gel 60 F254 (0.25 mm, EM Separations Tech.). Preparative thin-layer chromatography was carried out on glass sheets precoated with silica gel GF (2 mm, Analtech). Flash column chromatography was performed on Merck silica gel 60 (230–400 mesh). Melting points (mp) were determined in open capillary tubes on a Mel-Temp apparatus and are uncorrected.

Procedures for the Synthesis of the Dihydropyrimidine Intermediates

5-METHOXYCARBONYL-4-METHOXYMETHYL-1,2,3,6-TETRAHYDRO-2-OXO-6-(3,4-DIFLUOROPHENYL)-PYRIMIDINE: To a stirring mixture of methyl 4-methoxyacetoacetate (50.0 g, 0.342 mol), 3,4-difluorobenz-aldehyde (51.4 g, 0.362 mol), and urea (31.6 g, 0.527 mole) in THF (300 mL) at room Temperature were added copper(I) oxide (5.06 g, 0.035 mole) and acetic acid (2.05 mL), sequentially, followed by dropwise addition of boron trifluoride diethyl etherate (56.0 mL, 0.442 mole). The mixture was stirred and refluxed for 8 h, whereupon TLC (1/1 EtOAc/hexanes) analysis indicated completion of the reaction. The reaction mixture was cooled and poured into a mixture of ice and sodium bicarbonate (100 g) and the resulting mixture was filtered through Celite. The Celite pad was washed with dichloromethane (400 mL). The organic layer was separated from the filtrate and the aqueous layer was extracted with more dichloromethane (3×300 mL). The combined organic extracts were dried (sodium sulfate) and the solvent evaporated. The crude product was purified by flash column (ethyl acetate/hexanes, 1/1; then ethyl acetate), giving the product as pale yellow foam, which on trituration with hexane became white powder (103 g, 97%). $^1$H NMR d 3.48 (s, 3H), 3.65 (s, 3H), 4.65 (s, 2H), 5.39 (s, 1H), 6.60 (br s, 1H, NH), 7.00–7.20 (m, 3H), 7.72 (br s, 1H, NH).

(+)-5-METHOXYCARBONYL-4-METHOXYMETHYL-1,2,3,6-TETRAHYDRO-2-OXO-6-(3,4-DIFLUOROPHENYL)-PYRIMIDINE: The racemic intermediate 5-methoxycarbonyl-4-methoxymethyl-1,2,3,6-tetrahydro-2-oxo-6-(3,4-difluorophenyl)pyrimidine was resolved by chiral HPLC [Chiralcel OD 20×250 mm #369-703-30604; lambda 254 nm; hexanes/ethanol 90/10; 85 mg per injection; retention time of the desired enantiomer: 16.94 min., the first enantiomer peak to elute], giving (+)-5-methoxycarbonyl-4-methoxymethyl-1,2,3,6-tetrahydro-2oxo-6-(3,4-difluorophenyl)-pyrimidine (40–42 wt % isolation of the desired enantiomer from the racemate); $[\alpha]_D$=+ 83.8 (c=0.5, chloroform). The (−)-isomer was also isolated as the later eluting fraction from the chiral chromatography column.

(+)-5-METHOXYCARBONYL-4-METHOXYMETHYL-1,2,3,6-TETRAHYDRO-2-OXO-6-(3,4-DIFLUOROPHENYL)-1-[(4-NITROPHENYLOXY)CARBONYL]PYRIMIDINE: To a solution of (+)-5-methoxycarbonyl-4-methoxymethyl-1,2,3,6-tetrahydro-2-oxo-6-(3,4-difluorophenyl)-pyrimidine (1.98 g, 6.34 mmol) in anhydrous THF (20 mL) at −78° C. under argon atmosphere, a solution of lithium hexamethyldisilazide in THF (1M, 18.0 mL, 18.0 mmol) was added over 2–3 min. and the mixture was stirred for 10 min. This solution was added over 6 min., via a cannula, to a stirred solution of 4-nitrophenyl chloroformate (4.47 g, 22.2 mmol) in THF (20 mL) at −78° C. Stirring was continued for 10 min. and the mixture was poured onto ice (50 g) and extracted with chloroform (2×50 mL). The combined extracts were dried (sodium sulfate) and the solvent was evaporated. The residue was purified by flash column chromatography (hexanes/ ethyl acetate, 4/1 to 3.5/1) as the eluent. The product was obtained as yellow syrup which upon trituration with hexanes became a white powder (2.40 g, 79%): $^1$H NMR d 3.52 (s, 3H), 3.74 (s, 3H), 4.65–4.80 (q, J=16.5 Hz, 2H), 6.32 (s, 1H), 7.10–7.30 (m, 4H), 7.36 (d, J=9 Hz, 2H), 8.27 (d, J=9 Hz, 2H).

BENZYL 3-[(3,4-DIFLUOROPHENYL)METHYLENE]-4-OXOPENTANOATE: A solution of benzyl propionylacetate (36.3 g, 176 mmol), 3,4-difluorobenzaldehyde (25.0 g, 176 mmol), piperidine (0.86 mL, 9.0 mmol) and acetic acid (0.49 mL, 9.0 mmol) was refluxed with removal of water using a Dean-Stark apparatus for 5 h. The solvent was removed in vacuo and the residue was dissolved in EtOAc. The reaction mixture was washed with water (100 mL), followed by brine (100 mL) and dried over anhydrous $Na_2SO_4$. The solvent was evaporated, giving a pale yellow syrup (60.2 g). The product was used in the next step without further purification.

5-(BENZYLOXYCARBONYL)-1,6-DIHYDRO-2-METHOXY-4-ETHYL-6-(3,4-DI-FLUOROPHENYL)PYRIMIDINE: A suspension of benzyl 3-[(3,4-difluorophenyl)methylene]-4-oxopentanoate (16.0 g, 48.0 mmol), O-methylisourea hydrogen sulfate (16.7 g, 97.0 mmol) and NaHCO3 (16.3 g, 130 mmol) in DMF (190 mL) was stirred at 70° C. for 20 h. After cooling to room temperature, the mixture was filtered and the filtrate was diluted with EtOAc (300 mL) and then washed with water (4×100 mL), brine (200 mL) and dried over $Na_2SO_4$. After removal of solvent, the residue was purified by column chromatography (EtOAc/Hexane, 1/9 to 3/7), giving the title compound as a colorless oil (10.6 g, 58%). The NMR analysis showed it to be a mixture of amine/imine tautomers and was used as is in the next step.

5-(BENZYLOXYCARBONYL)-4-ETHYL-1,6-DIHYDRO-2-METHOXY-6-(3,4-DI-FLUOROPHENYL)-1-[(4-NITROPHENYLOXY)CARBONYL]PYRIMIDINE: To a stirring solution of 5-(benzyloxycarbonyl)-1,6-dihydro-2-methoxy-4-ethyl-6-(3,4-difluorophenyl)pyrimidine (17.0 g, 44.0 mmol) and 4-dimethylaminopyridine (7.00 g, 57.3 mmol) in CH₂Cl₂ (200 mL) was added 4-nitrophenyl chloroformate as a powder (11.5 g, 57.1 mmol) at room temperature. The reaction mixture was stirred for 12 h and then the solvent was removed in vacuo. The residue was purified by chromatography (EtOAc/Hexane, 1/9 to 3/7), giving 5-(benzyloxycarbonyl)-4-ethyl-1,6-dihydro-2-methoxy-6-(3,4-difluorophenyl)-1-[(4-nitrophenyloxy)carbonyl]pyrimidine as a colorless viscous oil (12.6 g, 50%). ¹H NMR d 1.24 (t, J=7.2 Hz, 3H), 2.81–2.98 (m, 3H), 3.97 (s, 3H), 5.14 (ABq, A=5.08, B=5.20, J=12.3 Hz, 2H), 6.28 (s, 3H), 7.03–7.29 (m, 8H), 7.35 (d, J=9.2 Hz, 2H), 8.26 (d, J=9.2 Hz, 2H).

5-(BENZYLOXYCARBONYL)-4-ETHYL-1,6-DIHYDRO-1-{N-[1-PHENYL)ETHYL]}-CARBOXAMIDO-2-METHOXY-6-(3,4-DIFLUOROPHENYL)PYRIMIDINE: To a stirred mixture of 5-(benzyloxycarbonyl)-4-ethyl-1,6-dihydro-2-methoxy-6-(3,4-difluorophenyl)-1-[(4-nitrophenyloxy)carbonyl]pyrimidine (12.6 g, 22.9 mmol) in THF (150 mL) was added a solution of R-(+)-α-methyl benzylamine (3.53 mL, 27.1 mmol) at room temperature. The stirring was continued for 12 h and the solvent was removed in vacuo. The yellow residue was dissolved in chloroform (200 mL) and was washed with 10% K₂CO₃ solution (2×30 mL). The organic layer was dried over Na₂SO₄, filtered and solvent was removed in vacuo. The resulting mixture of diastereomers was separated by column chromatography (petroleum ether/ether, 9/1 to 4/1). The first major product to elute was (+)-5-(benzyloxycarbonyl)-4-ethyl-1,6-dihydro-1-{N-[1-phenyl)-ethyl]}carboxamido-2-methoxy-6-(3,4-difluorophenyl)pyrimidine. Colorless oil; Rf=0.31 (petroleum ether/ether, 4/1); yield: 3.8 g (31%); [α]$_D$=+267.05 (c=0.76, CHCl₃); ¹H NMR d 1.22 (t, J=7.5 Hz, 3H), 1.52 (d, J=6.9 Hz, 3H), 2.88 (q, J=6.0 Hz, 2H), 3.99 (s, 3H), 4.99 (m, 1H), 5.09 (ABq, A=5.00, B=5.19, J=12.6 Hz, 2H), 6.66 (s, 1H), 6.99–7.36 (m, 13H). The second major product to elute was (−)-5-(benzyloxycarbonyl)-4-ethyl-1,6-dihydro-1-{N-[2-phenyl)ethyl]}carboxamido-2-methoxy-6-(3,4-difluorophenyl)pyr-imidine. Colorless oil; Rf=0.22 (petroleum ether/ether, 4/1); yield: 3.20 g (26%); [α]$_D$=−146.89 (c=0.38, CHCl₃); ¹H NMR δ 1.22 (t, J=7.2 Hz, 3H), 1.49 (d, J=6.6 Hz, 3H),2.88 (q, J=6.0 Hz, 2H), 3.94 (s, 3H), 5.03 (m, 1H), 5.11 (ABq, A=5.02, B=5.19, J=12.6 Hz, 2H), 6.68 (s, 1H), 6.91–7.34 (m, 13H).

(+)-5-(BENZYLOXYCARBONYL)-1,6-DIHYDRO-2-METHOXY-4-ETHYL-6-(3,4-DI-FLUOROPHENYL)PYRIMIDINE: To a stirred solution of (+)-5-(benzyloxycarbonyl)-4-ethyl-1,6-dihydro-1-{N-[2-phenyl)ethyl]}carbox-amido-2-methoxy-6-(3,4-difluorophenyl)pyrimidine (1.00 g, 1.83 mmol) in toluene (10 mL) was added 1,8-diazabicyclo[5,4,0]-undec-7-ene (0.120 mL, 0.810 mmol) at room temperature and the resulting solution was heated at reflux temperature for 5 h and then stirred for 12 h at room temperature. The solvent was evaporated and the residue was purified by flash column (EtOAc/Hexanes, 1/3), giving (+)-5-(benzyloxycarbonyl)-1,6-dihydro-2-methoxy-4-ethyl-6-(3,4-difluorophenyl)pyrimidine (0.560 g, 77%).

(+)-5-(BENZYLOXYCARBONYL)-4-ETHYL-1,6-DIHYDRO-2-METHOXY-6-(3,4-DI-FLUOROPHENYL)-1-[(4-NITROPHENYLOXY)CARBONYL]PYRIMIDINE: To a stirring solution of (+)-5-(benzyloxycarbonyl)-1,6-dihydro-2-methoxy-4-ethyl-6-(3,4-difluorophen-yl)pyrimidine (17.0 g, 44.0 mmol) and 4-dimethylaminopyridine (6.99 g, 57.3 mmol) in CH₂Cl₂ (200 mL) was added 4-nitrophenyl chloroformate (11.6 g, 57.3 mmol) at room temperature. The reaction mixture was stirred for 12 h and then the solvent was removed in vacuo. The residue was purified by chromatography (EtOAc/Hexane, 1/9 to 3/7), giving (+)-5-(benzyloxycarbonyl)-4-ethyl-1,6-dihydro-2-methoxy-6-(3,4-difluorophenyl)-1-[(4-nitrophenyloxy) carbonyl]pyrimidine as a viscous colorless oil (19.3 g, 76%).

5-METHYLBENZFUROXAN: 4-Methyl-2-nitroaniline (100 g, 0.650 mol) was suspended in saturated methanolic sodium hydroxide solution (1.50 L). This suspension was cooled (5° C.) and aqueous sodium hypochlorite until the red color disappeared. The resulting fluffy yellow precipitate was filtered, washed with cold water and recrystallized from ethanol, giving 5-methylbenzfuroxan (88.2 g, 89% yield) as a pale yellow solid: ¹H NMR d 2.39 (s, 3 H), 6.90–7.40 (br m. 3 H).

5-METHYLBENZOFURAZAN: To 5-Methylbenzfuroxan (88.2 g, 0.590 mol) in refluxing EtOH (75 mL) was added dropwise P(OEt)₃ (150 mL). Heating was continued at reflux temperature for h. The solvent was removed in vacuo and the residue was shaken with water (200 mL) and allowed to stand overnight at (0–5° C.). The resulting brown solid was filtered, washed with water. The crude product was purified by flash chromatography, giving 5-methylbenzofurazan (70.0 g, 87%) as white needles; ¹H NMR δ 2.41 (s, 1 H), 7.19 (dd, J=9.3, 1.1 Hz, 1 H), 7.48 (d, J=1.1 Hz, 1 H), 7.66 (d, J=9.3 Hz, 1H).

5-DIBROMOMETHYLBENZOFURAZAN: An anhydrous solution of 5-methylbenzofurazan (70.0 g, 0.520 mol), N-bromosuccinamide (325 g), and benzoyl peroxide (0.50 g) in carbon tetrachloride (1.5 L) was heated at reflux temperature with stirring for 30 h. The reaction mixture was washed with water (2×500 mL), dried (NaSO₄), and the solvent was removed in vacuo. The residue was chromatograghed (EtOAc/hexane, 1/150), giving 122 g (80%) of the title compound as a white solid: ¹H NMR d 6.69 (s, 1 H), 7.69 (d, J=9.6 Hz, 1 H), 7.77 (s, 1 H), 7.89 (d, J=9.6 Hz, 1 H).

5-FORMYLBENZOFURAZAN: AgNO₃ (163 g) in 2 L of water was added to a refluxing mixture of dibromomethylbenzofurazan (122 g, 418 mmol) in EtOH (1 L). Heating at reflux temperature was continued for 2 h. The mixture was cooled, the precipitated AgBr was removed by filtration through Celite, and the solvent was concentrated. The resulting solution was extracted with toluene (10×100 mL), dried over magnesium sulfate, and the solvent was removed in vacuo. The residue was chromatograghed (EtOAc/hexane, 1/125), giving the title aldehyde (48.2 g, 78%) as a white solid: ¹H NMR δ 7.92 (m, 2H), 8.39 (s, 1 H), 10.10 (s, 1 H).

METHYL 2-{(BENZOFURAN-5-YL)METHYLENE}-3-OXOBUTYRATE: A mixture of 5-formylbenzofurazan (0.60 g, 4.1 mmol), methyl acetoacetate (0.52 g, 4.5 mmol), piperidine (0.019 g, 0.23 mmol), and acetic acid (0.014 g, 0.23 mmol) in benzene (30 mL) was heated at reflux temperature (equipped with a Dean-Stark trap) for 8 h. Benzene was evaporated in vacuo, the residue was dissolved in ethyl acetate (80 mL) and washed with brine (50 mL), saturated potassium bisulfate solution (50 mL), and saturated sodium bicarbonate solution. The ethyl acetate solution was dried over magnesium sulfate, the solvent removed under reduced pressure and the residue was purified by column chromatography (EtOAc/hexane, 1/9 to 3/20). The desired product was obtained as oil (0.98 g, 98%) and was used in the next step without any further characterization.

6-(BENZOFURAZAN-5-YL)-1,6-DIHYDRO-2-METHOXY-5-METHOXYCARBONYL-4-METHYLPYRIMIDINE: A mixture of methyl 2-{(benzofuran-5-yl)-methylene}-3-oxobutyrate (1.02 g, 4.10 mmol), O-methylisourea hydrogen sulfate (1.06 g, 6.20 mmol), and NaHCO₃ (1.30 g, 16.4 mmol) in DMF (15 mL) was stirred and heated at 70° C. for 16 h. The mixture was cooled, diluted with EtOAc (50 mL) and washed with water (5×50 mL), brine (50 mL) and dried over magnesium sulfate. The solvent was evaporated and the crude product was purified by flash chromatography (EtOAc/hexane, 1/9 to 1/5), giving the desired product as an oil (0.520 g, 43%): ¹HNMR δ 2.38 and 2.42 (2 s, 3 H), 3.60 and 3.66 (2 s, 3 H), 3.74 and 3.82 (2 s, 3 H), 5.53 and 5.68 (2 s, 1 H), 6.31 and 6.32 (br s, 1 H), 7.0–7.8 (m, 3 H).

6-(BENZOFURAZAN-5-YL)-1,6-DIHYDRO-2-METHOXY-5-METHOXYCARBONYL-4-METHYL-1-[(4-NITROPHENYLOXY)CARBONYL]PYRIMIDINE: To a solution of 6-(benzofuran-5-yl)-1,6-dihydro-2-methoxy-5-methoxycarbonyl-4-methylpyrimidine (0.485 g, 1.6 mmol) and 4-dimethylaminopyridine (0.200 g, 1.64 mmol) in CH₂Cl₂ (20 mL) at 0–5° C. was added 4-nitrophenyl chloroformate (0.307 g, 1.52 mmol). The mixture was then allowed to warm to room temperature. After 12 h, the solvent was evaporated and the residue was purified by flash chromatography (EtOAc/hexane, 1/9 to 3/20), giving the desired product as white crystals (0.665 g, 89%); mp 180–183° C.; ¹H NMR δ 2.54 (s, 3 H), 3.75 (s, 3 H), 3.98 (s, 3 H), 6.37 (s, 1 H), 7.40 (d, J=9.3 Hz, 2 H), 7.52 (d, J=9.0 Hz, 1 H), 7.68 (s, 1 H), 7.84 (d, J=9.0 Hz, 1 H), 8.32 (d, J=9.3 Hz, 2 H).

(+) and (−)-6-(BENZOFURAZAN-5-YL)-1,6-DIHYDRO-2-METHOXY-5-METHOXYCARBONYL-1-[N-(S)-1-(1-PHENYLETHYL)]-4-METHYLPYRIMIDINE: A solution of 6-(benzofurazan-5-yl)-1,6-dihydro-2-methoxy-5-methoxycarbonyl-4-methyl-1-(4-nitrophenoxy)carbonylpyrimidine (800 mg, 1.71 mmol) and (S)-(−)-a-methylbenzylamine (269 mg, 2.22 mmol) in THF (50 mL) was stirred at room temperature for 12 h. The THF was removed in vacuo and the residue was dissolved in EtOAc (100 mL), washed by 10% aqueous K₂CO₃ solution (3×50 mL), brine (50 mL) and dried (Na₂SO₄). After removal of the solvent, the residue was purified by chromatography (EtOAc/hexane, 1/20 to 3/20), separating the two diastereomers. The isomers of 6-(benzofurazan-5-yl)-1,6-dihydro-2-methoxy-5-methoxycarbonyl-1-[N-(S)-1-(1-phenylethyl)]-4-methylpyrimidine were obtained as colorless oils. 1st Isomer (367 mg, 47.7%): [α]$_D$=+278 (c=0.50, CHCl₃); ¹H NMR δ 1.54 (d, J=6.9 Hz, 3H), 2.45 (s, 3H), 3.68 (s, 3H), 3.99 (s, 3H), 5.02 (quintet, J=6.9 Hz, 1H), 6.71 (s, 1H), 6.89 (d, J=6.6 Hz, 1H), 7.2–7.9 (m, 8H). 2nd Isomer (205 mg, 26.6%):[α]$_D$=−81 (c=0.43, CHCl₃); ¹H NMR δ 1.52 (d, J=6.6 Hz, 3H) 2.48 (s, 3H), 3.71 (s, 3H), 3.96 (s, 3H), 5.00 (quintet, J=6.6 Hz, 1H), 6.74 (s, 1H), 6.90 (d, J=6.5 Hz, 1H), 7.2–7.9 (m, 8H)

6-(BENZOFURAZAN-5-YL)-1,6-DIHYDRO-2-METHOXY-5-METHOXYCARBONYL-4-METHYLPYRIMIDNE: A solution of the 1st isomer of 6-(benzofura-zan-5-yl)-1,6-dihydro-2-methoxy-5-methoxycarbon-yl-1-[N-(S)-1-(1-phenylethyl)]-4-methylpyrimidine (960 mg, 2.14 mmol) and 1,8-diazabicyclo[5,4,0]undec-7-ene (107 mg, 0.705 mmol) in toluene (50 mL) was stirred at 100° C. for 5 h. After cooling to room temperature, toluene was removed in vacuo and the residue was purified by chromatography (EtOAc/hexane, 1/9 to 3/7). 6-(Benzofurazan-5-yl)-1,6-dihydro-2-methoxy-5-methoxycarbonyl-4-methylpyrimidine was obtained as a colorless oil (635 mg, 98.3%). ¹H NMR δ 2.38 (s, 3H), 3.66 (s, 3H), 3.74 (s, 3H), 5.68 (s, 1H), 6.32 (br s, 1H) 7.0–7.8 (m, 3H).

6-(BENZOFURAZAN-5-YL)-1,6-DIHYDRO-2-METHOXY-5-METHOXYCARBONYL-4-METHYL-1-(4-NITROPHENOXY)CARBONYLPYRIMIDINE: To a solution of 6-(benzofuran-5-yl)-1,6-dihydro-2-methoxy-5-methoxycarbonyl-4-methylpyrimidine (0.485 g, 1.60 mmol) and 4-dimethylamino-pyridine (0.200 g, 1.60 mmol) in CH₂Cl₂ (20 mL), at 0–5° C., was added 4-nitrophenyl chloroformate (0.307 g, 1.52 mmol). After addition, the mixture was allowed to warm to room temperature. After 12 hours, the solvent was evaporated and the residue was purified by flash column chromatography (EtOAc/hexane, 1/9 to 3/20), giving the desired product as white crystals (0.665 g, 89%): mp 180–183° C.; ¹H NMR δ 2.54 (s, 3 H), 3.75 (s, 3 H), 3.98 (s, 3 H), 6.37 (s, 1 H), 7.40 (d, J=9.3 Hz, 2 H), 7.52 (d, J=9.0 Hz, 1 H), 7.68 (s, 1 H), 7.84 (d, J=9.0 Hz, 1 H), 8.32 (d, J=9.3 Hz, 2 H); [α]$_D$=+266 (c=2.70, CH₂Cl₂).

METHYL 2-{(3,4-DIFLUOROPHENYL) METHYLENE}-3-OXOBUTYRATE: A mixture of 3,4-difluorobenzaldehyde (14.2 g, 0.100 mol), methyl acetoacetate (12.2 g, 0.105 mol), piperidine (0.430 g, 5 mmol), and acetic acid (0.30 g, 5 mmol) in benzene (150 mL) was stirred and heated at reflux temperature (equipped with a Dean-Stark trap) for 8 h. The benzene was evaporated and the residue was dissolved in ethyl acetate (200 mL). The resulting solution was washed with brine (50 mL), saturated potassium bisulfate solution (50 mL), and saturated sodium bicarbonate solution. The ethyl acetate solution was dried over magnesium sulfate and the solvent was removed under reduced pressure. The residue was purified by column chromatography (EtOAc/hexane, 1/9 to 3/20), giving the desired product as a yellow oil (9.80 g, 41%) which was used in the subsequent step without any further characterization.

6-(3,4-DIFLUOROPHENYL)-1,6-DIHYDRO-2-METHOXY-5-METHOXYCARBONYL-4-METHYLPYRIMIDINE: A mixture of methyl 2-{(3,4-difluorophenyl)-methylene}-3-oxobutyrate (8.80 g, 36.3 mmol), O-methylisourea hydrogen sulfate (9.40 g, 546 mmol), and NaHCO3 (12.3 g, 146 mol) in DMF (30 mL) was heated at 70° C. with stirring for 16 h. The mixture was cooled, diluted with EtOAc (300 mL) and washed with water (5×300 mL), brine (300 mL), and dried over magnesium sulfate. The solvent was evaporated and the crude product was purified by flash chromatography (EtOAc/hexane, 1/9 to 3/7) as the gradient eluent, giving the desired product as an oil (3.82 g, 35%).

6-(3,4-DIFLUOROPHENYL)-1,6-DIHYDRO-2-METHOXY-5-METHOXYCARBONYL-4-METHYL-1-[(4-NITROPHENYLOXY)CARBONYL]PYRIMIDINE: 4-Nitrophenyl chloroformate (1.82 g, 9.04 mmol) was added to a solution of 6-(3,4-difluorophenyl)-1,6-dihydro-2-methoxy-5-methoxycarbonyl-4-methylpyrimidine (2.82 g, 9.46 mmol) and 4-dimethylaminopyridine (1.16 g, 9.52 mmol) in CH₂Cl₂ (50 mL), at 0–5° C. and the mixture was then allowed to warm to room temperature. After 12 h, the solvent was evaporated and the residue was purified by flash chromatography (EtOAc/hexane, 1/9 to 3/20), giving the desired product as white crystals (3.72, 85%): mp 172–174° C.

6-(3,4-DIFLUOROPHENYL)-1,2,3,6-TETRAHYDRO-2-OXO-5-METHOXYCARBON-YL-4-METHYL-1-(4-NITROPHENOXY)CARBONYLPYRIMIDINE:

Aqueous 6 N hydrochloric acid (10 mL) was added to a stirring solution of 6-(3,4-difluorophenyl)-1,6-dihydro-2-methoxy-5-methoxycarbonyl-4-methyl-1-(4-nitrophenoxy) carbonylpyrimidine (10.0 g) in THF (200 mL) at room temperature. The stirring was continued for 3 h. The solvent was evaporated and the residue was dried under vacuum, giving the desired product as a white powder (9.70 g, 100%): mp 185–186° C.

(+)-1-(3-BROMO-PROPYLCARBAMOYL)-6-(3,4-DIFLUOROPHENYL)-4-METHYL-2-OXO-1,6-DIHYDRO-PYRIMIDINE-5-CARBOXYLIC ACID METHYL ESTER: A solution of 10% aqueous HCl (5 mL) was added to a stirring solution of (+)-6-(3,4-difluorophenyl)-1,6-dihydro-2-methoxy-5-methoxycarbonyl-4-methyl-1-[(4-nitrophenyloxy)carbonyl]pyrim-idine (4.10 g, 9.10 mmol) in THF (20 mL) at room temperature and the resulting solution was stirred overnight. The THF was removed in vacuo and the resulting residue was extracted with EtOAc (3×20 mL), washed with brine (10 mL) and then dried over $Na_2SO_4$. The solvent was removed in vacuo, giving (+)-6-(3,4-di-fluorophenyl)-1,6-dihydro-2-oxo-5-methoxycarbonyl-4-methyl-1-[(4-nitrophenyloxy)carbonyl]pyrimidine as a viscous oil (3.8 g, 8.5 mmol). The oil was dissolved in THF (20 mL) and 3-bromo-propylamine hydrobromide (2.33 g, 10.8 mmol) and $NaHCO_3$ (1.81 g, 21.5 mmol) were added. The resulting suspension was stirred at room temperature overnight. The THF was removed in vacuo and the resulting residue was dissolved in water (10 mL) and then extracted with EtOAc (3×20 mL). The EtOAc extracts were combined, dried over $Na_2SO_4$, filtered and the solvent was removed, giving (+)-1-(3-bromopropylcarbamoyl)-6-(3,4-difluorophenyl)-4-methyl-2-oxo-1,6-dihydropyrimidine-5-carboxylic acid methyl ester (3.28 g, 83%): $^1H$ NMR δ 2.05–2.15 (m, 2 H), 2.43 (s, 3 H), 3.40–3.56 (m, 4 H), 3.72 (s, 3 H), 6.69 (s, 1 H), 7.08–7.27 (m, 3 H), 7.57 (br s, 1 H), 8.84 (br t, 1 H). Anal. Calcd for $C_{17}H_{18}N_3O_4 F_2Br$: C, 45.76; H, 4.07; N, 9.42. Found: C, 45.70; H, 3.99; N, 9.16.

3-{(3,4,5-TRIFLUOROPHENYL)METHYLENE}-2,4-PENTANEDIONE: A stirring mixture of 3,4,5-trifluorobenzaldehyde (4.20 g, 26.2 mmol), 2,4-pentanedione (2.62 g, 26.2 mmol), piperidine (0.430 g, 5.00 mol) in benzene (150 mL) was heated at reflux temperature (equipped with a Dean-Stark trap) for 8 h. The benzene was evaporated and the yellow oily residue, 2-{(3,4,5-trifluorophenyl)methylene}-2,4-pentanedione, was used in the next step without further purification.

6-(3,4,5-TRIFLUOROPHENYL)-1,6-DIHYDRO-2-METHOXY-5-ACETYL-4-METHYLPYRIMIDINE: A mixture of 2-{(3,4,5-trifluorophenyl)methylene}-2,4-pentanedione (26.2 mmol), O-methylisourea hydrogen sulfate (3.22 g, 39.3 mmol), and $NaHCO_3$ (6.6 g, 78.6 mmol) in EtOH (400 mL) was stirred and heated at 95–100° C. for 6 h. The mixture was filtered and the solid residue was washed with ethanol (100 mL). The solvent was evaporated from the combined filtrates and the crude product was purified by flash column chromatography (EtOAc/hexane, 1/9 to 1/4), giving the desired product as an oil (2.80 g, 36%).

6-(3,4,5-TRIFLUOROPHENYL)-1,6-DIHYDRO-2-METHOXY-5-ACETYL-4-METH-YL-1-[(4-NITROPHENYLOXY)CARBONYL]PYRIMIDINE: 4-Nitrophenyl chloroformate (1.89 g, 9.38 mmol) was added to a solution of 6-(3,4,5-trifluorophenyl)-1,6-dihydro-2-methoxy-5-acetyl-4-meth-ylpyrimidine (2.80 g, 9.38 mmol) and pyridine (10 mL) in $CH_2Cl_2$ (200 mL) at 0–5° C., and the resulting mixture was allowed to warm to room temperature. After 12 h, the solvent was evaporated and the residue was purified by flash chromatography (dichloromethane/EtOAc, 1/9 to 3/20), giving the desired product as a white powder (4.00 g, 92%).

6-(3,4,5-TRIFLUOROPHENYL)-1,2,3,6-TETRAHYDRO-2-OXO-5-ACETYL-4-METHYL-1-[(4-NITROPHENYLOXY)CARBONYL]PYRIMIDINE: A solution of 6 N aqueous HCl (4 mL) was added to a stirring solution of 6-(3,4,5-trifluorophenyl)-1,6-dihydro-2-methoxy-5-acetyl-4-methyl-1-[(4-nitrophenyloxy)carbonyl]pyrimidine (4.00 g, 8.63 mmol) in THF (100 mL) at 0–5° C., and the mixture was allowed to warm to room temperature. After 2 h, solvent was evaporated and the product dried under vacuum. The product was obtained as a pure single component and used in the next step without any further purification (3.88 g, 100%).

Procedures for the Synthesis of the Piperidine Intermediates (reference for the general procedure for Pd coupling of vinyl triflate and boronic acids or tributyl tin reagents: See, Wuston, Wise *Synthesis* (1991), 993)

TERT-BUTYL 4-{[(TRIFLUOROMETHYL)SULFONYL]OXY}-1,2,3,6-TETRA-HYDRO-1-PYRIDINECARBOXYLATE: n-Butyllithium (17.6 mL, 44.2 mmol, 2.5 M in hexanes) was added to a solution of diisopropyl amine (96.2 mL, 44.2 mmol) in 40 mL of dry THF at 0° C. and stirred for 20 minutes. The reaction mixture was cooled to −78° C. and tert-butyl 4-oxo-1-piperidinecarboxylate (40.0 mmol) in THF (40 mL) was added dropwise to the reaction mixture and stirred for 30 minutes. $Tf_2NPh$ (15.0 g, 42.0 mmol) in THF (40 mL) was added dropwise to the reaction mixture and the mixture was stirred at 0° C. overnight. The reaction mixture was concentrated in vacuo, re-dissolved in hexanes/EtOAc (9/1), passed through a plug of alumina and washed with hexanes/EtOAc (9/1). The combined extracts were concentrated to yield 16.5 g of the desired product that was contaminated with a small amount of $Tf_2$ Nph. $^1H$ NMR δ 5.77 (s, 1 H), 4.05 (dm, 2 H, J=3.0 Hz), 3.63 (t, 2 H, J=5.7 Hz), 2.45 (m, 2 H), 1.47 (s, 9 H).

TERT-BUTYL 4-[3-(ACETYLAMINO)PHENYL]-1,2,3,6-TETRAHYDRO-1-PYRIDINECARBOXYLATE: A mixture of saturated of aqueous $Na_2CO_3$ solution (25 mL), tert-butyl 4-{[(trifluoromethyl)sulfonyl]oxy}-1,2,3,6-tetrahydro-1-pyridine-carboxylate (20 mmol), 3-acetamidophenylboronic acid (30 mmol) and tetrakis-triphenylphosphine palladium (0) (1.15 g) and dimethoxyethane (40 mL) was heated at reflux temperature overnight. The organic layer of the cooled reaction mixture was separated and the aqueous layer was washed with ethyl acetate (3×). The combined organic extracts were dried and concentrated in vacuo. The crude product was chromatograghed, giving the desired product $^1H$ NMR δ 8.11 (br s, 1 H), 7.57 (br s, 1 H), 7.41 (br d, 1 H, J=7.8 Hz), 7.25 (apparent t, 1 H, J=7.8 Hz), 7.08 (br d, 1 H, J=7.8 Hz), 5.99 (b s, 1 H), 4.03 (br m, 2 H, J=2.7 Hz), 3.59 (t, 2 H, J=5.7 Hz), 2.46 (m, 2 H,), 2.16 (s, 3 H), 1.49 (s, 9 H).

N1-[3-(1,2,3,6-TETRAHYDRO-4-PYRIDINYL)PHENYL]ACETAMIDE: A solution of 4 M HCl in dioxane (10 mL) was added to tert-butyl 4-[3-(acetylamino)phenyl]-1,2,3,6-tetrahydro-1-pyridinecarboxyl-ate (8.25 mmol) in dichloromethane (30 mL). The reaction mixture was stirred at room temperature overnight, concentrated in vacuo, giving the desired product as the hydrochloride salt (2.1 g). $^1H$ NMR δ 7.41–7.00 (m, 4 H), 6.10 (br, 1 H), 3.55 (m, 2 H), 3.16 (t, 2 H, J=5.7 Hz), 2.44 (m, 2 H), 2.19 (s, 3 H).

TERT-BUTYL N-(3-BROMOPROPYL)CARBAMATE: Prepared from 3-bromopropylamine hydrobromide and $BOC_2O$ in the presence of base in dichloromethane: $^1H$ NMR δ 5.07 (br, 1 H), 3.31 (t, 2 H, J=6.6 Hz), 3.12 (apparent br q, 2 H, J=6.0 Hz), 1.92 (p, 2 H, J=6.6 Hz), 1.30 (s, 9H).

REACTION OF N1-[3-(1,2,3,6-TETRAHYDRO-4-PYRIDINYL)PHENYL]ACETAMIDE WITH TERT-BUTYL N-(3-BROMOPROPYL)CARBAMATE

TERT-BUTYL N-(3-{4-[3-(ACETYLAMINO)PHENYL]-1,2,3,6-TETRAHYDRO-1-PYRIDINYL}PROPYL)CARBAMATE: A solution of N1-[3-(1,2,3,6-tetrahydro-4-pyridinyl) phenyl]acetamide hydrochloride (8.24 mmol), tert-butyl N-(3-bromopropyl) carbamate and potassium carbonate (33 mmol) in dry dioxane (30 mL) was heated at reflux temperature overnight. The solids were removed by filtration, the solution was concentrated in vacuo and the product was chromatographed, giving the desired product (110 mg). $^1$H NMR δ 7.65 (s, 1 H), 6.98 (s, 1 H), 7.45 (d, 1 H, J=7.8 Hz), 7.16 (apparent t, 1 H, J=7.8 Hz), 7.10 (d, 1 H, J=7.8 Hz), 6.02 (s, 1 H), 5.23 (b, 1 H), 3.40 (b, 2 H), 3.30–1.80 (m, 10 H), 2.18 (s, 3 H), 1.45 (s, 9 H)

Deprotection of BOC:

N1-{3-[1-(3-AMINOPROPYL)-1,2,3,6-TETRAHYDRO-4-PYRIDINYL]PHENYL}ACETAMIDE: A 1:1 solution of TFA:CH$_2$Cl$_2$ (5 mL) was added to tert-butyl N-(3-{4-[3-(acetylamino)phenyl]-1,2,3,6-tetrahydro-1-pyridinyl}propel)carbamate in dichloromethane (5 mL). The resulting solution was stirred at room temperature for 1–3 days, saturated NaHCO3 was added until pH>6, the organic layer was separated, and dried in vacuo, giving the desired product (45 mg): $^1$H NMR δ 7.68 (br, 1 H), 7.35 (dm, 1 H, J=7.8 Hz), 7.25 (apparent t, 1 H, J=7.8 Hz), 7.15 (dm, 1 H, J=7.8 Hz), 6.12 (m, 1 H), 3.22 (m, 2 H), 3.03 (t, 2 H, J=7.3 Hz), 2.78 (t, 2 H, J=5.5 Hz), 2.70–2.50 (m, 4 H), 2.10 (s, 3 H), 1.87 (p, 2 H, J=7.3 Hz).

TERT-BUTYL 4-[3-(ACETYLAMINO)PHENYL]-1-PIPERIDINECARBOXYLATE: A mixture tert-butyl 4-[3-(acetylamino)phenyl]-1,2,3,6-tetra-hydro-1-pyridinecarboxylate (710 mg) and 5% Pd/C (100 mg) in EtOH (10 mL) was hydrogenated (balloon technique) at room temperature overnight. The reaction mixture was passed through a pad of Celite 545 and the pad of Celite was washed with ethanol. The combined ethanol extracts were concentrated and chromataghed, giving the desired product (660 mg). $^1$H NMR δ 7.80 (s, 1 H), 7.41–7.20 (m, 3 H), 6.94 (d, 1 H, J=7.5 Hz), 4.21 (m, 2 H), 2.75 (m, 2 H), 2.62 (m, 1 H), 2.16 (s, 3 H), 1.78 (m, 2 H), 1.56 (m, 2 H), 1.48 (s, 9 H).

N1-[3-(4-PIPERIDYL)PHENYL]ACETAMIDE: A solution of HCl in dioxane (4N, 5 mL) was added to tert-butyl 4-[3-(acetylamino)-phenyl]-1-piperidinecarboxylate (660 mg) in dry dichloromethane (15 mL). The reaction mixture was stirred at room temperature overnight and concentrated in vacuo, giving the desired product (550 mg): mp 102–104° C.; $^1$H NMR δ 2.02 (d, J=13.2 Hz, 2H), 2.11–2.45 (m, 5H), 2.67–2.77 (m, 1H), 3.00–3.10 (m, 2H), 3.51 (d, J=10.5 Hz, 2H), 6.94 (d, J=7.5 Hz, 1H), 7.20–7.46 (m, 3H), 7.60 (s, 1H)

TERT-BUTYL N-(3-{4-[3-(ACETYLAMINO)PHENYL]PIPERIDINO}PROPYL)-CARBAMATE: A solution of N1-[3-(4-piperidyl)phenyl]acetamide (550 mg, 0.210 mmol), tert-butyl N-(3-bromopropyl)-carbamate (550 mg, 0.230 mmol), K$_2$CO$_3$ (1.10 g, 0.890 mmol), diisopropylethyl amine (1.50 mL) and a few crystals of KI in dioxane (20 mL) was heated at reflux temperature for 2 days. The precipitated salts were removed by filtration, concentrated in vacuo and the crude product was chromatographed, giving the desired product (340 mg). $^1$H NMR δ 8.15 (s, 1 H), 7.47–7.44 (m, 2 H), 7.22 (t, 1 H, J=7.8 Hz), 6.94 (d, 1 H, J=7.8 Hz), 5.53 (b, 1 H), 3.23 (b, 6 H), 2.80–1.60 (m, 9 H), 2.20 (s, 3 H), 1.45 (s, 9 H).

N1-{3-[1-(3-AMINOPROPYL)-4-PIPERIDYL]PHENYL}ACETAMIDE: TFA (1.0 mL) was added to a solution of tert-butyl N-(3-{4-[3-(acetyl-amino)phenyl]piperidino}propyl)carbamate (340 mg) in dry dichloromethane (10 mL) and stirred at room temperature for 5 h. A 10% aqueous solution of KOH was added to the reaction mixture until pH >6 and then the dichloromethane was removed in vacuo. The aqueous layer was frozen and lyophilized, giving a solid which was then extracted with methanol. Removal of methanol gave the desired product (120 mg) as an oil. $^1$H NMR δ 8.56–8.46 (s, 1H), 7.43–7.30 (m, 2H), 7.23–7.16 (apparent t, 1H, J=7.5 Hz), 6.95–6.92 (m, 1H), 3.03–2.99 (m, 2H), 2.77–2.73 (t, 2H, J=6.6 Hz), 2.50–1.60 (m, 10 H), 2.13 (s, 3 H).

1-BENZYL-4-HYDROXY-4-(4-FLUORO-2-METHYLPHENYL)PIPERIDINE: $^1$H NMR δ 7.40–7.26 (M, 5 H), 6.91–6.76 (m, 3 H), 3.57 (s, 2 H), 2.83–2.72 (m, 2 H), 2.61 (s, 3 H), 2.58–2.43 (m, 2 H), 2.23–2.12 (m, 2 H).

1-BENZYL-4-(4-FLUORO-2-METHYLPHENYL)-1,2,3,6-TETRAHYDROPYRIDINE: $^1$H NMR δ 7.41–7.26 (m, 5 H), 7.05 (dd, 1 H, J=6.0, 8.1 Hz), 6.87–6.80 (m, 2 H), 5.52–5.50 (m, 2 H), 3.65 (s, 2 H), 3.13 (q, 2 H, J=3.3 Hz), 2.69–2.66 (t, 2 H, J=5.1 Hz), 2.35–2.31 (m, 2 H), 2.27 (s, 3 H).

4-(4-FLUORO-2-METHYLPHENYL)PIPERIDINE: $^1$H NMR δ 7.17 (t, 1 H, J=7.2 Hz), 6.83–6.80 (m, 2 H), 3.22 (m, 2 H), 2.81–2.73 (m, 2 H), 2.66 (br s, 1 H), 2.33 (s, 3 H), 1.80–1.60 (m, 4 H).

1-BENZYL-4-(3,4,5-TRIFLUOROPHENYL)-1,2,3,6-TETRAHYDROPYRIDINE: $^1$H NMR δ 7.50–7.20 (m, 7 H), 5.67 (m, 1 H), 3.69 (s, 2 H), 3.19 (apparent q, 2 H, J=2.7 Hz), 2.75 (t, 2 H, J=5.7 Hz), 2.34 (m, 2 H).

4-(3,4,5-TRIFLUOROPHENYL)PIPERIDINE: mp 197–199° C.; $^1$H NMR δ 2.05 (d, J=13.2 Hz, 2H),), 2.33 (dd, J=25.5 Hz, J=12.9 Hz, 2H), 3.06–3.23 (m, 3H), 3.73 (d, J=12.0 Hz, 2H) 6.94–7.04 (m, 2H).

4-(3,4,5-TRIFLUOROPHENYL)PIPERIDINE: $^1$H NMR δ 7.20–6.80 (m, 2 H), 3.73 (m, 2 H), 3.14 (m, 3 H), 2.33 (m, 2 H), 2.05 (m, 2 H)

TERT-BUTYL N-3-[4-(3,4,5-TRIFLUOROPHENYL)PIPERIDINO]PROPYL-CARBAMATE: $^1$H NMR δ 6.91 (m, 2 H), 5.62 (b, 1 H), 4.31 (t, 2 H, J=5.4 Hz), 3.63 (m, 2 H), 3.39 (dt, J=2.1, 6.0 Hz), 3.40–2.70 (m, 7 H), 2.46 (t, 2 H, J=6.9 Hz), 2.10–1.60 (m, 4 H), 1.45 (s, 9 H).

3-[4-(3,4,5-TRIFLUOROPHENYL)PIPERIDINO]-1-PROPANAMINE: $^1$H NMR δ 6.93 (m, 2 H), 4.30 (b, 1 H), 3.36 (b, 1 H), 3.06 (m, 2 H), 2.77 (m, 2 H), 2.43 (m, 2 H), 2.20–1.40 (m, 9 H).

1-BENZYL-4-(5-FLUORO-2-METHOXYPHENYL)-4-PIPERIDINOL: $^1$H NMR δ 7.40–6.80 (m, 8 H), 3.94 and 3.85 (s, 3 H), 3.61 and 3.58 (s, 2 H), 2.80–1.90 (m, 8 H).

1-BENZYL-4-(5-FLUORO-2-METHOXYPHENYL)-1,2,3,6-TETRAHYDROPYRIDINE: $^1$H NMR δ 7.40–6.70 (m, 8 H), 5.84 (m, 1 H), 3.77 (s, 3 H), 3.64 (s, 2 H), 3.17 (m, 2 H), 2.68 (t, 2 H, J=5.7 Hz), 2.54 (m, 2 H).

4-(5-FLUORO-2-METHOXY)PHENYL PIPERIDINE: mp 254–258° C.; $^1$H NMR δ 1.53–1.68 (m, 2H), 1.79 (d, J=11.7 Hz, 2H), 2.12 (dt, J=2.1 Hz, J=11.7 Hz, 1H), 2.77 (dt, J=1.8 Hz, J=12.3 Hz, 1H), 2.90–3.05 (m, 1H), 3.10–3.22 (m, 2H), 3.68 (s, 1H), 3.79 (s, 3H), 6.72–6.93 (m, 3H). Anal. Calcd. For C$_{12}$H$_{17}$NOFCl+0.14 CH$_2$Cl$_2$: C, 56.60; H, 6.76; N, 5.44. Found: C, 56.60; H, 6.92; N, 5.28.

TERT-BUTYL N-3-[4-(5-FLUORO-2-METHOXYPHENYL)PIPERIDINO]PROPYL-CARBAMATE: $^1$H NMR δ 6.90–6.70 (m, 3 H), 5.76 (b, 1 H), 3.80 (s, 3 H), 3.68 (m, 1 H), 3.40–2.90 (m, 4 H), 2.45 (t, 2 H, J=6.6 Hz), 2.20–1.60 (m, 9 H), 1.45 (s, 9 H)

3-[4-(5-FLUORO-2-METHOXYPHENYL)PIPERIDINO]-1-PROPANAMINE: $^1$H NMR δ 7.00–6.80

(m, 3 H), 3.80 (s, 3 H), 3.05 (d, 2 H, J=11.4 Hz), 2.76 (t, 2 H, J=6.9 Hz), 2.43 (dd, 2 H, J=7.8 Hz), 2.05 (dt, 2 H, J=2.4, 11.7 Hz), 1.90–1.20 (m, 10 H).

TERT-BUTYL 4-(1-NAPHTHYL)-1,2,3,6-TETRAHYDRO-1-PYRIDINECARBOXYL-ATE: $^1$H NMR δ 8.00–7.80 (m, 2 H), 7.76 (d, 1 H, J=8.1 Hz), 7.50–7.44 (m, 2 H), 7.42 (d, 1 H, J=8.1 Hz), 7.27 (d, 1 H, J=8.1 Hz), 5.76 (br, 1 H), 4.14 (m, 2 H), 4 or 3.29 (t, 2 H, J=5.7 Hz), 2.52 (br m, 2 H), 1.53 (s, 9H).

4-(1-NAPHTHYL)PIPERIDINE: HCl salt; mp 330–332° C.; $^1$H NMR δ 1.66–1.70 (m, 2H), 2.20–2.26 (m, 2H), 2.30–2.43 (m, 2H), 2.72–2.84 (m, 1H), 3.15–3.26 (m, 2H), 7.42–7.56 (m, 4H), 7.78 (d, J=8.1 Hz, 1H), 7.90 (d, J=8.1 Hz, 1H), 8.04 (d, J=8.1 Hz, 1H). Anal. Calcd. For $C_{15}H_{18}NOCl+0.20\ CH_2Cl_2$: C, 68.96; H, 7.00; N, 5.29. Found: C, 68.64; H, 7.04; N, 5.24.

TERT-BUTYL N-3-[4-(1-NAPHTHYL)PIPERIDINO] PROPYLCARBAMATE: $^1$H NMR δ 8.09 (d, 1 H, J=8.4 Hz), 7.86 (dd, 1 H, J=1.8, 7.5 Hz), 7.71 (dd, 1 H, J=2.4, 6.9 Hz), 7.60–7.30 (m, 4 H), 6.31 (br, 1 H), 5.75 (br, 1 H), 4.26 (t, 1 H, J=5.4 Hz), 3.40–3.00 (m, 6 H), 2.54 (t, 2 H, J=6.9 Hz), 2.24 (dt, 2 H, J=3.0, 11.4 Hz), 2.00–1.60 (m, 6 H), 1.45 (s, 9 H).

4-(3-METHYL-2-PYRIDYL)-4-PIPERIDINOL: $^1$H NMR δ 8.21 (dd, 1 H, J=1.2, 4.5 Hz), 7.36 (dd, 1 H, J=6.6, 7.8 Hz), 7.02 (dd, 1 H, J=4.8, 7.5 Hz), 3.07 (dt, 2 H, J=2.7, 12.3 Hz), 2.89 (m, 2 H), 2.46 (s, 3 H), 2.22 (dt, 2 H, J=4.8, 12.3 Hz), 1.39 (dm, 2 H, J=12.3 Hz).

TERT-BUTYL 4-(3-METHYL-2-PYRIDYL)-1,2,3,6-TETRAHYDRO-1-PYRIDINE-CARBOXYLATE: $^1$H NMR δ 8.16 (dd, 1 H, J=1.2, 3.3 Hz), 7.51 (dm, 1 H, J=7.5 Hz), 7.15 (dd, 1 H, J=4.8, 7.5 Hz), 5.73 (br, 1 H), 4.01 (m, 2 H), 3.59 (t, 2 H, J=5.7 Hz), 2.40 (m, 2 H), 1.44 (s, 9 H).

TERT-BUTYL N-3-[4-(3-METHYL-2-PYRIDYL) PIPERIDINO]PROPYLCARBAMATE: $^1$H NMR δ 8.37 (dd, 1 H, J=4.2, 4.8 Hz), 7.51 (dd, 1 H, J=7.2, 7.5 Hz), 7.20 (dd, 1 H, J=4.5, 7.5 Hz), 6.73 (br, 1 H), 3.26 (m, 4 H), 3.05 (d, 2 H, J=12.0 Hz), 2.80–2.40 (m, 4 H), 2.61 (s, 3 H), 1.82 (p, 2 H, J=6.3 Hz), 1.54 (d, 2 H, J=12.0 Hz).

TERT-BUTYL 4-(3-METHOXYPHENYL)-1,2,3,6-TETRAHYDRO-1-PYRIDINECARBOXYLATE: $^1$H NMR δ 7.23 (t, 1 H, J=8.1 Hz), 6.96 (d, 1 H, J=7.5 Hz), 6.89 (d, 1 H, J=1.8 Hz), 6.80 (dd, 1 H, J=2.4, 8.1 Hz), 6.02 (br, 1 H), 4.20–4.00 (m, 3 H), 3.80 (s, 3 H), 3.62 (t, 2 H, J=5.7 Hz), 2.51 (br, 2 H), 1.49 (s, 9 H).

1-BENZYL-4-METHYL-PIPERIDIN-4-OL: Methyllithium (1.4 M in Et$_2$O, 54.0 mL) was added to a solution of 1-benzyl-4-piperidone (5.00 mL, 27.0 mmol) in anhydrous ether at −78° C. under argon. Stirring was continued at −78° C. for 1.5 hours. Ether (200 mL) and water (40 mL) were added, and the two phases were separated. The aqueous solution was extracted with Et$_2$O (3×50 mL). The combined organic solutions were dried over magnesium sulfate and concentrated. The residue was chromatographed (EtOAc to EtOAc-MeOH 9/1), giving 4.81 g (87%) of the desired product as a colorless oil: $^1$H NMR δ 1.21 (s, 3 H), 1.56 (dt, J=13, 3 Hz, 2 H), 1.65 (td, J=10, 4 Hz, 2 H), 2.35 (td, J=10, 3 Hz, 2 H), 2.53 (m, 2 H), 7.24 (m, 1 H), 7.29 (m, 4 H); $^{13}$C NMR δ 30.44, 39.37, 50.39, 63.80, 68.50, 127.56, 128.80, 129.80, 139.17.

1-BENZYL-4-METHYL-4-PHENYLPIPERIDINE: 1-Benzyl-4-methylpiperidin-4-ol (4.81 g, 23.4 mmol) was added to a suspension of AlCl$_3$ (15.62 g, 117 mmol) in benzene (100 mL) at room temperature under argon. The mixture was stirred at reflux for 24 hours, then cooled and poured cautiously into ice water (100 g of ice, 50 mL of water). The aqueous phase was adjusted to pH 11–12 by addition of 6 N aqueous NaOH at 0° C., and extracted with EtOAc (3×100 mL). The combined organic solutions were dried over magnesium sulfate and concentrated. The residue was chromatographed (hexane-Et$_2$O 19/1 to 9/1, followed by hexane-EtOAc 3/1), giving the desired product (3.23 g, 52%) as a brown oil: $^1$H NMR δ 1.25 (s, 3 H), 1.80 (m, 2 H), 2.17 (m, 2 H), 2.44 (m, 2 H), 2.55 (m, 2 H), 3.50 (s, 2 H), 7.25 (m, 1 H), 7.35 (m, 4 H); $^{13}$C NMR δ 36.82, 37.65, 50.95, 54.93, 64.08, 126.19, 126.51, 127.59, 128.83, 128.95, 129.05, 129.89, 139.24.

4-METHYL-4-PHENYLPIPERIDINE: Freshly prepared methanolic formic acid solution (4.4% by weight, 70 mL) was added to 1-benzyl-4-methyl-4-phenylpiperidine (3.23 g, 12.2 mmol). To the resulting solution was added 10% palladium on carbon (2.00 g). The mixture was stirred at room temperature for 24 hours. The solid was filtered out and washed with MeOH (30 mL), H$_2$O (15 mL), CH$_2$Cl$_2$ (30 mL) and MeOH (15 mL). The combined filtrate and washings were concentrated, and the residue was dissolved in CH$_2$Cl$_2$ (50 mL) and H$_2$O (10 mL). The aqueous phase was adjusted to pH 11 by addition of 1 N aqueous NaOH. The organic phase was separated, dried over magnesium sulfate and concentrated. The residual oil was purified by flash chromatography (CHCl$_3$/MeOH/2 N NH$_3$ in MeOH 100/4/0 to 100/20/10), giving 1-benzyl-4-methyl-4-phenylpiperidine (1.20 g) and 1.10 g (51%, 82% based on consumed starting material) of 4-methyl-4-phenylpiperidine: $^1$H NMRδ 1.24 (s, 3 H), 1.71 (m, 2 H), 2.06 (m, 2 H), 2.82 (m, 3 H), 2.94 (m, 2 H), 7.19 (m, 1 H), 7.32 (m, 4 H); $^{13}$C NMR δ 37.22, 38.54, 43.44, 47.74, 126.31, 127.43, 129.01, 149.73.

3-AMINOPROPYL-4-METHYL-4-PHENYLPIPERIDINE: A solution of 4-methyl-4-phenylpiperidine (1.00 g, 5.70 mmol), 3-bromopropylamine hydrobromide (1.87 g, 8.55 mmol) and potassium carbonate (1.97 g, 14.2 mmol) in refluxing dioxane (20 mL) was stirred for 36 hours. After removal of the solvent, water (50 mL) was added and the pH adjusted to 11–12 by the addition of 1 N aqueous NaOH. The mixture was extracted with CH$_2$Cl$_2$ (150 mL+3×100 mL) The combined organic solutions were dried over magnesium sulfate and concentrated. The residue was purified by flash chromatography (CHCl$_3$/MeOH/2 N NH$_3$ in MeOH 100/20/10), giving the desired product as a colorless oil (241 mg, 18%): $^1$H NMR δ 1.18 (s, 3 H), 1.61 (p, J=7 Hz, 2 H), 1.75 (m, 2 H), 2.10 (m, 2 H), 2.33 (t, J=7 Hz, 2 H), 2.40 (m, 2 H), 2.45 (m, 2 H), 2.72 (t, J=6 Hz, 2 H), 3.02 (br s, 2 H), 7.14 (m, 1 H), 7.30 (m, 4 H); $^{13}$C NMR δ 30.28, 36.78, 37.64, 41.51, 50.96, 57.51, 126.16, 126.40, 128.91, 149.20.

Preparation of 3-[4-(4-Fluorophenyl)piperidin-1-yl] propylamine 4-(4-FLUOROPHENYL)PIPERIDINE HYDROCHLORIDE: To a solution of 4-(4-fluorophenyl)-1,2,3,6-tetrahydropyridine hydrochloride (10 g) in methanol (200 mL) was added 10% palladium on charcoal (0.5 g) and the mixture was hydrogenated at 50 psi for 3 h. The catalyst was removed by filtration and solvent was evaporated, leaving the product (10.0 g) as a white powder, which was used in the next step without purification. The product appeared to be pure based on $^1$H NMR and TLC analysis. $^1$H NMR δ 1.95–2.03 (br d, 2H), 2.14–2.29 (m, 2H), 2.70–2.80 (m, 1H), 2.91–3.07 (br q, 2H), 3.60–3.64 (br d, 2H), 6.96–7.03 (m, 2H), 7.19–7.22 (m, 2H), 9.60 (br s, 1H), 9.71 (br s, 1H).

4-(4-FLUOROPHENYL)PIPERIDINE: mp ° C.; $^1$H NMR δ 1.51–1.66 (m, 2H), 1.80 (d, J=7.2 Hz, 2H), 2.53–2.64 (m, 1H), 2.67–2.77 (m, 2H), 3.17 (d, J=12.0 Hz, 2H), 6.94–7.03 (m, 2H), 7.13–7.21 (m, 2H).

Anal. Calcd. For $C_{11}H_{14}NF+C_4H_4O_4$: C, 58.70; H, 5.83; N, 4.18. Found: C, 58.72; H, 5.84; N, 3.98.

3-[4-(4-FLUOROPHENYL)PIPERIDIN-1-YL] PROPYLPHTHALIMIDE: A mixture of 4-(4-fluorophenyl) piperidine hydrochloride (5.08 g, 23.2 mmol), 3-bromopropylphthalimide (6.22 g, 23.2 mmol), and potassium carbonate (15 g) in DMF (100 mL) was stirred at 95–100° C. for 12 h. About 80% of the solvent was evaporated under reduced pressure. The residue was diluted with ethyl acetate (200 mL) and washed with brine (3×100 mL) and dried ($Na_2SO_4$). The solvent was evaporated from the ethyl acetate solution and the residue was purified by column chromatography (1/1 hexane-ethyl acetate to 100% ethyl acetate), giving crude product (7.50 g, 88%). This crude product was crystallized from isopropanol, giving a white crystalline solid (4.50 g, 1st crop). This material was used in the next step. Concentration of the mother liquor and cooling gave the second crop of desired product (1.0 g). $^1$H NMR δ 1.43–1.52 (m, 2H), 1.67–1.75 (m, 2H), 1.80–1.96 (m, 4H), 2.33–2.46 (m, 3H), 2.94–2.99 (br d, 2H), 3.78 (t, J=7 Hz, 2H), 6.90–7.04 (m, 4H), 7.70–7.74 (m, 2H), 7.84–7.87 (m, 2H).

3-[4-(4-FLUOROPHENYL)PIPERIDIN-1-YL] PROPYLAMINE: Hydrazine (4 mL) was added to a solution of 3-[4-(4-fluorophenyl)piperidin-1-yl] propylphthalimide (4.50 g, 12.3 mmol) in methanol (200 mL), and the mixture was stirred at reflux for 8 h. The solution was cooled to room temperature, and the resulting white solid which formed was filtered and washed with methanol (20 mL). The solvent was evaporated from the filtrate and residue was dried under vacuum for 4 h. The crude product was dissolved in 50 mL of chloroform, stirred for 1 h, and filtered. The white solid was washed with additional chloroform (20 mL), the solvent was evaporated from the combined filtrates to leave the crude product as an oil. The oil was purified by column chromatography (dichloromethane/methanol/2 M ammonia in methanol, 10/3/1), giving the desired product (2.70 g, 93%). $^1$H NMR δ 1.60–1.83 (m, 6H), 1.96–2.07 (m, 4H), 2.40–2.55 (m, 3H), 2.70–2.85 (br t, 2H), 3.03–3.07 (br d, 2H), 6.93–7.00 (m, 2H), 7.14–7.20 (m, 2H).

4-(4-METHYL-4-(3,5-DIMETHYLPHENYL) PIPERIDINE: hygroscopic; $^1$H NMR δ 1.20 (s, 3H) 1.74–1.80 (m, 2H), 2.08–2.16 (m, 2H), 2.30 (s, 6H), 2.50–2.56 (m, 2H), 2.64–2.68 (m, 2H), 2.97–3.04 (m, 1H), 6.87 (s, 1H), 6.94 (s, 2H).

Piperidine Side Chain Intermediates

TERT-BUTYL 4-{[(TRIFLUOROMETHYL) SULFONYL]OXY}-1,2,3,6-TETRAHYDRO-1-PYRIDINECARBOXYLATE:

n-Butyl lithium (17.6 mL, 44.2 mmol, 2.5 M in hexanes) was added to a solution of diisopropyl amine (96.2 mL, 44.2 mmol) in 40 mL of dry THF at 0° C. and stirred for 20 minutes. The reaction mixture was cooled to −78° C. and tert-butyl 4-oxo-1-piperidinecarboxylate (Aldrich Chemical Company, 40.0 mmol) in THF (40 mL) was added dropwise to the reaction mixture and stirred for 30 minutes. $Tf_2NPh$ (42.0 mmol, 15.0 g) in THF (40 mL) was added dropwise to the reaction mixture and stirred at ° C. overnight. The reaction mixture was concentrated in vacuo, re-dissolved in hexanes:EtOAc (9:1), passed through a plug of alumina and the alumina plug was washed with hexanes:EtOAc (9:1). The combined extracts were concentrated to yield 16.5 g of the desired product that was contaminated with some starting $Tf_2NPh$.

$^1$H NMR (400 MHz, CDCl$_3$) δ 5.77 (s, 1 H), 4.05 (dm, 2 H, J=3.0 Hz), 3.63 (t, 2 H, J=5.7 Hz), 2.45 (m, 2 H), 1.47 (s, 9 H).

TERT-BUTYL 4-[3-(AMINO)PHENYL]-1,2,3,6-TETRAHYDRO-1-PYRIDINECARBOXYLATE:

A mixture of 2 M aqueous $Na_2CO_3$ solution (4.2 mL), tert-butyl 4-{[(trifluoromethyl)sulfonyl]oxy}-1,2,3,6-tetrahydro-1-pyridine-carboxylate (0.500 g, 1.51 mmol), 3-aminophenylboronic acid hemisulfate (0.393 g, 2.11 mmol), lithium chloride (0.191 g, 4.50 mmol) and tetrakis-triphenylphosphine palladium (0) (0.080 g, 0.075 mmol) in dimethoxyethane (5 mL) was heated at reflux temperature for 3 hours, under an inert atmosphere (an initial degassing of the mixture is recommended to prevent the formation of triphenylphosphine oxide). The organic layer of the cooled reaction mixture was separated and the aqueous layer was washed with ethyl acetate (3×). The combined organic extracts were dried and concentrated in vacuo. The crude product was chromatograghed (silica, hexanes:EtOAc:dichloromethane (6:1:1) with 1% added isopropylamine to protect the BOC group from hydrolysis) to give 0.330 g of the desired product in 81% yield:

$^1$H NMR (400 MHz, CDCl$_3$) δ 7.12 (t, 1H, J=7.60 Hz), 6.78 (d, 1H, J=8.4 Hz), 6.69 (t, 1H, J=2.0 Hz), 6.59 (dd, 1H, J=2.2, 8.0 Hz), 6.01 (m, 1H), 4.10–4.01 (d, 2H, J=2.40 Hz), 3.61 (t, 2H, J=5.6 Hz), 2.52–2.46 (m, 2H), 1.49 (s, 9H); ESMS m/e: 275.2 (M+H)$^+$.

Anal. Calc. for $C_{16}H_{24}N_2O_2$: C, 70.04; H, 8.08; N, 10.21. Found: C, 69.78; H, 7.80; N, 9.92

TERT-BUTYL 4-[3-(AMINO)PHENYL]-1-PIPERIDINECARBOXYLATE

A mixture of 3.10 g of tert-butyl 4-(3-aminophenyl)-1,2,3,6-tetrahydropyridine-1-carboxylate (11.3 mmol) and 1.0 g of 10% Pd/C in 200 mL of ethanol was hydrogenated at room temperature using the balloon method for 2 days. The reaction mixture was filtered and washed with ethanol. The combined ethanol extracts were concentrated in vacuo and the residue was chromatographed on silica (dichloromethane: methanol 95:5 with 1% isopropylamine added to protect the BOC group from hydrolysis) to give 2.63 g of the desired product (84%).

TERT-BUTYL 4-(3-NITROPHENYL)-3,6-DIHYDRO-1(2H)-PYRIDINECARBOXYLATE

1H NMR (400 MHz, CHCl$_3$) δ 8.23 (s, 1H), 8.11 (d, 1H, J=8.0 Hz), 7.69 (d, 1H, J=8.0 Hz), 7.51 (t, 1H, J=8.0 Hz), 6.20 (m, 1H), 4.17–4.08 (m, 2H), 3.67 (t, 2H, J=5.6 Hz), 2.61–2.52 (m, 2H), 1.50 (s, 9H); ESMS m/e: 249.1 (M+H-$C_4H_8$)$^+$.

1,2,3,6-TETRAHYDRO-4-(3-NITROPHENYL) PYRIDINE: Into a stirred solution of 5.00 g (16.0 mmol) of tert-butyl 1,2,3,6-tetrahydro-4-(3-nitrophenyl)pyridine-1-carboxylate in 100 ml of 1,4-dioxane at 0° C. was bubbled HCl gas for 10 minutes. The reaction mixture was allowed to warm to room temperature and the bubbling of the HCl gas was continued for an additional 1 hour. The solvent was removed in vacuo, the residue was dissolved in 50 mL of water and was neutralized by the addition of KOH pellets. The aqueous solution was extracted with 3×80 mL of dichloromethane and the combined organic extracts were dried (MgSO$_4$), filtered and concentrated in vacuo. The residue was purified by column chromatography (silica, 9:1, dichloromethane methanol+1% isopropyl amine) to afford 2.85 g (87.5% yield) of the desired product: $^1$H NMR (400 MHz, CDCl$_3$) δ 8.24 (s, 1H), 8.09 (d, 1H, J=8.4 Hz), 7.71 (d, 1H, J=8.0 Hz), 7.49 (t, 1H, J=8.0 Hz), 6.35–6.25 (m, 1H), 3.58 (apparent q, 2H, J=3.0 Hz), 3.14 (t, 2H, J=5.6 Hz), 2.54–2.46 (m, 2H)

TERT-BUTYL 3-(4-(3-NITROPHENYL)-3,6-DIHYDRO-1(2H)-PYRIDINYL)PROPYLCARBAMATE: A mixture of 2.80 g (14.0 mmol) of 1,2,3,6-tetrahydro-4-(3-nitrophenyl)pyridine, 3.60 g (15.0 mmol) of tert-butyl N-(3-bromopropyl)carbamate, 11.6 g (84.0 mmol) of K$_2$CO$_3$, 14.6 mL (84.0 mmol) of diisopropylethylamine and 0.78 g (2.00 mmol) of tetrabutylammonium iodide in 250 mL of 1,4-dioxane was heated at reflux temperature for 14 hours. The reaction mixture was filtered and the filtrate was dried (MgSO$_4$), concentrated in vacuo and the residue was purified by column chromatography (silica, 9:1, dichloromethane:methanol+1% isopropyl amine) to afford 4.35 g (85.7% yield) of the desired product: $^1$H NMR (400 MHz, CDCl$_3$) δ 8.24 (t, 1H, J=1.9 Hz), 8.09 (dd, 1H, J=1.9, 8.0 Hz), 7.70 (apparent d, 1H, J=8.0 Hz), 7.49 (t, 1H, J=8.0 Hz), 6.23 (m, 1H), 3.29–3.18 (m, 4H) 2.75 (t, 2H, J=5.6 Hz), 2.64–2.54 (m, 4H), 1.82–1.70 (m, 2H), 1.44 (s, 9H); ESMS m/e: 362.2 (M+H)$^+$.

3-(4-(3-NITROPHENYL)-3,6-DIHYDRO-1(2H)-PYRIDINYL)-1-PROPANAMINE: Into a stirred solution of 4.35 (12.0 mmol) of tert-butyl 3-(4-(3-nitrophenyl)-3,6-dihydro-1(2H)-pyridinyl)propylcarbamate in 100 ml of 1,4-dioxane at 0° C. was bubbled HCl gas for 10 minutes. The reaction mixture was allowed to warm to room temperature and the bubbling was continued for an additional 1 hour. The solvent was removed in vacuo, the residue was dissolved in 50 mL of water and was neutralized by the addition of KOH pellets. The aqueous solution was extracted with 3×80 mL of dichloromethane, the combined organic extracts were dried (MgSO$_4$), filtered and concentrated in vacuo. The residue was purified by column chromatography (silica, 9:1, dichloromethane:methanol+1% isopropyl amine) to afford 3.05 g (97.0% yield) of the desired product: $^1$H NMR (400 MHz, CDCl$_3$) δ 8.24 (t, 1H, J=1.8 Hz), 8.09 (dd, 1H, J=1.8, 8.2 Hz), 7.69 (dd, 1H, J=1.8, 8.2 Hz), 7.48 (t, 1H, J=8.2 Hz), 6.24 (m, 1H), 3.21 (d, 2H, J=3.6 Hz), 2.84 (t, 2H, J=6.6 Hz), 2.75 (t, 2H, J=5.8 Hz), 2.64–2.54 (m, 4H), 1.76 (m, 2H); ESMS m/e: 262.2 (M+H)$^+$; Anal. Calc. for C$_{14}$H$_{19}$N$_3$O$_2$ (0.06 CHCl$_3$): C, 62.90; H, 7.16; N, 15.65. Found: C, 63.20; H, 7.16; N, 15.65.

METHYL (4S)-3-[({3-[4-(3-AMINOPHENYL)-1-PIPERIDINYL]PROPYL}AMINO)CARBONYL]-4-(3,4-DIFLUOROPHENYL)-6-(METHOXYMETHYL)-2-OXO-1,2,3,4-TETRAHYDRO-5-PYRIMIDINECARBOXYLATE: A mixture of 3.02 g (6.33 mmol) 5-methyl 1-(4-nitrophenyl) (6S)-6-(3,4-difluorophenyl)-4-(methoxymethyl)-2-oxo-3,6-dihydro-1,5(2H)-pyrimidinedicarboxylate, 1.50 g (5.80 mmol) of 3-(4-(3-nitrophenyl)-3,6-dihydro-1(2H)-pyridinyl)-1-propanamine, 7.94 g (75.5 mmol) of K$_2$CO$_3$ and 1.00 mL of methanol in 200 mL dichloromethane (under argon) was stirred at room temperature for 1 hour. The reaction mixture was filtered and concentrated in vacuo. The residue was dissolved in 100 mL of ethyl acetate and washed 3×50 mL of 5% aqueous NaOH solution, the organic layer was dried (MgSO$_4$) and concentrated in vacuo. The residue was dissolved in 100 mL of anhydrous ethanol containing 0.50 g 10% Pd/C and the reaction mixture was stirred under a hydrogen balloon for 24 hours. The reaction mixture was passed through a column of Celite 545 filtering agent, washed with ethanol, the filtrate was dried (MgSO$_4$) and concentrated in vacuo. The residue was purified by column chromatography (silica, 9.5:0.5, dichloromethane:methanol+1% isopropyl amine) to afford 1.65 g (52.0% yield) of the desired product.

TERT-BUTYL 4-[3-(ISOBUTYRYLAMINO)PHENYL]-3,6-DIHYDRO-1(2H)-PYRIDINECARBOXYLATE: Into a solution of 4.00 g (16.0 mmol) of tert-butyl 4-(3-aminophenyl)-3,6-dihydro-1(2H)-pyridinecarboxylate and 5.60 mL (32.0 mmol) of diisopropylethylamine in 100 mL dichloromethane was slowly added 1.90 mL (19.0 mmol) of isobutyryl chloride. The reaction mixture was stirred at room temperature for 2 hours, washed with water, dried (MgSO$_4$), and concentrated in vacuo. The residue was purified by column chromatography (silica, 50:46:3:1, hexanes:dichloromethane:methanol:isopropyl amine) to afford 2.90 g (52.0% yield) of the desired product: $^1$H NMR (400 MHz, CDCl$_3$) δ 7.69 (s, 1 H), 7.34 (d, 1 H, J=7.8 Hz), 7.27 (t, 1H, J=7.8 Hz), 7.11 (d, 1H, J=7.8 Hz), 6.04 (s, 1H), 4.05 (s, 2H), 3.62 (apparent t, 2 H, J=4.9 Hz), 2.51 (m, 3H), 1.49 (s, 9H), 1.25 (d, 6H, J=7.4 Hz); ESMS m/e: 345.5 (M+H)$^+$. Anal. Calc. for C$_{20}$H$_{28}$N$_2$O$_3$+0.175 CHCl$_3$: C, 66.33; H, 7.77; N, 7.67. Found: C, 66.20; H, 7.41; N, 7.88

TERT-BUTYL 4-[3-(ISOBUTYRYLAMINO)PHENYL]-1-PIPERIDINECARBOXYLATE: A mixture of 2.90 g (8.40 mmol) of tert-butyl 4-[3-(isobutyrylamino)phenyl]-3,6-dihydro-1(2H)-pyridinecarboxylate and 0.80 g of 10% yield Pd/C in 100 mL of ethanol was stirred under a hydrogen balloon for 24 hours. The reaction mixture was passed through a column of Celite 545 filtering agent, the filtrate was dried (MgSO$_4$) and concentrated in vacuo. The residue was purified by column chromatography (silica, 9.5:0.5, dichloromethane:methanol+1% isopropyl amine) to afford 2.40 g (84.0% yield) of the desired product: $^1$H NMR (400 MHz, CDCl$_3$) δ 7.49–7.44 (m, 2H), 7.24 (t, 1H, J=7.6 Hz), 6.93 (d, 1H, J=7.6 Hz), 4.20–4.10 (m, 2H), 2.86–2.45 (m, 4H), 1.86–1.75 (m, 4H), 1.48 (s, 9H), 1.24 (d, 6H, J=6.8 Hz); ESMS m/e: 345.2 (M+H)$^+$; Anal. Calc. for C$_{20}$H$_{30}$N$_2$O$_3$+0.3H$_2$O: C, 68.27; H, 8.77; N, 7.96. Found: C, 68.25; H, 8.54; N, 7.84.

2-METHYL-N-[3-(4-PIPERIDINYL)PHENYL]PROPANAMIDE: Into a stirred solution of 2.20 (6.50 mmol) of tert-butyl 4-[3-(isobutyrylamino)phenyl]-1-piperidinecarboxylate in 100 ml of 1,4-dioxane at 0° C. was bubbled HCl gas for 10 minutes. The reaction mixture was allowed to warm to room temperature and the bubbling of the HCl gas was continued for 1 hour. The solvent was removed in vacuo, the residue was dissolved in 50 mL of water and was neutralized by the addition of KOH pellets. The aqueous solution was extracted with 3×80 mL of dichloromethane, the combined organic extracts were dried (MgSO$_4$), filtered and concentrated in vacuo. The residue was purified by column chromatography (silica, 9:1, dichloromethane:methanol+1% isopropyl amine) to afford 0.700 g (46.0% yield) of the desired product: $^1$H NMR (400 MHz, CDCl$_3$) δ 7.47 (s, 1H), 7.40 (d, 1H, J=7.8 Hz), 7.24 (t, 1H, J=7.8 Hz), 7.00 (d, 1H, J=7.8 Hz), 3.23–3.14 (m, 5H), 2.82–2.57 (m, 4H), 1.20 (d, 6H, J=6.8 Hz); ESMS m/e: 247.2 (M+H)$^+$; The hydrochloride salt was used for the combustion analysis: Anal. Calc. for C$_{15}$H$_{22}$N$_2$O+HCl+0.15 CHCl$_3$: C, 60.51; H, 7.76; N, 9.32. Found: C, 60.57; H, 7.83; N, 8.88.

3-(4-PIPERIDINYL)ANILINE: $^1$H NMR (400 MHz, CDCl$_3$) δ 7.01 (t, 1H, J=7.6 Hz), 6.62–6.54 (m, 3H), 3.16 (br d, 2H, J=10.3 Hz), 2.75 (dt, 2H, J=2.7, 12.3 Hz), 2.56 (tt, 1H, J=3.6, 12.3 Hz), 1.81 (br d, 2H, J=12.3 Hz), 1.65 (dq, 2H, J=4.0, 12.3 Hz); ESMS m/e: 177.2 (M+H)$^+$.

TERT-BUTYL 4-(4-NITROPHENYL)-3,6-DIHYDRO-1(2H)-PYRIDINECARBOXYLATE: To a 25-mL RB flask, equipped with a condensor, was added tert-butyl 4-{[(trifluoromethyl)sulfonyl]oxy}-3,6-dihydro-1(2H)-pyridinecarboxylate (1.0 g), 4-nitrophenylboronic acid (0.71 g), sodium carbonate (0.430 mL of 2M solution), lithium chloride (0.382 g), tetrakis(triphenylphosphine)-palladium (0) (0.173 g) and ethylene glycol dimethyl ether (10 mL). The reaction mixture was flushed with Argon three times, then the reaction mixture was heated to 100° C. for 3 hrs. After cooling to room temperature, the reaction mixture was diluted with methylene chloride (30 mL) and water (30 mL) and the organic layer was separated. The aqueous layer was extracted with methylene chloride (3×20 mL) and the combined organic extracts were washed with sat NH$_4$Cl (20 mL) and brine (20 mL), dried over MgSO$_4$ and concentrated under reduced pressure. The residue was purified by chromatography (6:1=hexane:ethyl acetate with 1% NH$_3$) to afford the product (0.55 g, 59.9%) as a yellow oil. The compound is not stable at room temperature and should be used as prompt as practical: $^1$H NMR (400 MHz, CDCl$_3$) δ 8.20 (d, 2H, J=8.6 Hz), 7.51 (d, 2H, J=8.6 Hz), 6.24 (m, 1H), 4.13 (m, 2H), 3.67 (apparent t, 2H, J=5.5 Hz), 2.55 (m, 2H), 1.49 (s, 9H).

4-(4-NITROPHENYL)-1,2,3,6-TETRAHYDROPYRIDINE: 4-(4-Nitrophenyl)-1,2,3,6-tetrahydropyridine was prepared by a similar procedure to that used for the preparation of 2-methyl-N-[3-(4-piperidinyl)phenyl]propanamide using HCl gas and tert-Butyl 4-(4-Nitrophenyl)-3,6-dihydro-1(2H)-pyridinecarboxylate (130 mg) in dioxane (5.0 mL) at room temperature. The reaction mixture was concentrated in vacuo to give the crude product (69.8 mg) that used in the next reaction without further purification.

Dihydropyrimidine Intermediates 3-(3,4,5-TRIFLUOROBENZYLIDENE)-2,4-PENTANEDIONE: A stirring mixture of 3,4,5-trifluorobenzaldehyde (4.20 g, 26.2 mmol), 2,4-pentanedione (2.62 g, 26.2 mmol), piperidine (0.430 g, 5.00 mmol) in benzene (150 mL) was heated at reflux temperature in a Dean-Stark apparatus for 8 h. The benzene was evaporated and the yellow oily residue was used in the next step without further purification.

1-[2-METHOXY-4-METHYL-6-(3,4,5-TRIFLUOROPHENYL)-1,6-DIHYDRO-5-PYRIMIDINYL]ETHANONE: A mixture 3-(3,4,5-trifluorobenzylidene)-2,4-pentanedione (26.2 mmol), O-methylisourea hydrogen sulfate (3.22 g, 39.3 mmol), and NaHCO$_3$ (6.6 g, 78.6 mmol) in EtOH (400 mL) was stirred and heated at 95–100° C. for 6 h. The mixture was filtered and the solid filter cake was washed with ethanol (100 mL). The solvent was evaporated from the combined filtrates and the crude product was purified by flash column chromatography (EtOAc/hexane, 1/9 to 1/4), to afford the desired product as an oil (2.80 g, 36%).

4-NITROPHENYL 5-ACETYL-2-METHOXY-4-METHYL-6-(3,4,5-TRIFLUOROPHENYL)-1(6H)-PYRIMIDINECARBOXYLATE: 4-Nitrophenyl chloroformate (1.89 g, 9.38 mmol) was added to a solution of 1-[2-methoxy-4-methyl-6-(3,4,5-trifluorophenyl)-1,6-dihydro-5-pyrimidinyl]ethanone (2.80 g, 9.38 mmol) and pyridine (10 mL) in CH$_2$Cl$_2$ (200 mL) at 0–5° C., and the resulting mixture was allowed to warm to room temperature. After 12 h, the solvent was evaporated and the residue was purified by flash chromatography (dichloromethane/EtOAc, 1/9 to 3/20), to give the desired product as a white powder (4.00 g, 92%).

4-NITROPHENYL 5-ACETYL-4-METHYL-2-OXO-6-(3,4,5-TRIFLUOROPHENYL)-3,6-DIHYDRO-1(2H)-PYRIMIDINECARBOXYLATE:

A solution of 6 N aqueous HCl (4 mL) was added to a well-stirred solution of 4-nitrophenyl 5-acetyl-2-methoxy-4-methyl-6-(3,4,5-trifluorophenyl)-1(6H)-pyrimidinecarboxylate (4.00 g, 8.63 mmol) in THF (100 mL) at 0–5° C., and the mixture was allowed to warm to room temperature. After 2 h, solvent was evaporated and the product dried under vacuum. The product was obtained as a pure single component and used in the next step without further purification (3.88 g, 100%).

$^1$H NMR (DMSO) δ 10.29 (s, 1H), 8.23 (d, 2H, J=9.1 Hz), 7.51 (d, 2H, J=9.1 Hz), 7.15–7.07 (m, 2H), 6.18 (s, 1H), 2.30 (s, 3H), 2.28 (s, 3H); ESMS m/e: 450.2 (M+H)$^+$; Anal. Calc. for C$_{20}$H$_{14}$F$_3$N$_3$O$_6$: C, 53.46; H, 3.14; N, 9.35. Found: C, 53.26; H, 3.21; N, 9.35.

BENZYL 2-PROPIONYL-3-(3,4,5-TRIFLUOROPHENYL)-2-PROPENOATE. A solution of benzyl propionylacetate (36.3 g, 176 mmol), 3,4-difluorobenzaldehyde (25.0 g, 176 mmol), piperidine (0.86 mL, 9.0 mmol) and acetic acid (0.49 mL, 9.0 mmol) were heated at reflux temperature with removal of water using a Dean-Stark apparatus for 5h. The solvent was removed in vacuo and the residue was dissolved in EtOAc. The organic layer was washed with water (100 mL) followed by brine (100 mL) and dried over anhydrous Na$_2$SO$_4$. The solvent was evaporated to afford a pale yellow syrup (60.2 g), which was used in the next step without further purification.

BENZYL 6-(3,4-DIFLUOROPHENYL)-4-ETHYL-2-METHOXY-1,6-DIHYDRO-5-PYRIMIDINECARBOXYLATE. A suspension of benzyl 2-propionyl-3-(3,4,5-trifluorophenyl)-2-propenoate (16.0 g, 48.0 mmol), O-methylisourea hydrogen sulfate (16.65 g, 97.02 mmol), NaHCO$_3$ (16.3 g, 130.2 mmol) in DMF (190 mL) was stirred at 70° C. for 20h. After cooling to room temperature, the reaction mixture was filtered and the filtrate was diluted with EtOAc (300 mL) and then washed with water (4×100 mL), brine (200 mL) and dried over Na$_2$SO$_4$. After removal of solvent, the residue was purified by column chromatography (SiO$_2$, EtOAc/Hexane, 10%–30%) to afford benzyl 6-(3,4-difluorophenyl)-4-ethyl-2-methoxy-1,6-dihydro-5-pyrimidinecarboxylate as a colorless oil (10.6 g, 58% yield). The product was directly used in the next step after $^1$H NMR spectroscopy which showed it to be a mixture of amine/imine tautomers.

5-BENZYL 1-(4-NITROPHENYL) 6-(3,4-DIFLUOROPHENYL)-4-ETHYL-2-METHOXY-1,5(6H)-PYRIMIDINEDICARBOXYLATE.

Into a well-stirred solution of benzyl 6-(3,4-difluorophenyl)-4-ethyl-2-methoxy-1,6-dihydro-5-pyrimidinecarboxylate (27.5 g, 68.75 mmol) and pyridine (9.2 mL) in CH$_2$Cl$_2$ (300 mL) was added 4-nitrophenyl chloroformate (14.49 g, 82.5 mmol) at room temperature. The reaction mixture was stirred for 4 h and then washed with 10% aqueous KOH solution (2×150 mL). The organic layer was separated and dried over Na$_2$SO$_4$. The solvent was removed in vacuo and the residue was used in the next step without further purification: $^1$H NMR (CDCl$_3$) δ 1.24 (t, J=7.2 Hz, 3H), 2.81–2.98 (m, 3H), 3.97 (s, 3H), 5.14 (AB$_q$, 2H), 6.28 (s, 3H), 7.03–7.29 (m, 8H), 7.35 (d, J=9.2 Hz, 2H), 8.26 (d, J=9.2 Hz, 2H).

BENZYL 6-(3,4-DIFLUOROPHENYL)-4-ETHYL-2-METHOXY-1-({[(1R)-1-PHENYLETHYL]AMINO}CARBONYL)-1,6-DIHYDRO-5-PYRIMIDINECARBOXYLATE.

Into a stirred mixture of 5-benzyl 1-(4-nitrophenyl) 6-(3,4-difluorophenyl)-4-ethyl-2-methoxy-1,5(6H)-pyrimidinedicarboxylate (12.6 g, 22.86 mmol) in THF (150 mL) was added a solution of R-(+)-α-methyl benzylamine (3.53 mL, 27.44 mmol) at room temperature. The stirring was continued for 12 h and the solvent was removed in vacuo. The yellow residue was dissolved in chloroform (200 mL) and was washed with 10% K$_2$CO$_3$ solution (2×30 mL). The organic layer was dried over Na$_2$SO$_4$, filtered and the solvent was removed in vacuo. The resulting mixture of diastereomers was separated by column chromatography over silica gel with 9:1 pet. ether:ether to 4:1 pet. ether:ether. First major product to elute was (+)-benzyl 6-(3,4- difluorophenyl)-4-ethyl-2-methoxy-1-({[(1R)-1-phenylethyl]amino}carbonyl)-1,6-dihydro-5-pyrimidinecarboxylate: Colorless oil, Rf=0.31(4:1 pet ether:ether); wt.=3.8 g (60% yield); [α]$_D$=+267.05 (c=0.76, CHCl$_3$); $^1$H NMR (CDCl$_3$) δ 1.22 (t, J=7.5 Hz, 3H), 1.52 (d, J=6.9 Hz, 3H), 2.88 (q, J=6.0 Hz, 2H), 3.99 (s, 3H), 4.99 (m, 1H), 5.09 (AB$_q$, 2H), 6.66 (s, 1H), 6.99–7.36 (m, 13H); The second major product to elute was (−)-benzyl 6-(3,4-difluorophenyl)-4-ethyl-2-methoxy-1-({[(1R)-1-phenylethyl]amino}carbonyl)-1,6-dihydro-5-pyrimidinecarboxylate: Colorless oil; R$_f$=0.22 (4:1 pet ether:ether); wt.=3.2 g (51.2% yield); [α]$_D$=−146.89 (c=0.38, CHCl$_3$); $^1$H NMR (CDCl$_3$) δ 1.22 (t, J=7.2 Hz, 3H), 1.49 (d, J=6.6 Hz, 3H), 2.88 (q, J=6.0 Hz, 2H), 3.94 (s, 3H), 5.03 (m, 1H), 5.11 (AB$_q$, 2H), 6.68 (s, 1H) 6.91–7.34 (m, 13H).

(+)-BENZYL 6-(3,4-DIFLUOROPHENYL)-4-ETHYL-2-METHOXY-1,6-DIHYDRO-5-PYRIMIDINECARBOXYLATE. Into a stirred solution of (+)-benzyl 6-(3,4-difluorophenyl)-4-ethyl-2-methoxy-1-({[(1R)-1-phenylethyl]amino}carbonyl)-1,6-dihydro-5-pyrimidinecarboxylate (17.1 mmol, 9.35 g) in CH$_2$Cl$_2$ was added 1,8-diazabicyclo[5,4,0]-undec-7-ene (17.1 mmol, 2.56 mL) and stirring was continued for 16 h at room temperature. The solvent was evaporated and the residue was purified by flash column chromatography on silica gel with 3:1 EtOAc/Hexanes as the eluting system. 5.27 g of the (+)-benzyl 6-(3,4-difluorophenyl)-4-ethyl-2-methoxy-1,6-dihydro-5-pyrimidinecarboxylate was obtained (77% yield).

(+)-5-BENZYL 1-(4-NITROPHENYL) 6-(3,4-DIFLUOROPHENYL)-4-ETHYL-2-METHOXY-1,5(6H)-PYRIMIDINEDICARBOXYLATE. Into a well-stirred solution of (+)-benzyl 6-(3,4-difluorophenyl)-4-ethyl-2-methoxy-1,6-dihydro-5-pyrimidinecarboxylate (6.4 g, 16.0 mmol) and pyridine (1.5 mL) in CH$_2$Cl$_2$ (150 mL) was added 4-nitrophenyl chloroformate (3.41 g, 19.2 mmol) at room temperature. The reaction mixture was stirred for 4 h and then it was washed with 10% aqueous KOH solution (2×100 mL). The organic layer was separated and dried over Na$_2$SO$_4$. The solvent was removed in vacuo. The residue of (+)-5-benzyl 1-(4-nitrophenyl) 6-(3,4-difluorophenyl)-4-ethyl-2-methoxy-1,5(6H)-pyrimidinedicarboxylate was used in the next step without further purification.

a. 2-(4-METHOXYBENZYL)-2-THIOPSEUDOUREA HYDROCHLORIDE.

Into a well-stirred suspension of thiourea (7.6 g, 0.1 mol) in THF (50 mL) at 0° C., 4-methoxybenzyl chloride (16 g, 0.1 mol) was added in 10 min and the reaction mixture was allowed to warm to room temperature. After 2 hours the reaction mixture was heated to 65° C. and kept at that temperature for 5 hours. The reaction mixture was cooled to room temperature and diluted with diethyl ether (200 mL). The white precipitate that formed was filtered and dried (22.5 g, 96% yield); m. p. 161–163° C.

b. METHYL 2-{(4-NITROPHENYL)METHYLENE}-3-OXOBUTYRATE.

A mixture of 4-nitrobenzaldehyde (15.1 g, 0.1 mol), methyl acetoacetate (12.773 g, 0.11 mol), piperidine (0.41 g, 4.80 mmol), and acetic acid (0.288 g, 4.8 mmol) in 2-propanol (400 mL) was stirred at room temperature for 48 hours. The resulting white solid, methyl 2-{(4-nitrophenyl)methylene}-3-oxobutyrate was filtered, washed with 2-propanol (2×50 mL) and dried (21.8 g, 93% yield).

c. 1,6-DIHYDRO-5-METHOXYCARBONYL-2-[{(4-METHOXYPHENYL)METHYL}THIO]-4-METHYL-6-(4-NITROPHENYL)PYRIMIDINE.

A mixture of methyl 2-{(4-nitrophenyl)methylene}-3-oxobutyrate (8.96 g, 0.04 mol), 2-(4-methoxybenzyl)-2-thiopseudourea hydrochloride (9.28 g, 0.04 mol), and NaOAc (3.28 g, 0.04 mol) in DMF (100 mL) was stirred and heated at 70–75° C. for 4.5 hours. The reaction mixture was cooled to room temperature, poured into ice-water (300 mL) and extracted with EtOAc (2×400 mL). The combined EtOAc extracts were washed with 10% NaHCO$_3$ solution (2×60 mL), brine (100 mL), and then dried (MgSO$_4$). The solvent was evaporated and the crude product was purified by flash column chromatography on silica gel using 10% through 30% EtOAc in hexane as the gradient eluent. The desired product was obtained as an oil, which on trituration with EtOAc/hexane became a yellow solid (11.4 g, 66.7% yield) which was shown by $^1$H NMR to be a mixture of tautomers: m.p. 138–139° C.; $^1$H NMR (CDCl$_3$) δ 2.15 (s, 3 H), 3.62 (s, 3 H), 3.72 (s, 3 H) 4.05 and 5.78 (s and d, J=3 Hz, 1 H), 4.08, 4.20 (AB q, J=12.5 Hz, 2 H), 4.21 and 6.40 (s and d, J=3 Hz, 1 H), 6.66 (2 d, J=8.5 Hz, 2 H), 7.08 (2 d, J=8.5 Hz, 2 H), 7.37 (2 d, J=8.8 Hz, 2 H), 8.7 (2 d, J=8.8 Hz, 2 H); Anal. Calcd. for C$_{21}$H$_{21}$N$_3$O$_5$S: C, 59.00; H, 4.95; N, 9.83. Found: C, 59.02; H, 4.93; N, 9.77.

d. 1,6-DIHYDRO-5-METHOXYCARBONYL-2-[{(4-METHOXYPHENYL)METHYL}THIO]-4-METHYL-6-(4-NITROPHENYL)-1-[(4-NITROPHENYLOXY)CARBONYL]PYRIMIDINE.

Into a well-stirred mixture of 1,6-dihydro-5-methoxycarbonyl-2-[{(4-methoxyphenyl)methyl}thio]-4-methyl-6-(4-nitrophenyl)pyrimidine (4.50 g, 10.5 mmol), NaHCO$_3$ (3.69 g, 0.044 mol), CH$_2$Cl$_2$ (200 mL), and water (50 mL) at 0–5° C., 4-nitrophenyl chloroformate (2.40 g, 12.0 mmol) was added over a 5 min period and the reaction mixture was allowed to warm to room temperature. After 10 hours, the TLC analysis of the reaction mixture showed the presence of a small amount of starting pyrimidine, therefore, more 4-nitrophenyl chloroformate (0.65 g, 0.0032 mol) was added and the stirring was continued for an additional 4 hours. The two layers were separated, the CH$_2$Cl$_2$ layer was washed with saturated aqueous NaHCO$_3$ solution (3×50 mL), dried (MgSO$_4$), and the solvent evaporated. The residue was recrystallized from CH$_2$Cl$_2$ and hexane to give the product as white crystals (5.50 g, 88.4% yield): m.p. 156–157° C.; $^1$H-NMR (CDCl$_3$) δ 2.53 (s, 3 H), 3.70 (s, 3 H), 3.81 (s, 3 H), 4.06, 4.36 (ABq, J=13.5 Hz, 2 H), 6.30 (s, 1 H), 6.78 (d, J=8.6 Hz, 2 H), 7.17 (d, J=8.6 Hz, 2 H), 7.20 (d, J=8.8 Hz, 2 H), 7.32 (d, J=8.8 Hz, 2 H), 7.97 (d, J=8.8 Hz, 2 H), 8.25 (d, J=8.8 Hz, 2 H); Anal. Calcd. for C$_{28}$H$_{24}$N$_4$O$_9$S: C, 56.75; H, 4.08; N, 9.45. Found: C, 56.49; H, 4.28; N, 9.25.

a. 6-(BENZOFURAZAN-5-YL)-1,6-DIHYDRO-2-OXO-5-METHOXYCARBONYL-4-BROMOMETHYL-1-[(4-NITROPHENYLOXY)CARBONYL]PYRIMIDINE.

Into a well-stirred solution of 6-(benzofurazan-5-yl)-1,6-dihydro-2-methoxy-5-methoxycarbonyl-4-methyl-1-[(4-nitrophenyl-oxy)carbonyl]pyrimidine (0.310 mmol, 0.140 g) in 1.5 mL of chloroform was added a solution of bromine (0.310 mmol, 0.020 mL) in 1.5 mL of chloroform at 0° C. and the solution was allowed to attain room temperature over 1.5 h. The solvent was removed in vacuo and the residue was again dissolved in CHCl$_3$ (10 mL) and washed with brine. The organic layer was separated, dried over Na$_2$SO$_4$, filtered and the solvent was removed in vacuo to obtain 0.15 g (88% yield) of 6-(benzofurazan-5-yl)-1,6-dihydro-2-oxo-5-methoxycarbonyl-4-bromomethyl-1-[(4-nitrophenyl-oxy)carbonyl]pyrimidine as a yellow foam. The crude product was used in the next step without purification. $^1$H NMR (CDCl$_3$) δ 3.79 (s, 3 H), 4.72 (ABq, 2 H), 6.47 (s, 1 H), 7.37 (d, J=9.1 Hz, 2 H), 7.51 (d, J=7.8 Hz, 1 H), 7.80 (s, 1 H), 7.92 (d, J=9.1 Hz, 1 H), 8.30 (d, J=9.1 Hz, 2 H).

c. 4-NITROPHENYL 4-(2,1,3-BENZOXADIAZOL-5-YL)-2,5-DIOXO-1,2,5,7-TETRAHYDROFURO[3,4-D]PYRIMIDINE-3(4H)-CARBOXYLATE.

6-(3,4-Benzofurazan-5-yl)-1,6-dihydro-2-oxo-5-methoxycarbonyl-4-bromomethyl-1-[(4-nitrophenyloxy)carbonyl]pyrimidine (0.27 mmol, 0.15 g) was heated in oil bath for 3 h (bath temperature 130° C. The brownish-yellow residue thus obtained was washed with CHCl$_3$ and 4-nitrophenyl 4-(2,1,3-benzoxadiazol-5-yl)-2,5-dioxo-1,2,5,7-tetrahydrofuro[3,4-d]pyrimidine-3(4H)-carboxylate was obtained as an off-white solid which was used in the next step without further purification (crude wt. 0.11 g, 93% yield): $^1$H NMR (DMSO-d$_6$) δ 8.38–7.56 (m, 7H), 6.33 (s, 1H), 5.02 (s, 2H); Anal. Calc. for C$_{19}$H$_{11}$N$_5$O$_8$+2.3H$_2$O: C, 47.85; H, 3.28; N, 14.63. Found: C, 47.73; H, 2.51; N, 14.77.

5-METHYL 1-(4-NITROPHENYL) 4-(BROMOMETHYL)-6-(3,4-DIFLUOROPHENYL)-2-OXO-3,6-DIHYDRO-1,5(2H)-PYRIMIDINEDICARBOXYLATE: Into a well-stirred solution of 6-(3,4-Difluorophenyl)-1,6-dihydro-2-methoxy-5-methoxycarbonyl-4-methyl-1-[(4-nitrophenyloxy)carbonyl]pyrimidine (1.5 mmol, 0.66 g) in 5 mL of chloroform was added a solution of bromine (1.5 mmol, 0.09 mL) in 3 mL of chloroform at 0° C. and the solution was allowed to attain room temperature over 1.5 h. The solvent was removed in vacuo and the residue was again dissolved in CHCl$_3$ (20 mL) and washed with brine. The organic layer was separated, dried over Na$_2$SO$_4$, filtered and the solvent was removed in vacuo to afford the desired product as a yellow foam, which was used in the next step without purification. $^1$H NMR δ 3.75 (s, 3 H), 4.67 (ABq, 2 H), 6.35 (s, 1 H), 7.09–7.19 (m, 4 H), 7.37 (d, J=9.0 Hz, 2 H), 8.27 (d, J=9.0 Hz, 2 H).

4-NITROPHENYL 4-(3,4-DIFLUOROPHENYL)-2,5-DIOXO-1,2,5,7-TETRAHYDROFURO[3,4-D]PYRIMIDINE-3(4H)-CARBOXYLATE.

5-methyl 1-(4-nitrophenyl) 4-(bromomethyl)-6-(3,4-difluorophenyl)-2-oxo-3,6-dihydro-1,5(2H)-pyrimidinedicarboxylate (1.5 mmol, 0.81 g) was heated in an oil bath for 3 h (bath temperature 130° C.). The brown residue thus obtained was washed with CHCl$_3$ and the desired product was obtained as a pale brown solid which was used in the next step without further purification (crude wt. 0.51 g): $^1$H NMR (DMSO-d$_6$) δ 4.94 (br s, 2 H), 6.08 (s, 1 H), 7.20–7.43 (m, 4 H), 8.35 (d, J=10.2 Hz, 2 H).

4-NITROPHENYL 4-(1,3-BENZODIOXOL-5-YL)-2,5-DIOXOHEXAHYDROFURO[3,4-D]PYRIMIDINE-3(4H)-CARBOXYLATE: $^1$H NMR (DMSO) δ 11.35 (s, 1H), 8.16 (d, 2H, J=9.5 Hz), 7.32 (d, 2H, J=8.9 Hz), 6.81–6.65 (m, 3H), 5.88 (s, 1H), 4.85 (ABq, 2H); ESMS m/e: 440.1 (M+H)$^+$; Anal. Calc. for C$_{20}$H$_{15}$N$_3$O$_9$+1.5H$_2$O: C, 51.29; H, 3.87; N, 8.97. Found: C, 51.38; H, 2.85; N, 8.73.

5-METHYL 1-(4-NITROPHENYL) (6S)-6-(3,4-DIFLUOROPHENYL)-4-METHYL-2-OXO-3,6-DIHYDRO-1,5(2H)-PYRIMIDINEDICARBOXYLATE: $^1$H NMR (400 MHz, CDCl$_3$) δ 8.29 (d, 2H, J=9.1 Hz), 7.36 (d, 2H, J=8.9 Hz), 7.25–7.11 (m, 3H), 6.37 (s, 1H), 3.75 (s, 3H), 2.46 (s, 3H); ESMS m/e: 448.1 (M+H)$^+$; Anal. Calc. for C$_{20}$H$_{15}$F$_2$N$_3$O$_7$: C, 53.70; H, 3.38; N, 9.39. Found: C, 53.35; H, 3.36; N, 9.27.

BENZYL 4-{[(TERT-BUTOXYCARBONYL)AMINO]METHYL}CYCLOHEXYLCARBAMATE: Oxalyl chloride (1.1 equivalents) was added dropwise to a mixture of 4-[[(tert-butoxycarbonyl)-amino]methyl]-cyclohexanecarboxylic acid (1 equivalent, Maybridge) in toluene. The reaction mixture was stirred at room temperature for 2–6 h. The solvent was removed in vacuo, the residue was dissolved in acetone and the resulting mixture was added dropwise to an aqueous solution of sodium azide (1.2 equivalents) at a rate such as to maintain a temperature of 10–15° C. After the completion of the reaction, the reaction mixture was extracted with ethyl acetate, the combined extracts were dried and concentrated in vacuo. The residue was dissolved in acetone and added slowly to warm (60° C.) benzene. After the completion of the reaction, benzyl alcohol was added to the reaction mixture, stirred for 2 days and the desired product was isolated (For Typical References, See: G. Schroeter Ber. 1909, 42, 3356; and Allen, C. F. H.; Bell, A. *Org. Syn. Coll. Vol.* 3 (1955) 846.).

A solution of benzyl 4-{[(tert-butoxycarbonyl)amino]methyl}-cyclohexyl carbamate in MeOH containing 10% Pd/C was hydrogenated at 50 psi overnight. The reaction mixture was filtered through Celite 545 and the Celite 545 was washed with methanol. The combined methanol extracts were concentrated in vacuo, giving trans-tert-butyl 4-aminocyclohexylmethylcarbamate (95%).

9H-9-FLUORENYLMETHYL N-[4-(AMINOMETHYL)CYCLOHEXYL]CARBAMATE:: $^1$H NMR δ 8.02 (br, 1 H), 7.33 (m, 5 H), 5.07 (s, 2 H), 3.71 (s, 1 H), 3.40 (br m, 1 H), 2.80 (br m, 2 H), 1.94 (ABq, 4 H), 1.68 (br, 1 H), 1.30–1.00 (m, 5 H).

N1-[4-(AMINOMETHYL)CYCLOHEXYL]-1-NAPHTHAMIDE: HCl in dioxane (10 mL, 4 N) was added to a solution of tert-butyl[4-(1-naphthoyl-amino)cyclohexyl]methylcarbamate (0.350 g) in dichloromethane (20 mL), stirred overnight, concentrated in vacuo, giving the desired product: $^1$H NMR δ 8.24 (dd, 1 H, J=1.2, 8.7 Hz), 7.85 (dt, 2 H, J=2.7, 9.7 Hz), 7.60–7.30 (m, 4 H), 5.98 (m, 1 H), 4.02 (m, 1 H), 3.80–3.40 (m, 4 H), 2.53 (d, 2 H, J=6.0 Hz), 2.02 (ABq, 4 H), 1.41–1.90 (m, 4 H).

TERT-BUTYL N-(4-[(1-NAPHTHYLCARBONYL)AMINO]CYCLOHEXYLMETHYL)-CARBAMATE: A mixture of 1-naphthoic acid (1.00 mmol, 0.172 g), DMAP (2.00 mmol, 0.250 g) and ECD (0.383 g, 2.00 mmol) in dry dichloromethane (20 mL) was stirred at room temperature for 0.5 h followed by the addition of tert-butyl(4-amino)cyclohexyl)methylcarbamate amine (1.09 mmol, 0.250 g). The reaction mixture was stirred at room temperature overnight and purified by flash chromatography, giving the desired product as a white solid (0.160 g): $^1$H NMR δ 8.29 (dd, 1 H, J=1.8, 9.1 Hz), 7.89 (m, 2 H), 7.60–7.40 (m, 4 H), 5.85 (br d, 1 H, J=6.3 Hz), 4.65 (m, 1 H), 4.04 (m, 1 H), 3.02 (t, 1 H, J=6.3 Hz), 2.05 (ABq, 4 H), 1.62 (m, 2 H), 1.46 (s, 9 H), 1.40–1.10 (m, 4 H).

4-ACETYL-1-(3-AMINOPROPYL)-4-PHENYLPIPERIDINE: A solution of 4-Acetyl-4-phenylpiperidine (7, 1.53 g, 7.50 mmol), 3-bromopropylamine hydrobromide (1.64 g, 7.50 mmol) and potassium carbonate (1.24 g, 9.00 mmol) was stirred in refluxing 1,4-dioxane (50 mL) for 12 h. After removal of dioxane, water (50 mL) was added and the pH was adjusted to 11–12 by addition of 1 N aqueous NaOH. The mixture was extracted with CH$_2$Cl$_2$ (100 mL+3×50 mL). The combined organic solutions were dried over magnesium sulfate and concentrated. The residue was purified by flash chromatography (EtOAc-MeOH-Et3N 100/40/20), giving the desired product as a colorless oil (780 mg, 40%): $^1$H NMR δ 1.56 (p, J=7 Hz, 2 H), 1.84 (s, 3 H), 1.98 (m, 2 H), 2.15 (br t, J=12 Hz, 2 H), 2.29 (t, J=7 Hz, 2 H), 2.41 (br d, J=12 Hz, 2 H), 2.66 (t, J=7 Hz, 4 H), 7.18–7.30 (m, 5 H); $^{13}$C NMR δ 26.28, 31.11, 33.43, 41.47, 51.62, 55.31, 57.19, 77.32, 77.74, 78.17, 126.95, 127.69, 129.44, 142.25, 210.15.

For the preparation of benzo-4',5'[H]furanpiperidine refer to W. E. Parham et al, *J. Org. Chem.* (1976) 41, 2268.

TERT-BUTOXY{[3-(BENZO-4',5'[H]FURANPIPERIDIN-1-YL)PROPYL]AMINO}METHANOL: To a stirred solution of the N-[4-(benzo-4',5'[H]furanpiperidine (0.566 g, 3.27 mmol) in dioxane (20 mL), N-(tert-butoxycarbonyl)-3-bromopropylamine (0.772 g, 3.27 mmol) and potassium carbonate (0.904 g, 6.54 mmol) were added and the solution was refluxed for 24 h. The reaction mixture was cooled to room temperature, concentrated and partitioned between chloroform (40 mL) and water (5 mL). The organic layer was dried over sodium sulfate, filtered and concentrated. The crude product was purified by column chromatography (ethyl acetate/methanol, 4.5/0.5), giving the desired product as a colorless oil (0.856 g, 79%); $^1$H NMR (1.45 (s, 9 H), 1.63–2.04 (m, 6 H), 2.33–2.52 (m, 4 H), 2.87 (d, J=11.0 Hz, 2 H), 3.2 (br s, 2 H), 5.07 (s, 2 H), 5.6 (br s, 1 H), 7.13–7.28 (m, 4 H).

3-(4-METHYL-4-PHENYL-1-PIPERDINYL) PROPYLAMINE: Trifluoroacetic acid (1 mL) was added to tert-butoxy{[3-(4-methyl-4-phenyl-1-piperdinyl)propyl]amino}methanol (0.500 g, 1.51 mmol) in dichloromethane (5 mL) and the solution was stirred at room temperature for 1 h. The solution was concentrated, neutralized with 10% KOH solution and extracted with dichloromethane (25 mL). The organic layer was dried over sodium sulfate, filtered and concentrated, giving 0.340 g (98%) of 3-(4-methyl-4-phenyl-1-piperdinyl)propylamine which was used without further purification in the subsequent step.

Procedures for the Reaction of the Amine Side Chains with the p-Nitrophenylcarbamate Intermediates:

General Procedure:

An equimolar solution of an amine side chain such as 3-(4-methyl-4-phenyl-1-piperdinyl)propylamine and a p-nitrophenylcarbamate intermediate such as 5-methoxycarbonyl-4-methoxymethyl-1,2,3,6-tetrahydro-2-oxo-6-(3,4-difluorophenyl)-1-[(4-nitrophenyloxy)carbonyl]pyrimidine and 1–2 equivalents of a base such as diisopropylethylamine in dichloromethane were stirred at room temperature overnight. The reaction mixture was concentrated and purified by flash chromatography, giving the desired product. In case of 2-methoxy intermediates, conversion to the oxo derivatives was accomplished by treatment of the 2-methoxy product with HCl in dioxane.

2-OXO-3-{SPIRO[1H-INDANE-1,4'-PIPERIDINE] PROPYLAMINE(0.03 19 g, 0.123 mmol) was added to (±)-6-(3,4-difluorophenyl)-1,6-dihydro-2-methoxy-5-methoxycarbonyl-4-ethyl-1-(4-nitrophenoxy) carbonylpyrimidine (0.052 g, 0.112 mmol) in dry dichloromethane (10 mL) and the solution was stirred at room temperature for 24 h. The reaction mixture was stirred for another 1 h after addition of 6 N HCl (2 mL). After neutralization with aqueous 10% KOH solution, the reaction mixture was extracted into dichloromethane (3×10 mL). The organic layer was dried over sodium sulfate, filtered and concentrated. The crude product was purified by flash chromatography (EtOAc/MeOH, 4.5/0.5), giving of the desired product (0.040 g) as a syrup.

1 N HCl in ether (5 mL) was added to the free base (0.040 g, 0.072 mmol) in dichloromethane (4 mL) and the solution was concentrated under reduced pressure. The crude product was recrystallized from ether, giving the desired compound (0.042 g, 99%) as a pale yellow solid; mp 178–182° C.; Anal. Calcd. for $C_{29}H_{34}F_2N_4O_5Cl_2+0.6\ H_2O$: C, 57.87; H, 5.73, N 9.31. Found: C, 58.11; H 5.90; N 8.95.

General Procedure for the Reaction of the Piperidines and Piperazines with 1-(3-bromo-propylcarbamoyl)-6-(3,4-difluoro-phenyl)-4-methyl-2-oxo-1,6-dihydro-pyrimidine-5-carboxylic Acid Methyl Ester:

The amine (0.15 mmol) was added to a solution of 1-(3-bromo-propylcarbamoyl)-6-(3,4-difluorophenyl)-4-methyl-2-oxo-1,6-di-hydropyrimidine-5-carboxylic acid methyl ester (43.0 mg, 0.100 mmol) in anhydrous acetone (10 mL), followed by NaHCO$_3$ (41 mg, 0.3 mmol) and KI (16 mg, 0.1 mmol). The resulting suspension was heated to reflux for 10 h and then cooled to room temperature. The solvent was removed in vacuo and the residue was purified by flash column chromatography (EtOAc, followed by EtOAc/MeOH, 9/1). The product was then dissolved in 2 mL of chloroform, acetone or EtOAc and HCl in Et$_2$O (1 M, 0.5 mL) was added at room temperature. The solvent was removed in vacuo, giving the desired compound as an HCl salt.

EXAMPLE 1

(−)-1,2,3,6-TETRAHYDRO-1-{N-[4-(3,-ACETAMIDO)-PHENYLPIPERIDIN-1-YL]PROPYL}CARBOXAMIDO-4-METHOXYMETHYL-6-(3,4-DIFLUORO-PHENYL)-2-OXOPYRIMIDINE-5-CARBOXYLIC ACID METHYL ESTER: ESMS, 612.25 (M+1); $^1$H NMR δ 1.76–1.87 (m, 6H), 2.03–2.13 (m, 2H), 2.18 (s, 3H), 2.49 (t, J=6.9 Hz, 3H), 3.10 (d, J=11.1 Hz, 2H), 3.30–3.42 (m, 2H), 3.45 (s, 3H), 3.71 (s, 3H), 4.68 (s, 2H), 6.68 (s, 1H), 6.96 (d, J=7.5 Hz, 1H), 7.04–7.11 (m, 2H), 7.16–7.26 (m, 2H), 7.34 (d, J=6.3 Hz, 1H), 7.45 (s, 1H), 7.94 (s, 1H), 8.98 (t, J=5.4 Hz, 1H).

EXAMPLE 2

METHYL 3-[(3-4-[3-(ACETYLAMINO)PHENYL]-1,2,3,6-TETRAHYDRO-1-PYR-IDINYLPROPYL)AMINO]CARBONYL-4-(3,4-DIFLUOROPHENYL)-6-(METHOXY-METHYL)-2-OXO-1,2,3,4-TETRAHYDRO-5-PYRIMIDINECARBOXYLATE: $^1$H NMR δ 8.90 (t, 1 H, J=3.6 Hz), 7.75 (s, 1 H), 7.50–7.00 (m, 8 H), 6.68 (s, 1 H), 6.03 (br s, 1 H), 4.67 (s, 2 H), 3.71 (s, 3 H), 3.47 (s, 3 H), 3.38 (ABm, 2 H), 3.16 (m, 2 H), 2.71 (t, 2 H, J=5.4 Hz), 2.56 (m, 4 H), 2.35–1.90 (br, 2 H), 2.17 (s, 3 H), 1.82 (p, 2 H, J=7.2 Hz); ESMS, 612.25 (M+1).

EXAMPLE 3

(1)-1,2,3,6-TETRAHYDRO-1-{N-[3-(4-O-ACETYL)-4-PHENYLPIPERIDIN-1-YL]PROPYL}CARBOXAMIDO-5-METHOXYCARBONYL-4-METHOXYMETHYL-6-(3,4-DIFLUOROPHENYL)-2-OXOPYRIMIDINE: 4-Acetyl-1-(3-aminopropyl)-4-phenylpiperidine (190 mg, 0.687 mmol) was added to a stirring solution of 5-methoxy carbonyl-4-methoxymethyl-1,2,3,6-tetra-hydro-2-oxo-6-(3,4-difluorophenyl)-1-[(4-nitrophenyloxy)carbonyl] pyrimidine (281 mg, 0.573 mmol) in dry dichloromethane (3 mL) and THF (4 mL). The reaction mixture was stirred at room temperature for 12 h. The reaction mixture was quenched with aqueous 6 N HCl. The reaction mixture was concentrated to a small volume, partitioned between dichloromethane and water (100 mL each), the mixture was adjusted to pH 8 by addition of Na$_2$CO$_3$, the layers were separated, and the aqueous layer was extracted with dichloromethane (3×30 mL). The combined organic extracts were dried (Na$_2$SO$_4$) and the product was chromatographed, giving the desired product. The HCl salt was prepared by the addition of 1 N HCl in ether to a solution of the product in CH$_2$Cl$_2$. The precipitated salt was filtered, washed with ether and dried in vacuo, giving (1)-1,2,3,6-tetrahydro-1-{N-[3-(4-O-acetyl)-4-phenylpiperidin-1-yl]propyl}carboxamido-5-methoxycarbonyl-4-methoxymethyl-6-(3,4-difluorophenyl)-2-oxopyrimidine (170 mg, 47%) as the hydrochloride salt: ($C_{31}H_{36}N_4F_2O_7$+ HCl+0.6 $CH_2Cl_2$); mp 82–84° C.

EXAMPLE 4

Benzyl ester precursor to the product of Example 4: (+)-1,2,3,6-TETRAHYDRO-1-{N-[4-(BENZO-4',5'(H)FURAN)PIPERIDIN-1-YL]PROPYL}-CARBOXAMIDO-4-ETHYL-6-(3,4-DIFLUOROPHENYL)-2-OXO-PYRIMIDINE-5-CARBOXYLIC ACID PHENYLMETHYL ESTER: $^1$H NMR δ 7.60–7.00 (m, 12 H), 6.85 (br, 1 H), 6.62 (s, 1 H), 5.10 (ABq, 2 H), 5.67 (s, 2 H), 4.03 (br, 1 H), 4.01 (s, 3 H), 3.40 (apparent q, 2 H, J=6.8 Hz), 3.20–1.60 (m, 12 H), 2.86 (q, 2 H, J=2.5 Hz), 1.19 (t, 3 H, J=7.5 Hz).

(+)-1,2,3,6-TETRAHYDRO-1-{N-[4-(BENZO-4',5'(H)FURAN)PIPERIDIN-1-YL]PROPYL}-CARBOXAMIDO-4-ETHYL-6-(3,4-DIFLUOROPHENYL)-2-OXO-PYRIMIDINE-5 CARBOXYLIC ACID HYDROCHLORIDE: $^1$H NMR δ 8.95 (br s, 1 H), 8.22 (br s, 1 H), 7.40–6.95 (m, 7 H), 6.95 (s, 1 H), 6.63 (s, 1 H), 5.10–4.95 (m, 2 H), 3.40–3.20 (m, 4 H), 3.10–2.80 (m, 4 H), 2.55–2.20 (m, 1 H), 2.15 (m, 1 H), 1.85 (m, 2 H), 1.55–1.30 (m, 4 H), 1.20 (t, 3 H, J=7.6 Hz); Anal. Calc. For $C_{29}H_{32}N_4O_5F_2$+HCl+1.5 $H_2O$: C, 56.36; H, 5.87; N, 8.06. Found: C, 56.72; H, 6.11; N, 7.61.

EXAMPLE 5

1,2,3,4-TETRAHYDRO-1-OXO-2-NAPHTHACETIC ACID METHYL ESTER: Under argon, α-tetralone (5.00 g, 34.2 mmol) in dry THF (300 mL) was treated with LDA in THF (2 M, 18.8 mL) at −78° C. The solution was stirred at −78° C. for 1 h. Methyl bromoacetate (15.7 g, 0.103 mole) was then added to the solution, the mixture was stirred overnight and allowed to warm to room temperature. The solvent was evaporated and the residue was dissolved into $CHCl_3$ (300 mL), washed with water and saturated brine, and then dried over $Na_2SO_4$. After filtration and removal of solvent, the residue was vacuum distilled. The product, a colorless oil (7.21 g, 96.5%) was collected at 180° C./1 mm Hg; $^1$H NMR (400 Mhz) δ 1.98 (m, 1H), 2.25 (m, 1H), 2.44 (m, 1H), 2.90–3.20 (m, 4H), 3.73 (s, 3H), 7.10–8.10 (m, 4H); EI mass spectrum M+at m/z 218.

1-HYDROXY-2-(2-HYDROXYETHYL)-1,2,3,4-TETRAHYDRONAPHTHALENE: A solution of 1,2,3,4-tetrahydro-1-oxo-naphthacetic acid methyl ester (6.15 g, 28.2 mmol) in THF (150 mL) was treated with $LiAlH_4$ (2.82 g, 70.5 mmol) and then the reaction mixture was heated at reflux temperature for 5 h. The suspension was cooled to 0° C. and quenched by addition of solid $Na_2SO_4.10 H_2O$. The mixture was stirred at room temperature for 4 hrs. The solid was removed by filtration and concentration of the filtrate in vacuo gave a yellow oil (5.33 g, 98.3%); $^1$H NMR indicated the formation of an isomeric mixture. EI mass spectrum M+ at m/z 192. The mixture was directly used in next reaction without further purification.

2-(2-HYDROXYETHYL)-1,2,3,4-TETRAHYDRO-1-OXO-NAPHTHALENE: A solution of isomeric mixture of 1-hydroxy-2-(2-hydroxyethyl)-1,2,3,4-tetrahydronaphthalene (3.00 g, 15.6 mmol) in $CH_2Cl_2$ (100 mL) was treated with $MnO_2$ (20.4 g, 0.234 mole). The suspension was stirred at room temperature for 16 h and the solids were removed by filtration. Concentration of the filtrate in vacuo gave a brown oil, which was further purified by flash chromatography (MeOH/$CHCl_3$, 5/95), giving a yellow oil (2.00 g, 67.4%): $^1$H NMR δ 1.76 (m, 1H), 1.98 (m, 1H), 2.21 (m, 2H), 2.57 (br, 1H), 2.70 (m, 2H), 3.20 (m, 2H), 3.81 (m, 2H), 7.00–8.20 (m, 4H); CI mass spectrum (M+1)+ at m/z 191.

2-(2-BROMOETHYL)-1,2,3,4-TETRAHYDRO-1-OXONAPHTHALENE: A solution of 2-(2-hydroxethyl)-1,2,3,4-tetrahydro-1-oxo-naphthalene (2.00 g, 10.5 mmol) in $CH_2Cl_2$ (100 mL) was treated with $PBr_3$ (948 mg, 3.50 mmol) at 0° C. The mixture was stirred at room temperature for 72 h and then poured onto 100 g of ice. The organic layer was separated, washed with aqueous 10% $K_2CO_3$ solution, $H_2O$, saturated NaCl and dried over $Na_2SO_4$. After filtration and removal of the solvent, the residue was purified by chromatography (EtOAc/hexane, 1/10), giving a yellow oil (1.18 g, 44.4%); $^1$H NMR δ 1.49 (m, 2 H), 2.24 (m, 1H), 2.60 (m, 1H), 2.75 (m, 1H), 3.03 (m, 2H), 3.64 (m, 2H) 7.10–8.10 (m, 4H); EIMS M+ m/z 223, M/M+2=1:1.

2-[2-(4-BENZAMINO-1-PIPERIDYL)ETHYL]-1,2,3,4-TETRAHYDRO-1-OXO-NAPHTHALENE: A mixture of 2-(2-bromoethyl)-1,2,3,4-tetrahydro-1-oxonaphthalene (1.18 g, 4.66 mmol), 4-benzamidopiperidine (952 mg, 4.66 mmol) and $K_2CO_3$ (1.29 g, 9.32 mmol) in acetone (200 mL) was stirred at room temperature for 48 h. The solids were removed by filtration. Concentration of filtrate in vacuo gave a yellow solid which was purified by chromatography (MeOH:$CHCl_3$, 5/95). The product was recrystallized from an EtOAc/hexane mixture, giving a white powder (268 mg, 15.3%); mp 158–159° C.; $^1$H NMR δ 1.53 (m, 2H), 1.67 (m, 1H), 1.91 (m, 1H), 2.02 (m, 2H), 2.21 (m, 4H), 2.50 (m, 3H), 2.95 (m, 4H), 4.01 (m, 1H), 5.95 (d, J=8.0 Hz, 1H), 7.20–8.10 (m, 9H); CI MS (M+1) +m/z 377; Anal. Calcd for $C_{24}H_{29}N_2O_2$: C, 76.55; H. 7.51; N, 7.44. Found: C, 76.28; H, 7.46; N, 7.37.

EXAMPLE 6

METHYL 4-(2,1,3-BENZOXADIAZOL-5-YL)-3-[(1-[4-(DIBUTYLAMINO)BENZYL]-4-PIPERIDYLMETHYL)AMINO]CARBONYL-6-METHYL-2-OXO-1,2,3,4-TETRAHYDRO-5-PYRIMIDINECARBOXYLATE: $^1$H NMR δ 7.72 (dd, 1 H, J=0.6, 9.6 Hz), 7.70–7.50 (m, 2 H), 7.11 (d, 2 H, J=8.7 Hz), 6.59 (d, 2 H, J=8.7 Hz), 5.90 (s, 1 H), 3.94 (s, 3 H), 3.63 (s, 2h), 3.24 (t, 4 H, J=7.8 Hz), 2.80 (m, 2 H), 2.49 (d, 2 H, J=6.3 Hz), 2.38 (s, 3 H), 2.90–1.00 (m, 5 H), 1.54 (p, 4 H, J=7.8 Hz), 1.35 (sextet, 4 H, J=7.8 Hz), 0.94 (t, 6 H, J=7.8 Hz).

EXAMPLE 7

(+)-1,2,3,6-TETRAHYDRO-1-{N-[4-(N'-ETHYL)-N-BENZIMIDAZOLYL-PIPERIDIN-1YL]PROPYL}CARBOXAMIDO-4-METHYL-6-(3,4-DIFLUOROPHENYL)-2-OXOPYRIMIDINE HYDROCHLORIDE: $^1$H NMR δ 8.95 (t, 1 H, J=3.6 Hz), 7.61 (b, 1 H), 7.60–6.95 (m, 7 H), 6.69 (s, 1 H), 4.36 (m, 1 H), 3.94 (q, 2 H, J=7.2 Hz), 3.72 (s, 3 H), 3.42 (ABm, 4 H), 3.30 (m, 2 H, 4.76 (m, 4 H), 2.43 (s, 3 H), 2.13 (m, 2 H), 1.77 (m, 4 H), 1.33 (t, 3 H, J=7.2 Hz).

EXAMPLE 8

6-(BENZOFURAZAN-5-YL)-1,2,3,6-TETRAHYDRO-5-METHOXYCARBONYL-4-METHYL-2-OXO-1-{N-[3-(4-PHENYLPIPERIDIN-1-YL)PROPYL]}CARBOXAMIDO-PYRIMIDINE: A solution of 6-(benzofurazan-5-yl)-1,6-dihydro-2-methoxy-5-methoxycarbonyl-4-methyl-1-{N-[3-(4-phenylpiperidin-1- yl)propyl]}carboxamidopyrimidine in MeOH was treated with 6 N HCl at 0° C. The solution was stirred at room temperature for 2 h and the MeOH was removed in vacuo. 6-(Benzofurazan-5-yl)-1,2,3,6-tetrahydro-5-methoxycarbonyl-4-methyl-2-oxo-1-{N-[3-(4-phenylpiperidin-1-yl)propyl]}carboxamidopyrimidine hydrochloride was obtained as a white powder: mp 134–137° C.

EXAMPLE 9

4-(3-METHOXY)-PHENYL PIPERIDINE: HCl salt; mp 150–154° C.; $^1$H NMR δ 2.04 (s, br, 2H), 2.25 (s, br, 2H), 2.80 (s, br, 1H), 3.09 (s, br, 2H), 3.66 (s, 2H), 3.78 (s, 3H), 6.79 (s, br, 3H), 7.23 (s, 1H), 9.41 (s, br, 1H). Anal. Calcd. For $C_{12}H_{18}NOCl+0.30\ CH_2Cl_2$: C, 58.34; H, 7.40; N, 5.53. Found: C, 58.30; H, 7.71; N, 5.35.

(+)-1,2,3,6-TETRAHYDRO-1-N-[4-(3-METHOXY)-PHENYL}-PIPERIDIN-1-YL]-PROPYL-CARBOXAMIDO-4-METHOXYMETHYL-6-(3,4-DIFLUOROPHENYL)-2-OXOPYRIMIDINE-5-CARBOXYLIC ACID METHYL ESTER: mp 80–84° C.; $[\alpha]_D$=+94.7, (c=0.25, MeOH); $^1$H NMR δ 1.74–1.84 (m, 6H), 1.99–2.09 (m, 2H), 2.38–2.51 (m, 3H), 3.03 (d, J=11.1 Hz, 2H), 3.24–3.43 (m, 2H), 3.48 (s, 3H), 3.71 (s, 3H), 3.80 (s, 3H), 4.72 (s, 2H), 6.68 (s, 1H), 6.72–6.84 (m, 3H), 7.05–7.11 (m, 2H), 7.15–7.27 (m, 2H), 7.72 (s, 1H), 8.84 (t, J=5.4 Hz, 1H). Anal. Calcd. For $C_{10}H_{37}N_4O_6F_2Cl$: C, 57.8; H, 6.0; N, 9.0. Found: C, 57.61; H, 6.57; N, 6.97.

EXAMPLE 10

(+)-1,2,3,6-TETRAHYDRO-1-{N-[4-(3,-ACETAMIDO)-PHENYL-PIPERIDIN-1-YL]PROPYL}CARBOXAMIDO-4-METHOXYMETHYL-6-(3,4-DIFLUORO-PHENYL)-2-OXOPYRIMIDINE-5-CARBOXYLIC ACID METHYL ESTER: mp 135–138° C.; $[\alpha]_D$=+105.5, (c=0.11, MeOH); ESMS, 614.25 (M+1); $^1$H NMR δ 1.76–1.87 (m, 6H), 2.03–2.13 (m, 2H), 2.18 (s, 3H), 2.49 (t, J=6.9 Hz, 3H), 3.10 (d, J=11.1 Hz, 2H), 3.30–3.42 (m, 2H), 3.46 (s, 3H), 3.71 (s, 3H), 4.68 (s, 2H), 6.68 (s, 1H), 6.96 (d, J=7.5 Hz, 1H), 7.04–7.11 (m, 2H), 7.16–7.26 (m, 2H), 7.34 (d, J=6.3 Hz, 1H), 7.45 (s, 1H), 7.94 (s, 1H), 8.97 (t, J=5.4 Hz, 1H); ESMS, M+1614.25

The compound of Example 10 may also be prepared via hydrogenation of the compoun of example 2 ($H_2$ balloon method, methanol, Pd/C, overnight). A synthetic path analogous to the latter route (Scheme 11) was used in the preparation of the tritiated analog, which in turn, was used as a radioligand in the MCH pharmacological assays.

EXAMPLE 11

3-(4-PHENYLPIPERIDIN-1-YL)PROPIONITRILE: Acrylonitrile (3.1 mL, 44 mmol, 2.5 eq) was added to a solution of 4-phenylpiperidine (3.00 g, 18.0 mmol) in EtOH (40 mL) and the mixture was stirred at room temperature for 1.5 h. The volatiles were removed, giving 3.80 g of the desired product (brown oil, 99%).

3-(4-PHENYLPIPERIDIN-1-YL)PROPYLAMINE: A solution of $BH_3$ in THF (1.0 M, 83.0 mL, 83.0 mmol, 3.5 eq) was added to a stirring solution of 3-(4-phenylpiperidin-1-yl)propionitrile (5.10 g, 24.0 mmol) in anhydrous THF (20 mL) under argon at room temperature. The mixture was heated at reflux temperature for 4.5 hours and then cooled to room temperature. Aqueous 6 N HCl (130 mL) was added and stirring was continued for 2 hours at 50–70° C. The mixture was basified to pH 9 by addition of aqueous 6 N NaOH and extracted with EtOAc (100 mL) and $CH_2Cl_2$ (3×100 mL). The combined organic extracts were dried over magnesium sulfate and concentrated. The residue was dissolved in $CH_2Cl_2$ (20 mL) and treated with HCl in ether (1.0 M, 50 mL). The solvents were removed, ether (250 mL) was added, the mixture was filtered, and the filter cake was washed with ether. Water (60 mL) was added to the resulting white solid, 1 N NaOH was added until pH 10–11 was reached, and then the aqueous phase was extracted with $CH_2Cl_2$ (3×50 mL). The combined extracts were dried over magnesium sulfate and the solvents were evaporated, giving the desired product (4.50 g, 87%).

6-(3,4-DIFLOUROPHENYL)-1,2,3,6-TETRAHYDRO-5-METHOXYCARBONYL-4-METHYL-2-OXO-1-{N-[3-(4-PHENYLPIPERIDIN-1-YL) PROPYL]}CARBOXAMIDO-PYRIMIDINE: A solution of 6-(3,4-difluorophenyl)-1,6-dihydro-2-methoxy-5-methoxycarbonyl-4-methyl-1-{N-[3-(4-phenyl-piperidin-1-yl)propyl]}carboxamidopyrimidine (100 mg, 0.185 mmol, mp=43–45° C.) in MeOH (5 mL) was treated with aqueous 6 N HCl (1.5 mL) at 0° C. The solution was stirred at room temperature for 2 hrs and MeOH was removed in vacuo. 6-(3,4-Diflourophenyl)-1,2,3,6-tetrahydro-5-methoxycarbonyl-4-methyl-2-oxo-1-{N-[3-(4-phenylpiperidin-1-yl)propyl]}carboxamidopyrimidine hydrochloride was obtained as a white powder (89 mg, 86%). mp 133–136° C.

EXAMPLE 12

3-{(3,4,5-TRIFLUOROPHENYL)METHYLENE}-2,4-PENTANEDIONE: A stirring mixture of 3,4,5-trifluorobenzaldehyde (4.2 g, 26.2 mmol), 2,4-pentanedione (2.62 g, 26.2 mmol), piperidine (0.430 g, 5 mmol) in benzene (150 mL) was heated at reflux temperature (equipped with a Dean-Stark trap) for 8 h. The benzene was evaporated, the yellow oily residue, 2-{(3,4,5-trifluorophenyl)-methylene}-2,4-pentanedione, was used in the next step without further purification.

6-(3,4,5-TRIFLUOROPHENYL)-1,6-DIHYDRO-2-METHOXY-5-ACETYL-4-METHYLPYRIMIDINE: A stirring mixture of 2-{(3,4,5-trifluoro-phenyl)methylene}-2,4-pentanedione (26.2 mmol), O-methylisourea hydrogen sulfate (3.22 g, 39.3 mmol), and $NaHCO_3$ (6.60 g, 78.6 mmol) in EtOH (400 mL) was heated at 95–100° C. for 6 h. The mixture was filtered, the solid residue was washed with ethanol (100 mL). The solvent was evaporated from the combined filtrates and the crude product was purified by flash column chromatography (EtOAc/hexane, 9/1 to 4/1), giving the desired product as an oil (2.80 g, 36%).

6-(3,4,5-TRIFLUOROPHENYL)-1,6-DIHYDRO-2-METHOXY-5-ACETYL-4-METHYL-1-[(4-NITROPHENYLOXY)CARBONYL]PYRIMIDINE: 4-Nitrophenyl chloroformate (1.886 g, 9.38 mmol) was added to a solution of 6-(3,4,5-trifluorophenyl)-1,6-dihydro-2-methoxy-5-acetyl-4-methylpyrimidine (2.80 g, 9.38 mmol) and pyridine (10 mL) in $CH_2Cl_2$ (200 mL) at 0–5° C. and then the mixture was allowed to warm to room temperature. After 12 h, the solvent was evaporated and the residue was purified by flash chromatography ($CH_2Cl_2$/ EtOAc, 9/1 to 20/3), giving the desired product as a white powder (4.0 g, 92%).

6-(3,4,5-TRIFLUOROPHENYL)-1,2,3,6-TETRAHYDRO-2-OXO-5-ACETYL-4-METHYL-1-[(4-NITROPHENYLOXY)CARBONYL]PYRIMIDINE: Aqueous 6 N aqueous HCl (4 mL) was added to a stirring solution of 6-(3,4,5-trifluorophenyl)-1,6-dihydro-2- methoxy-5-acetyl-4-methyl-1-[(4-nitrophenyloxy) carbonyl]pyrimidine (4.0 g, 8.63 mmol) in THF (100 mL) at 0–5° C., and the mixture was allowed to warm to room temperature. After 2 h, the solvent was evaporated and the product was dried under vacuum, giving the desired product as a pure single component which was used in the next step without further purification (3.88 g, 100%).

(+)-1,2,3,6-TETRA HYDRO-1-{N-[4-(4-FLUOROPHENYL)PIPERIDINE-1-YL]-PROPYL} CARBOXAMIDO-5-ACETYL-2-OXO-6-(3,4,5-TRI FLUORO PHENYL)-4-METHYL PYRIMIDINE HYDROCHLORIDE: $^1$H NMR δ 7.20–6.86 (m, 6 H), 6.64 (s, 1 H), 5.56 (s, 1 H), 3.70–3.80 (m, 2 H), 3.43–3.35 (m, 2 H), 3.19–2.98 (m, 2 H), 2.40 (s, 3 H), 2.28 (s, 3 H), 2.50–1.60 (m, 8 H).

EXAMPLE 13

N1-[4-([4-(DIBUTYLAMINO)BENZYL] AMINOMETHYL)CYCLOHEXYL]-1-NAPHTHAMIDE: $^1$H NMR δ 8.26 (dd, 1 H, J=2.1, 7.2 Hz), 7.87 (m, 2 H), 7.51 (m, 2 H), 7.40 (apparent t, 1 H, J=7.8 Hz), 7.17 (d, 1 H, J=8.7 Hz), 6.61 (d, 2 H, J=8.7 Hz), 5.94 (d, 1 H, J=8,1 Hz), 4.04 (m, 1 H), 3.76 (m, 1 H), 3.63 (m, 2 H), 3.21 (t, 4 H, J=7.6 Hz average), 2.53 (d, 2 H, J=6.7 Hz), 2.10, ABm, 4 H), 1.55 (p, 4 H, J=7.7 Hz average), 1.34 (sept, 4 H, J=7.6 Hz average), 1.17 (m, 4 H), 0.95 (t, 6 H, J=7.6 Hz average).

EXAMPLE 14

(+)-1,2,3,6-TETRAHYDRO-1-{N-[4-(1-NAPHTHYL)-PIPERIDIN-1-YL]PROP-YL}CARBOXAMIDO-4-METHOXYMETHYL-6-(3,4-DIFLUOROPHENYL)-2-OXO-PYRIMIDINE-5-CARBOXYLIC ACID METHYL ESTER: mp 168–172° C.; $[α]_D$=+94.7, (c=0.25, MeOH); $^1$H NMR δ 1.75–1.84 (m, 2H), 1.87–2.01 (m, 4H), 2.14–2.28 (m, 2H), 2.47 (t, J=7.2 Hz, 2H), 3.10 (d, J=11.1 Hz, 2H), 3.28–3.45 (m, 3H), 3.48 (s, 3H), 3.71 (s, 3H), 4.68 (s, 2H), 6.70 (s, 1H), 7.05–7.12 (m, 2H), 7.16–7.24 (m, 1H), 7.42–7.54 (m, 4H), 7.69–7.75 (m, 2H), 7.85 (d, J=11.4 Hz, 1H), 8.09 (d, J=11.1 Hz, 1H), 8.91 (t, J=5.4 Hz, 1H).

EXAMPLE 15

4-(5-FLUORO-2-METHOXY)PHENYL PIPERIDINE: mp 254–258° C.; $^1$H NMR δ 1.53–1.68 (m, 2H), 1.79 (d, J=11.7 Hz, 2H), 2.12 (dt, J=2.1 Hz, J=11.7 Hz, 1H), 2.77 (dt, J=1.8 Hz, J=12.3 Hz, 1H), 2.90–3.05 (m, 1H), 3.10–3.22 (m, 2H), 3.68 (s, 1H), 3.79 (s, 3H), 6.72–6.93 (m, 3H). Anal. Calcd. For $C_{12}H_{17}NOFCl+0.14\ CH_2Cl_2$: C, 56.60; H, 6.76; N, 5.44. Found: C, 56.60; H, 6.92; N, 5.28.

(+)-1,2,3,6-TETRAHYDRO-1-{N-[4-(5-FLUORO-2-METHOXY)PHENYL PIPERI-DIN-1-YL] PROPYL}CARBOXAMIDO-4-METHOXYMETHYL-6-(3,4-DIFLUORO-PHENYL)-2-OXOPYRIMIDINE-5-CARBOXYLIC ACID METHYL ESTER: $^1$H NMR δ 8.93 (t, 1 H, J=5.4 Hz), 7.76 (br, 1 H), 7.30–6.69 (m, 7 H), 4.69 (s, 2 H), 3.79 (s, 3 H), 3.71 (s, 3 H), 3.48 (s, 3 H), 3.38 (m, 2 H), 3.10–2.80 (m, 3 H), 2.42 (t, 2 H, J=7.2 Hz), 2.07 (dt, 2 H, J=3.0, 8.4 Hz), 2.00–1.60 (m, 6 H).

EXAMPLE 16

(+)-1,2,3,6-TETRAHYDRO-1-{N-[4-HYDROXY-4-(2-PYRIDYL)-PIPERIDIN-1-YL]PROPYL) CARBOXAMIDO-4-METHOXYMETHYL-6-(3,4-DIFLUOROPHENYL)-2-OXOPYRIMIDINE-5-CARBOXYLIC ACID METHYL ESTER: mp 132–135° C.; $[α]_D$=+94.7, (c=0.25, MeOH); $^1$H NMR δ 1.47 (d, J=11.7 Hz, 2H), 1.74–1.85 (m, 2H), 2.43–2.63 (m, 9H), 2.87 (d, J=10.2 Hz, 2H), 3.30–3.47 (m, 2H), 3.49 (s, 3H), 3.71 (s, 3H), 4.69 (s, 2H), 6.69 (s, 1H), 7.04–7.21 (m, 4H), 7.49 (dd, J=0.6 Hz, J=6.9 Hz, 1H), 7.72 (s, br, 1H), 8.36 (dd, J=1.2, 4.8 Hz, 1H), 8.89 (t, J=5.4 Hz, 1H).

EXAMPLE 17

1-(3-AMINOPROPYL)-4-[2-PYRIDYL]PYRIDINIUM BROMIDE HYDROBROMIDE: A solution of 2,4'-dipyridyl (25.0 g, 160 mmol) and 3-bromopropyl-amine hydrobromide (35.0 g, 160 mmol) in DMF (60 mL) was heated at 90–95° C. for 10 h. After cooling to room temperature, anhydrous ether (500 mL) was added to the mixture, the resulting white solid was filtered, washed with Et$_2$O and dried, giving 1-(3-aminopropyl)-4-[2-pyridyl] pyridinium bromide hydrobromide (60 g, 100%)). $^1$H NMR (DMSO-d$_6$) δ 2.35–2.44 (m, 2 H), 3.08–3.13 (m, 2 H), 4.76–4.81 (m, 2 H), 7.58 (dd, J=4.8 Hz, J=7.5 Hz, 1 H), 8.03 (dt, J=1.8 Hz, J=7.8 Hz, 1 H), 8.32 (d, J=-7.8 Hz, 1 H), 8.77–8.81 (m, 3 H), 9.12 (d, J=6.3 Hz, 2 H). Anal. Calcd. for $C_{13}H_{16}N_3Br+HBr+0.5\ H_2O$: C, 40.65; H, 4.72; N, 10.94. Found: C, 40.83; H, 4.37; N, 11.05.

3-(3',6'-DIHYDRO-2'-H-[2,4']BIPYRIDINYL-1'-YL)-PROPYLAMINE: NaBH$_4$ (2 g, 53 mmol) in small portions was added to a solution of 1-(3-aminopropyl)-4-[2-pyridyl] pyridinium bromide hydrobromide (6 g, 16 mmol) in MeOH (150 mL) at 0–5° C. over a period of 2 h. The reaction mixture was stirred overnight at room temperature and then the solvent was evaporated. The residue was suspended in ether (200 mL) and treated with aqueous 50% NaOH solution (100 mL). The ether layer was separated and the aqueous layer was extracted with additional ether (2×50 mL). The combined ether extracts were dried over potassium carbonate and the solvent was removed, giving 3-(3',6'-dihydro-2'-H-[2,4']bipyridinyl-1'-yl)propylamine (3.48 g) as an oil. The crude product was used in the next step immediately without further purification.

3-AMINOPROPYL-4-(2-PYRIDYL)PIPERIDINE: A suspension of 3-(3',6'-dihydro-2'-H-[2,4']bipyridinyl-1'-yl)-propylamine (3.48 g crude, 15.9 mmol) and Pearlman's catalyst (1.0 g) in MeOH (40 mL) was hydrogenated under 120 psi for 10 h, after which the reaction mixture was filtered through a pad of Celite and the solvent was removed. The residue was purified by column chromatography over silica gel (30 g) [Note: If a large excess of silica gel is used the recovery of the product will be very low] (CH$_2$Cl$_2$/methanol/2M NH3 in MeOH, 90/8/4 to 90/40/40). The product was obtained as a pale yellow oil (3.21 g, 91%). $^1$H NMR δ (CD$_3$OD) 1.50–1.99 (m, 10 H), 2.02–2.06 (m, 2 H), 2.37–2.75 (m, 3 H), 3.02–3.06 (br m, 2 H), 7.05–7.09 (m, 4 H), 7.16 (dt, J=0.9 Hz, J=8.7 Hz, 1 H), 8.48 (dd, J=0.9 Hz, J=4.2 Hz, 1 H).

Part II (+)-6-(3,4-DIFLUOROPHENYL)-1-{N-[4-(2-PYRIDYL)PIPERIDIN-1-YL]-PROPYL] }CARBOXAMIDO-5-METHOXYCARBONYL-4-METHOXYMETHYL-2-OXO-1,2,3,6-TETRAHYDROPYRIMIDINE DIHYDROCHLORIDE 5-METHOXYCARBONYL-4-METHOXYMETHYL-1, 2,3,6-TETRAHYDRO-2-OXO-6-(3,4-DIFLUOROPHENYL)-PYRIMIDINE: Copper(I) oxide (5.06 g, 0.035 mole) and acetic acid (2.05 mL) were added sequentially to a stirring solution of methyl 4-methoxyacetoacetate (50.0 g, 0.351 mol), 3,4-difluorobenzaldehyde (51.4 g, 0.351 mmol), and urea (31.6 g, 0.527 mole) in THF (300 mL) at room temperature, followed by dropwise addition of boron trifluoride diethyl etherate (56.0 mL, 0.456 mole). The mixture was stirred at reflux temperature for 8 h, whereupon TLC (1/1 EtOAc/hexanes) indicated completion of the reaction. The reaction mixture was cooled and poured into a mixture of ice and sodium bicarbonate (100 g) and the resulting mixture was filtered through Celite. The Celite pad was washed with dichloromethane (400 mL). The organic layer was separated from the filtrate and the aqueous layer was extracted with more dichloromethane (3×300 mL). The combined organic extracts were dried (sodium sulfate) and the solvent was evaporated. The crude product was purified by flash chromatography (ethyl acetate/hexanes, 1/1;then ethyl acetate), giving the desired product as a pale yellow foam. The foam was triturated with hexanes, giving a white powder (103.3 g, 94%). $^1$H NMR δ 3.476 (s, 3H), 3.651 (s, 3H), 4.653 (s, 2H), 5.39 (s, 1H), 6.60 (br s, 1H, NH), 7.00–7.20 (m, 3H), 7.72 (br s, 1H, NH).

(+)-5-METHOXYCARBONYL-4-METHOXYMETHYL-1,2,3,6-TETRAHYDRO-2-OXO-6-(3,4-DIFLUOROPHENYL)-PYRIMIDINE: The racemic intermediate 5-methoxycarbonyl-4-methoxymethyl-1,2,3,6-tetrahydro-2-oxo-6-(3,4-difluorophenyl) pyrimidine was resolved by chiral HPLC [Chiralcel OD 20×250 mm #369-703-30604; lambda 254 nm; hexanes/ethanol 90/10; 85 mg per injection; retention time of the desired enantiomer: 16.94 min., the first enantiomer peak to elute], giving (+)-5-methoxycarbonyl-4-methoxymethyl-1,2,3,6-tetrahydro-2-oxo-6-(3,4-difluorophenyl)-pyrimidine (40–42 wt % isolation of the desired enantiomer from the racemate); $[\alpha]_D$=+83.8 (c=0.5, chloroform).

(+)-5-METHOXYCARBONYL-4-METHOXYMETHYL-1,2,3,6-TETRAHYDRO-2-OXO-6-(3,4-DIFLUOROPHENYL)-1-[(4-NITROPHENYLOXY)CARBONYL]PYRIMIDINE: A solution of lithium hexamethyldisilazide in THF (1M, 18.0 mL, 18.0 mmol) was added over 2–3 min. to a solution of (+)-5-methoxycarbonyl-4-methoxymethyl-1,2,3,6-tetrahydro-2-oxo-6-(3,4-difluorophenyl)-pyrimidine (1.98 g, 6.34 mmol) in anhydrous THF (20 mL) at −78° C. under argon atmosphere and the mixture was stirred for 10 min. The resulting solution was added over 6 min., via a cannula, to a stirred solution of 4-nitrophenyl chloroformate (4.47 g, 22.2 mmol) in THF (20 mL) at −78° C. The mixture was stirred for an additional 10 min. and the mixture was poured onto ice (50 g) and extracted with chloroform (2×50 mL). The combined extracts were dried (sodium sulfate) and the solvent evaporated. The residue was purified by flash chromatography (hexanes/ethyl acetate, 4/1 to 3.5/1), giving the product as a yellow syrup, which on trituration with hexanes became a white powder (2.40 g, 79%). $^1$H NMR δ 3.52 (s, 3H), 3.74 (s, 3H) 4.65–4.80 (q, J=16.5 Hz, 2H), 6.32 (s, 1H), 7.10–7.30 (m, 4H), 7.36 (d, J=9 Hz, 2H), 8.27 (d, J=9 Hz, 2H).

(+)-6-(3,4-DIFLUOROPHENYL)-1-{N-[4-(2-PYRIDYL)PIPERIDIN-1-YL]-PROPYL]}CARBOXAMIDO-5-METHOXYCARBONYL-4-METHOXYMETHYL-2-OXO-1,2,3,6-TETRAHYDROPYRIMIDINE DIHYDROCHLORIDE: A solution of (+)-5-methoxycarbonyl-4-methoxymethyl-1,2,3,6-tetrahydro-2-oxo-6-(3,4-difluorophenyl)-1-[(4-nitrophenyloxy)carbonyl]pyrimidine (2.38 g, 5 mmol), 3-aminopropyl-4-(2-pyridyl)piperidine (1.21 g, 5.5 mmol) in THF (20 mL) was stirred at room temperature for 12 h. The solvent was evaporated and the residue was re-dissolved in ethyl acetate (100 mL). The resulting solution was washed with ice-cold 1 N NaOH (4×50 mL), brine (2×50 mL) and dried over potassium carbonate. The solvent was evaporated in vacuo and the residue was purified by flash chromatography (dichloromethane/MeOH/2 M ammonia in MeOH, 980/10/10 to 940/30/30), giving a clean fraction of the desired product (2.45 g, 88%) as a foam and a slightly impure fraction (0.30 g, 10%). $^1$H NMR δ 1.60–2.00 (m, 6H), 2.05–2.15 (m, 2H), 2.38–2.43 (br t, 2H), 2.65–2.80 (m, 1H), 3.05–3.06 (br d, 2H), 3.30–3.45 (m, 2H), 3.48 (s, 3H), 3.704 (s, 3H), 4.68 (s, 2H), 6.68 (s, 1H), 7.05–7.20 (m, 5H), 7.58–7.63 (dt, 1H), 7.70 (s, 1H, NH), 8.50–8.52 (dd, 1H), 8.88 (br t, 1H).

The HCl salt was prepared by treatment of a solution of the free base in ether with 1 N HCl in ether. The white powder was dried under reduced pressure: $^1$H NMR δ 2.05–2.20 (m, 4H), 2.77–2.88 (m, 2H), 3.00–3.20 (m, 4H), 3.35–3.47 (m, 2H), 3.47 (s, 3H), 3.64–3.70 (m, 2H), 3.71 (s, 3H), 4.05 (br t, 1H), 4.67 (s, 2H), 6.59 (s, 1H), 7.05–7.20 (m, 3H), 7.79 (t, 1H), 8.00 (d, 1H), 8.43 (dt, 1H), 8.96 (br t, 1H, NH), 12.4 (br s, 1H). m.p. 188–191° C.; $[\alpha]_D$=+141.13 (c=0.265, MeOH); Anal. Calcd. for $C_{28}H_{34}N_5O_5F_2Cl+0.6$ $H_2O$:C, 52.36; H, 5.84; N, 10.90. Found: C, 52.24; H, 5.96; N, 10.80. (Note: NMR analysis of this product did not show the presence of any water. However, it was noted by the lab that performed the elemental analysis that this sample gains weight during handling by absorbing water from the atmosphere).

EXAMPLE 18

(1)-1,2,3,6-TETRAHYDRO-1-{N-[4-(ISOBENZOFURAN)PIPERIDINE-1-YL]-PROPYL}CARBOXAMIDO-5-METHOXYCARBONYL-2-OXO-6-(3,4-BENZOFURAZAN)-4-METHYLPYRIMIDINE HYDROCHLORIDE 4-(3,4-BENZOFURAZAN)-6-METHYL-2-OXO-3-{[3-(4-SPIRO[ISOBENZO-FURAN-1(3H),4'-PIPERIDINE]PROPYL}-1,2,3,4-TETRAHYDROPYRIMIDINE-5-CARBOXYLIC ACID METHYL ESTER: 1-(3-Aminopropyl)-4-spiro[iso-benzofuran-1 (3H),4'-piperidine] (0.028 g, 0.110 mmol) was added to (±)-6-(benzofurazan)-1,6-dihydro-2-methoxy-5-methoxycarbonyl-4-methyl-1-(4-nitrophenoxy)carbonylpyrimidine (0.047 g, 0.100 mmol) in dry dichloromethane (10 mL) and the solution was stirred at room temperature for 24 h. Aqueous 6 N HCl (2 mL) was added to the reaction mixture which was stirred for another 1 h. The reaction mixture was basified with aqueous 10% KOH solution (pH=9) and extracted into dichloromethane (3×10 mL). The organic layer was dried over sodium sulfate, filtered and concentrated. The crude product was purified by flash chromatography (EtOAc/MeOH, 4.5/0.5), giving the desired product (41.0 mg, 73%) as a syrup: $^1$H NMR δ 1.76–1.81 (m, 7 H), 1.94–2.04 (m, 6 H), 2.32–2.48 (m, 1 H), 2.83 (d, J=10.6 Hz, 2 H), 3.36–3.43 (m, 2 H), 3.75 (s, 3 H), 5.05 (s, 2 H), 6.83 (s, 1 H), 7.07–7.27 (m, 4 H), 7.54 (d, J=9.5 Hz, 1 H), 7.69 (s, 1 H), 7.78 (d, J=9.5 Hz, 1 H), 8.85 (d, J=5.2 Hz, 1 H).

HCl in ether (1 N, 5 mL) was added to the free base (0.041 g, 0.073 mmol) in dichloromethane (4 mL), and the solution was concentrated under reduced pressure. The product was recrystallized from ether, giving the hydrochloride salt as a pale yellow solid (42.0 mg, 96%); mp 180–182° C.; Anal. Calcd. for $C_{29}H_{34}N_6O_6Cl+0.5$ moles $H_2O$: C, 57.47; H, 5.65; N, 13.87. Found: C, 57.42; H, 5.71; N, 13.70.

EXAMPLE 19

2-(3,4-DIFLUOROPHENYL)4,5-DIHYDROIMIDAZOLE-1-CARBOXYLIC ACID {3-[4-

PHENYL-4-(4-BROMO-5-METHYLTHIOPNEN-2-YL)]PROPYL}-AMIDE: Anal. Calcd. for $C_{30}H_{30}N_4O_5ClF_3$+HCl+1.5 $H_2O$: C, 55.26; H, 6.03; N, 8.59. Found: C, 55.29; H, 5.95; N, 8.39.

EXAMPLE 20

4-(3,4-DIFLUORPHENYL)-6-METHYL-2-OXO-3-{[3-(4-SPIRO[ISOBENZO-FURAN-1(3H),4'-PIPERIDINE]PROPYL}-1,2,3,4-TETRAHYDROPYRIMIDINE-5-CARBOXYLIC ACID METHYL ESTER For the preparation of the ether piperidine precursor of the compound of Example 20, refer to W. E. Parham et al, *J. Org. Chem.* (1976) 41, 2268.

1-TERT-BUTOXYCARBONYL-3-(4-SPIRO[ISOBENZOFURAN-1(3H),4'-PIPERIDINE])PROPYLAMINE: N-(tert-utoxycarbonyl)-3-bromopropylamine (0.772 g, 3.27 mmol) and potassium carbonate (0.904 g, 6.54 mmol) were added to a stirring solution of the amine (0.566 g, 3.27 mmol) in dioxane (20 mL) and the reaction mixture was heated at reflux temperature for 24 h. The reaction mixture was cooled to room temperature, concentrated and partitioned between chloroform (40 mL) and water (5 mL). The organic layer was dried over sodium sulfate, filtered and concentrated. The crude product was purified by column chromatography (ethyl acetate/methanol, 4.5/0.5), giving the desired product (0.856 g, 79%) as a colorless oil; $^1H$ NMR δ 1.45 (s, 9 H), 1.63–2.04 (m, 6 H), 2.33–2.52 (m, 4 H), 2.87 (d, J=11.0 Hz, 2 H), 3.2 (br s, 2 H), 5.07 (s, 2 H), 5.6 (br s, 1 H), 7.13–7.28 (m, 4 H).

3-(4-SPIRO[ISOBENZO-FURAN-1(3H),4'-PIPERIDINE]) PROPYLAMINE: Trifluoroacetic acid (1 mL) was added to 1-tert-butoxycarbonyl 3-(4-spiro[isobenzo-furan-1(3H),4'-piperidine])propylamine (0.500 g, 1.51 mmol) in dichloromethane (5 mL) and the solution was stirred at room temperature for 1 h. The reaction mixture was concentrated, neutralized with 10% KOH solution and extracted into dichloromethane (25 mL). The organic layer was dried over sodium sulfate, filtered and concentrated, giving the desired amine (0.340 g, 98%) which was used in the subsequent step without further purification.

4-(3,4-DIFLUORPHENYL)-6-METHYL-2-OXO-3-{[3-(4-SPIRO[ISOBENZO-FURAN-1(3H),4'-PIPERIDINE]PROPYL}-1,2,3,4-TETRAHYDROPYRIMIDINE-5-CARBOXYLIC ACID METHYL ESTER: 3-(4-spiro[isobenzo-furan-1(3H),4'-piperidine]) propylamine (0.0319 g, 0.123 mmol) was added to (±)-6-(3,4-Difluorophenyl)-1,6-dihydro-2-methoxy-5-methoxycarbonyl-4-methyl-1-(4-nitrophenoxy)carbonylpyrimidine (0.052 g, 0.112 mmol) in dry dichloromethane (10 mL) and the solution was stirred at room temperature for 24 h. Aqueous 6 N HCl (2 mL) was added and the reaction mixture was stirred for an additional 1 h. After neutralization with 10% aqueous KOH solution, the reaction mixture was extracted with dichloromethane (3×10 mL). The organic layer was dried over sodium sulfate, filtered and concentrated. The crude product was purified by flash chromatography (EtOAc/MeOH, 4.5/0.5), giving the desired product (0.040 g, 64%) as a syrup; 1H-NMR δ 1.73–1.78 (m, 7 H), 1.93–2.04 (m, 2 H), 2.33–2.48 (m,, 6 H), 2.83 (d, J=11.8 Hz, 2 H), 3.35–3.41 (m, 2 H), 3.71 (s, 3 H), 5.06 (s, 2 H), 6.75 (s, 1 H), 7.04–7.26 (m, 7 H), 8.82 (t, J=5.1 Hz, 1 H).

A solution of 1 N HCl in ether (5 mL) was added to the free base (0.040 g, 0.072 mmol) in dichloromethane (4 mL) and the solution was concentrated in vacuo. The product was recrystallized from ether, giving the dihydrochloride as a pale yellow solid (0.042 g, 99%); mp 178–182° C.; Anal. Calcd. for $C_{29}H_{34}F_2N_4O_5Cl_2$+0.6 $H_2O$: C, 57.87; H, 5.73, N 9.31. Found: C, 58.11; H 5.90; N 8.95.

EXAMPLE 21

1,2,3,6-TETRAHYDRO-1-{N-[4-(DIHYDROINDENE)-1-YL}PROPYL}CARBOXAMIDO-5-METHOXYCARBONYL-2-OXO-6-(3,4-BENZOFURAZAN)-4-METHYLPYRIMID-INE

For the preparation of the indane piperidine precursor of the compound of Example 21, refer to M. S. Chambers *J. Med. Chem.* (1992) 35,2033.

N-(tert-butoxycarbonyl)3-(4-spiro[isobenzo-furan-1(3H), 4'-piperidine])propylamine(1.10 g, 4.64 mmol) and potassium carbonate (1.17 g, 8.44 mmol) were added to a stirring solution of the amine (0.790 g, 4.22 mmol) in dioxane (20 ml), and the resulting solution was heated at reflux temperature for 24 h. The reaction mixture was cooled to room temperature, concentrated and partitioned between chloroform (40 mL) and water (5 mL). The organic layer was dried over sodium sulfate, filtered and concentrated. The crude product was purified by column chromatography (ethyl acetate/methanol, 4.5/0.5), giving the desired product (0.886 g, 61%) as a colorless oil; $^1H$ NMR δ 1.46 (s, 9 H), 1.55 (d, J=11.3 Hz, 2 H), 1.69 (t, J=6.3 Hz, 2 H), 1.88–2.47 (m, 6 H), 2.47 (t, J=6.3 Hz, 2 H), 2.88 (t, J=3.3 Hz, 4 H), 3.23 (d, J=5.6 Hz, 2 H), 5.85 (br s, 1 H), 7.18 (s, 4 H).

Trifluoroacetic acid (1 ml) was added to 1-tert-butoxycarbonyl-3-(4-spiro[isobenzo-furan-1(3H),4'-piperidine])propylamine(0.180 g, 0.52 mmol) in dichloromethane (5 ml) and the resulting solution was stirred at room temperature for 1 hour. The solution was concentrated, neutralized with 10% KOH solution and extracted into dichloromethane (25 ml). The organic layer was dried over sodium sulfate, filtered and concentrated, giving propylamine (0.156 g, 100%) which was used in the subsequent step without further purification.

(±)-4-(3,4-BENZOFURAZAN)-6-METHYL-2-OXO-3-{SPIRO[1H-INDANE-1,4'-PIPERIDINE]PROPYL}-1,2,3,4-TETRAHYDROPYRIMIDINE-5-CARBOXYLIC ACID METHYL ESTER HYDROCHLORIDE: To (±)-4-(3,4-benzofurazan)-1,6-dihydro-2-methoxy-5-methoxycarbonyl-4-methyl-1-(4-nitrophenoxy)carbonylpyrimidine (0.059 g, 0.126 mmol) in dry dichloromethane (10 mL), 1-(3-aminopropyl)spiro [1H-indane-1,4'-piperidine] (0.062 g, 0.252 mmol) was added and the solution was stirred at room temperature for 24 h. The reaction mixture was stirred for another 1 h after addition of 2 mL of 6N HCl. The reaction mixture was basified with 10% aqueous KOH solution (pH=9) and extracted with dichloromethane (3×10 mL). The combined organic extracts were dried over sodium sulfate, filtered and concentrated. The crude product was purified by flash chromatography (EtOAc/MeOH, 4.5/0.5), giving 0.070 g (100%) of the desired product as a syrup: $^1H$ NMR δ 1.51 (d, J=12.5 Hz, 2 H), 1.76–2.08 (m, 4 H), 2.12 (t, J=10.3 Hz, 2 H), 2.45 (s, 5 H), 2.86–2.91 (m, 4 H), 3.30–3.45 (m, 2 H), 3.75 (s, 3 H), 6.83 (s, 1 H), 7.02 (br s, 1 H), 7.0 (m, 4 H), 7.54 (d, J=9.6 Hz, 1 H), 7.69 (s, 1 H), 7.78 (d, J=9.2 Hz, 1 H), 8.84, (t, J=5.2 Hz, 1 H).

To the free base (0.070 g, 0.125 mmol) in 4 mL of dichloromethane, 5 mL of 1 N HCl in ether was added, and the solution was concentrated under reduced pressure. Recrystallization from ether gave 0.088 g (100%) of (±)-4-(3,4-benzofurazan)-6-methyl-2-oxo-3-{spiro[1H-indane-1, 4'-piperidine]propyl}-1,2,3,4-tetrahydropyrimidine-5- carboxylic acid methyl ester hydrochloride as a white solid: m.p. 155–157° C.; Anal. Calcd. for $C_{31}H_{36}N_6O_5Cl$: C, 57.12; H, 5.76; N, 13.33. Found: C, 57.40; H, 5.96; N, 13.02.

EXAMPLE 22

(+)-1,2,3,6-TETRAHYDRO-1-{N-[4-(BENZO-4',5'(H)FURAN)PIPERIDIN-1-YL]PROPYL}CARBOXAMIDO-4-ETHYL-6-(3,4-DIFLUOROPHENYL)-2-OXO-PYRIMIDINE-5-CARBOXAMIDE HYDROCHLORIDE: DMAP.ECD (0.250 mmol, 0.050 g) was added to a stirred mixture of (+)-1,2,3,6-tetra-hydro-1-{N-[4-(benzo-4',5'(h)furan)piperidin-1-yl]propyl}carboxamido-4-ethyl-6-(3,4-difluorophenyl)-2-oxo-pyrimidine-5-carboxyl-ic acid hydrochloride (0.100 mmol, 0.055 g) and N-methylmorpholine (0.330 mL) in dry dichloromethane (10 mL). The resulting mixture was stirred at room temperature for 1 h and quenched with $NH_3$. The reaction mixture was stirred at room temperature overnight, concentrated and chromatographed, giving the desired product. The HCl salt was prepared by the addition of HCl in ether to a solution of the product in dichloromethane, followed by evaporation of the solvents. Anal. Calc. For $C_{29}H_{33}N_5O_4F_2$+HCl+0.7 $CHCl_3$: C, 52.96; H, 5.29; N, 9.40. Found: C, 52.81; H, 5.69; N, 8.97.

EXAMPLE 23

(1)-1,2,3,6-TETRAHYDRO-1-{N-[4-(3,4-DIHYDRO-2-OXOSPIRONAPHTHALENE-1(2H))-PIPERIDINE-1-YL]PROPYL}CARBOXAMIDO-5-METHOXYCARBONYL-2-OXO-6-(3,4-BENZOFURAZAN)-4-METHYLPYRIMIDINE HYDROCHLORIDE 1-(3-TERT-BUTOXYCARBONYLAMINOPROPYL)SPIRO[ISOCHROMAN-3,4' PIPERIDIN]-1-ONE: To a stirred solution of spiro[piperidine-4,1'-tetralin] To a stirred solution of spiro[isochroman-3,4'-piperidin]-1-one (K. Hashigaki et al. *Chem.Pharm.Bull.* (1984) 32, 3568.) (0.587 g, 2.58 mmol) in dioxane (20 mL), N-(tert-butoxycarbonyl)-3-bromopropylamine (0.615 g, 2.84 mmol) and potassium carbonate (0.714 g, 5.17 mmol) were added and the solution was refluxed for 24 h. The reaction mixture was cooled to room temperature, concentrated and partitioned between 40 mL chloroform and 5 mL water. The organic layer was dried over sodium sulfate, filtered and concentrated. The crude product was purified by column chromatography (ethyl acetate/methanol, 4.5/0.5) to yield 0.465 g (47%) of the desired product as a colorless oil; $^1H$ NMR δ 1.45 (s, 9 H), 1.64–2.18 (m, 7 H) 2.45–2.84 (m, 6 H), 3.19–3.95 (m, 4 H), 6.01 (br s, 1 H), 7.13–7.26 (m, 3 H), 7.42 (d, J=7.7 H).

Step B.

1-(3-AMINOPROPYL)SPIRO[ISOCHROMAN-3,4'PIPERIDIN]-1-ONE: To 1-(3-tert-Butoxycarbonylaminopropyl)spiro [isochroman-3,4'-piperidin]-1-one (0.144 g, 0.375 mmol) in 5 mL of dichloromethane, 1 mL of trifluoroacetic acid was added and the solution stirred at room temperature for 1 h. The solution was concentrated, neutralized with 10% KOH solution and extracted into 25 mL of dichloromethane. The organic layer was dried over sodium sulfate, filtered and concentrated, giving 0.110 g (100%) of the product which was used as such for the subsequent step.

(±)-4-(3,4-BENZOFURAZAN)-6-METHYL-2-OXO-3-{(SPIRO[ISOCHROMAN-3,4'-PIPERIDIN]-1-ONE)PROPYL}-1,2,3,4-TETRAHYDROPYRIMIDINE-5-CARBOXYL-IC ACID METHYL ESTER: To (±)-4-(3,4-Benzofurazan)-1,6-dihydro-2-methoxy-5-methoxycarbonyl-4-methyl-1-(4-nitrophenoxy)carbonylpyrimidine (40.0 mg, 0.0865 mmol) in 10 mL of dry dichloromethane, spiro[isochroman-3,4'piperidin]-1-one (44.0 mg, 0.173 mmol) was added and the solution was stirred at room temperature for 24 h. The reaction mixture was stirred for another 1 h after addition of 2 mL of 6N HCl. The reaction mixture was basified with 10% aqueous KOH solution (pH=9) and extracted into dichloromethane (3×10 mL). The organic layer was dried over sodium sulfate, filtered and concentrated. The crude product was purified by flash chromatography (EtOAc/MeOH, 4.5/0.5), giving 50.0 mg (100%) of the desired product as a syrup: $^1H$ NMR δ 1.67–2.13 (m, 8 H), 2.45 (m, 5 H), 2.70 (t, J=7.4 Hz, 2 H), 2.72–2.75 (m, 2 H), 3.19 (t, J=7.4 Hz, 2 H), 3.34–3.45 (m, 2 H), 3.75 (s, 3 H), 6.82 (s, 1 H), 6.87 (s, 1 H), 7.13–7.44 (m, 3 H), 7.54 (d, J=9.6 Hz, 1 H), 7.43 (d, J=7.4 Hz, 1 H), 7.69 (s, 1 H), 7.79 (d, J=9.6 Hz, 1 H), 8.87 (t, J=5.2 Hz, 1 H).

To the free base (50.0 mg, 0.084 mmol) in 4 mL of dichloromethane, 5 mL of 1 N HCl in ether was added, and the solution concentrated under reduced pressure. Recrystallization from ether gave 30.0 mg (86%) of the product as a white solid: m.p. 165–167° C.; Anal. Calcd. for $C_{31}H_{36}N_6O_6Cl$+1.5 $H_2O$: C, 57.81; H, 5.95. Found: C, 57.75; H, 5.91.

EXAMPLE 24

(1)-1,2,3,6-TETRAHYDRO-1-{N-[4-(3,4-DIHYDRO-2-OXOSPIRONAPHTHALENE-1(2H))-PIPERIDINE-1-YL]PROPYL}CARBOXAMIDO-5-METHOXY-CARBONYL-2-OXO-6-(3,4-DIFLUOROPHENYL)-4-METHYL-PYRIMIDINE (±)-4-(3,4-DIFLUOROPHENYL)-6-METHYL-2-OXO-3-{(SPIRO[ISOCHROMAN-3,4'PIPERIDIN]-1-ONE)PROPYL}-1,2,3,4-TETRAHYDROPYRIMIDINE-5-CARBOXYLIC ACID METHYL ESTER: To (±)-4-(3,4-Difluorophenyl)-1,6-dihydro-2-methoxy-5-methoxycarbonyl-4-methyl-1-(4-nitrophen-oxy)carbonylpyrimidine (40.0 mg, 0.0865 mmol) in 10 mL of dry dichloromethane, spiro[isochroman-3,4'piperidin]-1-one (44.0 mg, 0.173 mmol) was added and the solution was stirred at room temperature for 24 h. The reaction mixture was stirred for another 1 h after addition of 2 mL of 6N HCl. The reaction mixture was basified with 10% aqueous KOH solution (pH=9) and extracted into dichloromethane (3×10 mL). The organic layer was dried over sodium sulfate, filtered and concentrated. The crude product was purified by flash chromatography (EtOAc/MeOH, 4.5/0.5), giving 45.0 mg (90%) of (±)-4-(3,4-difluorophenyl)-6-methyl-2-oxo-3-{(spiro-[isochroman-3,4'piperidin]-1-one)propyl}-1,2,3,4-tetrahydropyrimi-dine-5-carboxylic acid methyl ester as a syrup; $^1H$ NMR δ 1.75–1.94 (m, 9H), 2.05–2.13 (m, 4 H), 2.36–2.41 (m, 5 H), 2.70 (t, J=7.35 Hz, 2 H), 2.77 (m, 2 H), 3.19 (t, J=7.4 Hz, 2 H), 3.39–3.43 (m, 2 H), 6.69 (s, 1 H), 7.04–7.45 (m, 8 H), 8.82 (t, J=5.2 Hz, 1 H).

To the free base (45.0 g, 0.077 mmol) in 4 mL of dichloromethane, 5 mL of 1 N HCl in ether was added, and the solution was concentrated in vacuo. Recrystallization from ether gave 0.050 g (100%) of (±)-4-(3,4-difluorophenyl)-6-methyl-2-oxo-3-{(spiro-[isochroman-3,4'piperidin]-1-one)propyl}-1,2,3,4-tetrahydro-pyrimidine-5-carboxylic acid methyl ester hydrochloride as a white solid: m.p. 150–152° C.; Anal. Calcd. for $C_{31}H_{38}F_2N_4OCl$+2 $H_2O$: C, 56.49; H, 5.96. Found: C, 56.40; H, 5.95.

EXAMPLE 25

5-[(Z)-1-(1-ETHYL-2,2,4-TRIMETHYL-1,2-DIHYDRO-6-QUINOLINYL)-METHYLIDENE]-2-THIOXO-1,3-THIAZOLAN-4-ONE

EXAMPLE 26

1-[BIS(4-FLUOROPHENYL)METHYL]-4-(3-PHENYL-2-PROPENYL)PIPERAZINE

EXAMPLE 27

4-[(4-IMIDAZO[1,2-A]PYRIDIN-2-YLPHENYL)IMINO]METHYL-5-METHYL-1,3-BENZENEDIOL

EXAMPLE 28

1-[3-(4-CHLOROBENZOYL)]PROPYL-4-BENZAMIDOPIPERIDINE

Preparation of 1-[3-(4-chlorobenzoyl)propyl]-4-benzamidopiperidine

1-[3-(4-CHLOROBENZOYL)PROPYL]-4-BENZAMIDOPIPERIDINE: A mixture of 3-(4-chlorobenzol)propyl bromide (640 mg, 2.45 mmol), 4-benzamidopiperidine (500 mg, 2.45 mmol) and $K_2CO_3$ (1.01 g, 7.34 mmol) in 50 ml of acetone was heated at reflux temperature for 48 h. The cooled reaction mixture was filtered to remove the solids, concentrated in vacuo, giving a yellow solid, which was purified by chromatography (MeOH/CHCl$_3$, 5/95). The product (320 mg 33.9%) was isolated as a white powder: $^1$H NMR δ 1.46 (dq, J1=1.0 Hz, J2=8.4 Hz, 2H), 1.90–2.10 (m, 4H), 2.16 (m, 2H), 2.43 (t, J=6.9 Hz, 2H), 2.80–2.90 (m, 2H), 2.97 (t, J=6.9 Hz, 2H), 3.97 (m, 1H), 5.92 (d, J=7.8 Hz, 1H, N—H), 7.40–8.00 (m, 9H). The product was converted to the HCl salt and recrystallized from MeOH/Et$_2$O, m.p. 243–244° C.; Anal. Calcd for $C_{22}H_{25}ClN_2O_2$+HCl+H$_2$O: C, 60.15; H, 6.37; N, 6.37; Found: C, 60.18; H, 6.34; N, 6.29.

EXAMPLE 29

4-[4-(4-CHLOROPHENYL)-4-HYDROXY-1-PIPERIDINYL]-1-(4-CHLOROPHEN-YL)-1-BUTANONE

EXAMPLE 30

N-METHYL-8-[4-(4-FLUOROPHENYL)-4-OXOBUTYL]-1-PHENYL-1,3,8-TRI-AZASPIRO-[4.5]DECAN-4-ONE

EXAMPLE 31

1H-1,2,3-BENZOTRIAZOL-1-YL (2-NITROPHENYL)SULFONE

EXAMPLE 32

(1)-1,2,3,6-TETRAHYDRO-1-{N-[4-(DIHYDROINDENE)-1-YL]PROPYL}-CARBOXAMIDO-5-METHOXYCARBONYL-2-OXO-6-(3,4-DIFLUORO)-4-METHYL-PYRIMIDINE 1-(3-TERT-BUTOXYCARBONYLAMINOPROPYL) SPIRO[1H-INDANE-1,4'-PIPERIDINE]: To a stirred solution of spiro[1H-indane-1,4'-piperidine] (M. S. Chambers et al. *J. Med. Chem.* (1992) 35, 2033.) (0.790 g, 4.22 mmol) in dioxane (20 mL), N-(tert-butoxy-carbonyl)-3-bromopropylamine (1.1 g, 4.64 mmol) and potassium carbonate (1.17 g, 8.44 mmol) were added and the resulting solution was heated at reflux temperature for 24 h. The reaction mixture was cooled to room temperature, concentrated and partitioned between 40 mL of chloroform and 5 mL of water. The organic layer was dried over sodium sulfate, filtered and concentrated. The crude product was purified by column chromatography (ethyl acetate/methanol, 4.5/0.5) to yield 0.886 g (61%) of the required product as a colorless oil: $^1$H NMR δ 1.46 (s, 9 H), 1.55 (d, J=11.3 Hz, 2 H), 1.69 (t, J=6.3 Hz, 2 H), 1.88–2.47 (m, 6 H), 2.47 (t, J=6.3 Hz, 2 H), 2.88 (t, J=3.3 Hz, 4 H), 3.23 (d, J=5.6 Hz, 2 H), 5.85 (br s, 1 H), 7.18 (s, 4 H).

1-(3-AMINOPROPYL)SPIRO[1H-INDANE-1,4'-PIPERIDINE]: To 1-(3-tert-Butoxycarbonylaminopropyl) spiro[1H-indane-1,4'-piperidine] (0.180 g, 0.52 mmol) in 5 mL of dichloromethane, 1 mL of trifluoroacetic acid was added and the solution stirred at room temperature for 1 h. The solution was concentrated, neutralized with 10% KOH solution and extracted into 25 mL of dichloromethane. The organic layer was dried over sodium sulfate, filtered and concentrated, giving 0.156 g (100%) of the product which was used as such for the subsequent step.

(±)-4-(3,4-DIFLUORO)-6-METHYL-2-OXO-3-{SPIRO [1H-INDANE-1,4'-PIPERIDINE]PROPYL}-1,2,3,4-TETRAHYDROPYRIMIDINE-5-CARBOXYLIC ACID METHYL ESTER: To (±)-4-(3,4-difluoro)1,6-dihydro-2-methoxy-5-methoxycarbonyl-4-methyl-1-(4-nitrophenoxy) carbonylpyrimidine (50.0 g, 0.108 mmol) in 10 mL of dry dichloromethane, 1-(3-aminopropyl) spiro[1H-indane-1,4'-piperidine] (53.0 mg, 0.216 mmol) was added and the solution was stirred at room temperature for 24 h. The reaction mixture was stirred for another 1 h after addition of 2 mL of 6N HCl. The reaction mixture was basified with 10% aqueous KOH solution (pH=9) and extracted into dichloromethane (3×10 mL). The organic layer was dried over sodium sulfate, filtered and concentrated. The crude product was purified by flash chromatography (EtOAc/MeOH, 4.5/0.5), giving 60.0 mg (100%) of the product as a syrup: $^1$H NMR δ 1.52 (d, J=13.2 Hz, 2 H), 1.70–2.07 (m, 8 H), 2.12 (t, J=10.3 Hz, 2 H), 2.42 (s, 4 H), 2.86–2.91 (m, 3 H), 3.32–3.43 (m, 2 H), 3.72 (s, 3 H), 6.71 (s, 1 H), 6.81 (br s, 1 H), 7.04–7.19 (m, 7 H), 8.82 (t, J=5.2 Hz, 1 H).

To the free base (0.060 g, 0.108 mmol) in 4 mL of dichloromethane, 5 mL of 1 N HCl in ether was added, and the solution was concentrated under reduced pressure. Recrystallization from ether gave 0.070 g (100%) of the product as a white solid; m.p. 150–153° C.; Anal. Calcd. for $C_{30}H_{36}F_2N_4O_6Cl$: C, 54.86; H,5.53; N, 8.54. Found: C, 54.96; H, 5.57; N, 8.27.

EXAMPLE 33

(+)-1,2,3,6-TETRAHYDRO-1-{N-[4-(3,4,5-TRIFLUORO)-PHENYL-PIPER-IDIN-1-YL] PROPYL}CARBOXAMIDO-4-METHOXYMETHYL-6-(3,4-DIFLUOROPHENYL)-2-OXOPYRIMIDINE-5-CARBOXYLIC ACID METHYL ESTER: mp ° C.; [α]$_D$=+ 123.0, (c=0.15, MeOH); $^1$H NMR δ 1.70–1.82 (m, 6H), 1.97–2.08 (m, 2H), 2.40 (t, J=6.9 Hz, 2H), 2.74–2.87 (m, 1H), 3.01 (d, J=11.1 Hz, 2H), 3.29–3.40 (m, 2H), 3.49 (s, 3H), 3.71 (s, 3H), 4.69 (s, 2H), 6. 68 (s, 1H), 6.88–6.95 (m, 2H), 7.05–7.11 (m, 2H), 7.15–7.22 (m, 1H), 7.71 (s, 1H), 8.90 (t, J=5.4 Hz, 1H).

EXAMPLE 34

(+)-1,2,3,6-TETRAHYDRO-1-{N-[2-(S)-METHYL)-4-(2-NITROPHENYL)-PIPERAZIN-1YL]PROPYL}-CARBOXAMIDO-4-METHYL-6-(3,4-DIFLUOROPHEN-YL)-2-OXO-PYRIMIDINE (S)-(+)-3-METHYL-1-(2-NITROPHENYL)-PIPERAZINE: To a solution of 2-bromonitrobenzene (0.600 g, 3.00 mmol) in 1,4-dioxane (15 mL) was added (S)-(+)-2-methylpiperazine (0.500 g, 0.500 mmol) and powdered $K_2CO_3$ (15.0 mmol, 1.50 g) and the resulting suspension was heated at reflux for 10 h. After the suspension was cooled, it was filtered through a sintered glass funnel and the solvent was removed in vacuo. The resulting residue was purified by column chromatography (1/1 hexane/EtOAc followed by 4/1 EtOAc/MeOH), giving (S)-(+)-3-methyl-1-(2-nitrophenyl)-piperazine as an orange oil (0.53 g, 80%).

(+)-1,2,3,6-TETRAHYDRO-1-{N-[2-(S)-METHYL]-4-(2-NITROPHENYL)PIPERAZIN-1YL]PROPYL}-CARBOXAMIDO-4-METHYL-6-(3,4-DIFLUOROPHENYL)-2-OXO-PYRIMIDINE: To a solution of (+)-1-(3-bromo-propylcarbamoyl)-6-(3,4-difluorophenyl)-4-methyl-2-oxo-1,6-dihydro-pyrimidine-5-carboxylic acid methyl ester (0.200 g, 0.500 mmol) and (S)-(+)-3-methyl-1-(2-nitrophenyl)-piperazine (0.170 g, 0.750 mmol) in 20 mL of anhydrous acetone was added powdered $K_2CO_3$ (0.34 g, 3.5 mmol) and KI (0.07 g, 0.5 mmol) and the resulting suspension was heated at reflux temperature for 10 h. TLC indicated a new spot for the product (Rf=0.3, 3/0.5 EtOAc/MeOH) and mostly the starting material. The suspension was cooled, filtered and the solvent was evaporated and the residue was purified by column chromatography (EtOAc/MeOH, 5/1). (+)-1,2,3,6-Tetrahydro-1-{N-[2-(S)-methyl)-4-(2-nitrophenyl)piperazin-1-yl]-propyl}-carboxamido-4-methyl-6-(3,4-difluorophenyl)-2-oxo-pyr-imidine was obtained as yellow oil (0.030 g, 10% yield). The HCl salt was prepared by the addition of HCl in ether to a solution of the product in dichloromethane, followed by evaporation of the solvents; mp 150–153° C.; $[\alpha]_D$=58.3 (c=0.3, MeOH); $^1$H NMR ($CD_3OD$)d 1.04 (d, J=6.0 Hz, 3 H), 1.71–1.78 (m, 2 H), 2.33–2.49 (m, 3 H), 2.42 (s, 3 H), 2.55–2.92 (m, 5 H), 3.00–3.10 (m, 3 H), 3.34–3.42 (m, 2 H), 3.72 (s, 3 H), 6.71 (s, 1 H), 7.01–7.32 (m, 6 H), 7.46 (dt, J=0.7 Hz, J=8.4 Hz, 1 H), 7.74 (dd, J=1.5, 8.4 Hz, 1 H), 8.82 (t, J=3.9 Hz, 1 H). Anal calcd. for $C_{28}H_{33}N_6F_2O_6$+0.20 $CH_2Cl_2$: C, 52.92; H, 5.26; N, 13.13. Found: C, 52.84; H, 5.68; N, 12.94.

EXAMPLE 35

1,2,3,6-TETRAHYDRO-1{N-[4-(2'-METHYL-PHENYL)PIPERAZIN-1-YL]-PROPYL}-CARBOXAMIDO-4-METHYL-6-(3,4-DIFLUOROPHENYL)-2-OXO-PYRIMIDINE: The amine used was 4-(2'-methyl-phenyl)piperazine. $^1$H NMR δ 1.75–1.80 (m, 2 H), 2.29 (s, 3 H), 2.42 (s, 3 H), 2.41–2.48 (m, 2 H), 2.58–2.62 (m, 4 H), 2.91–2.97 (m, 4 H), 3.35–3.42 (m, 2 H), 3.72 (s, 3 H), 6.71 (s, 1 H), 6.97–7.26 (m, 8 H), 8.81 (t, J=3.9 Hz, 1 H). The product was dissolved in ether and 1 N HCl in ether was added. The ether was evaporated, giving the dihydrochloride salt; mp 66–71° C. Anal calcd. for $C_{28}H_{35}N_5F_2O_4$ $Cl_3$+1.75 acetone: C, 55.73; H, 6.40; N, 9.78. Found: C, 56.16; H, 6.29; N, 10.06.

EXAMPLE 36

(+)-1,2,3,6-TETRAHYDRO-5-METHOXYCARBONYL-4-METHOXYMETHYL-2-OXO-1-{N-[3-(4-METHYL-4-PHENYL PIPERIDINE-1-YL]PROPYL}-6-(3,4-DIFLUOROPHENYL) PYRIMIDINE: Hygroscopic; $[\alpha]_D$=+82.1(c=0.31, MeOH); $^1$H NMR δ 1.14 (s, 3 H), 1.61–1.72 (m, 4 H), 2.03–2.08 (m, 2 H), 2.25 (t, J=7.2 Hz, 2 H), 2.30–2.42 (m, 4 H), 3.19–3.31 (m, 2 H), 3.40 (s, 3 H), 3.63 (s, 3 H), 4.60 (s, 2 H), 6.60 (s, 1 H), 6.97–7.29 (m, 8 H), 7.63 (br s, 1 H), 8.78 (t, J=5.7 Hz, 1 H). Anal calcd. for $C_{30}H_{37}N_4O_5F_2Cl$+$CH_2Cl_2$: C, 53.80; H, 5.68; N, 8.10. Found: C, 53.79; H, 6.03; N, 7.83.

EXAMPLE 37

5-(5-BUTYL-2-THIENYL)PYRIDO[2,3-d] PYRIMIDINE-2,4,7(1H,3H,8H)-TRIONE

General Procedure for the reaction of pyrimidine-3-carboxylic acid-4-nitrophenyl esters with amines: A solution of substituted pyrimidine-3-carboxylic acid-4-nitrophenyl ester ((0.29 mmol) and a substituted 4-phenyl-1-(3-propylaminopiperidine (0.30 mmol) in 10 mL of anhydrous THF was stirred overnight at room temperature. The solvent was removed in vacuo and the residue was purified by column chromatography.

EXAMPLE 38

METHYL (4S)-3-[({3-[4-(3-AMINOPHENYL)-1-PIPERIDINYL]PROPYL}AMINO)CARBONYL]-4-(3,4-DIFLUOROPHENYL)-6-(METHOXYMETHYL)-2-OXO-1,2,3,4-TETRAHYDRO-5-PYRIMIDINECARBOXYLATE: $^1$H NMR (400 MHz, $CDCl_3$) δ 7.80 (s, 1H), 7.22–7.02 (m, 2H), 6.95 (t, 2H, J=8.7 Hz), 6.63–6.44 (m, 4H), 4.56 (ABq, 2H), 3.62 (s, 3H), 3.33 (s, 3H), 3.32 (m, 4H), 2.96 (br s, 2H), 2.34 (t, 2H, J=7.5 Hz), 2.11–1.94 (m, 3H), 1.81–1.64 (m, 4H); ESMS m/e: 572.3 (M+H)$^+$.

EXAMPLE 39

The product was obtained according to the method described for Example 40.

METHYL (4S)-4-(3,4-DIFLUOROPHENYL)-3-({[3-(4-{3-[(METHOXYACETYL)AMINO]PHENYL}-1-PIPERIDINYL)PROPYL]AMINO}CARBONYL)-6-(METHOXYMETHYL)-2-OXO-1,2,3,4-TETRAHYDRO-5-PYRIMIDINECARBOXYLATE: 15.6 mg (69% yield); $^1$H NMR (400 MHz, $CDCl_3$) δ 9.01 (s, 1H), 8.25 (s, 1H), 7.60 (s, 1H), 7.37 (d, 1H, J=7.2 Hz), 7.30–7.05 (m, 5H), 7.02 (d, 1H, J=8.0 Hz), 6.71 (s, 1H), 4.70 (s, 2H), 4.03 (s, 2H), 3.73 (s, 3H), 3.53 (s, 3H), 3.47 (s, 3H), 3.42–3.33 (m, 2H), 3.08 (br s, 2H), 2.49 (br s, 2H), 2.20 (s, 2H), 2.07 (br s, 1H), 1.97–1.75 (m, 4H); ESMS m/e: 644.3 (M+H)$^+$

EXAMPLE 40

METHYL (4S)-4-(3,4-DIFLUOROPHENYL)-3-({[3-(4-{3-[(3,3-DIMETHYLBUTANOYL)AMINO]PHENYL}-1-PIPERIDINYL)PROPYL]AMINO}CARBONYL)-6-(METHOXYMETHYL)-2-OXO-1,2,3,4-TETRAHYDRO-5-PYRIMIDINECARBOXYLATE

To the 20 ml vial was added methyl (4S)-3-[({3-[4-(3-aminophenyl)-1-piperidinyl]propyl}amino)carbonyl]-4-(3,4-difluorophenyl)-6-(methoxymethyl)-2-oxo-1,2,3,4-tetrahydro-5-pyrimidinecarboxylate (0.035 mmol), an acid chloride or sulfonyl chloride (1.5 eq), N,N-diisopropylethylamine (5 eq) and dichloromethane (2 ml) at room temperature. The reaction mixture was stirred at room temperature for 24 h, at which time the TLC analysis indicated the reaction was completed. The reaction mixture was concentrated to a small volume and purified by preparative TLC (silica, 2000 microns, 95:5=dichloromethane:methanol with 1% of isopropylamine) to give 5.6 mg of methyl (4S)-4-(3,4-difluorophenyl)-3-({[3-(4-{3-[(3,3-dimethylbutanoyl)amino]phenyl}-1-piperidinyl)propyl]amino}carbonyl)-6-(methoxymethyl)-2-oxo-1,2,3,4-tetrahydro-5-pyrimidinecarboxylate: 24.6% yield; ¹H NMR (400 MHz, CDCl₃) δ 7.50 (s, 1H), 7.26 (d, 1H, J=8.3 Hz), 7.15–7.02 (m, 5H), 6.88 (d, 1H, J=8.3 Hz), 6.55 (s, 1H), 4.56 (ABq, 2H), 3.62 (s, 3H), 3.32 (s, 3H), 3.25 (t, 4H, J=9.0 Hz), 2.99 (d, 2H, J=10.8 Hz), 2.49–2.37 (m, 3H), 2.08 (t, 2H, J=11.7 Hz), 1.78–1.65 (m, 14H); ESMS m/e: 670.4 (M+H)⁺.

EXAMPLE 41

The product was obtained according to the method described for methyl (4S)-4-(3,4-difluorophenyl)-3-({[3-(4-{3-[(3,3-dimethylbutanoyl)amino]phenyl}-1-piperidinyl)propyl]amino}carbonyl)-6-(methoxymethyl)-2-oxo-1,2,3,4-tetrahydro-5-pyrimidinecarboxylate.

METHYL (4S)-4-(3,4-DIFLUOROPHENYL)-6-(METHOXYMETHYL)-2-OXO-3-{[(3-{4-[3-(PROPIONYLAMINO)PHENYL]-1-PIPERIDINYL}PROPYL)AMINO]CARBONYL}-1,2,3,4-TETRAHYDRO-5-PYRIMIDINECARBOXYLATE: 9.9 mg (45% yield) δ ¹H NMR (400 MHz, CDCl₃) δ 7.36 (s, 1H), 7.28 (d, 1H, J=8.0 Hz), 7.16–7.02 (m, 5H), 6.86 (d, 1H, J=7.6 Hz), 6.54 (s, 1H), 4.56 (ABq, 2H), 3.62 (s, 3H), 3.32 (s, 3H), 3.27–3.19 (m, 4H), 2.95 (d, 2H, J=10.3 Hz), 2.41 (m, 1H), 2.34 (t, 2H, J=7.7 Hz), 2.28 (q, 2H, J=7.6 Hz), 2.01 (t, 2H, J=11.1 Hz), 1.73–1.64 (m, 8H); ESMS m/e: 628.4 (M+H)⁺

EXAMPLE 42

The product was obtained according to the method described for methyl (4S)-4-(3,4-difluorophenyl)-3-({[3-(4-{3-[(3,3-dimethylbutanoyl)amino]phenyl}-1-piperidinyl)propyl]amino}carbonyl)-6-(methoxymethyl)-2-oxo-1,2,3,4-tetrahydro-5-pyrimidinecarboxylate.

METHYL (4S)-4-(3,4-DIFLUOROPHENYL)-6-(METHOXYMETHYL)-3-({[3-(4-{3-[(3-METHYLBUTANOYL)AMINO]PHENYL}-1-PIPERIDINYL)PROPYL]AMINO}CARBONYL)-2-OXO-1,2,3,4-TETRAHYDRO-5-PYRIMIDINECARBOXYLATE: 10.4 mg (45% yield) δ ¹H NMR (400 MHz, CDCl₃) δ 7.36 (s, 1H), 7.28 (d, 1H, J=7.9 Hz), 7.16–7.03 (m, 5H), 6.88 (d, 1H, J=7.4 Hz), 6.56 (s, 1H), 4.56 (ABq, 2H), 3.62 (s, 3H), 3.32 (s, 3H), 3.25 (t, 4H, J=6.7 Hz), 2.98 (d, 2H, J=11.1 Hz), 2.43 (m, 1H), 2.38 (t, 2H, J=7.5 Hz), 1.13 (d, 2H, J=7.5 Hz), 2.10–2.01 (m, 2H), 1.75–1.64 (m, 6H), 0.91 (d, 6H, J=5.8 Hz); ESMS m/e: 656.4 (M+H)⁺

EXAMPLE 43

The product was obtained according to the method described for methyl (4S)-4-(3,4-difluorophenyl)-3-({[3-(4-{3-[(3,3-dimethylbutanoyl)amino]phenyl}-1-piperidinyl)propyl]amino}carbonyl)-6-(methoxymethyl)-2-oxo-1,2,3,4-tetrahydro-5-pyrimidinecarboxylate.

METHYL (4S)-4-(3,4-DIFLUOROPHENYL)-3-{[(3-{4-[3-(ISOBUTYRYLAMINO)PHENYL]-1-PIPERIDINYL}PROPYL)AMINO]CARBONYL}-6-(METHOXYMETHYL)-2-OXO-1,2,3,4-TETRAHYDRO-5-PYRIMIDINECARBOXYLATE: 16.4 mg (73% yield) δ ¹H NMR (400 MHz, CDCl₃) δ 7.37 (s, 1H), 7.28 (d, 1H, J=7.3 Hz), 7.16–7.01 (m, 5H), 6.88 (d, 2H, J=7.3 Hz), 6.54 (s, 1H), 4.56 (ABq, 2H), 3.62 (s, 3H), 3.32 (s, 3H), 3.25 (t, 2H, J=6.8 Hz), 3.23–3.18 (m, 2H), 3.03 (d, 2H, J=11.7 Hz), 2.57–2.48 (m, 1H), 2.43 (t, 2H, J=8.0 Hz), 2.14 (t, 2H, J=9.4 Hz), 1.8–1.65 (m, 5H), 1.09 (d, 6H, J=6.3 Hz); ESMS m/e: 642.4 (M+H)⁺

EXAMPLE 44

The product was obtained according to the method described for methyl (4S)-4-(3,4-difluorophenyl)-3-({[3-(4-{3-[(3,3-dimethylbutanoyl)amino]phenyl}-1-piperidinyl)propyl]amino}carbonyl)-6-(methoxymethyl)-2-oxo-1,2,3,4-tetrahydro-5-pyrimidinecarboxylate.

METHYL (4S)-3-{[(3-{4-[3-(BUTYRYLAMINO)PHENYL]-1-PIPERIDINYL}PROPYL)AMINO]CARBONYL}-4-(3,4-DIFLUOROPHENYL)-6-(METHOXYMETHYL)-2-OXO-1,2,3,4-TETRAHYDRO-5-PYRIMIDINECARBOXYLATE: 14.7 mg (65.5% yield) δ ¹H NMR (400 MHz, CDCl₃) δ 7.38 (s, 1H), 7.26 (s, 1H), 7.17–6.99 (m, 5H), 6.87 (s, 1H), 6.55 (s, 1H), 4.56 (ABq, 2H), 3.63 (s, 3H), 3.33 (s, 3H), 3.28–3.17 (m, 6H), 3.0 (br s, 2H), 2.51–2.36 (m, 3H), 2.25 (t, 2H, J=5.0 Hz), 2.10 (br s, 2H), 1.8–1.56 (m, 6H), 0.90 (t, 3H, J=5.0 Hz); ESMS m/e: 642.4 (M+H)⁺.

EXAMPLE 45

(4R)-N-(3-{4-[3-(BUTYRYLAMINO)PHENYL]-1-PIPERIDINYL}PROPYL)-4-(3,4-DIFLUOROPHENYL)-6-(METHOXYMETHYL)-2-OXO-1,2,3,4-TETRAHYDRO-5-PYRIMIDINECARBOXAMIDE

Method:

(4R)-4-(3,4-difluorophenyl)-6-(methoxymethyl)-2-oxo-1,2,3,4-tetrahydro-5-pyrimidinecarboxylic acid: A stirred mixture of one mole equivalent of methyl (4R)-4-(3,4-difluorophenyl)-6-(methoxymethyl)-2-oxo-1,2,3,4-tetrahydro-5-pyrimidinecarboxylate (10.0 g, 32.0 mmol) and lithium hydroxide (2 equivalents, 1.53 g, 64.0 mol) in H₂O-THF (2:1, 300 mL) was heated at reflux temperature for 1 h. The reaction mixture was concentrated, dissolved in water, washed with ethyl acetate and acidified (1 N HCl) to pH 3–4 (pH paper). The precipitated product was collected, washed with water and dried under reduced pressure to give the desired product in 90% yield.

(4R)-4-(3,4-DIFLUOROPHENYL)-6-(METHOXYMETHYL)-N-[3-(4-(3-NITROPHENYL)-3,6-DIHYDRO-1(2H)-PYRIDINYL)PROPYL]-2-OXO-1,2,3,4-TETRAHYDRO-5-PYRIMIDINECARBOXAMIDE: A solution of (4R)-4-(3,4-difluorophenyl)-6-(methoxymethyl)-2-oxo-1,2,3,4-tetrahydro-5-pyrimidinecarboxylic acid (1.2 eq), EDC (1.5 Eq.), N-methylmorpholine (2.0 Eq.) in dichloromethane was stirred at room temperature for 15 minutes, followed by addition of 3-(4-(3-nitrophenyl)-3,6-dihydro-1(2H)-pyridinyl)-1-propanamine (1.0 eq.) to the reaction mixture. The resulting solution was stirred for 18 hours, concentrated and chromatographed on silica to give (4R)-4-(3,4-difluorophenyl)-6-(methoxymethyl)-N-[3-(4-(3-nitrophenyl)-3,6-dihydro-1(2H)-pyridinyl)propyl]-2-oxo-1,2,3,4-tetrahydro-5-pyrimidinecarboxamide.

(4R)-N-{3-[4-(3-AMINOPHENYL)-1-PIPERIDINYL]PROPYL}-4-(3,4-DIFLUOROPHENYL)-6-(METHOXYMETHYL)-2-OXO-1,2,3,4-TETRAHYDRO-5-PYRIMIDINECARBOXAMIDE: A mixture of (4R)-4-(3,4-difluorophenyl)-6-(methoxymethyl)-N-[3-(4-(3-nitrophenyl)-3,6-dihydro-1(2H)-pyridinyl)propyl]-2-oxo-1,2,3,4-tetrahydro-5-pyrimidinecarboxamide, 10% Pd/C in ethanol was hydrogenated (balloon method) for 2 days. The reaction mixture was filtered through Celite 545, washed with ethanol and concentrated to give the desired product.

(4R)-N-(3-{4-[3-(BUTYRYLAMINO)PHENYL]-1-PIPERIDINYL}PROPYL)-4-(3,4-DIFLUOROPHENYL)-6-(METHOXYMETHYL)-2-OXO-1,2,3,4-TETRAHYDRO-5-PYRIMIDINECARBOXAMIDE: Into a 20 mL vial was added(4R)-N-{3-[4-(3-aminophenyl)-1-piperidinyl]propyl}-4-(3,4-difluorophenyl)-6-(methoxymethyl)-2-oxo-1,2,3,4-tetrahydro-5- pyrimidinecarboxamide (0.040 mmol), acid chloride (1.5 eq) and N,N-diisopropylethylamine (5.0 eq) in 2.0 mL of dichloromethane at room temperature. After 24 hrs, the reaction mixture was concentrated in vacuo and purified by preparative TLC (silica, 2000 microns, 95:5= dichloromethane:methanol with 1% of isopropylamine) to give 9.2 mg (45% yield) of the desired product: $^1$H NMR (400 MHz, CD$_3$OD) δ 7.49 (s, 1H), 7.25 (d, 1H, J=7.6 Hz), 7.20–7.02 (m, 5H), 6.91 (d, 1H, J=8 Hz), 5.29 (s, 1H), 4.24 (ABq, 2H), 3.30 and 3.24 (two s, 3H), 3.46–3.12 (m, partially hidden by three s, 4H), 2.74 (br s, 4H), 2.25 (t, 2H, J=8.2 Hz), 2.04–1.69 (m, 7H), 1.63 (sextet, 2H, J=7.4 Hz), 0.91 (t, 3H, 7.4 Hz); ESMS m/e: 584.4 (M+H)$^+$.

EXAMPLE 46

The product was obtained according to the method described for (4R)-N-(3-{4-[3-(butyrylamino)phenyl]-1-piperidinyl}propyl)-4-(3,4-difluorophenyl)-6-(methoxymethyl)-2-oxo-1,2,3,4-tetrahydro-5-pyrimidinecarboxamide.

(4R)-4-(3,4-DIFLUOROPHENYL)-6-(METHOXYMETHYL)-2-OXO-N-(3-{4-[3-(PROPIONYLAMINO)PHENYL]-1-PIPERIDINYL}PROPYL)-1,2,3,4-TETRAHYDRO-5-PYRIMIDINECARBOXAMIDE: 5.6 mg (24.6% yield); $^1$H NMR (400 MHz, CD$_3$OD) δ 7.56 (s, 1H), 7.35 (d, 1H, J=6.9 Hz), 7.3–7.03 (m, 4H), 7.17 (br s, 1H), 6.99 (d, 1H, J=7.0 Hz), 5.45 (s, 1H), 4.33 (ABq, 2H), 3.41 (s, 3H), 3.37–3.23 (m, partially hidden, 4H), 2.8 (br s, 4H), 2.39 (d, 2H, J=9.3 Hz), 2.14–1.78 (m, 7H), 1.21 (t, 3H, J=7.6 Hz); ESMS m/e: 570.4 (M+H)$^+$.

EXAMPLE 47

The product was obtained according to the method described for (4R)-N-(3-{4-[3-(butyrylamino)phenyl]-1-piperidinyl}propyl)-4-(3,4-difluorophenyl)-6-(methoxymethyl)-2-oxo-1,2,3,4-tetrahydro-5-pyrimidinecarboxamide.

(4R)-4-(3,4-DIFLUOROPHENYL)-6-(METHOXYMETHYL)-N-[3-(4-{3-[(3-METHYLBUTANOYL)AMINO]PHENYL}-1-PIPERIDINYL)PPROPYL]-2-OXO-1,2,3,4-TETRAHYDRO-5-PYRIMIDINECARBOXAMIDE: 11.1 mg (46% yield); $^1$H NMR (400 MHz, CD$_3$OD) δ 7.81 (d, 1H, J=8.5 Hz), 7.6 (s, 1H), 7.55 (s, 1H), 7.36 (br s, 1 H), 7.31–7.17 (m, 3H), 7.01 (t, 1H, J=6.7 Hz) 6.64–6.61 (m, 1H), 5.45 (br s, 1H), 4.32 (ABq, 2H), 3.94 and 3.87 (two s, 3H), 3.42–3.12 (m, partially hidden, 2H), 3.1 (br s, 2H), 3.0 (t, 2H, J=11.1 Hz), 2.79–2.57 (m, 4H), 2.27–1.73 (m, 8H), 1.19 and 1.01 (two d, 6H, J=6.6 Hz); ESMS m/e: 598.4 (M+H)$^+$.

EXAMPLE 48

The product was obtained according to the method described for (4R)-N-(3-{4-[3-(butyrylamino)phenyl]-1-piperidinyl}propyl)-4-(3,4-difluorophenyl)-6-(methoxymethyl)-2-oxo-1,2,3,4-tetrahydro-5-pyrimidinecarboxamide.

(4R)-4-(3,4-DIFLUOROPHENYL)-6-(METHOXYMETHYL)-N-[3-(4-{3-[(2-METHYLBUTANOYL)AMINO]PHENYL}-1-PIPERIDINYL)PROPYL]-2-OXO-1,2,3,4-TETRAHYDRO-5-PYRIMIDINECARBOXAMIDE: 6.7 mg (28% yield); $^1$H NMR (400 MHz, CD$_3$OD) δ 7.59 (s, 1H), 7.35 (br s, 1H), 7.3–7.2 (m, 3H), 7.17 (br s, 1H), 7.01 (d, 1H, J=6.8 Hz), 5.45 (s, 1H), 4.33 (ABq, 2H), 3.39 (s, 3H), 3.29 (m, 2H), 2.84 (br s, 4H), 2.42 (m, 1H), 2.14–1.78 (m, 9H), 1.7 (m, 1H), 1.49 (m, 1H), 1.20 (d, 3H, J=6.7 Hz), 0.95 (t, 3H, J=6.6 Hz); ESMS m/e: 598.4 (M+H)$^+$.

EXAMPLE 49

The product was obtained according to the method described for (4R)-N-(3-{4-[3-(butyrylamino)phenyl]-1-piperidinyl}propyl)-4-(3,4-difluorophenyl)-6-(methoxymethyl)-2-oxo-1,2,3,4-tetrahydro-5-pyrimidinecarboxamide.

(4R)-4-(3,4-DIFLUOROPHENYL)-N-[3-(4-{3-[(3,3-DIMETHYLBUTANOYL)AMINO]PHENYL}-1-PIPERIDINYL)PROPYL]-6-(METHOXYMETHYL)-2-OXO-1,2,3,4-TETRAHYDRO-5-PYRIMIDINECARBOXAMIDE: 1.1 mg (4.4% yield); $^1$H NMR (400 MHz, CD$_3$OD) δ 7.6–6.91 (m, 7H), 5.43 (s, 1H), 4.31 (ABq, 2H), 3.40 (s, 3H), 3.27–1.26 (m, 17 H), 1.09 (s, 9H); ESMS m/e: 612.4 (M+H)$^+$.

EXAMPLE 50

The product was obtained according to the method described for (4R)-N-(3-{4-[3-(butyrylamino)phenyl]-1-piperidinyl}propyl)-4-(3,4-difluorophenyl)-6-(methoxymethyl)-2-oxo-1,2,3,4-tetrahydro-5-pyrimidinecarboxamide.

(4R)-4-(3,4-DIFLUOROPHENYL)-N-(3-{4-[3-(ISOBUTYRYLAMINO)PHENYL]-1-PIPERIDINYL}PROPYL)-6-(METHOXYMETHYL)-2-OXO-1,2,3,4-TETRAHYDRO-5-PYRIMIDINECARBOXAMIDE: 12.7 mg (54% yield); $^1$H NMR (400 MHz, CD$_3$OD) δ 7.59(s, 1H), 7.36 (d, 1H, J=8.6 Hz), 7.31–7.07 (m, 4H), 7.01 (d, 1H, J=6.5 Hz), 5.39 (s, 1H), 4.34 (ABq, 2H), 3.35 (s, 3H), 3.33–3.19 (m, partially hidden, 2H), 3.08–2.72 (m, 4H), 2.63 (t, 2H, J=7.2 Hz), 2.14–1.82 (m, 8H), 1.19 (d, 6H, J=6.9 Hz); ESMS m/e: 584.4 (M+H)$^+$.

EXAMPLE 51

The synthetic method is the same as described for the synthesis of (4S)-N-(3-{4-[3-(acetylamino)phenyl]-1-piperidinyl}propyl)-4-(3,5-difluorophenyl)-2-oxo-1,3-oxazolidine-3-carboxamide.

5-ACETYL-N-(3-{4-[3-(ACETYLAMINO)PHENYL]-1-PIPERIDINYL}PROPYL)-4-METHYL-2-OXO-6-(3,4,5-TRIFLUOROPHENYL)-3,6-DIHYDRO-1(2H)-PYRIMIDINECARBOXAMIDE: 14.5 mg (46% yield); $^1$H NMR (400 MHz, CDCl$_3$) δ 9.56 (s, 1H), 9.20 (s, 1 H), 8.21 (s, 1H), 7.52 (s, 1H), 7.18 (t, 1H, J=7.8 Hz), 7.07–6.75 (m, 5H), 3.59–3.37 (m, 1H), 3.48–3.38 (m, 1H), 3.08 (br s, 2H), 2.57–2.39 (m, 5H), 2.25 (s, 3H), 2.21 (s, 3H), 2.19–1.59 (m, 9H); ESMS m/e: 586.3 (M+H)$^+$; Anal. Calc. for C$_{30}$H$_{34}$F$_3$N$_5$O$_4$+0.1CHCl$_3$: C, 60.50; H, 5.75; N, 11.72. Found: C, 60.59; H, 5.40; N, 11.73.

EXAMPLE 52

The synthetic method is the same as described for the synthesis of (4S)-N-(3-{4-[3-(acetylamino)phenyl]-1-piperidinyl}propyl)-4-(3,5-difluorophenyl)-2-oxo-1,3-oxazolidine-3-carboxamide.

BENZYL 3-{[(3-{4-[3-(ACETYLAMINO)PHENYL]-1-PIPERIDINYL}PROPYL)AMINO]CARBONYL}-4-(2,4-DIFLUOROPHENYL)-6-ETHYL-2-OXO-1,2,3,4-TETRAHYDRO-5-PYRIMIDINECARBOXYLATE: 14.8 mg (41% yield); $^1$H NMR (400 MHz, CDCl$_3$) δ 9.05 (br s, 1H), 8.14 (s, 1H), 7.47 (s, 1H) 7.37–7.21 (m, 8H), 7.18 (t, 1H, J=7.7 Hz), 6.94 (d, 1H, J=6.9 Hz), 6.87 (d, 1H, J=7.4 Hz), 6.7–6.62 (m, 3H), 5.09 (q, 2H, J=17.8 Hz), 3.48–3.24 (m, 2H), 3.04 (ABq, 2H), 2.88–2.71 (m, 2H), 2.52–2.39 (m, 2H), 2.19 (s, 3H), 2.17–1.88 (m, 3H), 1.77–1.58 (m, 3H), 1.19 (t, 3H, J=7.5 Hz); ESMS m/e: 674.4 (M+H)$^+$.

EXAMPLE 53

The synthetic method is the same as described for the synthesis of (4S)-N-(3-{4-[3-(acetylamino)phenyl]-1-piperidinyl}propyl)-4-(3,5-difluorophenyl)-2-oxo-1,3-oxazolidine-3-carboxamide.

N-(3-{4-[3-(ACETYLAMINO)PHENYL]-1-PIPERIDINYL}PROPYL)-4-(1,3-BENZODIOXOL-5-YL)-2,5-DIOXO-1,2,5,7-TETRAHYDROFURO[3,4-D]PYRIMIDINE-3(4H)-CARBOXAMIDE: 8.75 mg (28% yield); $^1$H NMR (400 MHz, CDCl$_3$) δ 9.81 (s, 1H), 8.14 (s, 1H), 7.53 (s, 1H). 7.21 (t, 1H, J=7.7 Hz), 6.99 (d, 1H, J=7.7 Hz), 6.91–6.7 (m, 4H), 6.42 (s, 1H), 5.9 (s, 2H), 4.75 (s, 2H), 3.61–3.5 (m, 1H), 3.37–3.27 (m, 1H), 3.08 (br s, 2H), 2.56–2.40 (m, 3H), 2.18 (s, 3H), 2.16–1.85 (m, 4H), 1.78–1.6 (m, 5H); ESMS m/e: 576.3 (M+H)$^+$.

EXAMPLE 54

The synthetic method is the same as described for the synthesis of (4S)-N-(3-{4-[3-(acetylamino)phenyl]-1-piperidinyl}propyl)-4-(3,5-difluorophenyl)-2-oxo-1,3-oxazolidine-3-carboxamide.

METHYL 1-{[(3-{4-[3-(ACETYLAMINO)PHENYL]-1-PIPERIDINYL}PROPYL)AMINO]CARBONYL}-2-[(4-METHOXYBENZYL)SULFANYL]-4-METHYL-6-(4-NITROPHENYL)-1,6-DIHYDRO-5-PYRIMIDINECARBOXYLATE: 10.1 mg (26% yield); $^1$H NMR (400 MHz, CDCl$_3$) δ 8.02 (d, 2H, J=7.5 Hz), 7.53 (br s, 1H), 7.44–7.27 (m, 6H), 7.14 (d, 2H, J=8.5 Hz), 6.99 (d, 1H, J=7.6 Hz), 6.75 (d, 2H, J=8.5 Hz), 6.2 (s, 1H), 4.23 (ABq, 2H), 3.78 (s, 3H), 3.7 (s, 3H), 3.58–3.48 (m, 1H) 3.37–3.26 (m, 2H), 3.04 (m, 2H), 2.61–2.43 (m, 3H), 2.41 (s, 3H), 2.16 (s, 3H), 2.15–1.64 (m, 8H); ESMS m/e: 729.3 (M+H)$^+$.

EXAMPLE 55

The synthetic method is the same as described for the synthesis of (4S)-N-(3-{4-[3-(acetylamino)phenyl]-1-piperidinyl}propyl)-4-(3,5-difluorophenyl)-2-oxo-1,3-oxazolidine-3-carboxamide.

N-(3-{4-[3-(ACETYLAMINO)PHENYL]-1-PIPERIDINYL}PROPYL)-4-(2,1,3-BENZOXADIAZOL-5-YL)-2,5-DIOXO-1,2,5,7-TETRAHYDROFURO[3,4-D]PYRIMIDINE-3(4H)-CARBOXAMIDE: 7.7 mg (12% yield); $^1$H NMR (400 MHz, CDCl$_3$) δ 7.97–6.83 (m, 7H), 6.49 (s, 1H), 5.51(s, 1H) 3.43–2.02 (m, 17 H), 1.82 (s, 3H); ESMS m/e: 574.3 (M+H)$^+$.

EXAMPLE 56

The synthetic method is the same as described for the synthesis of (4S)-N-(3-{4-[3-(acetylamino)phenyl]-1-piperidinyl}propyl)-4-(3,5-difluorophenyl)-2-oxo-1,3-oxazolidine-3-carboxamide.

METHYL (4S)-3-{[(3-{4-[3-(ACETYLAMINO)PHENYL]-1-PIPERIDINYL}PROPYL)AMINO]CARBONYL}-4-(3,4-DIFLUOROPHENYL)-6-METHYL-2-OXO-1,2,3,4-TETRAHYDRO-5-PYRIMIDINECARBOXYLATE: 16.6 mg (52% yield); $^1$H NMR (400 MHz, CDCl$_3$) δ 9.55 (br s, 1H), 9.07 (s, 1H), 8.19 (s, 1H), 7.54 (s, 1H), 7.25–6.98 (m, 4H), 6.95 (d, 1H, J=8.0 Hz), 6.81 (d, 1H, J=7.5 Hz), 6.69 (s, 1H), 3.70 (s, 3H), 3.57–3.34 (m, 2H), 3.06 (t, 2H, J=11.6 Hz), 2.47 (t, 2H, J=8.1 Hz), 2.42 (s, 3H), 2.20 (s, 3H), 2.18–1.61 (m, 9H); ESMS m/e: 584.3 (M+H)$^+$; Anal. Calc. for C$_{30}$H$_{35}$F$_2$N$_5$O+ 0.25CHCl$_3$: C, 59.23; H, 5.79; N, 11.42. Found: C, 59.61; H, 5.31; N, 11.48.

Peptide Synthesis:

Abbreviations: Fmoc: 9-Fluorenyloxycarbonyl-; Trityl: triphenylmethyl-; tBu-: tertiary butyl ester; OtBu-: tertiary butyl ether; Ng: N-guanidinyl; Nin: N-Indole; MBHA: methylbenzhydlamine; DMF: N,N-dimethylformamide; NMP: N-Methylpyrrolidinone; DIEA: diisopripylethyl amine; TFA: trifluoroacetic acid.

Small scale peptide syntheses were performed either manually, by using a sintered glass column with argon pressure to remove solvents and reagents, or by using an Advanced ChemTech 396–9000 automated peptide synthesizer (Advanced ChemTech, Louisville, Ky.). Large scale peptide syntheses were performed on a CS Bio 536 (CS Bio Inc., San Carlos, Calif.). Fmoc-Alanine-OH, Fmoc-Cysteine (Trityl)-OH, Fmoc-Aspartic acid(tBu)-OH, Fmoc-Glutamic acid(tBu)-OH, Fmoc-Phenylalanine-OH, Fmoc-Glycine-OH, Fmoc-Histidine(Trityl)-OH, Fmoc-Isoleucine-OH, Fmoc-Lysine(Boc)-OH, Fmoc-Leucine-OH, Fmoc-Methionine-OH, Fmoc-Asparagine(Trityl)-OH, Fmoc-Proline-OH, Fmoc-Glutamine(Trityl)-OH, Fmoc-Arginine (Ng-2,2,4,6,7-Pentamethyldihydrobenzofuran-5-sulfonyl)-OH, Fmoc-Serine(OtBu-OH, Fmoc-Threonine(OtBu)-OH, Fmoc-Valine-OH, Fmoc-Tryptophan(NinBoc)-OH, Fmoc-Tyrosine(OtBu)-OH, Fmoc-Cyclohexylalanine-OH, and Fmoc-Norleucine, Fmoc -O-benzyl-phosphotyrosine were used as protected amino acids. Any corresponding D-amino acids had the same side-chain protecting groups, with the exception of Fmoc-D-Arginine, which had a Ng-2,2,5,7,8-pentamethyl-chroman-6-sulfonyl protecting group.

Peptides with C-terminal amides were synthesized on solid phase using Rink amide-MBHA resin. The Fmoc group of the Rink Amide MBHA resin was removed by treatment with 30% piperidine in DMF for 5 and 30 minutes respectively. After washing with DMF (3 times), methanol (2 times) and DMF/NMP (3 times), the appropriate Fmoc-protected amino acid (4 eq.) was coupled for 2 hours with HBTU or HATU (4 eq.) as the activating agent and DIEA (8 eq.) as the base. In manual syntheses, the ninhydrin test was used to test for complete coupling of the amino acids. The Fmoc groups were removed by treatment with 30% piperidine in DMF for 5 and 30 minutes respectively. After washing with DMF (3 times), methanol (2 times) and DMF/NMP (3 times), the next Fmoc-protected amino acid (4 eq.) was coupled for 2 hours with HBTU or HATU (4 eq.) as the activating agent and DIEA (8 eq.) as the base. This process of coupling and deprotection of the Fmoc group was continued until the desired peptide was assembled on the resin. The N-terminal Fmoc group was removed by treatment with 30% piperidine in DMF for 5 and 30 minutes respectively. After washing with DMF (3 times), methanol (2 times), the resin(s) was vacuum dried for 2 hours. Cleavage of the peptide-on-resin and removal of the side chain protecting groups was achieved by treating with TFA:ethanedithiol:thioanisole:m-cresol:water:triisopropylsilane:phenol, 78/5/3/3/3/5/3 (5 mL per 100 mg resin) for 2.5–3 hours. The cleavage cocktail containing the peptide was filtered into a round bottom flask and the volatile liquids were removed by rotary evaporation at 30–40° C. The peptides were precipitated with anhydrous ether, collected on a medium-pore sintered glass funnel by vacuum filtration, washed with ether and vacuum dried.

Peptides with C-terminal acids were synthesized using 2-chlorotrityl chloride resin. The first amino acid was attached to the resin by dissolving 0.6–1.2 eq. of the appropriate Fmoc-protected amino acid described above in dichloromethane (a minimal amount of DMF was added to facilitate the dissolution, if necessary). To this was added DIEA (4 eq. Relative to the Fmoc-amino acid) and the solution was added to the resin and shaken for 30–120 minutes. The solvents and the excess reagents were drained and the resin was washed with dichloromethane/methanol/DIEA (17/2/1) (3 times), dichloromethane (3 times), DMF (2 times), dichloromethane (2 times), and vacuum dried. The process of deprotection of the Fmoc group and coupling the appropriate Fmoc-protected amino acid was continued as described above, until the desired, fully protected peptide was assembled on the resin. The process for removal of the final Fmoc group and the cleavage and deprotection of the peptides was the same as described above for the peptides with C-terminal amides.

Purification of the peptides was achieved by preparative high performance column chromatography (HPLC), using a reverse-phase C-18 column (25×250 mm) (Primesphere or Vydac) with a gradient of acetonitrile (0.1% TFA) in water (0.1% TFA). The general gradient was from 10%–90% acetonitrile in water over 40 minutes. The fractions corresponding to each peak on the HPLC trace was collected, freeze dried and analyzed by electrospray mass spectrometery. The fraction having the correct mass spectral data corresponding to the desired peptide was then further analyzed by amino acid analysis, if necessary. All purified peptides were tested for homogeneity by analytical HPLC using conditions similar to that described above, but by using a 2.5×250 mm analytical column, and generally were found to have >95% purity.

REFERENCES

See our published dihydropyrimidinone and oxazolidinone patents as references for the synthesis of the templates and the piperidines.

Also, for the synthesis of the aminopropyl piperidines and the templates, see:

Lagu, Bharat, et al., Design and synthesis of novel $\alpha_{1a}$ adrenoceptor-selective antagonists. 3. Approaches to eliminate opioid agonist metabolites by using substituted phenylpiperazine side chains. J. Med. Chem. (1999), 42(23), 4794–4803. CODEN: JMCMAR ISSN:0022-2623. CAN 132:78527 AN 1999:680975 CAPLUS Dhar, T. G. Murali, et al., Design and Synthesis of Novel $\alpha_{1a}$ Adrenoceptor-Selective Antagonists. 2. Approaches To Eliminate Opioid Agonist Metabolites via Modification of Linker and 4-Methoxycarbonyl-4-phenyl piperidine Moiety. J. Med. Chem. (1999), 42(23), 4778–4793. CODEN: JMCMAR ISSN:0022–2623. CAN 132:18483 AN 1999:680971 CAPLUS Nagarathnam, Dhanapalan, et al., Design and Synthesis of Novel $\alpha_{1a}$ Adrenoceptor-Selective Antagonists. 1. Structure-Activity Relationship in Dihydropyrimidinones. J. Med. Chem. (1999), 42(23), 4764–4777. CODEN: JMCMAR ISSN:0022–2623. CAN 132:18482 AN 1999:680967 CAPLUS Wong, Wai C., et al., Design and Synthesis of Novel $\alpha_{1a}$ Adrenoceptor-Selective Antagonists. 4. Structure-Activity Relationship in the Dihydropyrimidine Series. J. Med. Chem. (1999), 42(23), 4804–4813. CODEN: JMCMAR ISSN:0022-2623. CAN 132:30317 AN 1999:680947 CAPLUS Marzabadi, Mohammad R., et al., Design and synthesis of novel dihydropyridine alpha-1A antagonists. Bioorg. Med. Chem. Lett. (1999), 9(19), 2843–2848. CODEN: BMCLE8 ISSN:0960-894X. CAN 132:44482 AN 1999:662323 CAPLUS Wong, Wai C., et al., Alpha-1a adrenoceptor selective antagonists as novel agents for treating benign prostatic hyperplasia. Book of Abstracts, 217th ACS National Meeting, Anaheim, Calif., Mar. 21–25 (1999), MEDI-156. CODEN: 67GHA6 AN 1999:92669 CAPLUS Nagarathnam, D., et al., Design, synthesis and evaluation of dihydropyrimidinones as alpha-1 a selective antagonists: 7. Modification of the piperidine moiety into 4-aminocyclohexane; identification and structure-activity relationship of SNAP 6991 analogs. Book of Abstracts, 217th ACS National Meeting, Anaheim, Calif., Mar. 21–25 (1999), MEDI-110. CODEN: 67GHA6 AN 1999:92624 CAPLUS Lagu, Bharat, et al., Heterocyclic substituted oxazolidinones for use as selective antagonists for human a 1A receptors. PCT Int. Appl. (1998), 258 pp. CODEN: PIXXD2 WO 9857940 A1 19981223 CAN 130:81508 AN 1999:9823 CAPLUS Wong, Wai C., et al., Preparation of piperidinylpropyl aminocarbonyldihydropyrimidones and related compounds as selective adrenergic a 1A receptor antagonists. PCT Int. Appl. (1998), 314 pp. CODEN: PIXXD2 WO 9851311 A2 19981119 CAN 130:25077 AN 1998:764290 CAPLUS Nagarathnam, Dhanapalan, et al., Design and synthesis of novel $\alpha_{1a}$ adrenoceptor-selective dihydropyridine antagonists for the treatment of benign prostatic hyperplasia. J. Med. Chem. (1998), 41(26), 5320–5333. CODEN: JMCMAR ISSN:0022-2623. CAN 130:110137 AN 1998:742998 CAPLUS For the general procedure for Pd coupling of vinyl triflate and bononic acids or tributyl tin reagents: See, Wusron, Wise Synthesis 1991, 993)

(For Typical References, See:Schroeter, G. Ber. (1909) 42, 3356; and Allen, C. F. H.; Bell, A. Org. Syn. Coll. Vol. 3, (1955) 846).

For the preparation of the ether N-[4-(benzo-4',5'[H]-furanpiperidine refer to W. E. Parham et al, J. Org. Chem. (1976) 41, 2268.

For the preparation of the ether piperidine precursor of Example 20, refer to W. E. Parham et al, J. Org. Chem. (1976) 41, 2268.

For the preparation of the indane piperidine precursor of Example 21, refer to M. S. Chambers J. Med. Chem. (1992) 35, 2033.

For the preparation of the piperidine precursor of Example 23, (K. Hashigaki et al. Chem.Pharm.Bull. (1984) 32, 3568.)

For the preparation of the piperidine precursor of Example 32, spiro[1H-indane-1,4'-piperidine], refer to M. S. Chambers et al. J. Med. Chem. (1992) 35, 2033.)

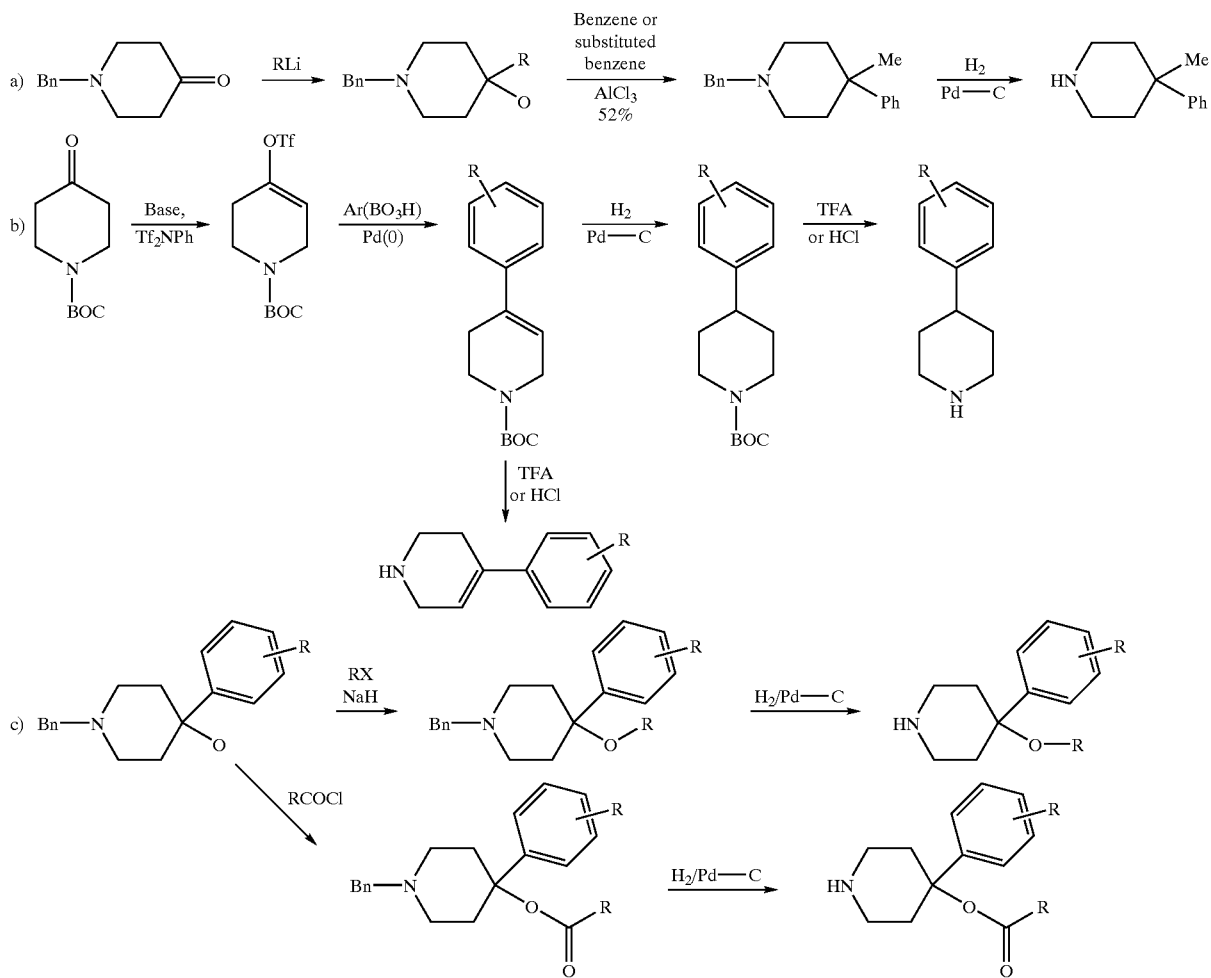
Scheme 1. Synthesis of Precursor Compounds
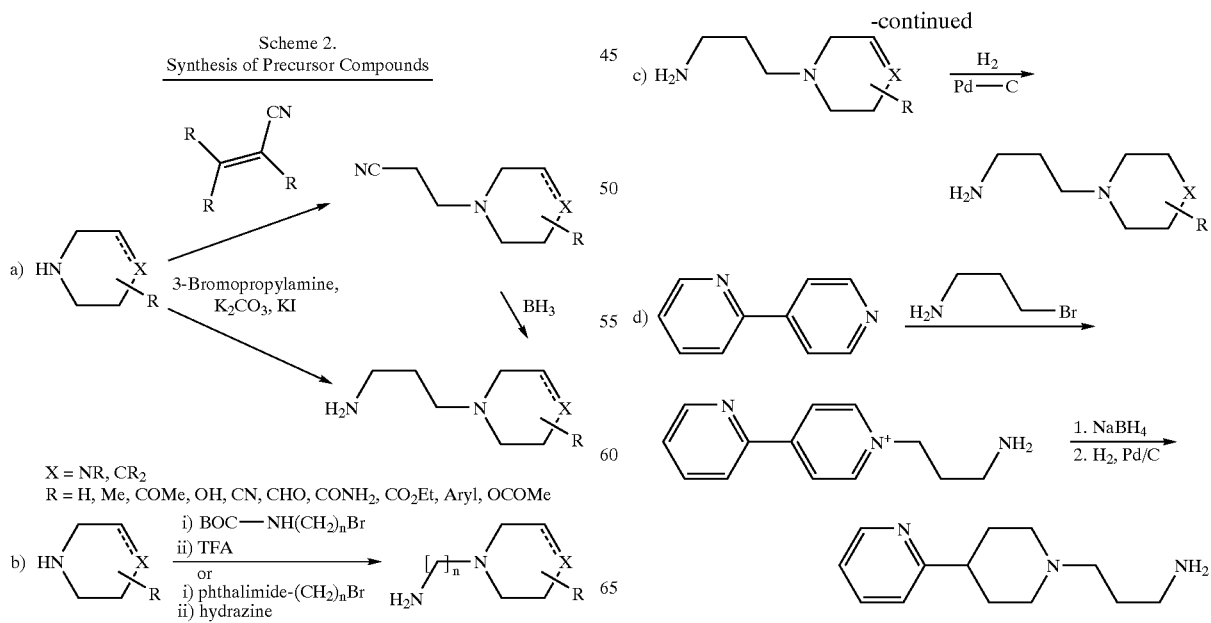
Scheme 2. Synthesis of Precursor Compounds

Scheme 3.
Synthesis of Precursor Compounds
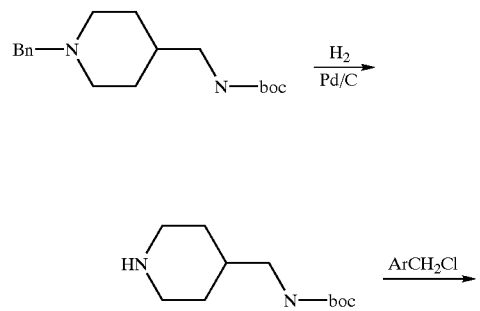
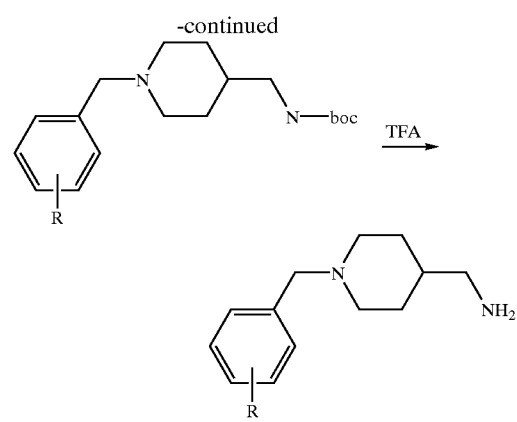
Scheme 4.
Synthesis of Various Dihydropyrimidinones
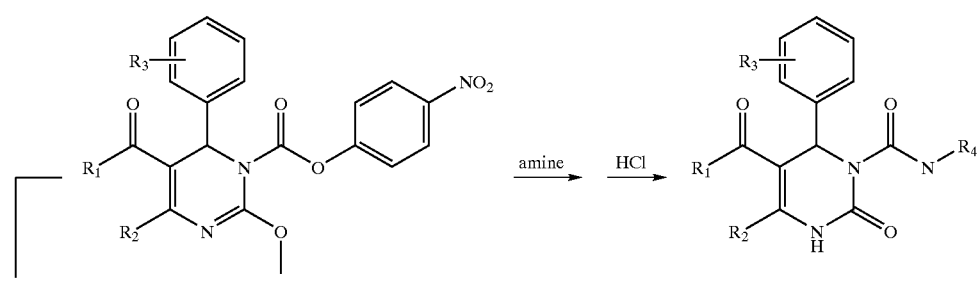
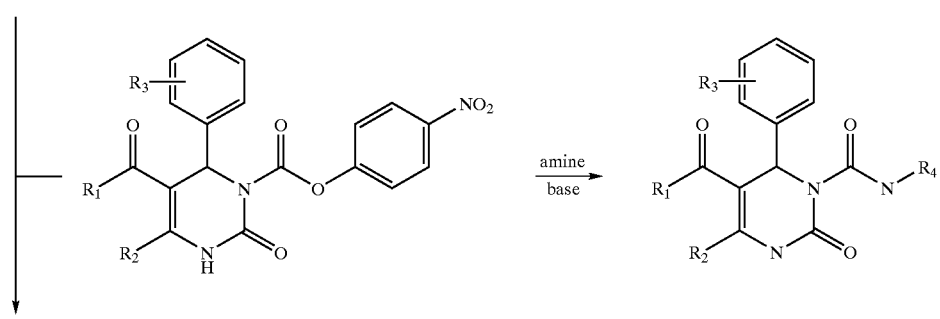
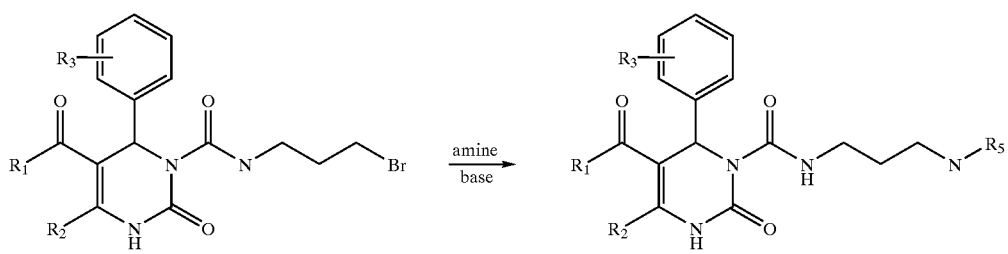

Scheme 5.
Synthesis of Dihydropyrimidinones
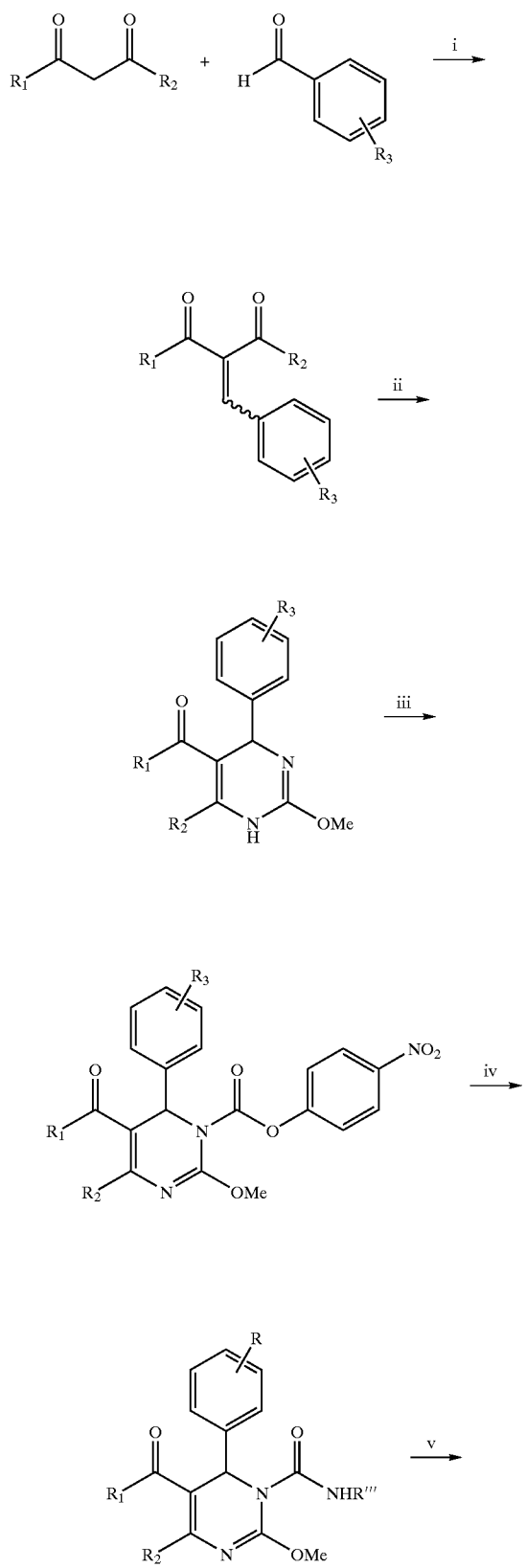
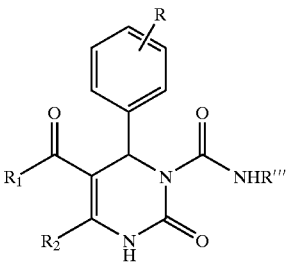
i. O-Methylisourea, NaHCO₃, DMF
ii. NaOAc/NaHCO₃, DMF
iii. 4-Nitrophenyl chloroformate, DMAP, CH₂Cl₂
iv. Amine
v. HCl/THF
Scheme 6.
Resolution of dihydropyrimidinones.
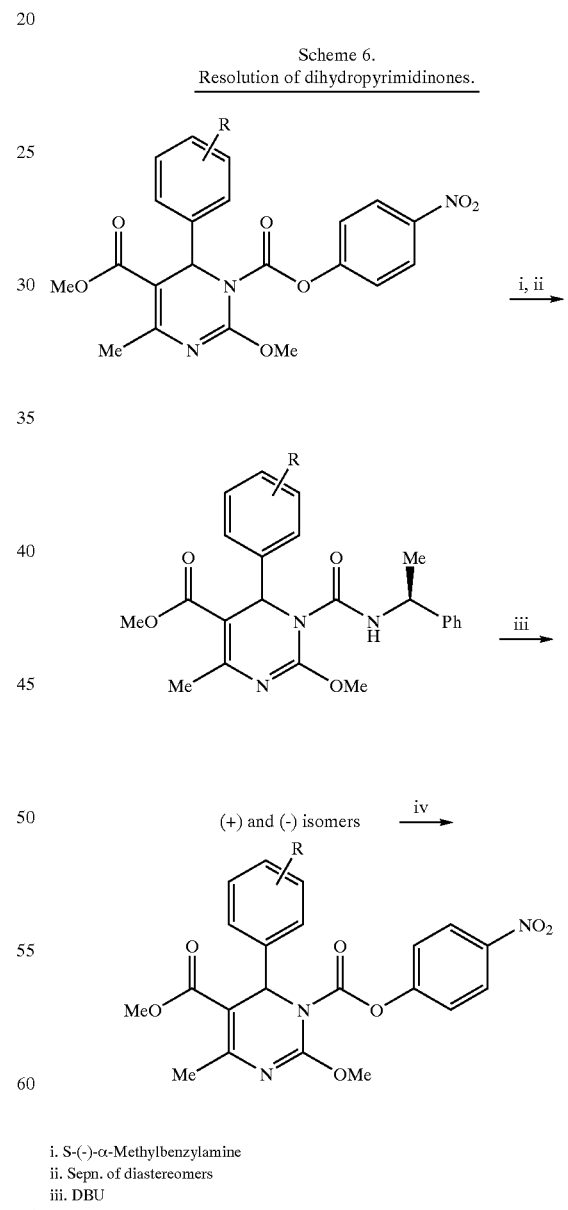
i. S-(-)-α-Methylbenzylamine
ii. Sepn. of diastereomers
iii. DBU
iv. p-nitrophenylchloroformate Scheme 7.
Synthesis of Example 5 and Analogs
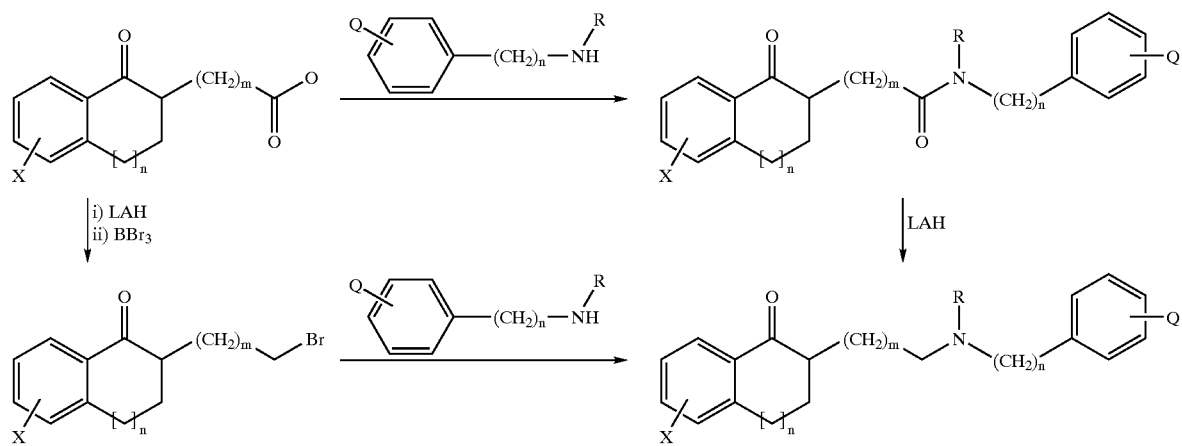
Scheme 8.
Synthesis of Example 13
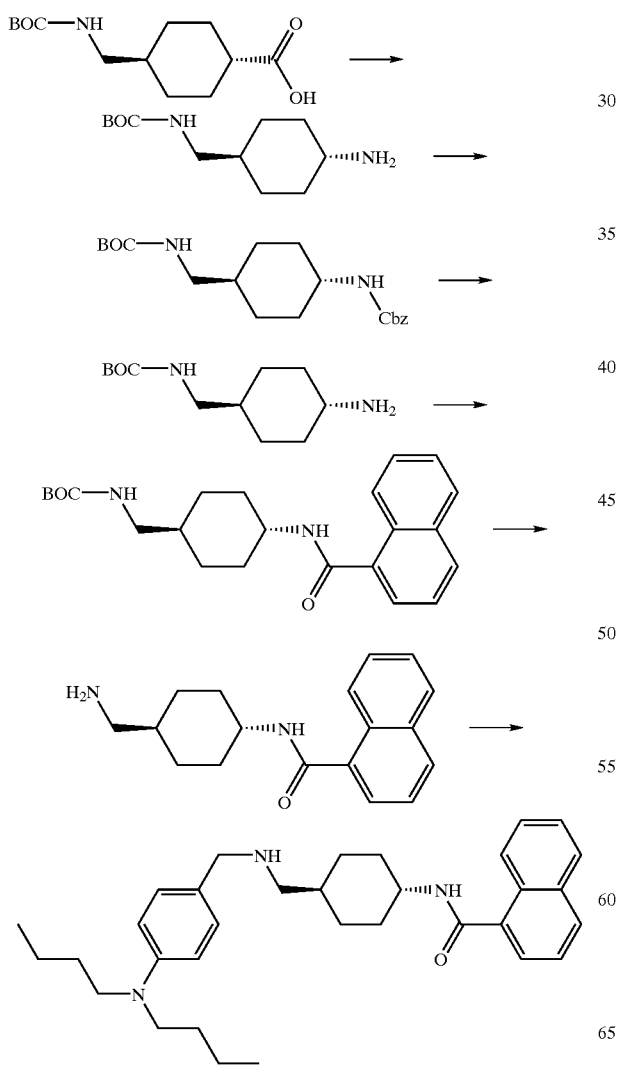
Scheme 9.
Synthesis of Example 12
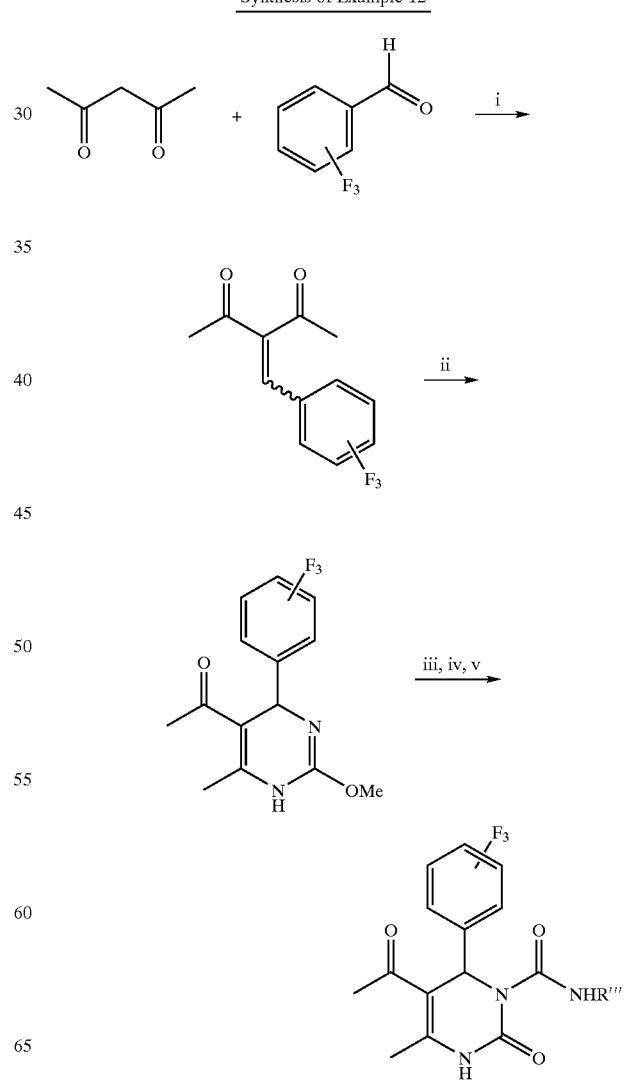

NHR''' = 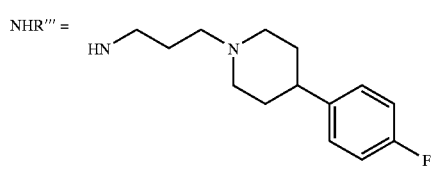

Amine 1 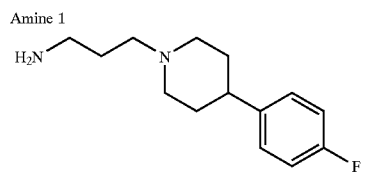

i. Piperidine, Benzene
ii. O-Methylisourea, NaHCO₃, DMF
iii. 4-Nitrophenyl chloroformate, Pyridine, CH₂Cl₂
iv. Amine 1
v. 6 N HCl Scheme 10.
Synthesis of Examples 4 and 22.

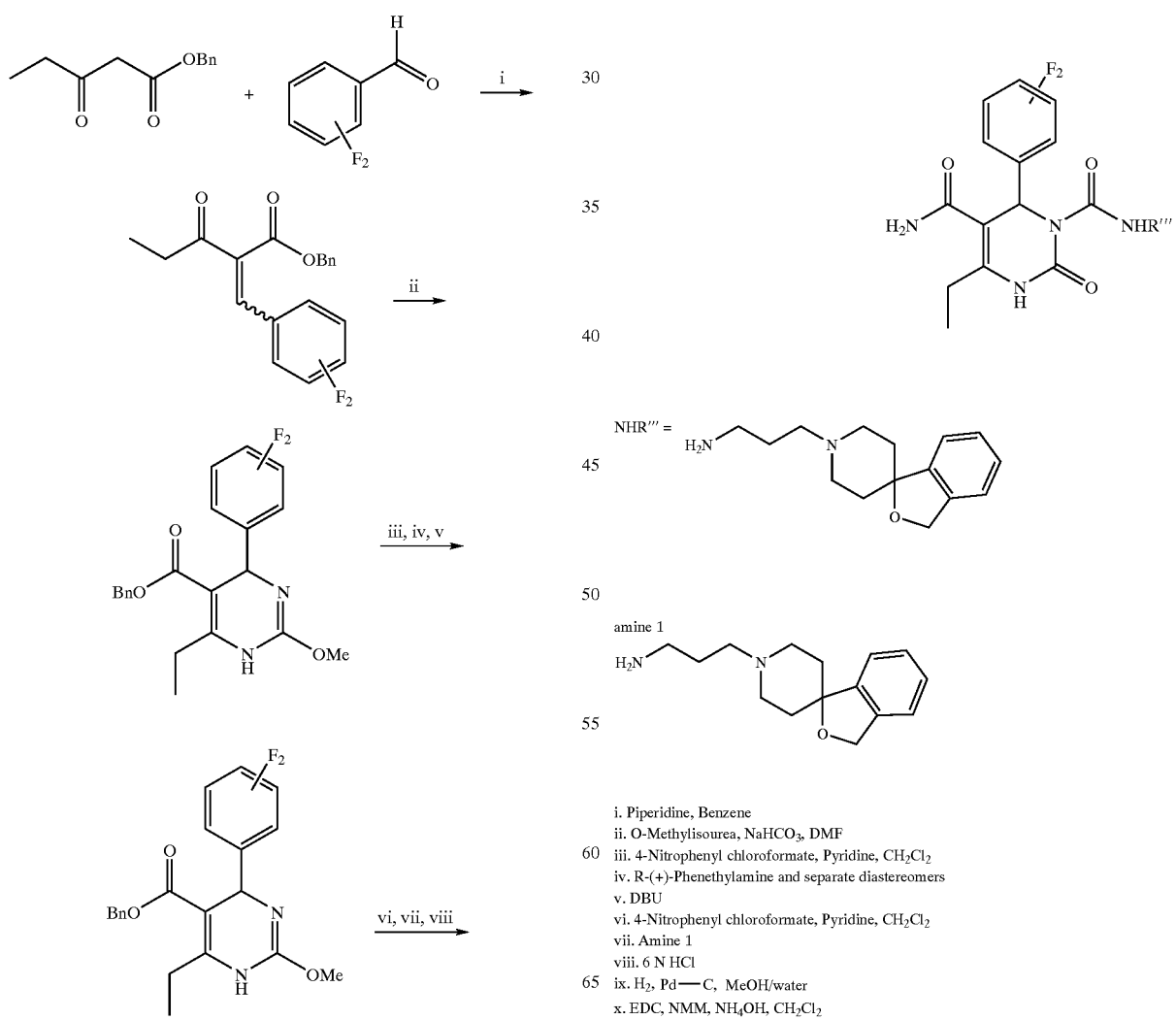

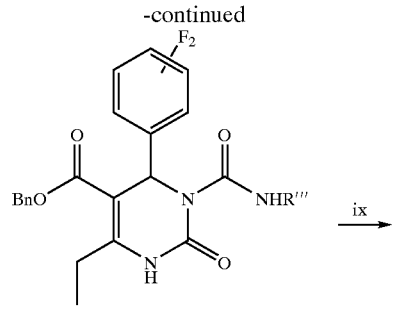

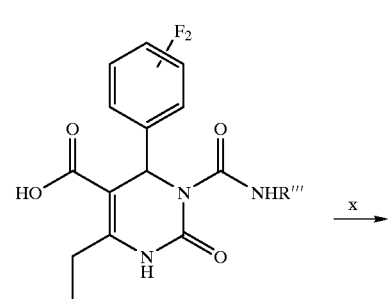

NHR''' = amine 1 i. Piperidine, Benzene
ii. O-Methylisourea, NaHCO₃, DMF
iii. 4-Nitrophenyl chloroformate, Pyridine, CH₂Cl₂
iv. R-(+)-Phenethylamine and separate diastereomers
v. DBU
vi. 4-Nitrophenyl chloroformate, Pyridine, CH₂Cl₂
vii. Amine 1
viii. 6 N HCl
ix. H₂, Pd—C, MeOH/water
x. EDC, NMM, NH₄OH, CH₂Cl₂

Scheme 11.
Synthesis of Example 10 and its Tritiated Analog
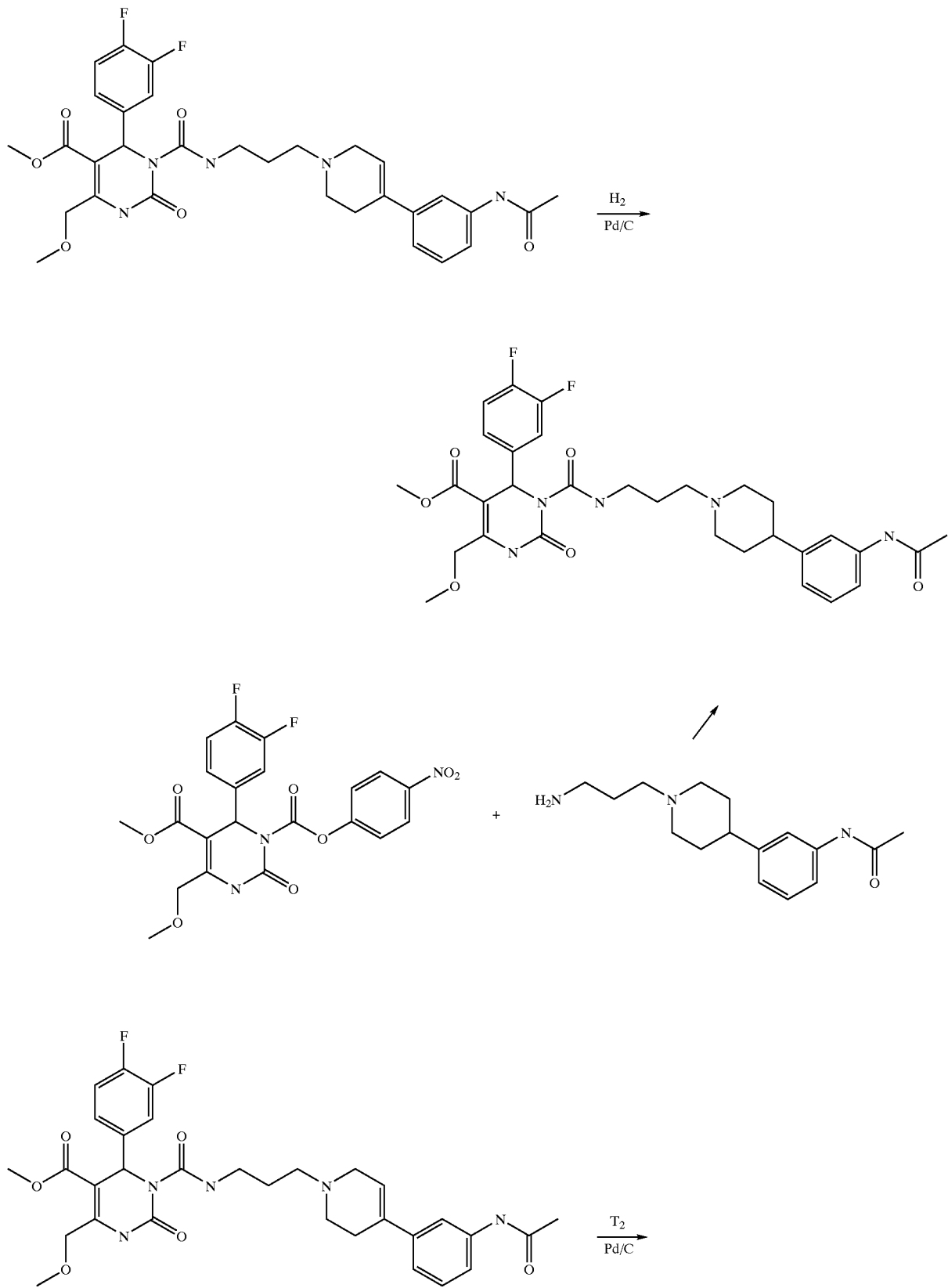

-continued

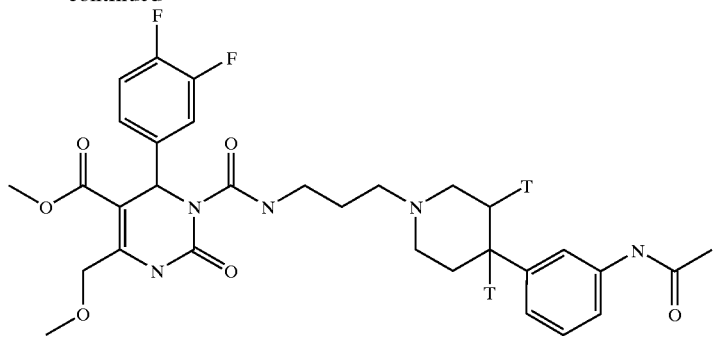

Scheme 12.
Synthesis of Dihydropyrimidines

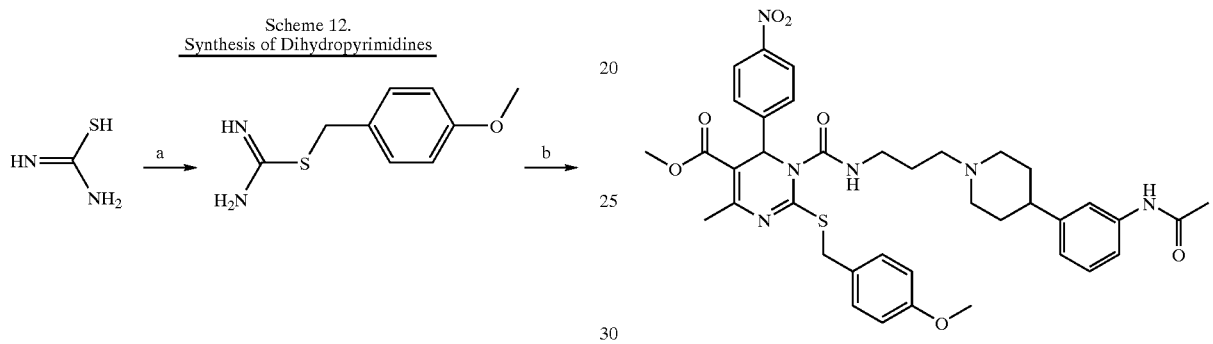

a. p-methoxybenzyl chloride, THF, 0 to 65 °C.;
b. Methyl 2-{(4-nitrophenyl)methylene}-3-oxobutyrate (prepared from p-nitrobenzaldehyde, methyl acetoacetate, piperidinium acetate in isopropanol), NaOAc, DMF, 65 °C.;
c. p-nitrophenyl chloroformate, NaHCO$_3$, dichloromethane
d. N-{3-[1-(3-aminopropyl)-4-piperidinyl]phenyl}acetamide Scheme 13.
Synthesis of Dihydropyrimidinone Fused Lactones

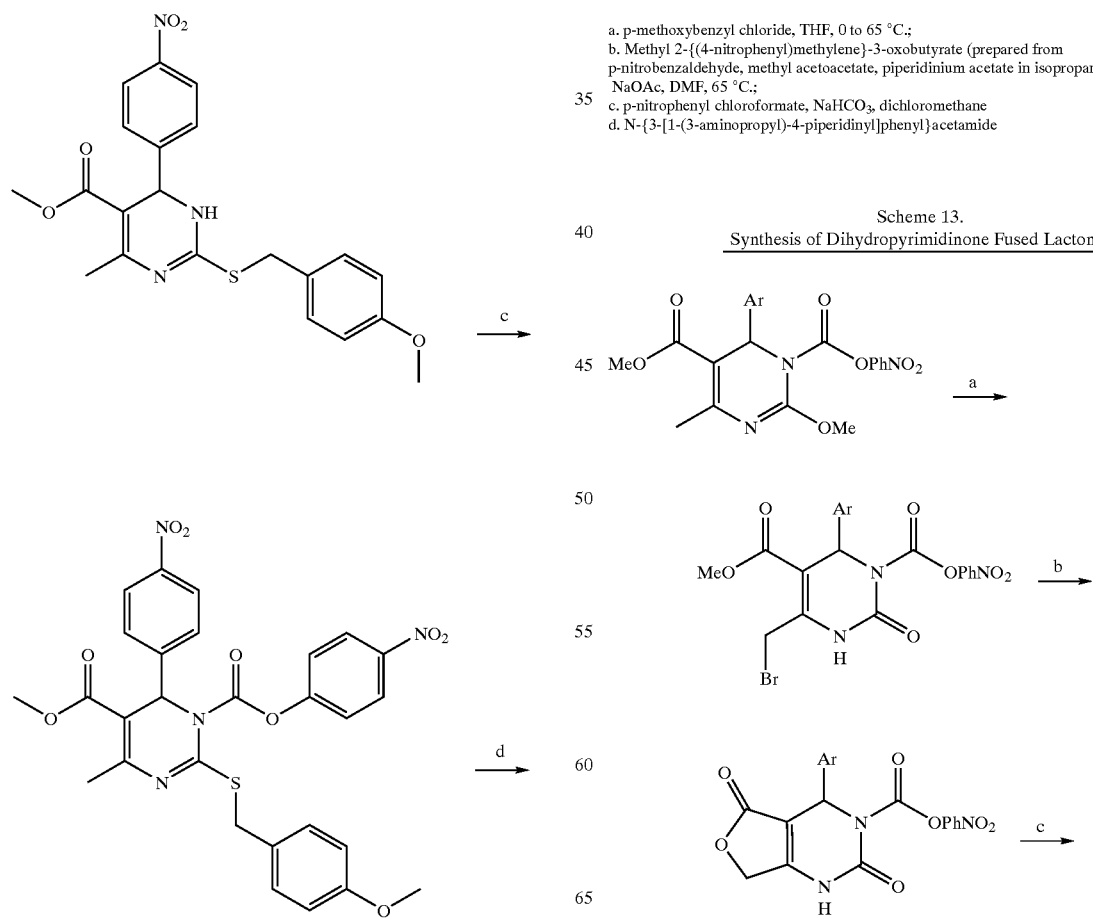

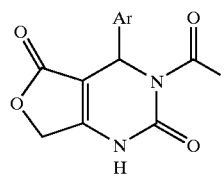

(a) Br$_2$, CHCl$_3$ (b) Heat, 130° C. (c) RNH$_2$, THF or CH$_2$Cl$_2$, 60–80% yield overall.

Ar =

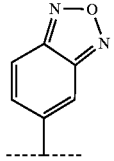 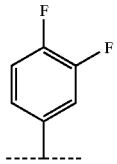 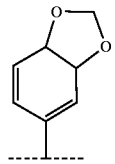

Scheme 14.
Synthesis of Substituted Dihyropyrimidinones
and Reverse Dihydropyrimidinones

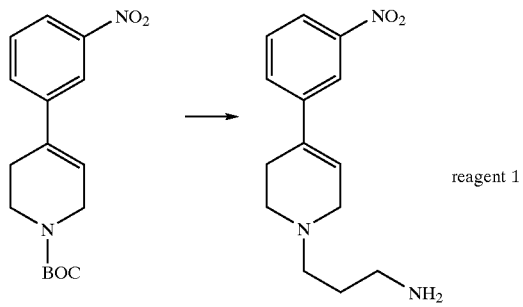

reagent 1

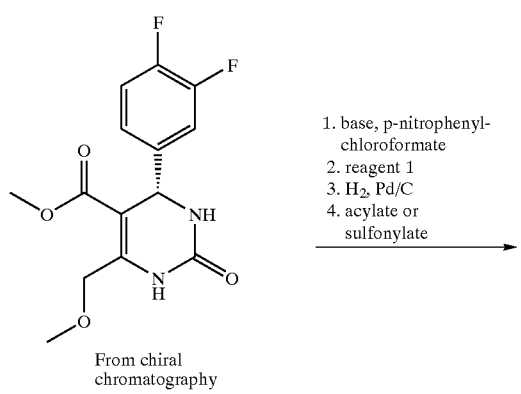

1. base, p-nitrophenyl-chloroformate
2. reagent 1
3. H$_2$, Pd/C
4. acylate or sulfonylate

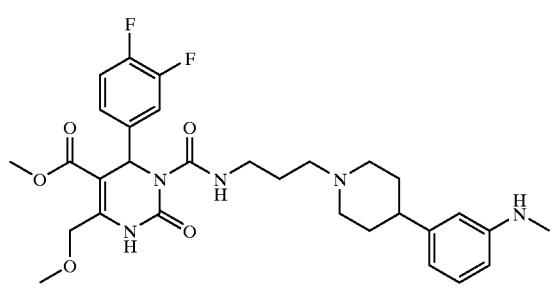

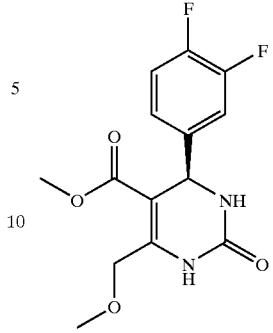

1. LiOH, heat
2. EDC, reagent 1
3. H$_2$, Pd/C
4. acylate or sulfonylate

From chiral chromatography

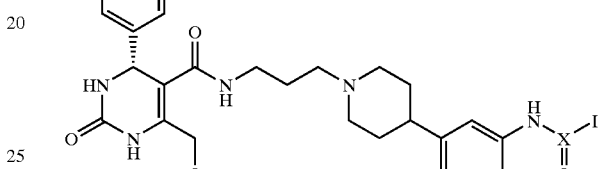

EDC = ethyl dimethylaminopropyl carbodiimide hydrochloride
X = C, S(=O)

II. Synthetic Methods for General Structures

The examples described in Section I are merely illustrative of the methods used to synthesize MCH1 antagonists. Further derivatives may be obtained utilizing generalized methods based on the synthetic methods used to synthesize the examples.

It may be necessary to incorporate protection and deprotection strategies for substituents such as amino, amido, carboxylic acid, and hydroxyl groups in the generalized synthetic methods to form further derivatives. Methods for protection and deprotection of such groups are well-known in the art, and may be found, for example in Green, T. W. and Wuts, P. G. M. (1991) *Protection Groups in Organic Synthesis*, 2nd Edition John Wiley & Sons, New York.

III. Oral Compositions

As a specific embodiment of an oral composition of a compound of this invention, 100 mg of one of the compounds described herein is formulated with sufficient finely divided lactose to provide a total amount of 580 to 590 mg to fill a size O hard gel capsule.

IV. Pharmacological Evaluation of Compounds at Cloned MCH1, NPY, Galanin, and 5-HT2C Receptors The pharmacological properties of the compounds of the present invention were evaluated at one or more of the cloned human MCH1, NPY1, NPY5, GALR1, GALR2, and GALR3 and rat 5-HT2C receptors using protocols described below.

Host Cells

A broad variety of host cells can be used to study heterologously expressed proteins. These cells include but are not restricted to assorted mammalian lines such as; Cos-7, CHO, LM(tk-), HEK293, etc.; insect cell lines such as; Sf9, Sf21, etc.; amphibian cells such as xenopus oocytes; and others.

COS-7 cells are grown on 150 mm plates in DMEM with supplements (Dulbecco's Modified Eagle Medium with 10% bovine calf serum, 4 mM glutamine, 100 units/ml penicillin/100 µg/ml streptomycin) at 37° C., 5% $CO_2$. Stock plates of COS-7 cells are trypsinized and split 1:6 every 3–4 days.

Human embryonic kidney 293 cells are grown on 150 mm plates in DMEM with supplements (10% bovine calf serum, 4 mM glutamine, 100 units/ml penicillin/100 µg/ml streptomycin) at 37° C., 5% $CO_2$. Stock plates of 293 cells are trypsinized and split 1:6 every 3–4 days.

Mouse fibroblast LM(tk-) cells are grown on 150 mm plates in D-MEM with supplements (Dulbecco's Modified Eagle Medium with 10% bovine calf serum, 4 mM glutamine, 100 units/ml penicillin/100 µg/ml streptomycin) at 37° C., 5% $CO_2$. Stock plates of LM(tk-) cells are trypsinized and split 1:10 every 3–4 days.

Chinese hamster ovary (CHO) cells were grown on 150 mm plates in HAM's F-12 medium with supplements (10% bovine calf serum, 4 mM L-glutamine and 100 units/ml penicillin/100 µg/ml streptomycin) at 37° C., 5% $CO_2$. Stock plates of CHO cells are trypsinized and split 1:8 every 3–4 days.

Mouse embryonic fibroblast NIH-3T3 cells are grown on 150 mm plates in Dulbecco's Modified Eagle Medium (DMEM) with supplements (10% bovine calf serum, 4 mM glutamine, 100 units/ml penicillin/100 µg/ml streptomycin) at 37° C., 5% $CO_2$. Stock plates of NIH-3T3 cells are trypsinized and split 1:15 every 3–4 days.

Sf9 and Sf21 cells are grown in monolayers on 150 mm tissue culture dishes in TMN-FH media supplemented with 10% fetal calf serum, at 27° C., no $CO_2$. High Five insect cells are grown on 150 mm tissue culture dishes in Ex-Cell 400™ medium supplemented with L-Glutamine, also at 27° C., no $CO_2$.

In some cases, cell lines that grow as adherent monolayers can be converted to suspension culture to increase cell yield and provide large batches of uniform assay material for routine receptor screening projects.

Transient Expression

DNA encoding proteins to be studied can be transiently expressed in a variety of mammalian, insect, amphibian and other cell lines by several methods including but not restricted to; calcium phosphate-mediated, DEAE-dextran mediated, Liposomal-mediated, viral-mediated, electroporation-mediated and microinjection delivery. Each of these methods may require optimization of assorted experimental parameters depending on the DNA, cell line, and the type of assay to be subsequently employed.

A typical protocol for the calcium phosphate method as applied to LM(tk-) cells is described as follows; Adherent cells are harvested approximately twenty-four hours before transfection and replated at a density of $1-2\times10^5$ cells/cm$^2$ in a 100 mm tissue culture dish and allowed to incubate over night at 37° C. at 5% $CO_2$. 250 µl of a mixture of $CaCl_2$ and DNA (20 µg DNA in 250 mM $CaCl_2$) is added to a 5 ml plastic tube and 250 ul of 2× HBS (250 mM NaCl, 10 mM KCl, 1.5 mM $Na_2HPO_4$, 12 mM dextrose, 50 mM HEPES) is slowly added with gentle mixing. The mixture is allowed to incubate for 20 minutes at room temperature to allow a DNA precipitate to form. The cells are then washed with complete medium, 10 ml of culture medium is added to each plate, followed by addition of the DNA precipitate. The cells are then incubated for 24 to 48 hours at 37° C. at 5% $CO_2$.

A typical protocol for the DEAE-dextran method as applied to Cos-7 cells is described as follows; Cells to be used for transfection are split 24 hours prior to the transfection to provide flasks which are 70–80% confluent at the time of transfection. Briefly, 8 µg of receptor DNA plus 8 µg of any additional DNA needed (e.g. $G_\alpha$ protein expression vector, reporter construct, antibiotic resistance marker, mock vector, etc.) are added to 9 ml of complete DMEM plus DEAE-dextran mixture (10 mg/ml in PBS). Cos-7 cells plated into a T225 flask (sub-confluent) are washed once with PBS and the DNA mixture is added to each flask. The cells are allowed to incubate for 30 minutes at 37° C., 5% $CO_2$. Following the incubation, 36 ml of complete DMEM with 80 µM chloroquine is added to each flask and allowed to incubate an additional 3 hours. The medium is then aspirated and 24 ml of complete medium containing 10% DMSO for exactly 2 minutes and then aspirated. The cells are then washed 2 times with PBS and 30 ml of complete DMEM added to each flask. The cells are then allowed to incubate over night. The next day the cells are harvested by trypsinization and reseeded as needed depending upon the type of assay to be performed.

A typical protocol for liposomal-mediated transfection as applied to CHO cells is described as follows; Cells to be used for transfection are split 24 hours prior to the transfection to provide flasks which are 70–80% confluent at the time of transfection. A total of 10 µg of DNA which may include varying ratios of receptor DNA plus any additional DNA needed (e.g. $G_\alpha$ protein expression vector, reporter construct, antibiotic resistance marker, mock vector, etc.) is used to transfect each 75 cm$^2$ flask of cells. Liposomal mediated transfection is carried out according to the manufacturer's recommendations (LipofectAMINE, GibcoBRL, Bethesda, Md.). Transfected cells are harvested 24 h post transfection and used or reseeded according the requirements of the assay to be employed.

A typical protocol for the electroporation method as applied to Cos-7 cells is described as follows; Cells to be used for transfection are split 24 hours prior to the transfection to provide flasks which are subconfluent at the time of transfection. The cells are harvested by trypsinization resuspended in their growth media and counted. $4\times10^6$ cells are suspended in 300 µl of DMEM and placed into an electroporation cuvette. 8 µg of receptor DNA plus 8 µg of any additional DNA needed (e.g. $G_\alpha$ protein expression vector, reporter construct, antibiotic resistance marker, mock vector, etc.) is added to the cell suspension, the cuvette is placed into a BioRad Gene Pulser and subjected to an electrical pulse (Gene Pulser settings: 0.25 kV voltage, 950 µF capacitance). Following the pulse, 800 µl of complete DMEM is added to each cuvette and the suspension transferred to a sterile tube. Complete medium is added to each tube to bring the final cell concentration to $1\times10^5$ cells/100 µl. The cells are then plated as needed depending upon the type of assay to be performed.

A typical protocol for viral mediated expression of heterologous proteins is described as follows for baculovirus infection of insect Sf9 cells. The coding region of DNA encoding the receptor disclosed herein may be subcloned into pBlueBacIII into existing restriction sites or sites engineered into sequences 5' and 3' to the coding region of the polypeptides. To generate baculovirus, 0.5 µg of viral DNA (BaculoGold) and 3 µg of DNA construct encoding a polypeptide may be co-transfected into 2×10$^6$ *Spodoptera frugiperda* insect Sf9 cells by the calcium phosphate co-precipitation method, as outlined in by Pharmingen (in "Baculovirus Expression Vector System: Procedures and Methods Manual"). The cells then are incubated for 5 days at 27° C. The supernatant of the co-transfection plate may be collected by centrifugation and the recombinant virus plaque purified. The procedure to infect cells with virus, to prepare stocks of virus and to titer the virus stocks are as described in Pharmingen's manual. Similar principals would in general apply to mammalian cell expression via retro-viruses, Simliki forest virus and double stranded DNA viruses such as adeno-, herpes-, and vacinia-viruses, and the like.

Stable Expression

Heterologous DNA can be stably incorporated into host cells, causing the cell to perpetually express a foreign protein. Methods for the delivery of the DNA into the cell are similar to those described above for transient expression but require the co-transfection of an ancillary gene to confer drug resistance on the targeted host cell. The ensuing drug resistance can be exploited to select and maintain cells that have taken up the heterologous DNA. An assortment of resistance genes are available including but not restricted to Neomycin, Kanamycin, and Hygromycin. For the purposes of receptor studies, stable expression of a heterologous receptor protein is carried out in, but not necessarily restricted to, mammalian cells including, CHO, HEK293, LM(tk−), etc.

Cell Membrane Preparation

For binding assays, pellets of transfected cells are suspended in ice-cold buffer (20 mM Tris.HCl, 5 mM EDTA, pH 7.4) and homogenized by sonication for 7 sec. The cell lysates are centrifuged at 200×g for 5 min at 4° C. The supernatants are then centrifuged at 40,000×g for 20 min at 4° C. The resulting pellets are washed once in the homogenization buffer and suspended in binding buffer (see methods for radioligand binding). Protein concentrations are determined by the method of Bradford (1976) using bovine serum albumin as the standard. Binding assays are usually performed immediately, however it is possible to prepare membranes in batch and store frozen in liquid nitrogen for future use.

Radioligand Binding Assays

Radioligand binding assays for the MCH1 receptor were carried out using plasmid pEXJ.HR-TL231 (ATCC Accession No. 203197). Plasmid pEXJ.HR-TL231 comprises the regulatory elements necessary for expression of DNA in a mammalian cell operatively linked to DNA encoding the human MCH1 receptor so as to permit expression thereof. Plasmid pEXJ.HR-TL231 was deposited on Sep. 17, 1998, with the American Type Culture Collection (ATCC), 12301 Parklawn Drive, Rockville, Md. 20852, U.S.A. under the provisions of the Budapest Treaty for the International Recognition of the Deposit of Microorganisms for the Purposes of Patent Procedure and was accorded ATCC Accession No. 203197.

Human embryonic kidney 293 cells (A293 cells) were stably transfected with DNA encoding the MCH1 receptor utilizing the calcium phosphate method and cell membranes were prepared as described above. Binding experiments with membranes from A293 cells transfected with the human MCH1 receptor were performed with 0.08 nM [$^3$H] Compound 10 (custom labeled by Amersham) using an incubation buffer consisting of 50 mM Tris pH 7.4, 10 mM MgCl$_2$, 0.16 mM PMSF, 1 mM 1,10 phenantroline and 0.2% BSA. Binding was performed at 25° C. for 90 minutes. Incubations were terminated by rapid vacuum filtration over GF/C glass fiber filters, presoaked in 5% PEI using 50 nM Tris pH 7.4 as wash buffer. In all experiments, nonspecific binding is defined using 10 µM Compound 10.

The methods to obtain the cDNA of the human NPY1, NPY5, GALR1, GALR2, and GALR3 and rat 5-HT2C receptors, express said receptors in heterologous systems, and carry out assays to determine binding affinity are described in the following publications and above: human NPY1 (Larhammar et al., 1992), human NPY5 (U.S. Pat. No. 5,602,024, the disclosure of which is hereby incorporated by reference in its entirety into this application), human Gal1 (Habert-Ortoli et al., 1994), human Gal2 (Smith et al., 1997), human Gal3 (Smith et al., 1998), and rat 5-HT2C (Julius et al., 1988).

Functional Assays

Cells may be screened for the presence of endogenous mammalian receptor using functional assays (described in detail below). Cells with no or a low level of endogenous receptor present may be transfected with the exoaenous receptor for use in the following functional assays.

A wide spectrum of assays can be employed to screen for receptor activation. These range from traditional measurements of phosphatidyl inositol, cAMP, Ca$^{++}$, and K$^+$, for example; to systems measuring these same second messengers but which have been modified or adapted to be higher throughput, more generic, and more sensitive; to cell based platforms reporting more general cellular events resulting from receptor activation such as metabolic changes, differentiation, and cell division/proliferation, for example; to high level organism assays which monitor complex physiological or behavioral changes thought to be involved with receptor activation including cardiovascular, analgesic, orexigenic, anxiolytic, and sedation effects, for example.

Functional Assay:

Intracellular Calcium Mobilization Assay

Intracellular calcium mobilization assays for the MCH1 receptor were carried out using plasmid pEXJ.HR-TL231 (ATCC Accession No. 203197). COS-7 cells were transiently transfected with DNA encoding the MCH1 receptor utilizing the DEAE-dextran method as described above. The intracellular free calcium concentration was measured by fluorescent imaging using the calcium sensitive fluorscent dye Fluo-3. COS-7 cells expressing the human MCH1 receptor were seeded onto sterile 96 well plates, washed with Hank's balanced salt solution (HBSS), containing 20 mM HEPES, 2.5 mM probenecid, and 0.1% BSA, and loaded with the same buffer containing 3.8 µM Fluo-3 for 1 hour at 37° C. After washing with HBSS to remove the fluo-3 solution, cells were equilibrated for 10 minutes. Cells were then incubated with, or without MCH, and the fluorescence is measured using a Fluorescence Imaging Plate Reader (FLIPR, Molecular Devices).

Materials

Cell culture media and supplements were from Specialty Media (Lavallette, N.J.). Cell culture plates (150 mm and 96-well microtiter) were from Corning (Corning, N.Y.). Sf9, Sf21, and High Five insect cells, as well as the baculovirus transfer plasmid, pBlueBacIII™, were purchased from Invitrogen (San Diego, Calif.). TMN-FH insect medium complemented with 10% fetal calf serum, and the baculovirus DNA, BaculoGold™, was obtained from Pharmingen (San Diego, Calif.). Ex-Cell 400™ medium with L-Glutamine was purchased from JRH Scientific. Polypropylene 96-well microtiter plates were from Co-star (Cambridge, Mass.). Commercially available MCH and related peptide analogs were either from Bachem California (Torrance, Calif.) or Peninsula (Belmont, Calif.). Bio-Rad Reagent was from Bio-Rad (Hercules, Calif.). Bovine serum albumin (ultra-fat free, A-7511) was from Sigma (St. Louis. Mo.). All other materials were reagent grade.

Functional Assay Results

The compounds of Examples 1–37 were assayed using the cloned human MCH1 receptor. The preferred compounds were found to be selective MCH1 antagonists. The results are summarized in Table 1.

TABLE 1

| EXAMPLE No. | STRUCTURE | Kb (nM) hMCH1 |
|---|---|---|
| 1 | 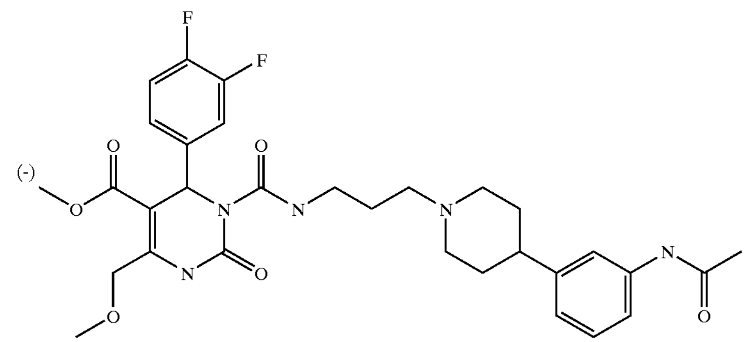 | 42 |
| 2 | 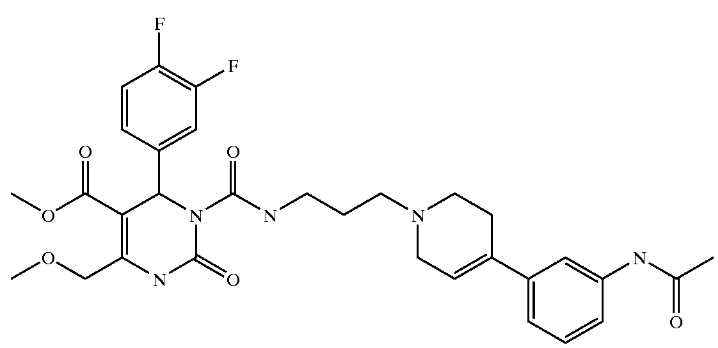 | 18 |
| 3 | 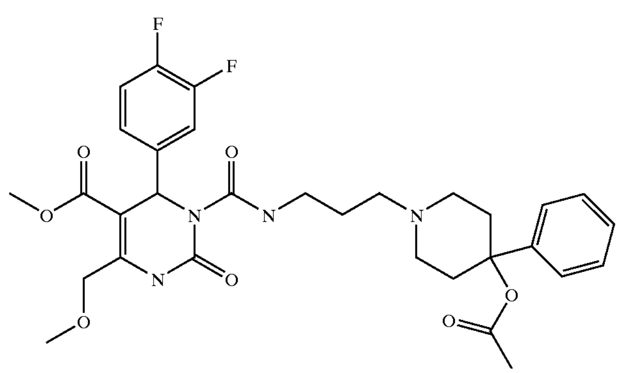 | 201 |

TABLE 1-continued

| EXAMPLE No. | STRUCTURE | Kb (nM) hMCH1 |
|---|---|---|
| 4 | 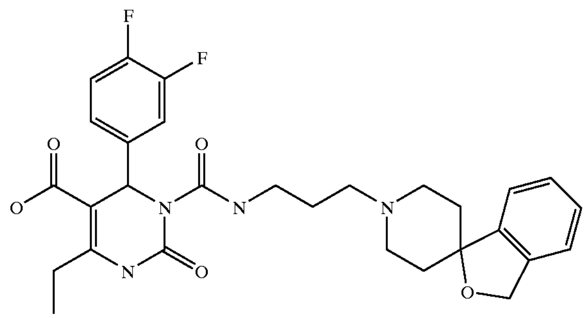 | 187 |
| 5 | 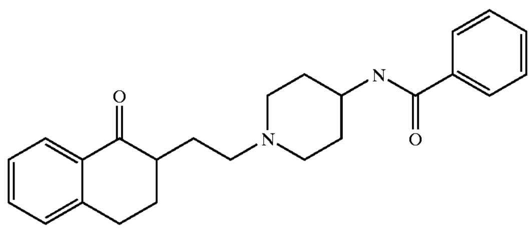 | 258 |
| 6 | 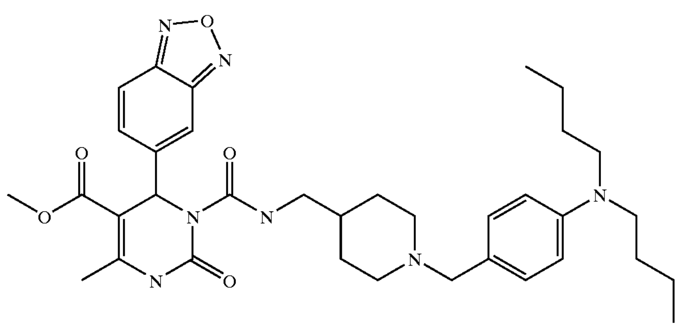 | 42 |
| 7 | 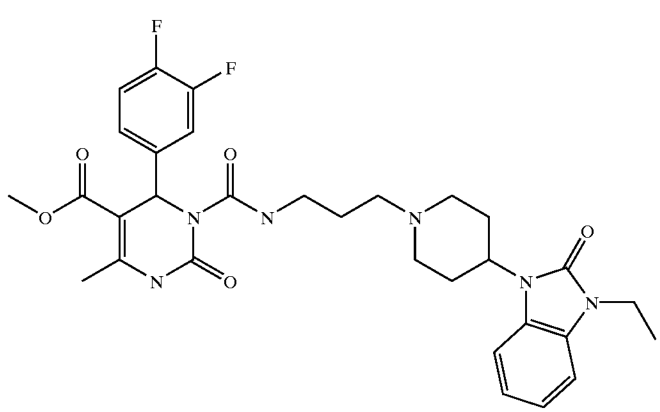 | 41 |

TABLE 1-continued

| EXAMPLE No. | STRUCTURE | Kb (nM) hMCH1 |
|---|---|---|
| 8 | 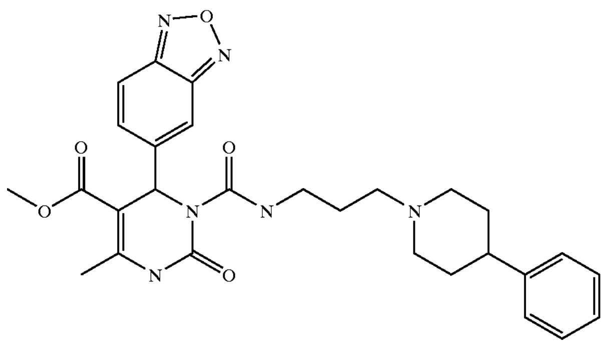 | 88 |
| 9 | 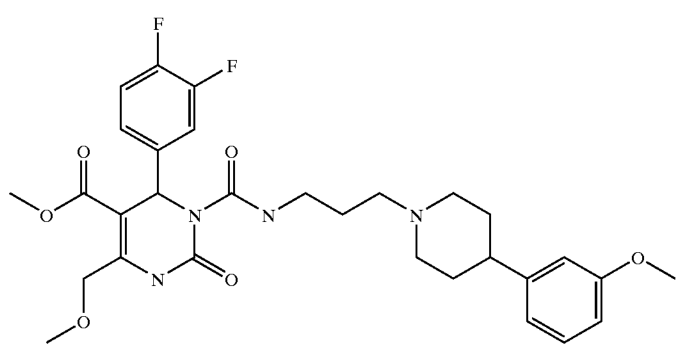 | 35 |
| 10 | 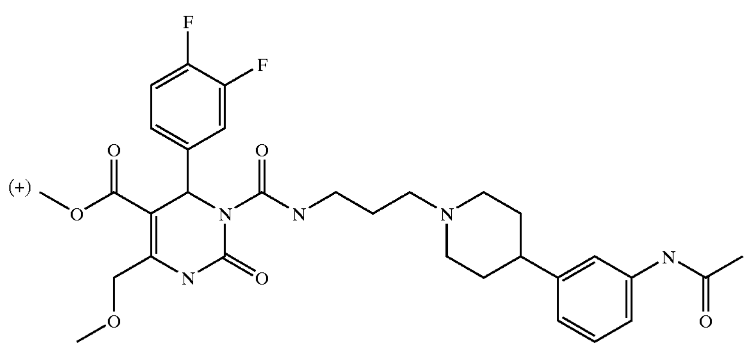 | 0.3 |
| 11 | 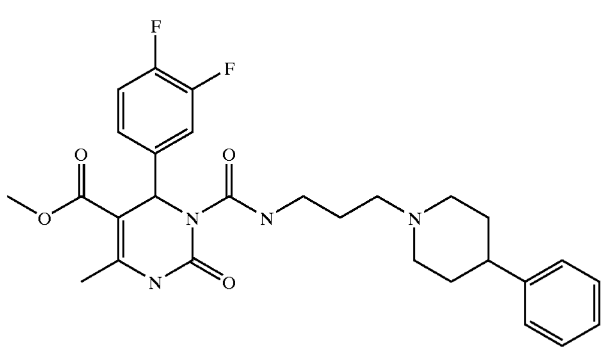 | 331 |

TABLE 1-continued

| EXAMPLE No. | STRUCTURE | Kb (nM) hMCH1 |
|---|---|---|
| 12 | 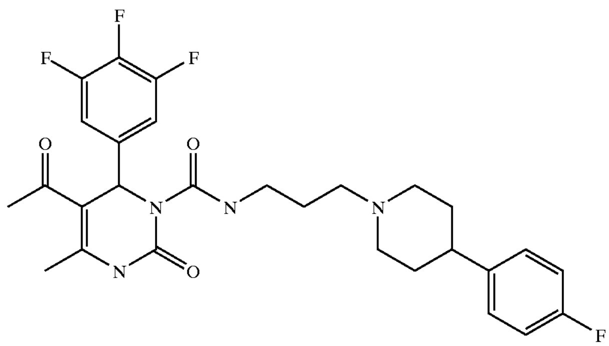 | 29 |
| 13 | 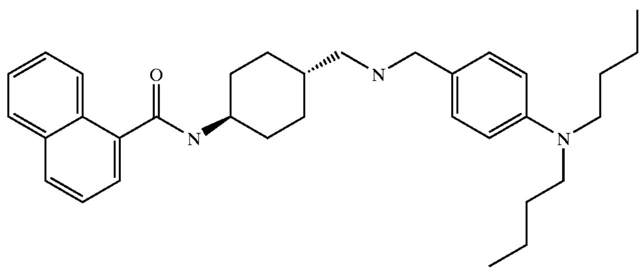 | 284 |
| 14 | 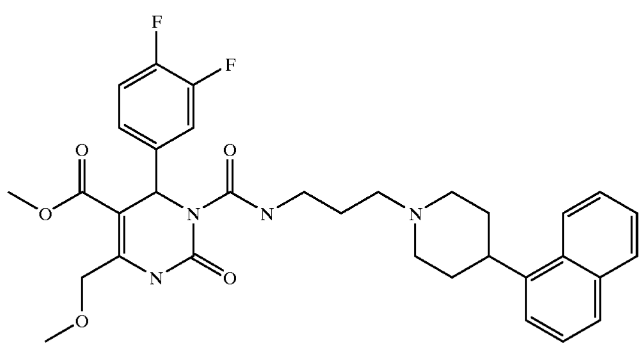 | 2 |
| 15 | 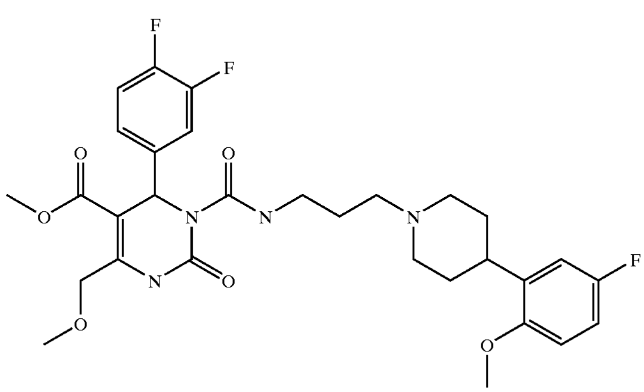 | 289 |

TABLE 1-continued

| EXAMPLE No. | STRUCTURE | Kb (nM) hMCH1 |
|---|---|---|
| 16 | 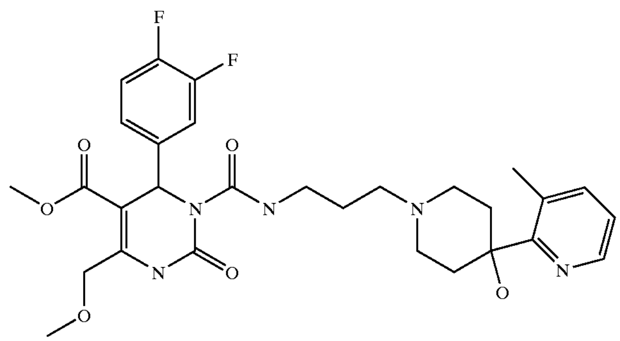 | 329 |
| 17 | 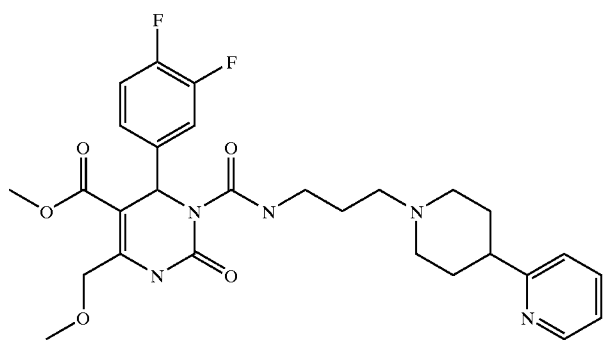 | 373 |
| 18 | 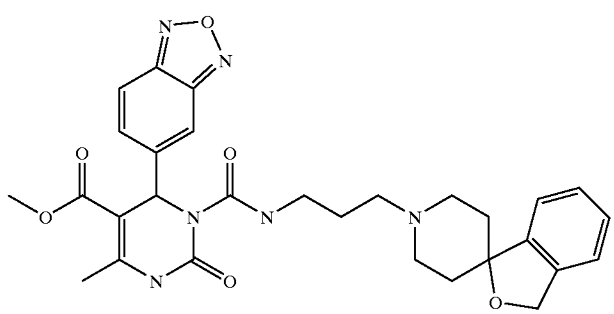 | 1 |
| 19 | 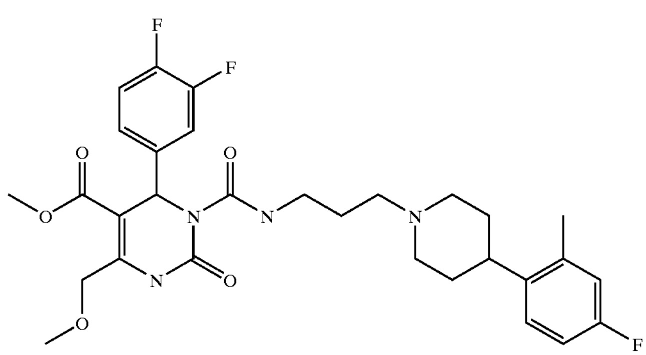 | 7 |

TABLE 1-continued

| EXAMPLE No. | STRUCTURE | Kb (nM) hMCH1 |
|---|---|---|
| 20 | 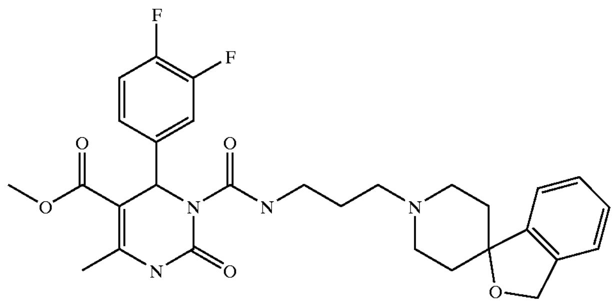 | 5 |
| 21 | 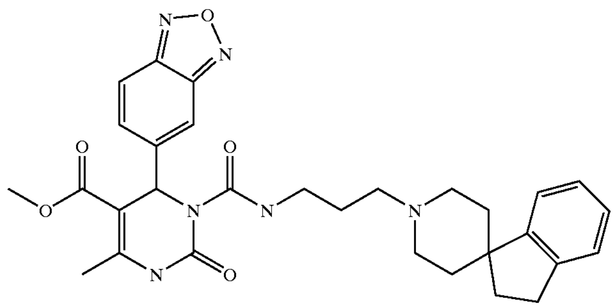 | 28 |
| 22 | 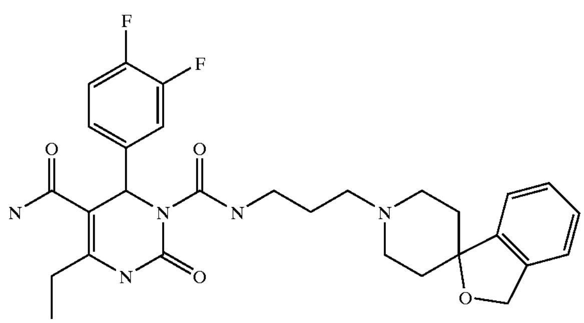 | 40 |
| 23 | 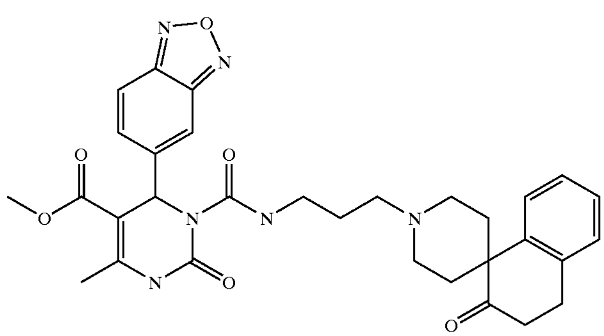 | 68 |

TABLE 1-continued

| EXAMPLE No. | STRUCTURE | Kb (nM) hMCH1 |
|---|---|---|
| 24 | 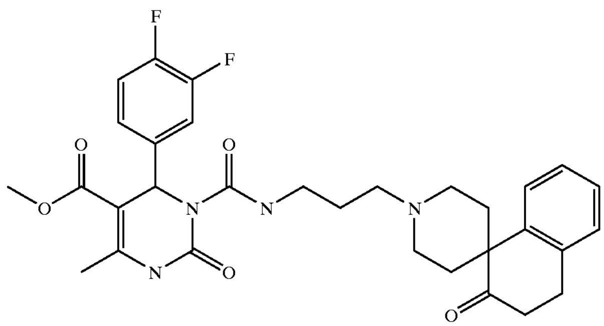 | 102 |
| 25 | 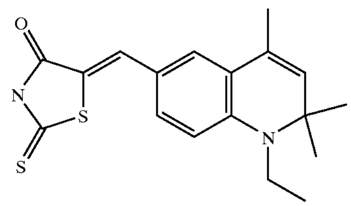 | 126 |
| 26 | 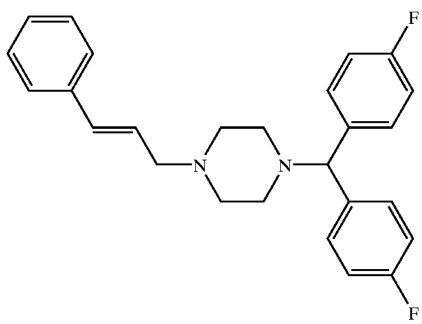 | 260 |
| 27 | 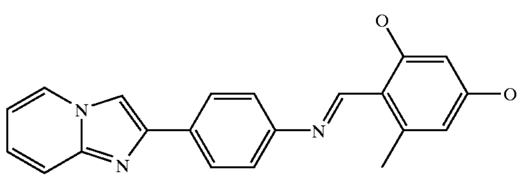 | 279 |
| 28 | 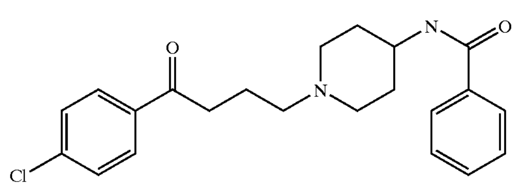 | 60 |
| 29 | 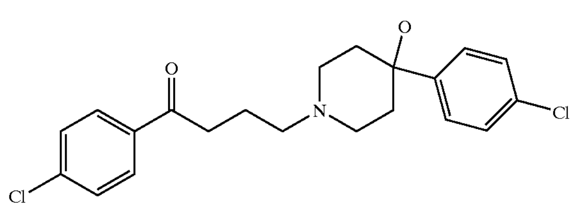 | 9 |

TABLE 1-continued
| EXAMPLE No. | STRUCTURE | Kb (nM) hMCH1 |
|---|---|---|
| 30 | 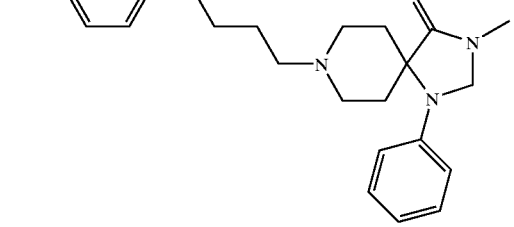 | 479 |
| 31 | 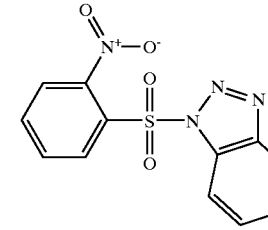 | 7 |
| 32 | 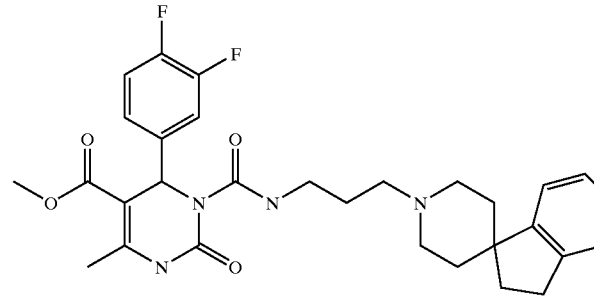 | 67 |
| 33 | 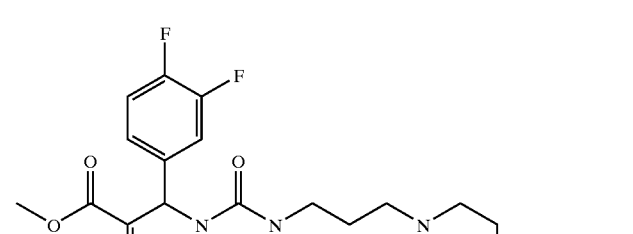 | 12 |

TABLE 1-continued

| EXAMPLE No. | STRUCTURE | Kb (nM) hMCH1 |
|---|---|---|
| 34 | 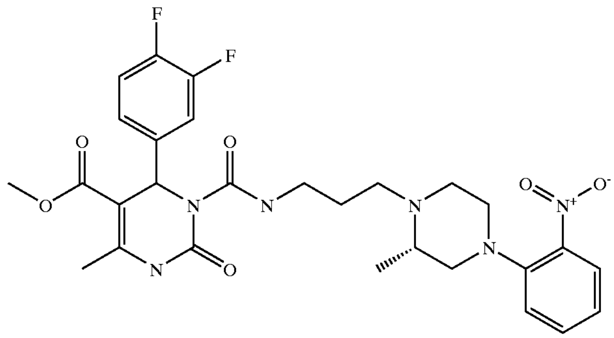 | 182 |
| 35 | 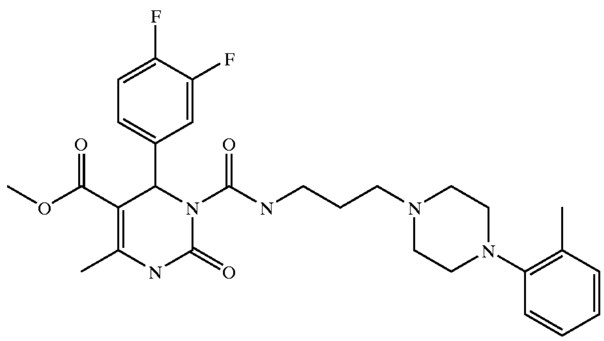 | 276 |
| 36 | 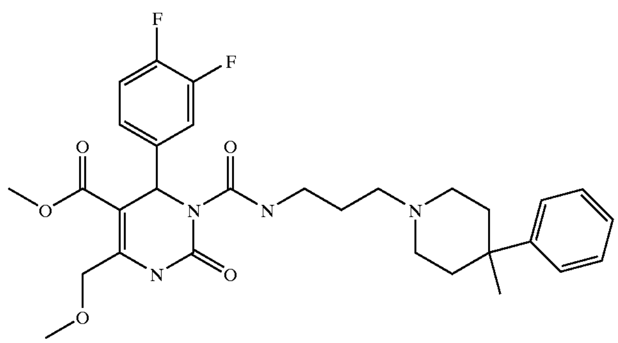 | 406 |
| 37 | 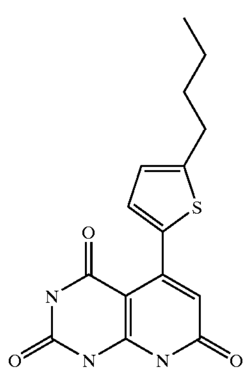 | 162 |

Radioligand Binding Assay Results

The compounds of Examples 1 to 37 were assayed using cloned human MCH1, NPY1, NPY5, GALR1, GALR2, and GALR3 and rat 5-HT2C receptors. The binding affinities of several compounds are shown in Tables 2 and 3.

The compounds of Examples 38 to 56 were assayed using the cloned rat MCH1 receptor. The binding affinities (Ki) of these compounds are shown in Table 4.

TABLE 2

Antagonist potency (Kb) at the human MCH1 receptor, and binding affiity (Ki) at NPY, galanin and 5HT2C receptors.

| Compound | hMCH1 Kb (nM) | hNPY1 Ki (nM) | hNPY5 Ki (nM) | hGALR1 Ki (nM) | hGALR2 Ki (nM) | hGALR3 Ki (nM) | r5HT2C Ki (nM) |
|---|---|---|---|---|---|---|---|
| 10 | 0.3 | >50000 | >50000 | >50000 | >50000 | >50000 | 29,585 |
| 18 | 1 | >50000 | >50000 | >50000 | >50000 | >50000 | 32,617 |
| 14 | 2 | ND | ND | >50000 | 42,603 | >50000 | 663 |
| 20 | 5 | 27,076 | >50000 | >50000 | >50000 | >50000 | 15,058 |
| 19 | 7 | >50000 | >50000 | >50000 | >50000 | >50000 | 11,720 |
| 29 | 9 | >50000 | 46,075 | >50000 | >50000 | >50000 | >50000 |
| 2 | 18 | ND | ND | >50000 | >50000 | >50000 | 39,837 |
| 6 | 42 | 6,667 | 4,735 | 11,057 | 14,921 | 21,095 | 25,549 |
| 1 | 42 | >50000 | >50000 | >50000 | >50000 | >50000 | >50000 |
| 28 | 60 | >50000 | >50000 | >50000 | >50000 | >50000 | 34,087 |
| 25 | 126 | >50000 | >50000 | >50000 | >50000 | >50000 | 41,009 |
| 37 | 162 | >50000 | >50000 | >50000 | >50000 | >50000 | >50000 |
| 4 | 187 | >50000 | >50000 | >50000 | >50000 | >50000 | 34,798 |
| 26 | 260 | >50000 | >50000 | >50000 | >50000 | >50000 | 2,900 |
| 27 | 279 | >50000 | >50000 | >50000 | >50000 | >50000 | >50000 |
| 13 | 284 | 9,601 | >50000 | 11,262 | 4,727 | 5,985 | 25,030 |
| 30 | 479 | >50000 | >50000 | >50000 | >50000 | >50000 | 8,859 |

TABLE 3

Antagonist potency (Kb) at the human MCH1 receptor, and binding affiity (Ki) at human MCH1, NPY1, NPY5, GALR1, GALR2, GALR3, and rat 5HT2C receptors.

| Compound | hMCH1 Kb (nM) | hMCH1 * Ki (nM) | hNPY1 Ki (nM) | hNPY5 Ki (nM) | hGALR1 Ki (nM) | hGALR2 Ki (nM) | hGALR3 Ki (nM) | r5HT2C Ki (nM) |
|---|---|---|---|---|---|---|---|---|
| 10 | 0.3 | 0.08 | >50000 | >50000 | >50000 | >50000 | >50000 | 29,585 |
| 19 | 7 | 3 | >50000 | >50000 | >50000 | >50000 | >50000 | 11,720 |
| 18 | 1 | 4 | >50000 | >50000 | >50000 | >50000 | >50000 | 32,617 |
| 20 | 5 | 6 | 27,076 | >50000 | >50000 | >50000 | >50000 | 15,058 |
| 1 | 42 | 40 | >50000 | >50000 | >50000 | >50000 | >50000 | >50000 |
| 2 | 18 | 49 | ND | ND | >50000 | >50000 | >50000 | 39,837 |
| 14 | 2 | 50 | ND | ND | >50000 | 42,603 | >50000 | 663 |
| 4 | 187 | 131 | >50000 | >50000 | >50000 | >50000 | >50000 | 34,798 |
| 13 | 284 | 171 | 9,601 | >50000 | 11,262 | 4,727 | 5,985 | 25,030 |
| 29 | 9 | 350 | >50000 | 46,075 | >50000 | >50000 | >50000 | >50000 |
| 6 | 42 | 463 | 6,667 | 4,735 | 11,057 | 14,921 | 21,095 | 25,549 |

* Binding affinity (Ki) was determined in competition binding assays using membrane preparations of A293 cells expressing the human MCH1 receptor and [3H]Compound 10 as the radioligand.

TABLE 4

| EXAMPLE No. | STRUCTURE | Ki (nM) rMCH1 |
|---|---|---|
| 38 | 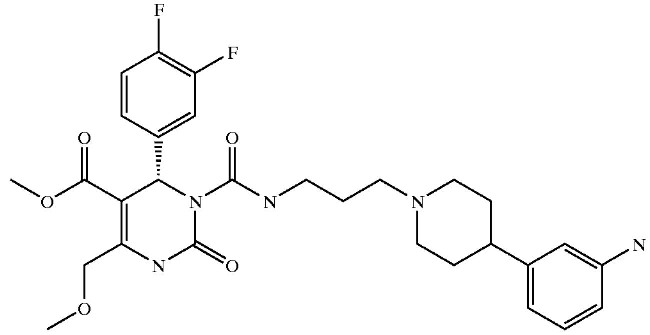 | 1.34 |

TABLE 4-continued

| EXAMPLE No. | STRUCTURE | Ki (nM) rMCH1 |
|---|---|---|
| 39 | 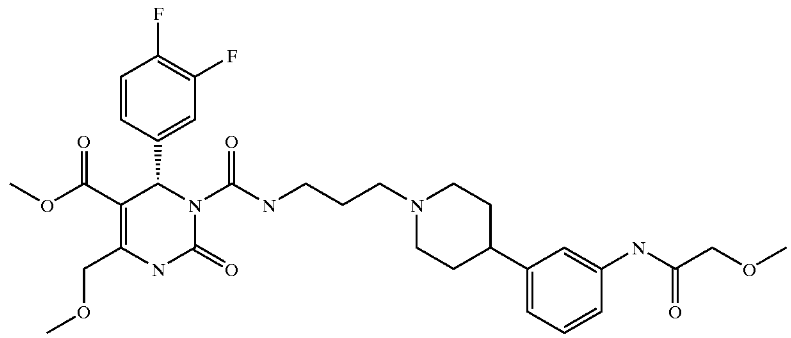 | 3.33 |
| 40 | 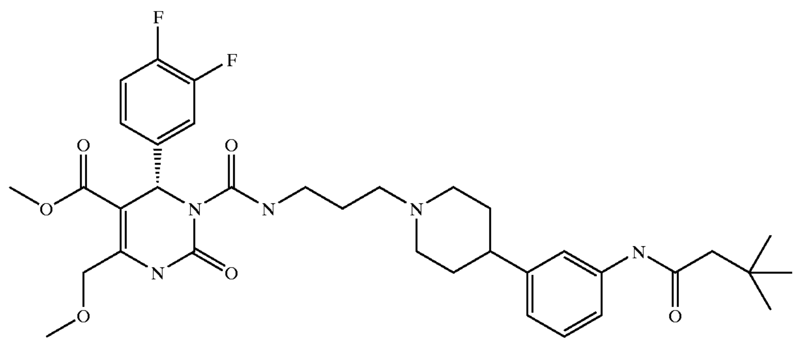 | 2.72 |
| 41 | 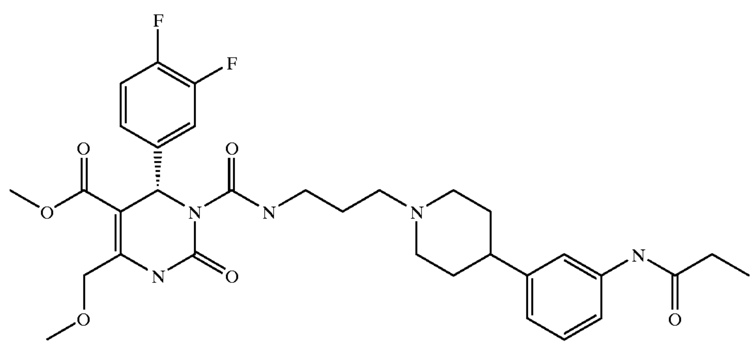 | 0.04 |
| 42 | 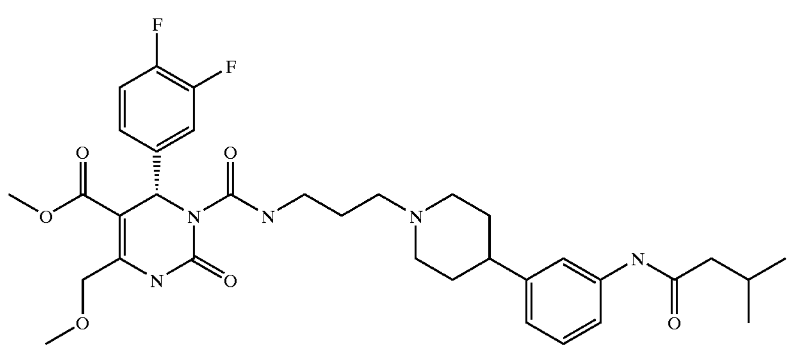 | 0.6 |

TABLE 4-continued

| EXAMPLE No. | STRUCTURE | Ki (nM) rMCH1 |
|---|---|---|
| 43 | 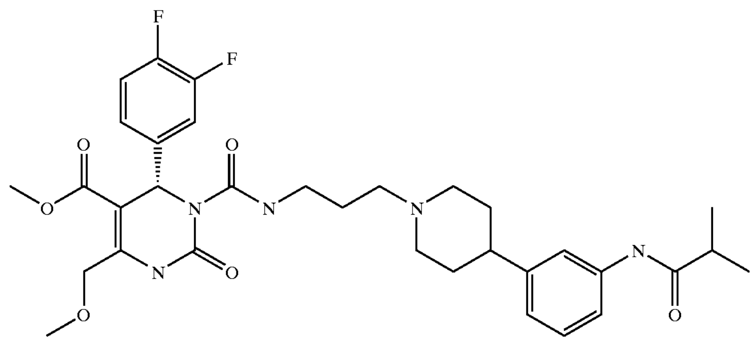 | 0.23 |
| 44 | 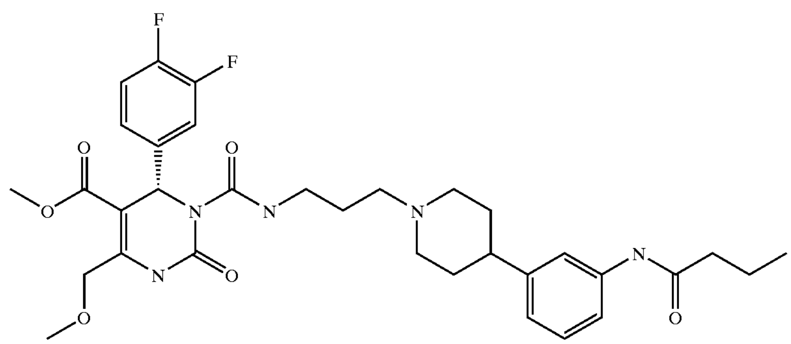 | 0.09 |
| 45 | 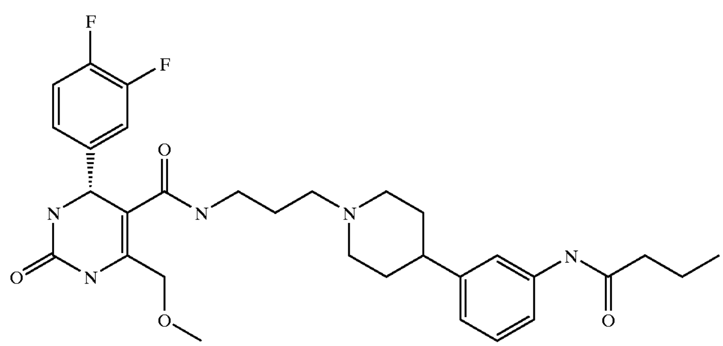 | 14.69 |
| 46 | 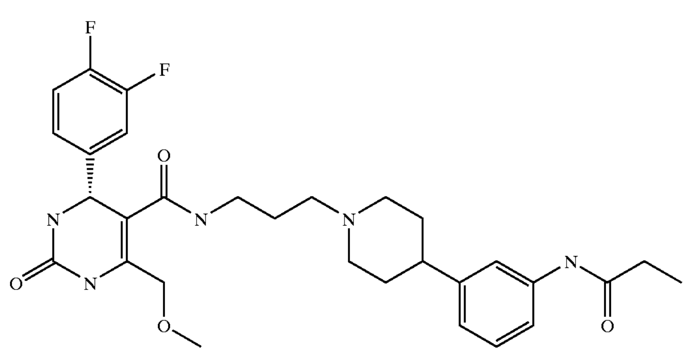 | 8.16 |

TABLE 4-continued

| EXAMPLE No. | STRUCTURE | Ki (nM) rMCH1 |
|---|---|---|
| 47 | 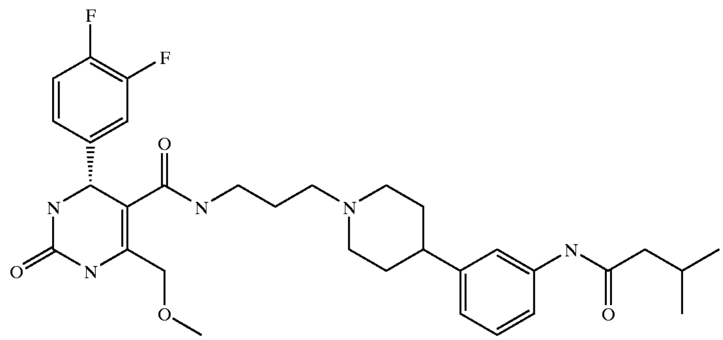 | 34.28 |
| 48 | 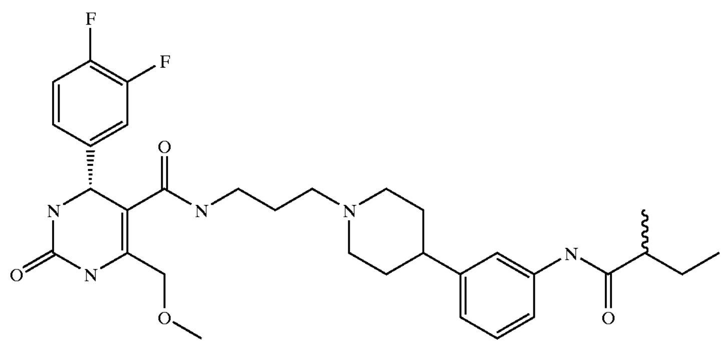 | 22.15 |
| 49 | 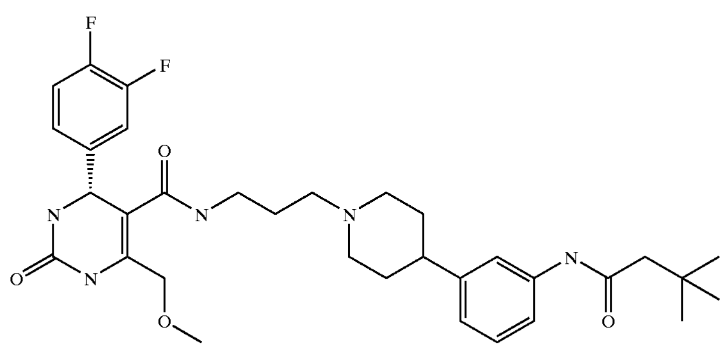 | 225.47 |
| 50 | 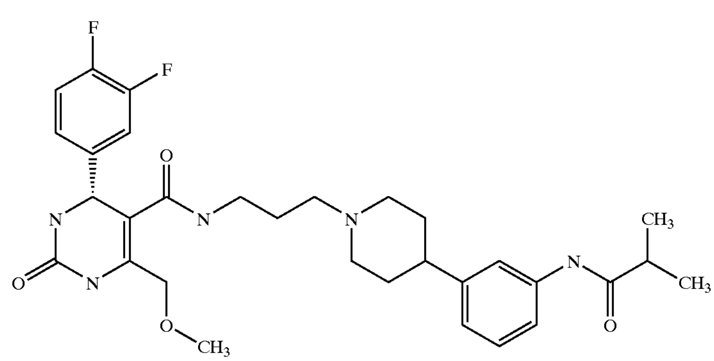 | 13.74 |

TABLE 4-continued

| EXAMPLE No. | STRUCTURE | Ki (nM) rMCH1 |
|---|---|---|
| 51 | 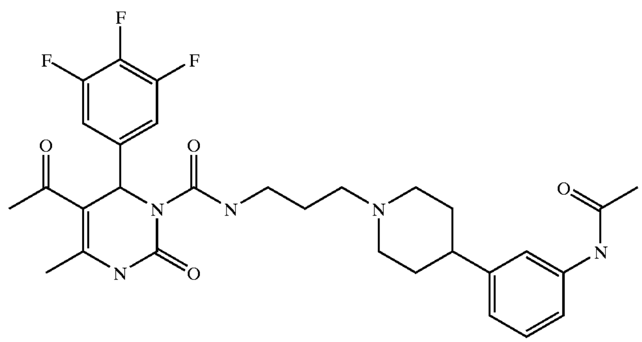 | 0.79 |
| 52 | 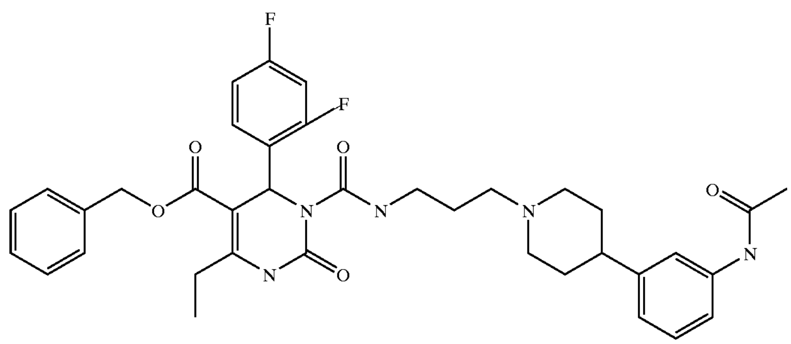 | 0.81 |
| 53 | 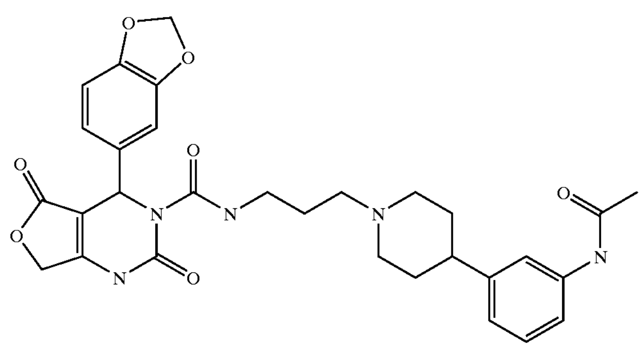 | 50.76 |
| 54 | 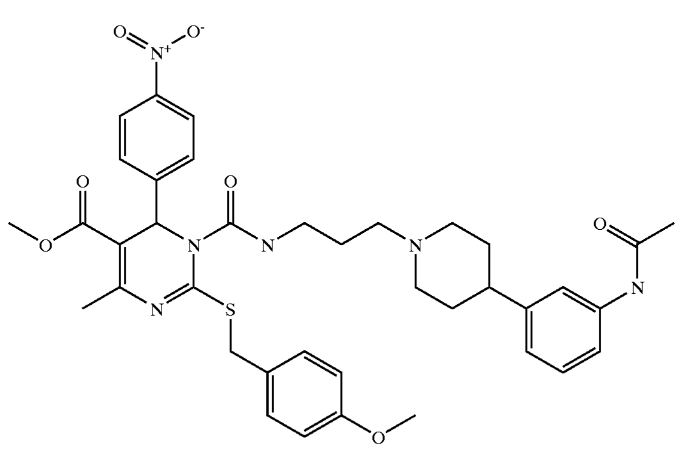 | 29.87 |

TABLE 4-continued

| EXAMPLE No. | STRUCTURE | Ki (nM) rMCH1 |
|---|---|---|
| 55 | 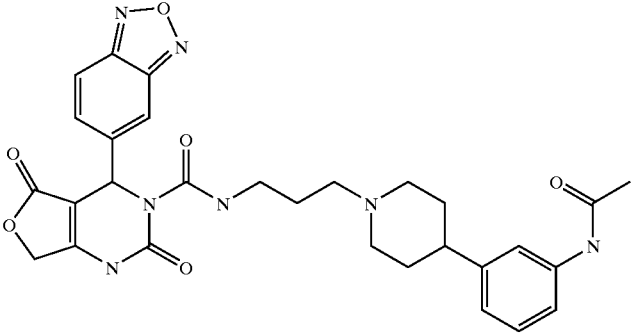 | 203.74 |
| 56 | 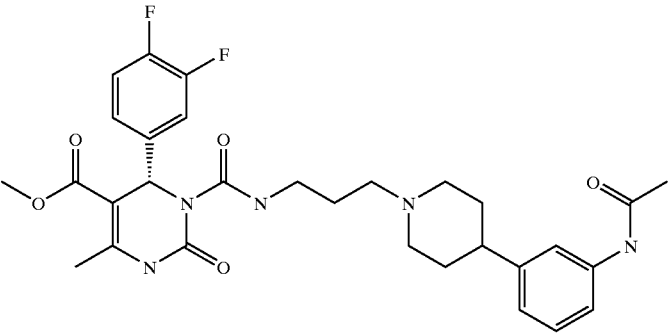 | 0.26 |

REFERENCES

Auburger, G., et al., (1992) Assignment of the second (Cuban) locus of autosomal dominant cerebellar ataxia to chromosome 12q23-24.1, between flanking markers D12S58 and PLA2. *Cytogenet. Cell. Genet.* 61:252–256.

Bahjaoui-Bouhaddi, M., et al., (1994) Insulin treatment stimulates the rat melanin-concentrating hormone-producing neurons. *Neuropeptides* 24:251–258.

Baker, B. I. (1991) Melanin-concentrating hormone: a general vertebrate neuropeptide. *Int. Rev. Cytol.* 126:1–47.

Baker, B. I. (1994) Melanin-concentrating hormone update: functional consideration. *TEM* 5:120–126.

Bassett, A. S., et al., (1988) Partial trisomy chromosome 5 cosegregating with schizophrenia. *Lancet* 1:799–801.

Bittencourt, J. C., et al., (1992) The melanin-concentrating hormone system of the rat brain: An immuno- and hybridization histochemical characterization. *J. Comp. Neurol.* 319:218–245.

Burgaud, J. L., et al., (1997) Melanin-concentrating hormone binding sites in human SVK14 keratinocytes. *Biochem.Biophys.Res.Commun.* 241(3):622–629.

Craddock, N., et al., (1993) The gene for Darier's disease maps to chromosome 12q23-q24.1. *Hum. Mol. Genet.* 2:1941–1943.

Drozdz, P. and Eberle, A. N. (1995) Binding sites for melanin-concentrating hormone (MCH) in brain synaptosomes and membranes from peripheral tissues identified with highly tritiated MCH. *J. Recept. Signal. Transduct. Res.* 15(1-4):487–502.

Drozdz, R., et al., (1995) Melanin-concentrating hormone binding to mouse melanoma cells in vitro. *FEBS* 359:199–202.

Drozdz, R., et al., (1998) Characterization of the receptor for melanin-concentrating hormone on melanoma cells by photocrosslinking. *Ann. NY Acad. Sci.* 839(1):210–213.

Gilliam, T. C., et al., (1989) Deletion mapping of DNA markers to a region of chromosome 5 that cosegregates with schizophrenia. *Genomics* 5:940–944.

Gonzalez, M. I., et al., (1997) Stimulatory effect of melanin-concentrating hormone on luteinizing hormone release. *Neuroendocrinology* 66(4):254–262.

Gonzalez, M. I., et al., (1997) α-melanocyte-stimulating hormone (α-MSH) and melanin-concentrating hormone (MCH) modify monoaminergic levels in the preoptic area of the rat. *Peptides* 18:387–392.

Gonzalez, M. I., et al., (1996) Behavioral effects of α-melanocyte-stimulating hormone (α-MSH) and melanin-concentrating hormone (MCH) after central administration in female rats. *Peptides* 17:171–177.

Grillon, S., et al., (1997) Exploring the expression of the melanin-concentrating hormone messenger RNA in the rat lateral hypothalamus after goldthioglucose injection. *Neuropeptides* 31(2):131–136.

Habert-Ortoli, E., et al., (1994) Molecular cloning of a functional human galanin receptor. *Proc Natl Acad Sci USA* 91:9780–9783.

Herve, C. and Fellmann, D. (1997) Changes in rat melanin-concentrating hormone and dynorphin messenger ribonucleic acids induced by food deprivation. *Neuropeptides* 31(3):237–242.

Hervieu, G., et al., (1996) Development and stage-dependent expression of melanin-concentrating hormone in mammalian germ cells. *Biology of Reproduction* 54:1161–1172.

Julius, D., et al.,(1988) Molecular characterization of a functional cDNA encoding the serotonin 1c receptor. *Science* 241:558–564.

Kauwachi, H., et al., (1983) Characterization of melanin-concentrating hormone in chum salmon pituitaries. *Nature* 305:321–333.

Knigge, K. M., et al., (1996) Melanotropic peptides in the mammalian brain: The melanin-concentrating hormone. *Peptides* 17:1063–1073.

Knigge, K. M. and Wagner, J. E. (1997) Melanin-concentrating hormone (MCH) involvement in pentylenetetrazole (PTZ)-induced seizure in rat and guinea pig. *Peptides* 18(7):1095–1097.

Larhammar, D., et al.,(1992) Cloning and functional expression of a human neuropeptide Y/peptide YY receptor of the Y1 type. *J Biol Chem.* 267:10935–10938.

Ludwig, D. S., et al., (1998) Melanin-concentrating hormone: a functional melanocortin antagonist in the hypothalamus. *Am. J. Physiol. Endocrinol. Metab.* 274(4) :E627-E633.

MacKenzie, F. J., et al., (1984) Evidence that the dopaminergic incerto-hypothalamic tract has a stimulatory effect on ovulation and gonadotropin release. *Neuroendocrinology* 39:289–295.

McBride, R. B., et al., (1994) The actions of melanin-concentrating hormone (MCH) on passive avoidance in rats: A preliminary study. *Peptides* 15:757–759.

Melki, J., et al., (1990) Gene for chronic proximal spinal muscular atrophies maps to chromosome 5q. *Nature (London)* 344:767–768.

Miller, C. L., et al., (1993) α-MSH and MCH are functional antagonists in a CNS auditory paradigm. *Peptides* 14:1–10.

Nahon, J. L., et al., (1989) The rat melanin-concentrating hormone mRNA encodes multiple putative neuropeptides coexpressed in the dorsolateral hypothalamus. *Endocrinology* 125:2056–2065.

Nahon, J-L. (1994) The melanin-concentrating hormone: from the peptide to the gene. *Critical Rev. in Neurobiol* 221:221–262.

Parkes, D. G. (1996) Diuretic and natriuretic actions of melanin concentrating hormone in conscious sheep. *J. Neuroendocrinol.* 8:57–63.

Pedeutour, F., et al., (1994) Assignment of the human pro-melanin-concentrating hormone gene (PMCH) to chromosome 12q23–24 and two variant genes (PMCHL1 and PMCHL2) to chromosome 5p14 and 5q12-q13. *Genomics* 19:31–37.

Presse, F., et al. (1992) Rat melanin-concentrating hormone messenger ribonucleic acid expression: marked changes during development and after stress and glucocorticoid stimuli. *Endocrinology* 131:1241–1250.

Qu, D., et al. (1996) A role for melanin-concentrating hormone in the central regulation of feeding behaviour. *Nature* 380:243–247.

Rossi, M., et al., (1997) Melanin-concentrating hormone acutely stimulates feeding, but chronic administration has no effect on body weight. *Endocrinology* 138:351–355.

Sahu, A. (1998) Evidence suggesting that galanin (GAL) melanin-concentrating hormone (MCH), neurotensin (NT), proopiomelanocortin (POMC) and neuropeptide Y (NPY) are targets of leptin signaling in the hypothalamus. *Endocrinology* 139(2):795–798.

Sakurai, T., et al., (1998) Orexins and orexin receptors: A family of hypothalamic neuropeptides and G protein-coupled receptors that regulate feeding behavior. *Cell* 92:573–585.

Sanchez, M., et al., (1997) Melanin-concentrating hormone (MCH) antagonizes the effects of α-MSH and neuropeptide E-I on grooming and locomotor activities in the rat. *Peptides* 18:393–396.

Sherrington, R., et al., (1988) Localization of a susceptibility locus for schizophrenia on chromosome 5. *Nature (London)* 336:164–167.

Smith. K. E., et al., (1998) Cloned human and rat galanin GALR3 receptors. Pharmacology and activation of G-protein inwardly rectifying K+ channels. *J Biol Chem* 273:23321–23326.

Smith, K. E., et al. (1997) Expression cloning of a rat hypothalamic galanin receptor coupled to phosphoinositide turnover. *J Biol Chem* 272:24612–24616.

Twells, R., et al., (1992) Chromosomal assignment of the locus causing olivo-ponto-cerebellar atrophy (SCA2) in a cuban founder population. Cytogent. Cell. Cenet. 61:262–265.

Westbrook, C. A., et al., (1992) Report of the second international workshop on human chromosome 5 mapping. Cytogenet. Cell. Genet. 61:225–231.

What is claimed is:

1. A compound having the structure:

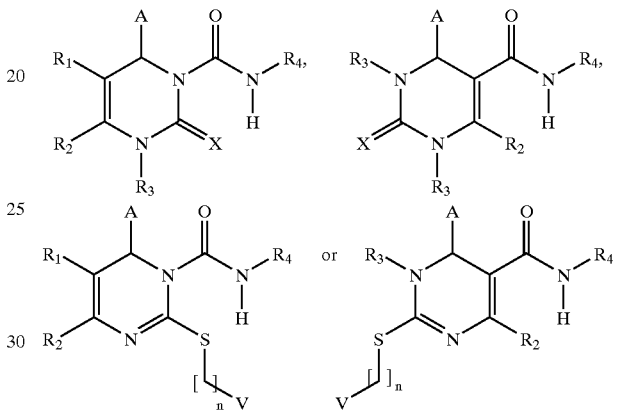

wherein A is

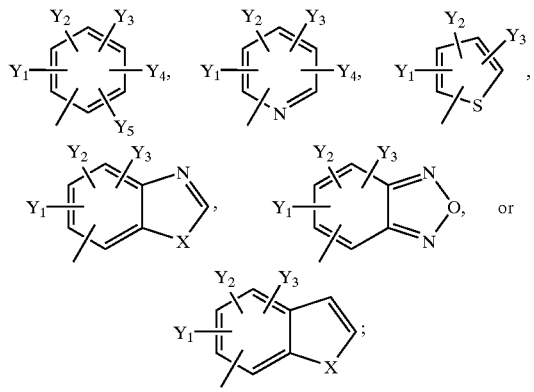

wherein each of $Y_1$, $Y_2$, $Y_3$, $Y_4$ and $Y_5$ is independently —H; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —F, —Cl, —Br, or —I, $NO_2$; —$N_3$; —CN; —$OR_3$; —$OCOR_3$, —$COR_3$, —$CON(R_3)_2$, or —$COOR_3$; or any two of $Y_1$, $Y_2$, $Y_3$, $Y_4$ and $Y_5$ present on adjacent carbon atoms can constitute a methylenedioxy group;

wherein each X is independently S; O; or $NR_3$;

wherein $R_1$ is —H; —$NO_2$; —CN; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —N(R$_3$)$_2$; —OR$_3$; —(CH$_2$)$_p$OR$_3$; —COR$_3$; —CO$_2$R$_3$; —CON(R$_3$)$_2$; or —CO$_2$(CH$_2$)$_n$V;

wherein R$_2$ is —H; straight chained or branched C$_1$–C$_7$ alkyl, hydroxyalkyl, alkoxyalkyl, monofluoroalkyl or polyfluoroalkyl; straight chained or branched C$_2$–C$_7$ alkenyl or alkynyl; C$_3$–C$_7$ cycloalkyl, monofluorocycloalkyl, polyfluorocycloalkyl or cycloalkenyl; C$_3$–C$_{10}$ cycloalkyl-C$_1$–C$_{10}$-alkyl, C$_3$–C$_{10}$ cycloalkyl-C$_1$–C$_{12}$-monofluoroalkyl or C$_3$–C$_{10}$ cycloalkyl-C$_1$–C$_{10}$-polyfluoroalkyl; —CN; —CH$_2$XR$_3$, —CH$_2$X(CH$_2$)$_p$NHR$_3$,—(CH$_2$)$_n$NHR$_3$, —CH$_2$X(CH$_2$)$_p$N(R$_3$)$_2$, —CH$_2$X(CH$_2$)$_p$N$_3$, or —CH$_2$X(CH$_2$)$_p$NHCXR$_7$; —OR$_3$; or wherein R$_2$ and R$_3$ together form a lactone ring;

wherein each R$_3$ is independently —H; straight chained or branched C$_1$–C$_7$ alkyl, monofluoroalkyl or polyfluoroalkyl; straight chained or branched C$_2$–C$_7$ alkenyl or alkynyl; C$_3$–C$_7$ cycloalkyl, monofluorocycloalkyl, polyfluorocycloalkyl or cycloalkenyl;

wherein R$_4$ is

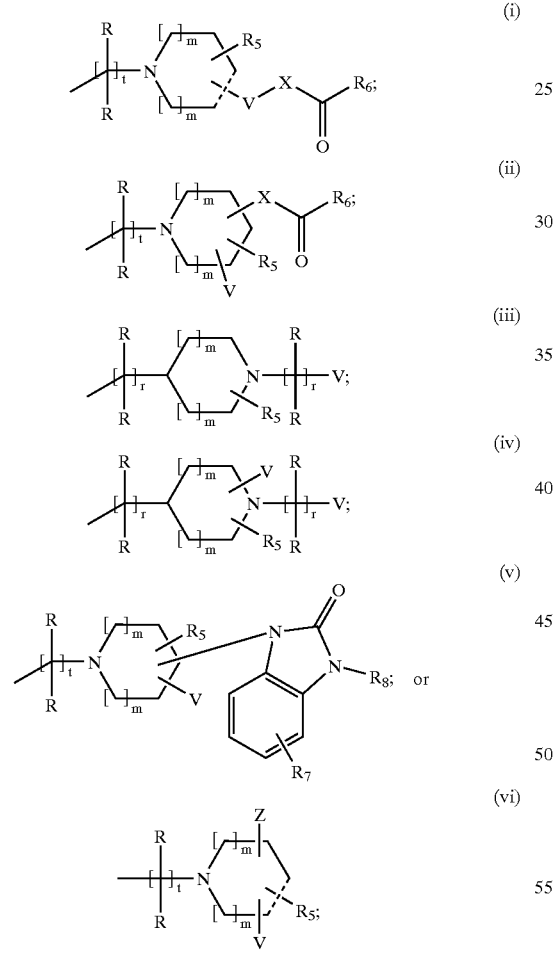

wherein the dashed line represents a single bond or a double bond;

wherein each R is independently —H; —F; straight chained or branched C$_1$–C$_7$ alkyl, monofluoroalkyl or polyfluoroalkyl; straight chained or branched C$_2$–C$_7$alkenyl or alkynyl; —N(R$_3$)$_2$; —NO$_2$; —CN; —CO$_2$R$_3$; —OR$_3$ or-CON(R$_3$)$_2$;

wherein each V is independently aryl or heteroaryl, optionally substituted with one or more F; Cl; Br; I; COR$_3$; CO$_2$R$_3$; —CON(R$_3$)$_2$; CN; —NO$_2$; —N(R$_3$)$_2$; —OR$_3$; —SR$_3$; (CH$_2$)$_q$OR$_3$; (CH$_2$)$_q$SR$_3$; straight chained or branched C$_2$–C$_7$ alkyl, monofluoroalkyl, polyfluoroalkyl, aminoalkyl, or carboxamidoalkyl; straight chained or branched C$_2$–C$_7$ alkenyl, C$_2$–C$_7$ alkynyl; C$_3$–C$_7$ cycloalkyl, monofluorocycloalkyl, polyfluorocycloalkyl or cycloalkenyl;

wherein each R$_5$ is —H; —NO$_2$; —N$_3$; —CN; straight chained or branched C$_1$–C$_7$ alkyl, monofluoroalkyl or polyfluoroalkyl; straight chained or branched C$_2$–C$_7$ alkenyl or alkynyl; C$_3$–C$_7$ cycloalkyl, monofluorocycloalkyl, polyfluorocycloalkyl or cycloalkenyl; —N(R$_3$)$_2$; —OR$_3$; —(CH$_3$)$_p$OR$_3$; —COR$_3$; —CO$_2$R$_3$; —CON(R$_3$)$_2$; aryl or heteroaryl, wherein the aryl or heteroaryl is optionally substituted with one or more F; Cl; Br; I; COR$_3$; CO$_2$R$_3$; —CON(R$_3$)$_2$; CN; —NO$_2$; —N(R$_3$)$_2$; —OR$_3$; —SR$_3$; (CH$_2$)$_q$OR$_3$; (CH$_2$)$_q$SR$_3$; straight chained or branched C$_1$–C$_7$ alkyl, monofluoroalkyl, polyfluoroalkyl, aminoalkyl, or carboxamidoalkyl; straight chained or branched C$_2$–C$_7$ alkenyl, C$_2$–C$_7$ alkynyl; C$_3$–C$_7$ cycloalkyl, monofluorocycloalkyl, polyfluorocycloalkyl or cycloalkenyl;

wherein R$_6$ is —H; straight chained or branched C$_1$–C$_7$ alkyl, monofluoroalkyl or polyfluoroalkyl; straight chained or branched C$_2$–C$_{14}$, alkenyl or alkynyl; C$_3$–C$_7$ cycloalkyl, monofluorocycloalkyl, polyfluorocycloalkyl or cycloalkenyl; —N(R$_3$)$_2$; —OR$_3$; —(CH$_3$)$_p$OR$_3$; —COR$_3$; —CO$_2$R$_3$; —CON(R$_3$)$_2$; aryl or heteroaryl, optionally substituted with one or more F; Cl; Br; I; COR$_3$; CO$_2$R$_3$; —CON(R$_3$)$_2$; CN; —NO$_2$; —N(R$_3$)$_2$; —OR$_3$; —SR$_3$; (CH$_2$)$_q$OR$_3$; (CH$_3$)$_q$SR$_3$; straight chained or branched C$_1$–C$_7$ alkyl, monofluoroalkyl, polyfluoroalkyl, aminoalkyl, or carboxamidoalkyl; straight chained or branched C$_2$–C$_7$ alkenyl, C$_2$–C$_7$ alkynyl; C$_3$–C$_7$ cycloalkyl, monofluorocycloalkyl, polyfluorocycloalkyl or cycloalkenyl;

wherein R$_7$ is H; F; Cl; Br; I; —NO$_2$; —N$_3$; —CN; straight chained or branched C$_1$–C$_7$ alkyl, monofluoroalkyl or polyfluoroalkyl; straight chained or branched C$_2$–C$_7$ alkenyl or alkynyl; C$_3$–C$_7$ cycloalkyl, monofluorocycloalkyl, polyfluorocycloalkyl or cycloalkenyl; —N(R$_3$)$_2$; —OR$_3$; —(CH$_2$)$_p$OR$_3$; —COR$_3$; —CO$_2$R$_3$; or —CON(R$_3$)$_2$;

wherein R$_8$ is independently straight chained or branched C$_1$–C$_7$ alkyl, monofluoroalkyl or polyfluoroalkyl; straight chained or branched C$_2$–C$_7$ alkenyl or alkynyl; C$_3$–C$_7$ cycloalkyl, monofluorocycloalkyl, polyfluorocycloalkyl or cycloalkenyl;

wherein Z is naphthyl, quinolinyl, isoquinolinyl, quinazolinyl, phthalazinyl, quinoxalinyl, indolyl, benzo[b]furanyl, or benzo[b]thiophenyl; wherein the naphthyl, quinolinyl, isoquinolinyl, quinazolinyl, phthalazinyl, quinoxalinyl, indolyl, benzo[b]furanyl, or benzo[b]thiophenyl may be substituted with one or more F; Cl; Br; I; COR$_3$; CO$_2$R$_3$; CON(R$_3$)$_2$; CN; —NO$_2$; —N(R$_3$)$_2$; —OR$_3$; —SR$_3$; (CH$_2$)$_q$OR$_3$; (CH$_2$)$_q$SR$_3$; straight chained or branched C$_1$–C$_7$ alkyl, monofluoroalkyl, polyfluoroalkyl, aminoalkyl, or carboxamidoalkyl; straight chained or branched C$_2$–C$_7$ alkenyl, C$_2$–C$_7$ alkynyl; C$_3$–C$_7$ cycloalkyl, monofluorocycloalkyl, polyfluorocycloalkYl or cycloalkenyl;

wherein each m is independently an integer from 0 to 3 inclusive;

wherein each n is independently an integer from 0 to 5 inclusive;
wherein each p is independently an integer from 1 to 7 inclusive;
wherein g is an integer from 1 to 3 inclusive;
wherein r is an integer from 0 to 3 inclusive;
wherein t is an integer from 2 to 6 inclusive;
or a pharmaceutically acceptable salt thereof.

2. A (+) enantiomer of the compound of claim 1.
3. A (−) enantiomer of the compound of claim 1.
4. The compound of claim 1 having the structure:

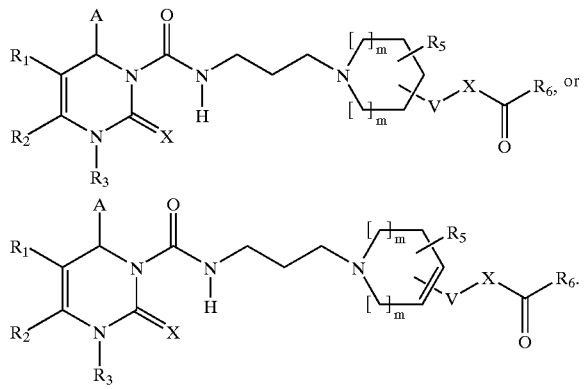

5. The compound of claim 4, having the structure:

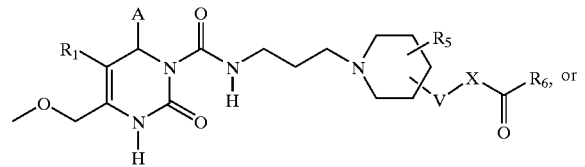

6. The compound of claim 5, having the structure:

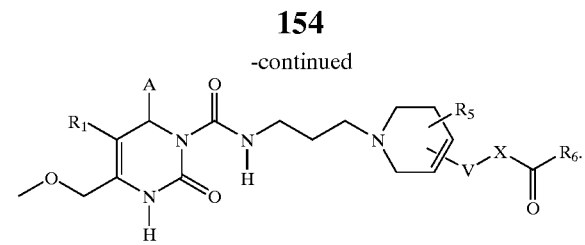

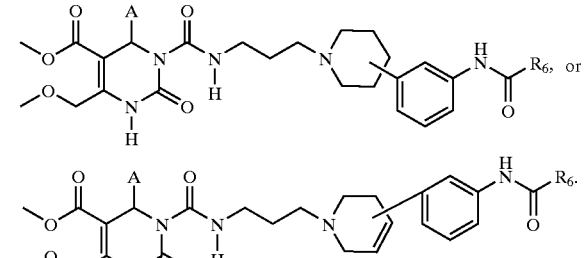

7. The compound of claim 6, wherein A is

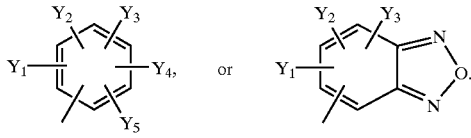

8. The compound of claim 7, wherein the compound is

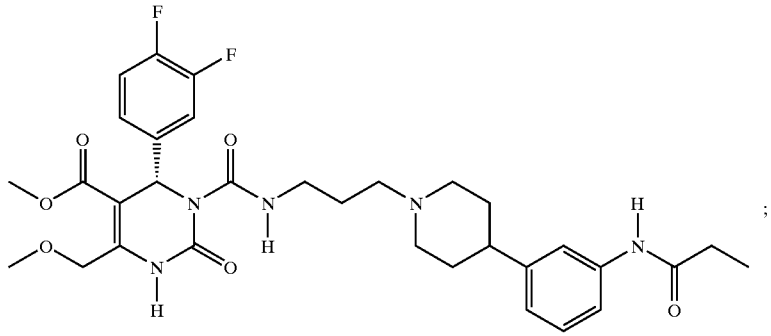

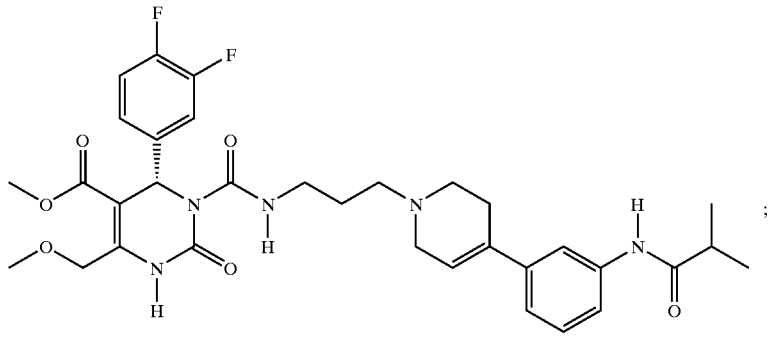

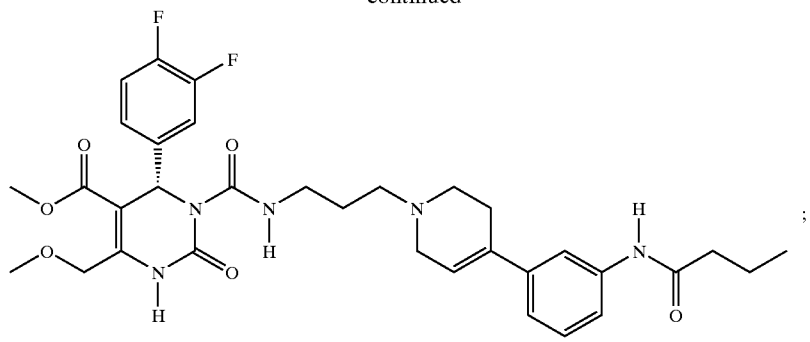
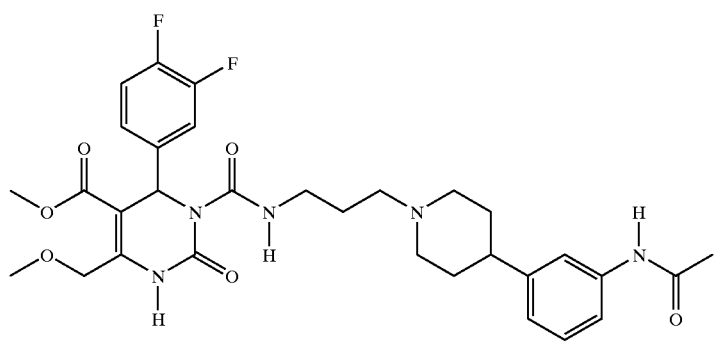
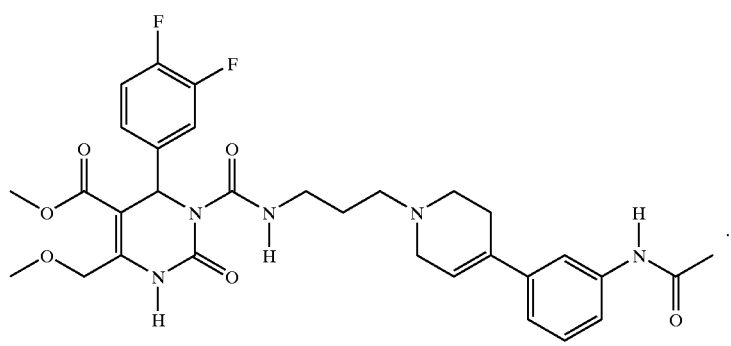
9. The compound of claim 1, having the structure:
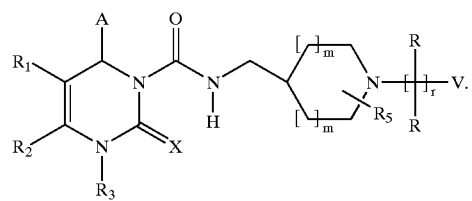
10. The compound of claim 9, having the structure:
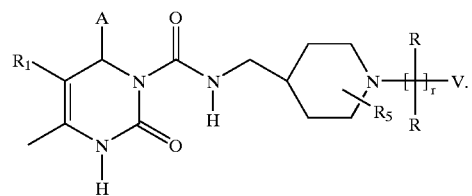
11. The compound of claim 10 having the structure:
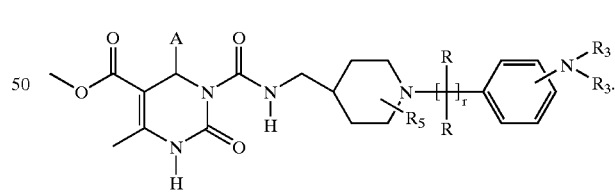
12. The compound of claim 11 wherein A is
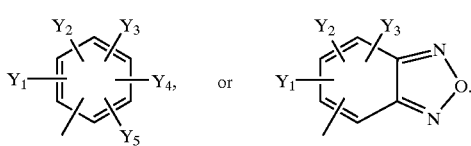

13. The compound of claim 12 having the structure:

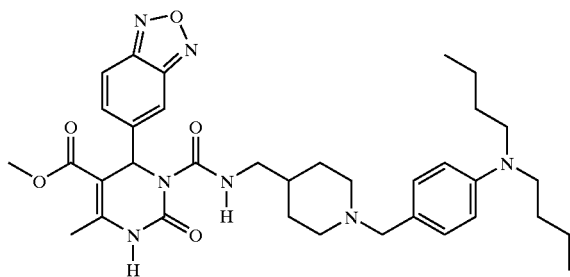

14. The compound of claim 1, wherein the compound is:
(+)-1,2,3,6-tetrahydro-1-{n [4-(3,-acetamido)-phenyl-piperidin-1-y 11propyl}carboxamido-4-methoxymethyl-6-(3,4-difluoro-phenyl)-2-oxo pyrimidine-5-carboxylic acid methyl ester.

15. The compound of claim 4 having the structure:

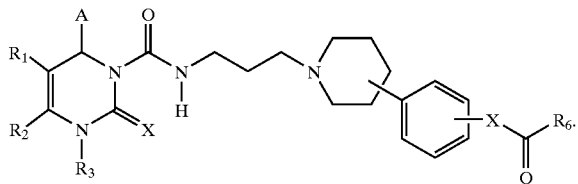

16. The compound of claim 15 having the structure:

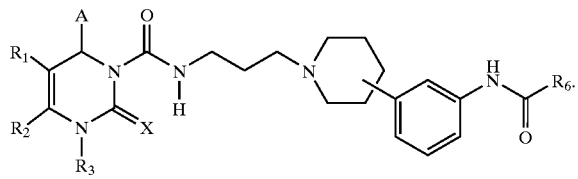

17. The compound of claim 16 having the structure:

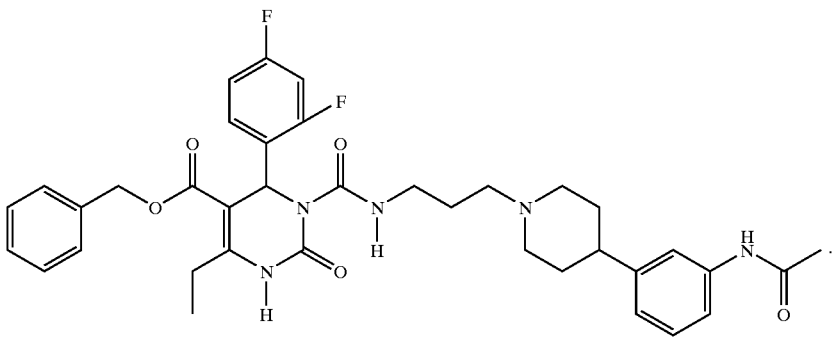

18. A method of reducing the body mass of a subject in need of such reduction, which comprises administering to the subject an amount of a compound effective to reduce the body mass of the subject wherein the compound has the structure:

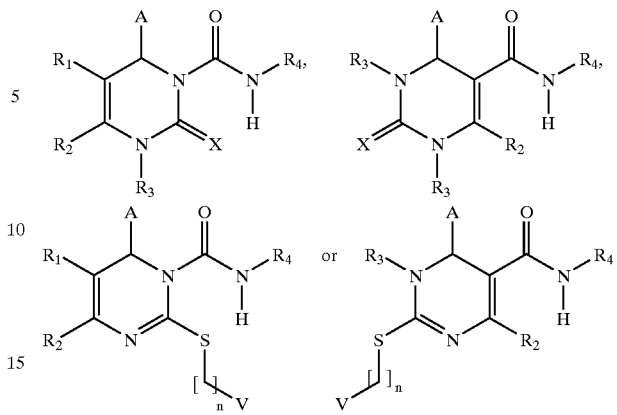

wherein A is

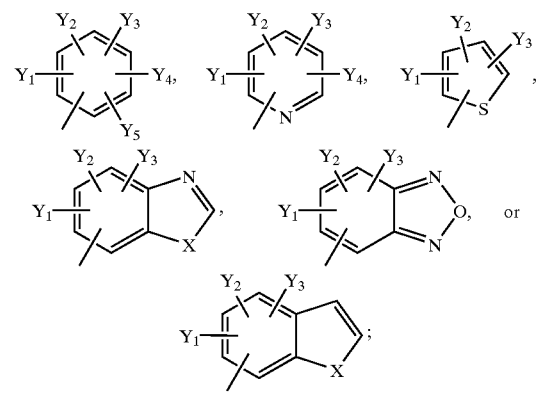

wherein each of $Y_1$, $Y_2$, $Y_3$, $Y_4$ and $Y_5$ is independently —H; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —F, —Cl, —Br, or —I, $NO_2$; —$N_3$; —CN; —$OR_3$, —$OCOR_3$, —$COR_3$, —$CON(R_3)_2$, or —$COOR_3$; or any two of $Y_1$, $Y_2$, $Y_3$, $Y_4$ and $Y_5$ present on adjacent carbon atoms can constitute a methylenedioxy group;

wherein each X is independently S; O; or $NR_3$;
wherein $R_1$ is —H; —$NO_2$; —CN; straight chained or branched $C_1$–$C_7$alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —N(R$_3$)$_2$; —OR$_3$; —(CH$_2$)$_p$OR$_3$; —COR$_3$; —CO$_2$R$_3$; —CON(R$_3$)$_2$; or —CO$_2$(CH$_2$)$_n$V;

wherein R$_2$ is —H; straight chained or branched C$_1$–C$_7$ alkyl, hydroxyalkyl, alkoxyalkyl, monofluoroalkyl or polyfluoroalkyl; straight chained or branched C$_2$–C$_7$ alkenyl or alkynyl; C$_3$–C$_7$ cycloalkyl, monofluorocycloalkyl, polyfluorocycloalkyl or cycloalkenyl; C$_3$–C$_{10}$ cycloalkyl-C$_1$–C$_{10}$ alkyl, C$_2$–C$_{10}$ cycloalkyl-C$_1$–C$_{10}$-monofluoroalkyl or C$_3$–C$_{10}$ cycloalkyl-C$_1$–C$_{10}$-polyfluoroalkyl; —CN; —CH$_2$XR$_3$, CH$_2$X(CH$_2$)$_p$NHR$_3$, —(CH$_2$)$_n$NHR$_3$, —CH$_2$X(CH$_2$)$_p$N(R$_3$)$_2$, —CH$_2$X(CH$_2$)$_p$N$_3$, or —CH$_2$X(CH$_2$)$_p$NHCXR$_7$; —OR$_3$; or wherein R$_2$ and R$_3$ together form a lactone ring;

wherein each R$_3$ is independently —H; straight chained or branched C$_1$–C$_7$ alkyl, monofluoroalkyl or polyfluoroalkyl; straight chained or branched C$_2$–C$_7$ alkenyl or alkynyl; C$_3$–C$_7$ cycloalkyl, monofluorocycloalkyl, polyfluorocycloalkyl or cycloalkenyl;

wherein R$_4$ is

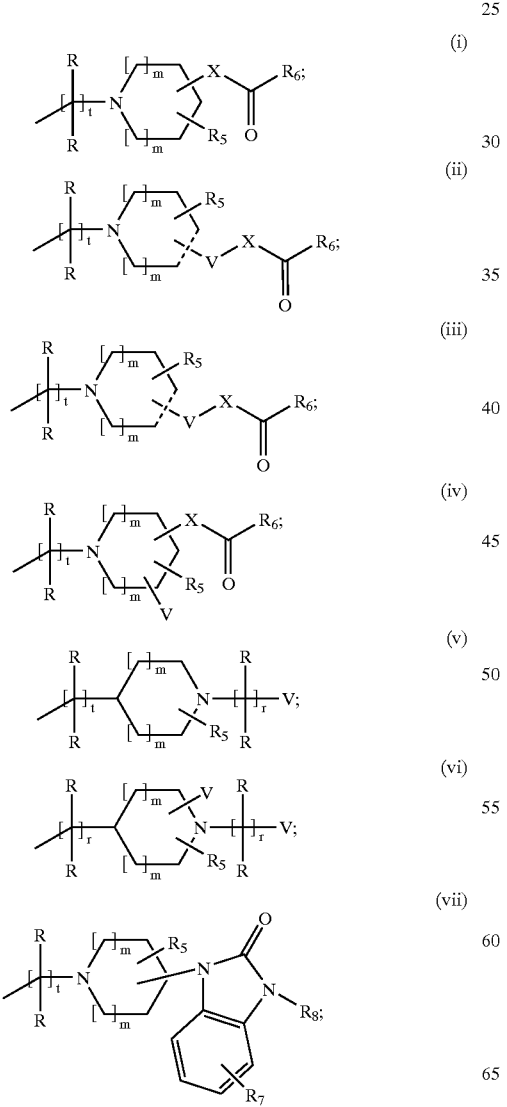

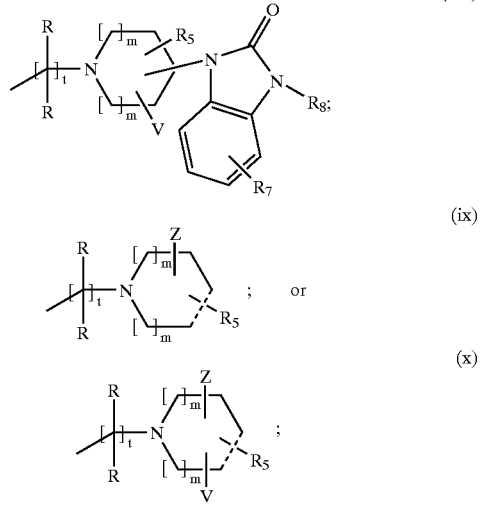

wherein the dashed line represents a single bond or a double bond;

wherein each R is independently —H; —F; straight chained or branched C$_1$–C$_7$ alkyl, monofluoroalkyl or polyfluoroalkyl; straight chained or branched C$_{2-C7}$ alkenyl or alkynyl; —N(R$_3$)$_2$; —NO$_2$; —CN; —CO$_2$R$_3$; —OR or —CON(R$_3$)$_2$;

wherein each V is independently aryl or heteroaryl, optionally substituted with one or more F; Cl; Br; I; COR$_3$; CO$_2$R$_3$; —CON(R$_3$)$_2$; CN; —NO$_2$; —N(R$_3$)$_2$; —OR$_3$; —SR$_3$; (CH$_2$)$_q$OR$_3$; (CH$_2$)$_q$SR$_3$; straight chained or branched C$_1$–C$_7$ alkyl, monofluoroalkyl, polyfluoroalkyl, aminoalkyl, or carboxamidoalkyl; straight chained or branched C$_2$–C$_7$ alkenyl, C$_2$–C$_7$ alkynyl; C$_3$–C$_7$ cycloalkyl, monofluorocycloalkyl, polyfluorocycloalkyl or cycloalkenyl;

wherein each R$_5$ is —H; —NO$_2$; —N$_3$; —CN; straight chained or branched C$_1$–C$_7$ alkyl, monofluoroalkyl or polyfluoroalkyl; straight chained or branched C$_2$–C$_7$ alkenyl or alkynyl; C$_3$—C$_7$ cycloalkyl, monofluorocycloalkyl, polyfluorocycloalkyl or cycloalkenyl; —N(R$_3$)$_2$; —OR$_3$; —(CH$_2$)$_p$OR$_3$; —COR$_3$; —CO$_2$R$_3$; CON(R$_3$)$_2$; aryl or heteroaryl, wherein the aryl or heteroaryl is optionally substituted with one or more F; Cl; Br; I; COR$_3$; CO$_2$R$_3$; —CON(R$_3$)$_2$; CN; —NO$_2$; —N(R$_3$)$_2$; —OR$_3$; —SR$_3$; (CH$_2$)$_q$OR$_3$; (CH$_2$)$_q$SR$_3$; straight chained or branched C$_1$–C$_7$ alkyl, monofluoroalkyl, polyfluoroalkyl, aminoalkyl, or carboxamidoalkyl; straight chained or branched C$_2$–C$_7$ alkenyl, C$_2$–C$_7$ alkynyl; C$_3$–C$_7$ cycloalkyl, monofluorocycloalkyl, polyfluorocycloalkyl or cycloalkenyl;

wherein R$_6$ is —H; straight chained or branched C$_3$–C$_7$ alkyl, monofluoroalkyl or polyfluoroalkyl; straight chained or branched C$_2$∫C$_7$ alkenyl or alkynyl; C$_3$–C$_7$ cycloalkyl, monofluorocycloalkyl, polyfluorocycloalkyl or cycloalkenyl; —N(R$_3$)$_2$; —OR$_3$; —(CH$_2$)$_p$OR$_3$; —COR$_3$; —CO$_2$R$_3$; —CON(R$_3$)$_2$; aryl or heteroaryl, optionally substituted with one or more F; Cl; Br; I; COR$_3$; CO$_2$R$_3$; —CON(R$_3$)$_2$; CN; —NO$_2$; —N(R$_3$)$_2$; —OR$_3$; —SR$_3$; (CH$_2$)$_q$OR$_3$; (CH$_2$)$_q$SR$_3$; straight chained or branched C$_3$–C$_7$ alkyl, monofluoroalkyl, polyfluoroalkyl, aminoalkyl, or carboxamidoalkyl; straight chained or branched C$_2$–C$_7$ alkenyl, $C_2$–$C_7$ alkynyl; $C_3$–$C_7$ cycloalkyl, monofluorocycloalkyl, polyfluorocycloalkyl or cycloalkenyl;

wherein $R_7$ is H; F; CL; Br; I; —$NO_2$; —$N_3$; —CN; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —$N(R_3)_2$; —$OR_3$; —$(CH_2)_pOR_3$; —$COR_3$; $CO_2R_3$; or —$CON(R_3)_2$;

wherein $R_8$ is independently straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl;

wherein Z is naphthyl, quinolinyl, isoquinolinyl, quinazoliflyl, phthalazinyl, quinoxalinyl, indolyl, benzo[b]furaflyl, or benzo[b]thiopheflyl; wherein the naphthyl, quinolinyl, isoquinolinyl, quinazolinyl, phthalazinyl, quinoxalinyl, indolyl, benzo[b]furanyl, or benzo[b]thiopheflyl may be substituted with one or more F; Cl; Br; I; $COR_3$; $CO_2R_3$; —$CON(R_3)_2$; CN; —$NO_2$; —$N(R_3)_2$; —$OR_3$; —$SR_3$; $(CH_2)_qOR_3$; $(CH_2)_qSR_3$; straight chained or branched $C_1$–$C_3$ alkyl, monofluoroalkyl, polyfluoroalkyl, aminoalkyl, or carboxamidoalkyl; straight chained or branched $C_2$–$C_7$ alkenyl, $C_2$–$C_7$ alkynyl; $C_3$–$C_7$ cycloalkyl, monofluorocycloalkyl, polyfluorocyclOalkYl or cycloalkenyl;

wherein each m is independently an integer from 0 to 3 inclusive;

wherein each n is independently an integer from 0 to 5 inclusive;

wherein each p is independently an integer from 1 to 7 inclusive;

wherein q is an integer from 1 to 3 inclusive;

wherein r is an integer from 0 to 3 inclusive;

wherein t is an integer from 2 to 6 inclusiver or a pharmaceutically acceptable salt thereof.

\* \* \* \* \*